US011104884B2

(12) United States Patent
Jordan et al.

(10) Patent No.: US 11,104,884 B2
(45) Date of Patent: Aug. 31, 2021

(54) VACCINIA VIRUS VECTORS RELATED TO MVA WITH EXTENSIVE GENOMIC SYMMETRIES

(71) Applicant: Probiogen AG, Berlin (DE)

(72) Inventors: Ingo Jordan, Berlin (DE); Volker Sandig, Berlin (DE)

(73) Assignee: Probiogen AB, Berlin (DE)

( * ) Notice: Subject to any disclaimer, the term of this patent is extended or adjusted under 35 U.S.C. 154(b) by 4 days.

(21) Appl. No.: 16/485,748

(22) PCT Filed: Feb. 23, 2017

(86) PCT No.: PCT/EP2017/054192
§ 371 (c)(1),
(2) Date: Aug. 13, 2019

(87) PCT Pub. No.: WO2018/153460
PCT Pub. Date: Aug. 30, 2018

(65) Prior Publication Data

US 2019/0367887 A1 Dec. 5, 2019

(51) Int. Cl.

| | |
|---|---|
| ***A61K 39/00*** | (2006.01) |
| ***A61K 39/12*** | (2006.01) |
| ***C12N 15/86*** | (2006.01) |
| ***C12N 7/00*** | (2006.01) |
| ***C12N 15/00*** | (2006.01) |
| ***A61K 39/285*** | (2006.01) |
| ***C07K 14/005*** | (2006.01) |

(52) U.S. Cl.
CPC .............. *C12N 7/00* (2013.01); *A61K 39/285* (2013.01); *C07K 14/005* (2013.01); *A61K 2039/525* (2013.01); *C12N 2710/24121* (2013.01); *C12N 2710/24122* (2013.01); *C12N 2710/24134* (2013.01); *C12N 2710/24143* (2013.01); *C12N 2710/24164* (2013.01)

(58) Field of Classification Search
CPC ............ A61K 2039/5256; A61K 39/12; C12N 2710/24143; C12N 15/86; A61P 35/00
See application file for complete search history.

(56) References Cited

FOREIGN PATENT DOCUMENTS

| | | | |
|---|---|---|---|
| WO | 2014/048500 A1 | | 4/2014 |
| WO | WO2014048500 | * | 4/2014 |

OTHER PUBLICATIONS

International Search Report in PCT/EP2017/054192, dated Oct. 2, 2017.
Elde, et al. "Poxviruses deploy genomic accordions to adapt rapidly against host antiviral defenses." Cell 150, No. 4 (2012): 831-841.
Jordan et al., "A Genotype of Modified Vaccinia Ankara (MVA) that Facilitates Replication in Suspension Cultures in Chemically Defined Medium," *Viruses*, vol. 5, No. 1, Jan. 21, 2013, 321-339.
Jordan et al., "Elements in the Development of a Production Process for modified Vaccinia Virus Ankara," *Microorganisms*, vol. 1, No. 1, Nov. 1, 2013, 100-121.
Kotwal, et al. "Analysis of a large cluster of nonessential genes deleted from a vaccinia virus terminal transposition mutant." Virology 167, No. 2 (1988): 524-537.
Meisinger-Henschel, et al. "Introduction of the six major genomic deletions of modified vaccinia virus Ankara (MVA) into the parental vaccinia virus is not sufficient to reproduce an MVA-like phenotype in cell culture and in mice." Journal of virology 84, No. 19 (2010): 9907-9919.
Suter, et al. "Modified vaccinia Ankara strains with identical coding sequences actually represent complex mixtures of viruses that determine the biological properties of each strain." Vaccine 27, No. 52 (2009): 7442-7450.
Tapi et al., "Propagation of Influenza and MVA Virus in Cascades of Continuous Stirred Tank Bioreactors: Challenging the 'Von Magnus Effect,'" *Vaccine Technology VI*, ECI Conference Albufeira, Portugal, 2016.

* cited by examiner

*Primary Examiner* — Barry A Chestnut
(74) *Attorney, Agent, or Firm* — Kilpatrick Townsend & Stockton LLP

(57) ABSTRACT

The present invention relates to a novel Modified Vaccinia Ankara (MVA) related virus. The present invention also relates to a method for culturing said MVA related virus and to a method for producing said MVA related virus. Further, the present invention relates to a pharmaceutical composition comprising said MVA related virus and one or more pharmaceutical acceptable excipient(s), diluent(s), and/or carrier(s). Furthermore, the present invention relates to a vaccine comprising said MVA related virus. In addition, the present invention relates to said MVA related virus for use in medicine.

15 Claims, 4 Drawing Sheets

Specification includes a Sequence Listing.

VACCINIA VIRUS VECTORS RELATED TO MVA WITH EXTENSIVE GENOMIC SYMMETRIES

The present invention relates to a novel Modified Vaccinia Ankara (MVA) related virus. The present invention also relates to a method for culturing said MVA related virus and to a method for producing said MVA related virus. Further, the present invention relates to a pharmaceutical composition comprising said MVA related virus and one or more pharmaceutical acceptable excipient(s), diluent(s), and/or carrier(s). Furthermore, the present invention relates to a vaccine comprising said MVA related virus. In addition, the present invention relates to said MVA related virus for use in medicine.

REFERENCE TO SUBMISSION OF A SEQUENCE LISTING AS A TEXT FILE

The Sequence Listing written in file 095697-1151072-003500US_SL.txt created on Apr. 15, 2021, 290,816 bytes, machine format IBM-PC, MS-Windows operating system, is hereby incorporated by reference in its entirety for all purposes.

BACKGROUND OF THE INVENTION

Vaccinia virus (VACV) belongs to the genus *Orthopoxvirus* of the Poxviridae family and has been used as a live vaccine in the successful eradication of variola. However, vaccinia virus can productively infect humans and its use as expression vector in laboratories has been affected by safety concerns and regulations. Concerns with the safety of standard strains of VACV have been addressed by the development of vaccinia vectors from highly attenuated virus strains which are characterized by their restricted replicative capacity in vitro and absence of virulence in vivo.

Modified Vaccinia Ankara (MVA) virus is a strain of vaccinia virus that has been obtained by adaptation of a strain of VACV to replication in cultures of primary chicken embryo fibroblasts (Mayr and Munz, 1964). It belongs to the highly attenuated poxviruses that can be used as a vaccine vector for safe and reactogenic expression of large transgenes to elicit a robust T-cell mediated immune response (Drillien et al., 2004; Liu et al., 2008; Sutter and Moss, 1992; Sutter et al., 1994). It is not inhibited by pre-existing immunity and investigated for protective and therapeutic treatment also of immunocompromised human patients (Cebere et al., 2006; McShane et al., 2002; Milligan et al., 2016; Webster et al., 2005).

Productive replication of MVA is restricted to avian cells and very few mammalian cells such as BHK and cell lines derived from the Egyptian fruit bat (Carroll and Moss, 1997; Drexler et al., 1998; Jordan et al., 2009a). The molecular basis for the narrow host range of MVA compared to the parental virus appears to be due to six deletions (deletion site I through VI, with the numerals increasing with the size of the deletion, not with position in the genome) and a number of more confined mutations that may have been caused by the adaptation to the avian cells (Blanchard et al., 1998; Meisinger-Henschel et al., 2007; Meyer et al., 1991).

The provision of adequate supply of the MVA virus is challenging. MVA has to be given at high doses of $10^8$ infectious units because it does not replicate and is therefore not amplified in the recipient (Wyatt et al., 2004). However, the MVA virus production systems which are presently available are time-consuming and expensive and cannot satisfy the needs of the pharmaceutical industry.

Here, for the first time, the present inventors isolated and characterized a novel MVA related virus. The present inventors found that the novel MVA related virus fundamentally differs in the genome structure from the (wild-type) MVA virus. The structural differences result in a virus having advantageous properties over the (wild-type) MVA virus. In particular, the novel MVA related virus releases a higher number of infectious units into the supernatant of infected cultures compared to those infected with the (wild-type) MVA virus. Further, the novel MVA related virus replicates to very high titers compared to the (wild-type) MVA virus. Furthermore, the novel MVA related virus induces fewer syncytia in adherent cultures.

The above described beneficial properties of the novel MVA related virus improve its industrial production. Particularly, they allow the production of the novel MVA related virus in high yields and, thus, also the production of heterologous proteins, e.g. antigens, which may be comprised therein. In addition, the novel MVA related virus can be isolated directly from the cell-free supernatant which facilitates purification and, thus, the logistic and the operation of bioreactors producing said MVA related virus. This, in turn, reduces the costs of its production.

SUMMARY OF THE INVENTION

In a first aspect, the present invention relates to a Modified Vaccinia Ankara (MVA) related virus comprising one or more of the following features:

(i) a nucleic acid sequence corresponding to a region that includes the right Inverted Terminal Repeat (ITR) and extends to but excludes deletion site III instead of (replacing) a nucleic acid sequence that includes the left Inverted Terminal Repeat (ITR) and extends to but excludes deletion site V, (ii) two copies of a nucleic acid sequence comprising deletion site IV and the right ITR, (iii) no nucleic acid sequence comprising deletion site I and the left ITR, (iv) no deletion site I, (v) two deletion sites IV, (vi) no open reading frame for at least one gene product selected from the group consisting of C11R, C10L, and D7L, (vii) two open reading frames for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R, and/or (viii) a nucleic acid sequence encoding a L3L gene product, wherein said nucleic acid sequence comprises at least one mutation resulting in an amino acid sequence modification of said gene product.

In a second aspect, the present invention relates to a genome of the MVA related virus according to the first aspect.

In a third aspect, the present invention relates to a cell comprising the MVA related virus according to the first aspect or the genome according to the second aspect.

In a fourth aspect, the present invention relates to a method for culturing a MVA related virus according to the first aspect comprising the steps of:

(a) providing a cell according to the third aspect, (b) culturing the cell, and (c) isolating the MVA related virus.

In a fifth aspect, the present invention relates to a method for producing a MVA related virus according to the first aspect comprising the steps of:

(a) infecting a cell with a MVA virus,
(b) culturing the cell,
(c) isolating the MVA virus, and
(d) repeating steps (a) to (c) with the MVA virus isolated in step (c) until a MVA related virus comprising one or more of the following features:
  (i) a nucleic acid sequence corresponding to a region that includes the right Inverted Terminal Repeat (ITR) and extends to but excludes deletion site III instead of (replacing) a nucleic acid sequence that includes the left Inverted Terminal Repeat (ITR) and extends to but excludes deletion site V,
  (ii) two copies of a nucleic acid sequence comprising deletion site IV and the right ITR,
  (iii) no nucleic acid sequence comprising deletion site I and the left ITR,
  (iv) no deletion site I,
  (v) two deletion sites IV,
  (vi) no open reading frame for at least one gene product selected from the group consisting of C11R, C10L, and D7L,
  (vii) two open reading frames for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R, and/or
  (viii) a nucleic acid sequence encoding a L3L gene product, wherein said nucleic acid sequence comprises at least one mutation resulting in an amino acid sequence modification of said gene product is detected.

In a sixth aspect, the present invention relates to a pharmaceutical composition comprising the MVA related virus according to the first aspect or the genome according to the second aspect and one or more pharmaceutical acceptable excipient(s), diluent(s), and/or carrier(s).

In a seventh aspect, the present invention relates to a vaccine comprising the MVA related virus according to the first aspect or the genome according to the second aspect.

In an eighth aspect, the present invention relates to a MVA related virus according to the first aspect or a genome according to the second aspect for use in medicine.

This summary of the invention does not describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in “A multilingual glossary of biotechnological terms: (IUPAC Recommendations)”, Leuenberger, H. G. W, Nagel, B. and Kolb', H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word “comprise”, and variations such as “comprises” and “comprising”, will be understood to imply the inclusion of a stated integer or step or group of integers or steps but not the exclusion of any other integer or step or group of integer or step. As used in this specification and the appended claims, the singular forms “a”, “an”, and “the” include plural referents, unless the content clearly dictates otherwise.

The term “attenuated virus”, as used herein, refers to a virus with compromised virulence in the intended recipient, e.g. human or animal recipient. Such a property can be achieved by adaptation of a virus to narrow temperature ranges or narrow host ranges and to other artificial replication environments, including chemically defined media. Replication of such a virus is restricted in cells derived from the intended recipient, e.g. human or animal recipient, or in cells removed from the tissue environment. It may replicate to high titers outside of the intended recipient (e.g. in a permissive cell culture or laboratory animal). An example of an attenuated virus strain is the Ender's attenuated measles virus Edmonston strain given to protect against serious measles disease or the vaccinia virus strain used in the pox eradication campaign of the World Health Organisation (WHO) in the 1970s.

The term “highly attenuated virus”, as used herein, refers to a virus with blocked virulence in the intended recipient, e.g. human or animal recipient. Such a property can be achieved by adaptation of a virus to narrow temperature ranges or narrow host ranges and to other artificial replication environments, including chemically defined media. Replication of such a virus is blocked in cells derived from the intended recipient, e.g. human or animal recipient, or in cells removed from the tissue environment. It may replicate to high titers outside of the intended recipient (e.g. in a permissive cell/cell culture or laboratory animal). The MVA virus of the present invention is a highly attenuated virus. It does not replicate in human or non-human primate cells.

The term “host-restricted virus”, as used herein, refers to a virus which (only or mainly) replicates in a specific host organism, e.g. in a cell such as an avian cell or in an animal such as a laboratory animal. It does not replicate or only replicates at very low levels in other organisms, e.g. in other cells than avian cells. A host-restricted virus may be achieved by (serial) virus passaging of a virus in a host organism, e.g. in avian cells. The MVA related virus of the present invention is restricted to avian cells. It does not replicate in human cells.

The term "virus passaging", as used herein, refers to a process which involves infecting a series of host organisms, e.g. cells or animals such as laboratory animals, with a virus. Each time the virus is given some time to incubate, and then the next host organism is infected with the incubated virus. This process can also be designated as "serial virus passaging". For example, serial virus passaging allows the generation of (highly) attenuated and/or host-restricted viruses. The MVA related virus of the present invention is a highly attenuated virus. It is restricted to avian cells. It does not replicate in human or non-human primate cells.

When a host organism, e.g. a cell such as an avian cell or an animal such as a laboratory animal, is defined by the term "permissive", it refers to the fact that the virus is able to circumvent defenses of said organism and is able to invade a cell, replicate in said cell, and escape from said cell. Usually this occurs when the virus has modulated one or several of the cellular intrinsic defenses of said organism and/or the immune system of said organism.

The term "recipient", as used herein, refers to a subject which may receive a virus, e.g. which may be vaccinated with a virus. The subject may be a human or an animal. Said animal may be a member of the mammalian species such as a canine, feline, lupine, mustela, rodent (e.g. a mouse, rat or hamster), an equine, a bovine, an ovine, a caprine, pig, bat (e.g. a megabat or microbat), or a non-human primate (e.g. a monkey such as a great ape). Particularly, the MVA related virus of the present invention does not replicate in human or non-human primate recipients.

The term "host organism", as used herein, refers to an organism which may be used for virus production and/or adaptation. The host organism may be a cell or an animal such as a laboratory animal. The cell may be an avian cell (e.g. a chicken, quail, goose, or duck cell such as a duck retina (CR) cell). The animal, particularly laboratory animal, may be a bird (e.g. a chicken, quail, goose, or duck), canine, mustela, rodent (e.g. a mouse, rat or hamster), an ovine, a caprine, pig, bat (e.g. a megabat or microbat) or a non-human primate (e.g. a monkey such as a great ape). Particularly, the MVA related virus of the present invention replicates in an avian cell (e.g. in a chicken, quail, goose, or duck cell) or in a bird (e.g. in a chicken, quail, goose, or duck).

The term "infectious", as used herein, refers to the ability of a virus to replicate in a cell and to produce viral particles. Infectivity can be evaluated either by detecting the virus load or by observing disease progression in a human or in an animal.

The term "vaccine", as used herein, refers to an agent that can be used to elicit protective immunity in a recipient, e.g. human or animal recipient. To be effective, a vaccine can elicit immunity in a portion of the immunized population, as some individuals may fail to mount a robust or protective immune response or, in some cases, any immune response. This inability may stem from the genetic background of the recipient or because of an immunodeficiency condition (either acquired or congenital) or immunosuppression (e.g., due to treatment with chemotherapy or use of immunosuppressive drugs). Vaccine efficacy can be established in animal models. The vaccine of the present invention comprises the MVA related virus according to the first aspect or the genome according to the second aspect. In this respect, it should be noted that the MVA related virus itself may be the vaccine. It confers protection against pox. However, said virus may further comprise a heterologous nucleic acid sequence, e.g. a sequence coding for an antigen, particularly an epitope of an antigen, against which an additional protective immunity in the recipient may be elicited. A MVA related virus comprising a heterologous nucleic acid sequence can also be designated as recombinant MVA related virus.

The term "vaccination", as used herein, means that a recipient, e.g. human or animal recipient, is challenged with an infectious virus, e.g. in an attenuated or inactivated form of said infectious virus, to induce a specific immunity. In the present invention, the recipient is challenged with the MVA related virus according to the first aspect or with the genome according to the second aspect to induce immunity against pox. However, in the context of the present invention, the term "vaccination" also covers the challenge of a recipient with a MVA related virus which further comprises a heterologous nucleic acid sequence. The heterologous sequence is a sequence against which an additional protective immunity should be elicited. It may code for an antigen, particularly an epitope of an antigen. A MVA related virus comprising a heterologous nucleic acid sequence can also be designated as recombinant MVA related virus. Examples of such epitopes which are heterologous to said virus cover, e.g. epitopes from proteins of other viruses such as the Influenza virus, Hepatitis virus, e.g. Hepatitis C virus, Human immunodeficiency virus (HIV), Flavivirus, Paramyxovirus, Hantavirus or Filovirus, or epitopes derived from proteins that are associated with the development of tumours and cancer. After the administration of the vaccine into the body of the recipient, the epitopes are expressed and are presented to the immune system and a specific immune response against these epitopes may be induced. The recipient is, thus, immunized against the protein containing the epitope.

The term "heterologous nucleic acid sequence", as used herein, refers to a nucleic acid sequence that is not normally found intimately associated with the virus, particularly with the MVA related virus according to the present invention, in nature. A MVA related virus comprising a heterologous nucleic acid sequence may also be designated as recombinant MVA related virus. The heterologous nucleic acid sequence is preferably selected from a sequence coding for (i) an antigen, particularly an epitope of an antigen, (ii) a diagnostic compound, and (iii) a therapeutic compound.

The term "epitope (also known as antigenic determinant)", as used herein, refers to the part of an antigen that is recognized by the immune system, specifically by antibodies, B cells, or T cells.

The term "protect", as used herein, means to prevent or treat, or both, as appropriate, the development or continuance of a disease (e.g. pox) in a recipient, e.g. human.

The term "protective immunity", as used herein, comprises a humoral (antibody) immunity or cellular immunity, or both, effective to, e.g. eliminate or reduce the load of a pathogen (e.g. virus, such as pox virus) or infected cell or produce any other measurable alleviation of the infection in an immunized (vaccinated) subject.

The term "excipient", as used herein, is intended to indicate all substances in a pharmaceutical composition which are not active ingredients such as binders, lubricants, thickeners, surface active agents, preservatives, emulsifiers, buffers, flavoring agents, or colorants.

The term "diluent", as used herein, relates to a diluting and/or thinning agent. Moreover, the term "diluent" includes a solution, suspension (e.g. liquid or solid suspension) and/or media.

The term "carrier", as used herein, relates to one or more compatible solid or liquid fillers, which are suitable for an administration, e.g. to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds. Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol, and water. Pharmaceutical carriers, diluents, and/or excipients can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose, and polyethylene glycol. Examples of suitable lubricants include sodium oleate, sodium stearate, magnesium stearate, sodium benzoate, sodium acetate, sodium chloride, and the like. Preservatives, stabilizers, dyes, and even flavoring agents may be provided in the pharmaceutical composition. Examples of preservatives include sodium benzoate, sorbic acid, and esters of p-hydroxybenzoic acid. Antioxidants and suspending agents may be also used.

The terms "primary cell" or "primary cell culture", as used herein, refer to a cell or culture which usually cannot be passaged beyond 50 population doublings before suffering senescence, culture arrest, or cell death. The terms a "secondary cell" or "secondary cell culture", as used herein, refer to a cell or culture which is directly derived from a primary cell or primary cell culture. The population doubling limit still applies. The terms an "immortalized cell" or "immortalized cell culture", as used herein, refer to a cell or culture and its progeny that is not limited by the number of potential cell doublings. A cell culture may consist of primary cells, secondary cells, or immortalized cells (i.e. cells of a cell line). In preferred embodiments of the present invention, the cells are from a CR or CR.pIX cell line. The CR and CR.pIX cell lines are derived from immortalized Muscovy duck retina cells (Jordan, et al. 2009 in Vaccine 27, 748-756), designed for vaccine production. The CR.pIX cell line has further stably integrated into its genome a gene encoding the Adenovirus pIX protein and expresses said gene. In other preferred embodiments of the present invention, the cells are chicken embryo fibroblast (CEF) cells. Said cells are primary cells.

The term "isolated cell", as used herein, refers to a cell that is removed from its native or culturing environment. Thus, an isolated cell may be free of some or all native or culture components, i.e. components of the organism in which the cell naturally occurs (e.g. organ particularly tissue) or in which it is cultured (e.g. culture medium or culture-related impurities such as culture remnants). The cell may be infected with a MVA related virus according to the first aspect or transfected with a genome according the second aspect. Techniques how to infect or transfect a cell are known to the skilled person.

The terms "non-adherent cell" and "suspension cell" are used interchangeable herein. In the context of the present invention, the terms "non-adherent cell" and "suspension cell" refer to a cell that is able to survive in a suspension culture without being attached to a surface (e.g. tissue culture plastic carrier or micro-carrier). Said cell may be a cell which can naturally live in suspension without being attached to a surface. Said cell may also be a cell which has been modified or adapted to be able to survive in a suspension culture without being attached to a surface (e.g. tissue culture plastic carrier or micro-carrier). Most cells are in their original, non-modified or non-adapted form, adherent cells. A non-adherent cell can usually be grown to a higher density than adherent conditions would allow. It is, thus, more suited for culturing in an industrial scale, e.g. in a bioreactor setting or in an agitated culture. Cells have usually to be adapted to a non-adherent cell culture. Because the original cells would undergo apoptosis under serum-free conditions and/or in the absence of a suitable surface, this adaptation is a prolonged process requiring passaging with diminishing amounts of serum (e.g. dilution rows from 10% to 0% Fetal Calve Serum (FCS)), thereby selecting an irreversibly modified cell population. Adapted non-adherent cells are known in the art. The skilled person is aware of protocols for transferring a cell from an adherent state into a non-adherent state (see, for example, Appl Microbiol Biotechnol. 2008 March; 78(3):391-9. Epub 2008 Jan. 9).

In contrast thereto, the term "adherent cell", as used herein, refers to a cell which requires a surface, such as tissue culture plastic carrier or micro-carrier. Said surface may be coated with extracellular matrix components to increase adhesion properties and provide other signals needed for growth and differentiation. Said cells require periodic passaging, but allow easy visual inspection under inverted microscope. Said cells have to be dissociated enzymatically (e.g. with trypsin). In addition, the growth of adherent cells is limited by surface area, which may limit product yields.

The term "serum-free conditions", as used herein, refers to conditions, wherein cells grow in medium which is devoid of animal serum. Instead, cells grow in medium devoid of any animal derived components and preferably in a medium without any complex mixtures of biologic components, a so called "chemically defined medium".

The term "cell proliferation medium", as used herein, refers to a medium that supports cell division for at least 10 cell doublings so that, for example, a seed of 8×10^5 cells by passage in that medium can be brought to approximately 4×10^8 cells, e.g. sufficient for a 200 Litre bioreactor. The term "proliferating cells", as used herein, refers to dividing cells, i.e. cells that can divide for another at least 10 cell doublings with a doubling rate of at least once in 48 hours or less.

The term "virus production medium", as used herein, refers to a medium that enhances production of a virus in a culture of proliferating cells. With the addition of a virus production medium, cell aggregates are induced and cell proliferation in the culture decreases by a factor of at least 2 or is stopped completely. It is preferred that the virus production medium comprises $CaCl_2$), $MgSO_4$ and/or NaCl. Preferably, the $CaCl_2$) content is in a range of between 150 and 250 mg/1, more preferably between 180 and 250 mg/1, and most preferably between 200 and 220 mg/1, e.g. 150, 155, 160, 165, 170, 175, 180, 185, 190, 195, 200, 205, 210, 215, 220, 225, 230, 235, 240, 245, or 250 mg/1, the $MgSO_4$ content is in a range of between 50 and 150 mg/1, more preferably between 70 and 150 mg/1, and most preferably between 90 and 120 mg/1, e.g. 50, 55, 60, 65, 70, 75, 80, 85, 90, 95, 100, 105, 110, 115, 120, 125, 130, 135, 140, 145, or 150 mg/1, and/or the NaCl content is in a range of between 5000 and 7500 mg/1, more preferably between 6000 and 7000 mg/1, and most preferably between 6500 and 6800 mg/1, e.g. 5000, 5500, 6000, 6500, 7000, or 7500 mg/l. For example, the virus production medium may include a salt content of 205 mg/l $CaCl_2$), 100 mg/l $MgSO_4$ and/or 6500 mg/1NaCl.

The term "productive replication", as used herein, means that more virus can be recovered at least once from an infected culture than virus that has been added to infect the culture. The virus may cause a cytopathic effect and replicates to levels that eventually result in massive cell death in the infected culture. As opposed to productive replication, reproductive replication can occur at very low levels without accompanying cytopathic effect and may eventually lead to loss of virus in a surviving culture.

The term "Modified Vaccinia Ankara (MVA) virus", as used herein, refers to a highly attenuated strain of vaccinia derived from the Ankara strain and developed for use as a vaccine and vaccine adjuvant. The original MVA virus was isolated from the wild-type Ankara strain by successive passage through chicken embryonic cells. Treated thus, it lost about 15% of the genome of wild-type vaccinia including its ability to replicate efficiently in primate (including human) cells.

The MVA virus contains a single copy of a double-stranded DNA genome, approximately 178 kb in length. The viral genomic DNA comprises a core region flanked by viral telomeres. In particular, the viral telomeres are located at the left and right site of the viral genomic DNA. Said telomeres further comprise Inverted Terminal Repeats (ITRs). The virus commonly accepted to be a MVA virus contains six characteristic deletion sites, called deletion sites I, II, III, IV, V, and VI. The numerals increase with the size of the deletion, not with position in the genome. The deletion site I is located in the left viral telomere, the deletion sites II, III, V, and VI are located in the core region. The deletion site IV is located in the right telomere. Only those viruses that contain all six deletion sites are considered bona fides MVA. The virus commonly accepted to be a MVA virus further comprises an (one) open reading frame for the (functional) gene products selected from the group consisting of C11R, C10L, D7L, A57R, B1R, B2R, B3R, B4R, B5R, B6R, B7R, B8R, B9R, B10R, B11R, B12R, B15R, B16R, B17L, B18R, B19R, and B22R. The method to describe such authentic/genuine MVAs has been published by Kremer et al. ((Kremer et al., 2012)). The MVA virus may have a sequence according to accession number U94848 (version U94848.1 and GI: 2772662).

The term "Modified Vaccinia Ankara (MVA) related virus", as used herein, refers to a virus which structurally differs from the (above described or wild-type) MVA virus. It can, thus, not be considered to constitute a typical MVA virus anymore. It is rather a virus related to MVA. Said MVA related virus may, for example, not comprise a specific deletion site anymore, e.g. deletion site I, and/or comprise a specific deletion site in duplicate, e.g. deletion site IV. Alternatively or additionally, said MVA related virus may, for example, not comprise the open reading frame for a specific gene product anymore, e.g. the gene product C11, and/or comprise the open reading frame for a specific gene product in duplicate, e.g. gene product B1. The MVA related virus of the present invention is specifically described in the first aspect. The MVA related virus may have/comprise a sequence according to SEQ ID NO: 37 or Genbank Accession number KY633487 (MVA-CR19. GFP).

The term "isolated MVA related virus", as used herein, refers to a virus that is removed from its native or culturing environment. Thus, an isolated MVA related virus may be free of some or all cellular components, i.e. components of the cells in which the virus naturally occurs or in which it is cultured (e.g. cytoplasmic or membrane components). It may also be free of some or all culturing components (e.g. culture medium or culture-related impurities such as culture-remnants).

The term "purified MVA related virus", as used herein, refers to a virus that has been isolated under conditions that reduce or eliminate the presence of unrelated materials, i.e. contaminants, including native materials, e.g. cellular debris, cellular remnants, cellular proteins, cellular DNA molecules, and/or cellular RNA molecules, from which the virus is obtained. The purified MVA related virus is preferably substantially free of cell and/or culture components. As used herein, the term "substantially free" is used operationally, in the context of analytical testing of the material. A purified MVA related virus which is substantially free of contaminants is preferably at least 50% pure, more preferably at least 90% pure, and even more preferably at least 99% or 100% pure. Purity can be evaluated by chromatography, gel electrophoresis, immunoassay, composition analysis, biological assay, and other methods known in the art.

The term "viral telomeres", as used herein, refers to sequences at the left and right site of the viral genomic DNA, e.g. of the MVA virus or MVA related virus. The sequence at the left site of the viral genomic DNA is designated as left viral telomere and the sequence at the right site of the viral genomic DNA is designated as right viral telomere. The viral telomeres contain inverted terminal repeats (ITRs) that comprise or consist of regions of complementarity between the left and right sides of the genomic DNA. The viral telomeres also comprise functional and disrupted (not functional) genes that may be duplicated at both ends of the genomic DNA or that may be unique for the left or right side of the genomic DNA. Thus, viral telomeres extend beyond the mere region of the ITRs and can comprise 30 000 bp (30 kbp) or more.

The term "Inverted Terminal Repeats (ITRs)", as used herein, refers to sequences comprising or consisting of regions of complementarity between the left and right sides of the viral genomic DNA, e.g. of the MVA virus or MVA related virus. The ITR at the left side of the genomic DNA is designated as "left ITR" and the ITR at the right side of the genomic DNA is designated as "right ITR". The ITRs are part of the viral telomeres, in particular the left ITR is comprised in the left viral telomere and the right ITR is comprised in the right viral telomere. ITRs can form hairpin structures and appear to provide the origin for replication of the viral genomic DNA that presumably occurs by strand displacement of a leading strand and Okazaki-fragments in the lagging strand.

The term "terminus", as used herein, refers to the left and right end of the viral genomic DNA, e.g. of the MVA virus or MVA related virus.

The term "core region", as used herein, refers to a region of the viral genomic DNA, e.g. of the MVA virus or MVA related virus, comprising deletion sites V and III. In particular, the term "core region", as used herein, refers to a region extending from deletion site V to deletion site III, wherein deletion sites V and III are included.

An "amino acid replacement" may also be designated herein as an "amino acid substitution". The term "amino acid insertion", as used herein, refers to an amino acid modification which takes place within the amino acid sequence of the L3L, A3L, A34R, and/or A9L gene product(s), while the term "amino acid addition", as used herein, refers to an amino acid modification which takes place at the N- or C-terminus of the L3L, A3L, A34R, and/or A9L gene product(s).

In the context of the present invention, amino acid residues in two or more gene products are said to "correspond" to each other if the residues occupy an analogous position in the gene product structures. As is well known in the art, analogous positions in two or more gene products can be determined by aligning the gene product sequences based on amino acid sequence or structural similarities. Such alignment tools are well known to the person skilled in the art and can be, for example, obtained on the World Wide Web, e.g., ClustalW (web site: ebi.ac.uk/clustalw) or Align (web site: ebi.ac.uk/emboss/align/index.html) using standard settings, preferably for Align EMBOSS::needle, Matrix: Blosum62, Gap Open 10.0, Gap Extend 0.5. Those skilled in the art understand that it may be necessary to introduce gaps in either sequence to produce a satisfactory alignment. Amino acid residues in two or more gene products are said to "correspond" if the residues are aligned in the best sequence alignment. The "best sequence alignment" between two gene products is defined as the alignment that produces the largest number of aligned identical residues. The "region of best sequence alignment" ends and, thus, determines the metes and bounds of the length of the comparison sequence for the purpose of the determination of the similarity score, if the sequence similarity, preferably identity, between two aligned sequences drops to less than 30%, preferably less than 20%, more preferably less than 10% over a length of 10, 20 or 30 amino acids. The same applies to nucleic acid sequence. That means that nucleic acid sequences are said to "correspond" to each other in the context of the present invention if the residues occupy an analogous position in the nucleic acid structures.

Here, for the first time, the present inventors isolated and characterized a novel MVA related virus. The present inventors found that the novel MVA related virus structurally differs from the (wild-type) MVA virus. It has a hitherto undescribed genotype. The structural differences result in a virus having advantageous properties over the (wild-type) MVA virus. In particular, the novel MVA related virus releases a higher number of infectious units into the supernatant of infected cultures compared to those infected with the (wild-type) MVA virus. Further, the novel MVA related virus replicates to very high titers compared to the (wild-type) MVA virus. Furthermore, the novel MVA related virus induces fewer syncytia in adherent cultures.

The above described beneficial properties of the novel MVA related virus improve its industrial production. Particularly, they allow the production of the novel MVA related virus in high yields and, thus, also the production of heterologous proteins, e.g. antigens, which may be comprised therein. In addition, the novel MVA related virus can be isolated directly from the cell-free supernatant which facilitates purification and, thus, the logistic and the operation of bioreactors producing said MVA related virus. This, in turn, reduces the costs of its production.

Accordingly, the first aspect of the present invention relates to a Modified Vaccinia Ankara (MVA) related virus comprising (which differs from (wild-type) MVA by) one or more, e.g. 1, 2, 3, 4, 5, 6, 7, or 8, of the following features:

(i) a nucleic acid sequence corresponding to a region that includes the right Inverted Terminal Repeat (ITR) and extends to but excludes deletion site III instead of (replacing) a nucleic acid sequence that includes the left Inverted Terminal Repeat (ITR) and extends to but excludes deletion site V,
(ii) two copies of a nucleic acid sequence comprising deletion site IV and the right ITR,
(iii) no nucleic acid sequence comprising deletion site I and the left ITR,
(iv) no deletion site I,
(v) two deletion sites IV,
(vi) no open reading frame for at least one gene product selected from the group consisting of C11R, C10L, and D7L,
(vii) two open reading frames for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R, and/or
(viii) a nucleic acid sequence encoding a L3L gene product, wherein said nucleic acid sequence comprises at least one mutation resulting in an amino acid sequence modification of said gene product.

The skilled person will understood that the nucleic acid sequences mentioned above are part of/comprised in the viral genomic DNA of the MVA related virus or are part of/comprised in the genome of the MVA related virus.

The MVA related virus may comprise the feature according to (i), (ii), (iii), (iv), (v), (vi), (vii), or (viii). The MVA related virus may also comprise the features according to (ii) and (iii); (ii), (iii), and (viii); (ii) and (iv); (ii), (iv), and (vi); (ii), (iv), and (viii); (ii), (iv), (vi), and (viii); (iii) and (v); (iii), (v), and (vii); (iii), (v), and (viii); (iii), (v), (vii), and (viii); (iv) and (v); (iv), (v), and (viii); (vi) and (vii); or (vi), (vii), and (viii).

In one embodiment, the MVA related virus comprises a nucleic acid sequence corresponding to a region that includes the right Inverted Terminal Repeat (ITR) and extends to but excludes deletion site III instead of (replacing) a nucleic acid sequence that includes the left Inverted Terminal Repeat (ITR) and extends to but excludes deletion site V (feature (i)).

Particularly, the region that includes the right ITR and extends to but excludes deletion site III comprises deletion site IV and/or an open reading frame for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R.

Particularly, the region that includes the left ITR and extends to but excludes deletion site V comprises deletion site I and/or at least one open reading frame for at least one gene product selected from the group consisting of C11R, C10L, and D7L.

More particularly, the region that includes the right ITR and extends to but excludes deletion site III comprises deletion site IV and/or an open reading frame for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R, and the region that includes the left ITR and extends to but excludes deletion site V comprises deletion site I and/or at least one open reading frame for at least one gene product selected from the group consisting of C11R, C10L, and D7L.

Thus, in one preferred embodiment, the MVA related virus comprises no deletion site I, two deletion sites IV, no open frame for at least one gene product selected from the group consisting of C11R, C10L, and D7L, and/or two open reading frames for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R.

Preferably, the MVA related virus comprises a nucleic acid sequence corresponding to a MVA region that includes the right Inverted Terminal Repeat (ITR) and extends to but excludes deletion site III instead of (replacing) a nucleic acid sequence of MVA that includes the left Inverted Terminal Repeat (ITR) and extends to but excludes deletion site V.

The MVA related virus may also comprise a nucleic acid sequence that includes the right Inverted Terminal Repeat (ITR) and extends to the unique sequence next to the right ITR but excludes deletion site III instead of (replacing) a nucleic acid sequence that includes the left Inverted Terminal Repeat (ITR) and extends to the unique sequence next to the left ITR but excludes deletion site V. In this respect, the unique sequence is a sequence that does not comprise complementary regions. It may be untranscribed and untranslated, may contain pseudogenes (previously coding regions that have lost their function), or may contain genes that are being expressed.

Alternatively, the MVA related virus may comprise a nucleic acid sequence that starts with and includes the right Inverted Terminal Repeat (ITR) and extends to but excludes deletion site III instead of (replacing) a nucleic acid sequence that starts with and includes the left Inverted Terminal Repeat (iii) and extends but excludes deletion site V.

In one embodiment, the MVA related virus comprises two copies of a nucleic acid sequence comprising deletion site IV and the right ITR (feature (ii)).

Particularly, the nucleic acid sequence comprising deletion site IV and the right ITR further comprises an open reading frame for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R.

Thus, in one preferred embodiment, the MVA related virus comprises two deletion sites IV, two right ITRs and two open reading frames for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R.

In one embodiment, the MVA related virus comprises no nucleic acid sequence comprising deletion site I and the left ITR (feature (iii)).

Particularly, the nucleic acid sequence comprising deletion site I and the left ITR further comprises an open reading frame for at least one gene product selected from the group consisting of C11R, C10L, and D7L.

Thus, in one preferred embodiment, the MVA related virus comprises no deletion site I, no left ITR, and no open reading frame for at least one gene product selected from the group consisting of C11R, C10L, and D7L.

Preferably (i) the region that includes the right ITR and extends to but excludes deletion site III has a nucleic acid sequence according to SEQ ID NO: 37 or Genbank Accession number KY633487 (preferably ranging from nucleotide position 162221 to 190549 or a nucleotide position corresponding thereto) or is a variant thereof which is at least 85%, at least 90%, at least 95% or 100%, e.g. at least 85, 86, 87, 88, 89, 90, 91, 92, 93, 94, 95, 96, 97, 98, 99% or 100%, identical to said nucleic acid sequence, (ii) the region that includes the left ITR and extends to but excludes deletion site V has a nucleic acid sequence according to SEQ ID NO: 37 or Genbank Accession number KY633487 (preferably ranging from nucleotide position 1 to 31261 or a nucleotide position corresponding thereto) or is a variant thereof which is at least 85%, at least 90%, at least 95% or 100%, e.g. at least 85, 86, 87, 88, 89, 90, 91, 92, 93, 94, 95, 96, 97, 98, 99% or 100%, identical to said nucleic acid sequence, and/or (iii) the nucleic acid sequence comprising deletion site IV and the right ITR has a nucleic acid sequence according to SEQ ID NO: 37 or Genbank Accession number KY633487 (preferably ranging from nucleotide position 179272 to 190549 or a nucleotide position corresponding thereto) or is a variant thereof which is at least 85%, at least 90%, at least 95% or 100%, e.g. at least 85, 86, 87, 88, 89, 90, 91, 92, 93, 94, 95, 96, 97, 98, 99% or 100%, identical to said nucleic acid sequence.

It is preferred that the above variants are functionally active variants. This means that the variation(s) does/do not negatively affect the beneficial properties of the MVA related virus according to the present invention compared to (wild-type) MVA viruses such as an increased infectious activity and/or a greater number of infectious units in the extracellular space during culturing. Said beneficial properties allow, for example, the production of the MVA related virus according to the present invention in high yields. Experiments to test whether said beneficial properties are still present in the above variants are described in the experimental section.

Said variants may also comprise nucleic acid changes due to the degeneracy of the genetic code which code for the same or a functionally equivalent amino acid as the nucleic acid sequence mentioned above.

In one embodiment, the MVA related virus comprises a nucleic acid sequence encoding a L3L gene product, wherein said nucleic acid sequence comprises at least one mutation resulting in an amino acid sequence modification of said gene product (feature (viii)). In one alternative embodiment, the MVA related virus comprises a nucleic acid sequence encoding an A3L gene product and/or an A34R gene product, wherein said nucleic acid sequence comprises at least one mutation resulting in an amino acid sequence modification of said gene product(s). It should be noted that the nucleic acid sequence encoding the above gene product(s) comprises at least one mutation (e.g. 1, 2, or 3 mutation(s)) resulting in an/at least one amino acid modification (e.g. 1, 2, or 3 amino acid sequence modification(s)) of said gene product(s). Said amino acid sequence modification(s) may be (an) amino acid deletion(s) (e.g. 1, 2, or 3 amino acid deletion(s)), amino acid insertion(s) (e.g. 1, 2, or 3 amino acid insertion(s)), amino acid addition(s) (e.g. 1, 2, or 3 amino acid addition(s)) and/or amino acid replacement(s) (e.g. 1, 2, or 3 amino acid replacements(s)).

Preferably, the nucleic acid sequence further encodes an A9L gene product, wherein said nucleic acid sequence comprises at least one mutation (e.g. 1, 2, or 3 mutation(s)) resulting in an/at least one amino acid sequence modification (e.g. 1, 2, or 3 amino acid modification(s)) of said gene product. Said amino acid sequence modification(s) may be (an) amino acid deletion(s) (e.g. 1, 2, or 3 amino acid deletion(s)), amino acid insertion(s) (e.g. 1, 2, or 3 amino acid insertion(s)), amino acid addition(s) (e.g. 1, 2, or 3 amino acid addition(s)) and/or amino acid replacement(s) (e.g. 1, 2, or 3 amino acid replacements(s)). The present inventors surprisingly found that the above mutation(s) further positively affected the virus yield.

More preferably, (i) the MVA related virus comprises a nucleic acid sequence encoding an A3L gene product and an A9L gene product, wherein said nucleic acid sequence comprises at least one mutation (e.g. 1, 2, or 3 mutation(s)) resulting in an/at least one amino acid sequence modification (e.g. 1, 2, or 3 amino acid modification(s)) of said gene products (i.e. said A3L gene product and said A9L gene product), (ii) the MVA related virus comprises a nucleic acid sequence encoding an A34R gene product and an A9L gene product, wherein said nucleic acid sequence comprises at least one mutation (e.g. 1, 2, or 3 mutation(s)) resulting in an/at least one amino acid sequence modification (e.g. 1, 2, or 3 amino acid modification(s)) of said gene products (i.e. said A34R gene product and said A9L gene product), (iii) the MVA related virus comprises a nucleic acid sequence encoding an A3L gene product, an A34R gene product and an A9L gene product, wherein said nucleic acid sequence comprise at least one mutation (e.g. 1, 2, or 3 mutation(s)) resulting in an/at least one amino acid sequence modification (e.g. 1, 2, or 3 amino acid modification(s)) of said gene products (i.e. said A3L gene product, said A34R gene product and said A9L gene product), (iv) the MVA related virus comprises a nucleic acid sequence encoding a L3L gene product and an A3L gene product, wherein said nucleic acid sequence comprise at least one mutation (e.g. 1, 2, or 3 mutation(s)) resulting in an/at least one amino acid sequence modification (e.g. 1, 2, or 3 amino acid modification(s)) of said gene products (i.e. said L3L gene product and said A3L gene product), (v) the MVA related virus comprises a nucleic acid sequence encoding a L3L gene product and an A34R gene product, wherein said nucleic acid sequence comprise at least one mutation (e.g. 1, 2, or 3 mutation(s)) resulting in an/at least one amino acid sequence modification (e.g. 1, 2, or 3 amino acid modification(s)) of said gene products (i.e. said 3L3 gene product and said A34R gene product), or (vi) the MVA related virus comprises a nucleic acid sequence encoding a L3L gene product, an A3L gene product, an A34R gene product and an A9L gene product, wherein said nucleic acid sequence comprise at least one mutation (e.g. 1, 2, 3, or 4 mutation(s)) resulting in an/at least one amino acid sequence modification (e.g. 1, 2, 3, or 4 amino acid modification(s)) of said gene products (i.e. said L3L gene product, said A3L gene product, said A34R gene product and said A9L gene product).

It is preferred that (i) the amino acid sequence modification is in a region spanning amino acid positions 634 to 644 of the A3L gene product according to SEQ ID NO: 1, or amino acid positions corresponding thereto, (ii) the amino acid sequence modification is in a region spanning amino acid positions 81 to 91 of the A34R gene product according to SEQ ID NO: 2, or amino acid positions corresponding thereto, (iii) the amino acid sequence modification is in a region spanning amino acid positions 70 to 80 of the A9L gene product according to SEQ ID NO: 3, or amino acid positions corresponding thereto, and/or (iv) the amino acid sequence modification is in a region spanning amino acid positions 105 to 115 of the L3L gene product according to SEQ ID NO: 13, or amino acid positions corresponding thereto.

Thus, the amino acid sequence modification (e.g. amino acid deletion or amino acid replacement) may be (i) at amino acid position 634, 635, 636, 637, 638, 639, 640, 641, 642, 643, or 644 of the A3L gene product according to SEQ ID NO: 1, or at an amino acid position corresponding thereto, (ii) at amino acid position 81, 82, 83, 84, 85, 86, 87, 88, 89, 90, or 91 of the A34R gene product according to SEQ ID NO: 2, or at an amino acid position corresponding thereto, (iii) at amino acid position 70, 71, 72, 73, 74, 75, 76, 77, 78, 79, or 80 of the A9L gene product according to SEQ ID NO: 3, or at an amino acid position corresponding thereto, and/or (iv) at amino acid position 105, 106, 107, 108, 109, 110, 111, 112, 113, or 115 of the L3L gene product according to SEQ ID NO: 13, or at an amino acid position corresponding thereto.

It is further preferred that (i) the amino acid sequence modification is at amino acid position 639 of the A3L gene product or at an amino acid position corresponding thereto, (ii) the amino acid sequence modification is at amino acid position 638 of the A3L gene product or at an amino acid position corresponding thereto, (iii) the amino acid sequence modification is at amino acid position 86 of the A34R gene product or at an amino acid position corresponding thereto, (iv) the amino acid sequence modification is at amino acid position 75 of the A9L gene product or at an amino acid position corresponding thereto, (v) the amino acid sequence modification is at amino acid position 74 of the A9L gene product or at an amino acid position corresponding thereto, and/or (vi) the amino acid sequence modification is at amino acid position 110 of the L3L gene product or at an amino acid position corresponding thereto.

It is more preferred that the amino acid sequence modification is an amino acid deletion or amino acid replacement, wherein (i) H at amino acid position 639 of the A3L gene product or at an amino acid position corresponding thereto is deleted or replaced by a hydrophobic amino acid, preferably A, V, I, L, M, F, Y or W, a negative amino acid, preferably D or E, or a polar uncharged amino acid, preferably S, T, N or Q, (ii) R at amino acid position 638 of the A3L gene product or at an amino acid position corresponding thereto is deleted or replaced by a hydrophobic amino acid, preferably A, V, I, L, M, F, Y or W, a negative amino acid, preferably D or E, or a polar uncharged amino acid, preferably S, T, N or Q, (iii) D at amino acid position 86 of the A34R gene product or at an amino acid position corresponding thereto is deleted or replaced by a hydrophobic amino acid, preferably A, V, I, L, M, F, Y or W, a positive amino acid, preferably R, H or K, or a polar uncharged amino acid, preferably S, T, N or Q, (iv) K at amino acid position 75 of the A9L gene product or at an amino acid position corresponding thereto which is deleted or replaced by a hydrophobic amino acid, preferably A, V, I, L, M, F, Y or W, a negative amino acid, preferably D or E, or a polar uncharged amino acid, preferably S, T, N or Q, (v) K at amino acid position 74 of the A9L gene product or at an amino acid position corresponding thereto which is deleted or replaced by a hydrophobic amino acid, preferably A, V, I, L, M, F, Y or W, a negative amino acid, preferably D or E, or a polar uncharged amino acid, preferably S, T, N or Q, and/or (vi) V at amino acid position 110 of the L3L gene product or at an amino acid position corresponding thereto which is deleted or replaced by a hydrophobic amino acid, preferably A, V, I, L, M, F, Y or W, a negative amino acid, preferably D or E, or a polar uncharged amino acid, preferably S, T, N or Q.

It is even more preferred that the amino acid replacement is an amino acid replacement of (i) H at amino acid position 639 of the A3L gene product or at an amino acid position corresponding thereto by Y (H639Y A3L gene product mutant), (ii) R at amino acid position 638 of the A3L gene product or at an amino acid position corresponding thereto by Y (R638Y A3L gene product mutant), (iii) D at amino acid position 86 of the A34R gene product or at an amino acid position corresponding thereto by Y (D86Y A34R gene product mutant), (iv) K at amino acid position 75 of the A9L gene product or at an amino acid position corresponding thereto by E (K75E A9L gene product mutant), (v) K at amino acid position 74 of the A9L gene product or at an amino acid position corresponding thereto by E (K74E A9L gene product mutant), and/or (vi) V at amino acid position 110 of the L3L gene product or at an amino acid position corresponding thereto by A (V110A L3L gene product mutant).

It is further even more preferred that the amino acid replacement is an amino acid replacement of (i) H at amino acid position 639 of the A3L gene product or at an amino acid position corresponding thereto by Y and D at amino acid position 86 of the A34R gene product or at an amino acid position corresponding thereto by Y (H639Y A3L/D86Y A34R gene product mutant), (ii) H at amino acid position 639 of the A3L gene product or at an amino acid position corresponding thereto by Y and K at amino acid position 75 of the A9L gene product or at an amino acid position corresponding thereto by E (H639Y A3L/K75E A9L gene product mutant), (iii) D at amino acid position 86 of the A34R gene product or at an amino acid position corresponding thereto by Y and K at amino acid position 75 of the A9L gene product or at an amino acid position corresponding thereto by E (D86Y A34R/K75E A9L gene product mutant), (iv) H at amino acid position 639 of the A3L gene product or at an amino acid position corresponding thereto by Y, D at amino acid position 86 of the A34R gene product or at an amino acid position corresponding thereto by Y, and K at amino acid position 75 of the A9L gene product or at an amino acid position corresponding thereto by E (H639Y A3L/D86Y A34R/K75E A9L gene product mutant), and/or (v) H at amino acid position 639 of the A3L gene product or at an amino acid position corresponding thereto by Y, D at amino acid position 86 of the A34R gene product or at an amino acid position corresponding thereto by Y, K at amino acid position 75 of the A9L gene product or at an amino acid position corresponding thereto by E, and V at amino acid position 110 of the L3L gene product or at an amino acid position corresponding thereto by A (H639Y A3L/D86Y A34R/K75E A9L/V110A L3L gene product mutant).

It is most preferred that (i) the A3L gene product with the H639Y mutation has an amino acid sequence according to SEQ ID NO: 4 or is a variant thereof which is at least 85%, preferably at least 90%, more preferably at least 95%, and most preferably at least 99% or 100%, e.g. at least 85, 86, 87, 88, 89, 90, 91, 92, 93, 94, 95, 96, 97, 98, 99% or 100%, identical to said amino acid sequence, wherein said variant (still) comprises the amino acid Y at amino acid position 639 or at an amino acid position corresponding thereto, (ii) the A34R gene product with the D86Y mutation has an amino acid sequence according to SEQ ID NO: 5 or is a variant thereof which is at least 85%, preferably at least 90%, more preferably at least 95%, and most preferably at least 99% or 100%, e.g. at least 85, 86, 87, 88, 89, 90, 91, 92, 93, 94, 95, 96, 97, 98, 99% or 100%, identical to said amino acid sequence, wherein said variant (still) comprises the amino acid Y at amino acid position 86 or at an amino acid position corresponding thereto, (iii) the A9L gene product with the K75E mutation has an amino acid sequence according to SEQ ID NO: 6 or is a variant thereof which is at least 85%, preferably at least 90%, more preferably at least 95%, and most preferably at least 99%, e.g. at least 85, 86, 87, 88, 89, 90, 91, 92, 93, 94, 95, 96, 97, 98, 99% or 100%, identical to said amino acid sequence, wherein said variant (still) comprises the amino acid E at amino acid position 75 or at an amino acid position corresponding thereto, and/or (iv) the L3L gene product with the V110A mutation has an amino acid sequence according to SEQ ID NO: 14 or is a variant thereof which is at least 85%, preferably at least 90%, more preferably at least 95%, and most preferably at least 99% or 100%, e.g. at least 85, 86, 87, 88, 89, 90, 91, 92, 93, 94, 95, 96, 97, 98, 99% or 100%, identical to said amino acid sequence, wherein said variant comprises the amino acid A at amino acid position 110 or at an amino acid position corresponding thereto.

It is particularly preferred that the sequence identity is (i) at least 85%, 90%, 95%, or 99% over a continuous stretch of at least 50, 60, 70, 80, 90, 100, 120, 150, 180, 200, 300, 400, 500, 600, or more amino acids of the respective reference amino acid sequence according to SEQ ID NO: 4, (ii) at least 85%, 90%, 95%, or 99% over a continuous stretch of at least 20, 30, 40, 50, 60, 70, 80, 90, 100, 110, 120, 130, 140, 150, 160, or more amino acids of the respective reference amino acid sequence according to SEQ ID NO: 5, (iii) at least 85%, 90%, 95%, or 99% over a continuous stretch of at least 20, 30, 40, 50, 60, 70, 80, 90, or more amino acids of the respective reference amino acid sequence according to SEQ ID NO: 6, or (iv) at least 85%, 90%, 95%, or 99% over a continuous stretch of at least 20, 30, 40, 50, 60, 70, 80, 90, or more amino acids of the respective reference amino acid sequence according to SEQ ID NO: 14. It is further particularly preferred that the sequence identity is at least 85% over the whole length, is at least 90% over the whole length, is at least 95% over the whole length, or is at least 99% over the whole length of the respective reference amino acid sequence according to SEQ ID NO: 4, SEQ ID NO: 5, SEQ ID NO: 6, or SEQ ID NO: 14.

Preferably, the above variants are functionally active variants. This means that the (additional) variation(s) in the amino acid sequence does/do not negatively affect the beneficial properties of the MVA related virus according to the present invention compared to known (wild-type) MVA viruses such as an increased infectious activity and/or a greater number of infectious units in the extracellular space during culturing. Said beneficial properties allow, for example, the production of the MVA related virus according to the present invention in high yields. Experiments to test that said beneficial properties are still present in the above variants are described in the experimental section.

The above mentioned A3L gene product (also designated as P4b protein) of MVA is one of three major core proteins and is processed by the I7L-encoded viral protease during the maturation of the spherical and non-infectious immature virion (IV) to the intracellular mature virion (IMV). The A3L gene product of MVA contributes to virion morphogenesis at a very early step to allow correct condensation and membrane rearrangements in the transition towards the infectious IMV. Further, the above mentioned A34R gene product of MVA destabilizes the outer membrane of the extracellular enveloped virus (EEV) and is, thus, extremely important for infectious activity in the extracellular space and for virus spread. The EEV has evolved as a vehicle to allow virus to spread to distant sites. The additional membrane of the EEV is not equipped to mediate fusion with the target cell and must be disrupted to release the IMV, the actual virus infectious unit. In addition, the A34R gene product of MVA modulates the rate at which the cell-associated enveloped virus (CEV) detaches from the producing cell. Furthermore, the A9L gene product of MVA is, like the A3L gene product, involved in the early steps of MVA maturation. It is a factor important for correct condensation of the core of the IMV. In addition, the L3L gene product of MVA is essential for very early steps immediately following entry of the virus into the host cell. L3L is a loosely packaged component of the virus particles and appears to be responsible for events that allow nascent mRNAs to leave the viral core and to appear in the cytoplasm of the newly infected host cell.

Preferably, the MVA related virus is an isolated MVA related virus. The isolated MVA virus may further be purified. Thus, more preferably, the MVA related virus is a purified MVA related virus.

It is preferred that the MVA related virus further comprises a heterologous nucleic acid sequence. The expression of the heterologous nucleic acid sequence may be under the transcriptional control of a MVA virus promoter. The heterologous nucleic acid sequence is inserted into the nucleic acid sequence of the MVA related virus. In a preferred embodiment of the present invention, the insertion of the heterologous nucleic acid sequence is into a non-essential region of the MVA related virus nucleic acid sequence/genome. In a more preferred embodiment of the present invention, the heterologous nucleic acid sequence is inserted at a naturally occurring deletion site (e.g. deletion site III) of the viral genomic DNA/genome. Methods how to insert heterologous nucleic acid sequences into the MVA related virus genome are known to a skilled person.

It is more preferred that the heterologous nucleic acid sequence is selected from a sequence coding for (i) an antigen, particularly an epitope of an antigen,
(ii) a diagnostic compound, and
(iii) a therapeutic compound.

The antigen or epitope may be useful as a vaccine to induce an immune response against said antigen or epitope. Examples of such antigens which are heterologous to said virus cover, e.g. proteins of other viruses such as the Influenza virus, Hepatitis virus, e.g. Hepatitis C virus, Human immunodeficiency virus (HIV), Flavivirus, Paramyxovirus, Hantavirus or Filovirus, or proteins that are associated with the development of tumours and cancer such as Her2/neu or MUC-1. Examples of such epitopes which are heterologous to said virus cover, e.g. epitopes from proteins derived from other viruses such as the Influenza virus, Hepatitis virus, e.g. Hepatitis C virus, Human immunodeficiency virus (HIV), Flavivirus, Paramyxovirus, Hantavirus or Filovirus, or epitopes derived from proteins that are associated with the development of tumours and cancer such as extracellular peptides of Her2/neu or MUC-1. The antigen may also be a vaccine antigen, e.g. a vaccine antigen derived from a viral, fungal, eukaryotic or bacterial pathogen, or derived from a tumor.

The therapeutic compound may be any compound with a therapeutic effect. For example, the therapeutic compound can be a compound that affects or participates in tissue growth, cell growth, cell differentiation, a compound that is able to invoke a biological action such as an immune response, or a compound that can play any other role in one or more biological processes. Particularly, said compound may be an anti-microbial compound, an anti-viral compound, an anti-fungal compound, an immunosuppressive compound, a growth factor, an enzyme, an anti-inflammatory compound, or an anti-allergic compound. The therapeutic compound may also be an antisense nucleic acid.

The diagnostic compound may be any compound with a diagnostic effect. For example, the diagnostic compound can be a marker/reporter protein such as an antibody, GFP, EGFP, ß-galactosidase, luciferase or an antibiotic resistance conferring protein such as bla (beta-lactamase) against ampicillin or npt (neomycin phosphotransferase) against neomycin or G418. Said marker/reporter protein may be used to identify or isolate the virus, e.g. by using hybridization technology, fluorescence microscopy, or ELISA assays. In addition, the antibiotic resistance conferring protein comprised in the virus confers resistance against antibiotic selection to the infected cell.

As already mentioned above, the MVA related virus is a highly attenuated virus.

In one embodiment of the present invention, the MVA related virus is capable of productive replication in avian cells. Said avian cells are preferably chicken, quail, goose, or duck cells (e.g. duck somite or duck retina cells). Said avian cells (e.g. chicken, quail, goose, or duck cells such as duck somite or duck retina cells) may be primary cells (or cells from a primary cell culture), secondary cells (or cells from a secondary cell culture), or immortalized cells (or cells from a cell line).

In another embodiment of the present invention, the MVA related virus is not capable of productive replication in mammalian cells, wherein said mammalian cells are not Baby Hamster Kidney (BHK) cells, Fruit bat R05T cells, Fruit bat R05R cells, or Fruit bat R06E cells. R05T, R05R, and R06E cells are cells obtained by immortalization of primary cells from the Egyptian rousette. These are one of the very few mammalian cell lines permissive for MVA (Jordan et al. 2009 in Virus Res 145, 54-62). In a preferred embodiment of the present invention, the MVA virus is not capable of productive replication in primate cells, more preferably human cells.

The MVA virus according to the present invention may comprise a nucleic acid sequence encoding a L3L gene product having an amino acid sequence prior to amino acid modification according to SEQ ID NO: 13, an A3L gene product having an amino acid sequence prior to amino acid modification according to SEQ ID NO: 1, and/or an A34R gene product having an amino acid sequence prior to amino acid modification according to SEQ ID NO: 2. Said nucleic acid sequence may further encode an A9L gene product having an amino acid sequence prior to amino acid modification according to SEQ ID NO: 3.

The V110A L3L gene product mutant has a sequence according to SEQ ID NO: 14, the H639Y A3L gene product mutant has a sequence according to SEQ ID NO: 4, the D86Y A34R gene product mutant has a sequence according to SEQ ID NO: 5, and/or the K75E A9L gene product mutant has a sequence according to SEQ ID NO: 6.

Further, the respective L3L gene may have a nucleic acid sequence prior to mutation according to SEQ ID NO: 15, the A3L gene may have a nucleic acid sequence prior to mutation according to SEQ ID NO: 7, the respective A34R gene may have a nucleic acid sequence prior to mutation according to SEQ ID NO: 8, and/or the respective A9L gene may have a nucleic acid sequence prior to mutation according to SEQ ID NO: 9.

Furthermore, the mutated L3L gene may have a nucleic acid sequence according to SEQ ID NO: 16, the mutated A3L gene may have a nucleic acid sequence according to SEQ ID NO: 10, the mutated A34R gene may have a nucleic acid sequence according to SEQ ID NO: 11, and/or the mutated A9L gene may have a nucleic acid sequence according to SEQ ID NO: 12. In addition, the MVA virus from which the MVA related virus (structurally) differs may comprise a nucleic acid sequence (prior to mutation/rearrangement) according to accession number AY603355 (version AY603355.1 and GI: 47088326).

In a second aspect, the present invention relates to a genome of the MVA related virus according to the first aspect.

In a third aspect, the present invention relates to a cell comprising the MVA related virus according to the first aspect or the genome according to the second aspect. The cell comprising the MVA related virus according to the first aspect or the genome according to the second aspect may also be designated as a host cell.

Said cell may be for culturing the MVA related virus according to the first aspect. Said cell may be any cell in which the MVA related virus according to the first aspect is capable to replicate. It is preferred that said cell is not a primate cell, particularly a human cell. It is further preferred that said cell is an avian cell. Said avian cell is preferably a chicken, quail, goose, or duck cell (e.g. a duck somite or duck retina cell). Said avian cell (e.g. chicken, quail, goose, or duck cell such as duck somite or duck retina cell) may be a primary cell (or a cell from a primary cell culture), a secondary cell (or a cell from a secondary cell culture), or an immortalized cell (or a cell from a cell line). In preferred embodiments of the present invention, the cell is from a CR or CR.pIX cell line. The CR and CR.pIX cell lines are derived from immortalized Muscovy duck retina cells (Jordan, et al. 2009 in Vaccine 27, 748-756), designed for vaccine production. The CR.pIX cell line has further stably integrated into its genome a gene encoding the Adenovirus pIX protein and expresses said gene. In other preferred embodiments of the invention, the cells are chicken embryo fibroblast (CEF) cells. Said cells are primary cells. Preferably, the cell is an isolated cell.

Said cell may be infected with the MVA related virus according to the first aspect or transfected with the genome according the second aspect. Techniques how to infect or transfect a cell are known to the skilled person.

It is further preferred that the cell is a non-adherent/suspension cell. Generally, cells can be grown in suspension or adherent cultures. Some cells naturally live in suspension, without being attached to a surface, such as cells that exist in the bloodstream (e.g. hematopoietic cells). Adherent cells (e.g. primary cells) require a surface, such as tissue culture plastic carrier or micro-carrier, which may be coated with extracellular matrix components to increase adhesion properties and provide other signals needed for growth and differentiation.

In preferred embodiments of the present invention, the non-adherent/suspension cell grows under serum-free conditions.

In a fourth aspect, the present invention relates to a method for culturing a MVA related virus according to the first aspect comprising the steps of:

(i) providing a cell according to the third aspect, (ii) culturing the cell, and (iii) isolating the MVA related virus.

The cell according to the third aspect comprises the MVA related virus according to the first aspect or the genome according to the second aspect.

The cell may be cultured in step (ii) in cell proliferation medium and subsequently in virus production medium, or the cell may be (solely) cultured in step (ii) in cell proliferation medium. Preferably, the cell is (solely) cultured in step (ii) in cell proliferation medium. The use of a single medium has the advantage that it facilitates the virus culturing process, particularly the industrial virus culturing process. For example, it facilitates the logistic and the operation of bioreactors producing said MVA related virus. It is preferred that the cell proliferation medium is serum-free. A serum-free medium is particularly devoid of animal serum. Instead, cells grow in medium devoid of any animal derived components and preferably in a medium without any complex mixtures of biologic components, a so called chemically defined medium. It is further preferred that the cell proliferation medium has a low protein content and/or a low salt content.

Preferably, the cell is cultured in step (ii) in an agitated culture or in a bioreactor.

In step (iii), the MVA related virus is preferably isolated from the cell-free supernatant and/or cell lysate. The isolation of the MVA related virus in step (iii) may be performed according to standard procedures readily available to the skilled person. Preferably, the MVA related virus is isolated from the cell-free supernatant. This facilitates the virus isolation process, particularly the industrial virus isolation process. This, in turn, reduces the costs of virus production. For example, cell lyses for virus isolation is not required anymore. In this way, the contamination of the virus isolate with cellular material, particularly cellular DNA, can be reduced. As a consequence, the DNA-limit values of the World Health Organisation for virus preparations can easier be obtained.

Various isolation procedures for viruses are known in the art. An isolation procedure which is useful according to the invention does not interfere with the virus to be isolated. For example, extended exposure to impeller shear forces and other factors that occur during isolation should be avoided. It is preferred that the isolation in step (iii) is achieved by separating the virus from the cells via centrifugation, sedimentation and/or filtration. The person skilled in the art is able to easily adapt/adjust the appropriate separation parameters, e.g. the acceleration-force/G-force and/or time using centrifugation for separation, filter size using filtration for separation, and/or sedimentation time using sedimentation for separation, in order to isolate the virus cultured in said cells.

In a fifth aspect, the present invention relates to a method for producing a MVA related virus according to the first aspect comprising the steps of:

(a) infecting a cell with a MVA virus,
(b) culturing the cell,
(c) isolating the MVA virus, and
(d) repeating steps (a) to (c) with the MVA virus isolated in step (c) until a MVA related virus comprising one or more of the following features:
(i) a nucleic acid sequence corresponding to a region that includes the right Inverted Terminal Repeat (ITR) and extends to but excludes deletion site III instead of (replacing) a nucleic acid sequence that includes the left Inverted Terminal Repeat (ITR) and extends to but excludes deletion site V,
(ii) two copies of a nucleic acid sequence comprising deletion site IV and the right ITR,
(iii) no nucleic acid sequence comprising deletion site I and the left ITR,
(iv) no deletion site I,
(v) two deletion sites IV,
(vi) no open reading frame for at least one gene product selected from the group consisting of C11R, C10L, and D7L,
(vii) two open reading frames for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R, and/or
(viii) a nucleic acid sequence encoding a L3L gene product, wherein said nucleic acid sequence comprises at least one mutation resulting in an amino acid sequence modification of said gene product is detected.

Steps (a) to (c) may be repeated until a MVA related virus comprising the feature according to (i), (ii), (iii), (iv), (v), (vi), (vii), or (viii) is detected. Steps (a) to (c) may also be repeated until a MVA related virus comprising the features according to (ii) and (iii); (ii), (iii), and (viii); (ii) and (iv); (ii), (iv), and (vi); (ii), (iv), and (viii); (ii), (iv), (vi), and (viii); (iii) and (v); (iii), (v), and (vii); (iii), (v), and (viii); (iii), (v), (vii), and (viii); (iv) and (v); (iv), (v), and (viii); (vi) and (vii); or (vi), (vii), and (viii) is detected.

In one embodiment, steps (a) to (c) are repeated until a MVA related virus comprising a nucleic acid sequence corresponding to a region that includes the right Inverted Terminal Repeat (ITR) and extends to but excludes deletion site III instead of (replacing) a nucleic acid sequence that includes the left Inverted Terminal Repeat (ITR) and extends to but excludes deletion site V is detected (feature (i)). Preferably, steps (a) to (c) are repeated until a MVA related virus comprising a nucleic acid sequence corresponding to a MVA region that includes the right Inverted Terminal Repeat (ITR) and extends to but excludes deletion site III instead of (replacing) a nucleic acid sequence of MVA that includes the left Inverted Terminal Repeat (ITR) and extends to but excludes deletion site V is detected. Steps (a) to (c) may also be repeated until a MVA related virus comprising a nucleic acid sequence that includes the right Inverted Terminal Repeat (ITR) and extends to the unique sequence next to the right ITR but excludes deletion site III instead of (replacing) a nucleic acid sequence that includes the left Inverted Terminal Repeat (ITR) and extends to the unique sequence next to the left ITR but excludes deletion site V is detected. In this respect, the unique sequence is a sequence that does not comprise complementary regions. It may be untranscribed and untranslated, may contain pseudogenes (previously coding regions that have lost their function), or may contain genes that are being expressed. Alternatively, steps (a) to (c) may be repeated until a MVA related virus comprising a nucleic acid sequence that starts with and includes the right Inverted Terminal Repeat (ITR) and extends to but excludes deletion site III instead of (replacing) a nucleic acid sequence that starts with and includes the left Inverted Terminal Repeat (iii) and extends but excludes deletion site V is detected.

In one embodiment, steps (a) to (c) are repeated until a MVA related virus comprising two copies of a nucleic acid sequence comprising deletion site IV and the right ITR is detected (feature (ii)).

In one embodiment, steps (a) to (c) are repeated until a MVA related virus comprising no nucleic acid sequence comprising deletion site I and the left ITR is detected (feature (iii)).

In one embodiment, steps (a) to (c) are repeated until a MVA related virus comprising a nucleic sequence encoding a L3L gene product, wherein said nucleic acid sequence comprises at least one mutation resulting in an amino acid sequence modification of said gene product, is detected. In one alternative embodiment, steps (a) to (c) are repeated until a MVA related virus comprising a nucleic acid sequence encoding an A3L gene product and/or an A34R gene product, wherein said nucleic acid sequence comprises at least one mutation resulting in an amino acid sequence modification of said gene product(s), is detected. Preferably, steps (a) to (c) are repeated until a MVA related virus comprising a nucleic acid sequence further encoding an A9L gene product, wherein said nucleic acid sequence comprises at least one mutation resulting in an amino acid sequence modification of said gene product, is detected. It should be noted that the nucleic acid sequence encoding the above gene products comprises at least one mutation (e.g. 1, 2, 3, or 4 mutation(s)) resulting in an/at least one amino acid modification (e.g. 1, 2, 3, or 4 amino acid sequence modification(s)) of each of said gene products. Said amino acid sequence modification(s) (e.g. 1, 2, 3, or 4 amino acid modification(s)) may be (an) amino acid deletion(s) (e.g. 1, 2, 3, or 4 amino acid deletion(s)), amino acid insertion(s) (e.g. 1, 2, 3, or 4 amino acid insertion(s)), amino acid addition(s) (e.g. 1, 2, 3, or 4 amino acid additions(s)) and/or amino acid replacement(s) (e.g. 1, 2, 3, or 4 amino acid replacement(s)). Further preferred embodiments are described in the context of the first aspect of the present invention. More preferably,
(i) a MVA related virus comprising a nucleic acid sequence encoding an A3L gene product and an A9L gene product, wherein said nucleic acid sequence comprises at least one mutation (e.g. 1, 2, or 3 mutation(s)) resulting in an/at least one amino acid sequence modification (e.g. 1, 2, or 3 amino acid modification(s)) of said gene products (i.e. said A3L gene product and said A9L gene product), is detected,
(ii) a MVA related virus comprising a nucleic acid sequence encoding an A34R gene product and an A9L gene product, wherein said nucleic acid sequence comprises at least one mutation (e.g. 1, 2, or 3 mutation(s)) resulting in an/at least one amino acid sequence modification (e.g. 1, 2, or 3 amino acid modification(s)) of said gene products (i.e. said A34R gene product and said A9L gene product), is detected,
(iii) a MVA related virus comprising a nucleic acid sequence encoding an A3L gene product, an A34R gene product and an A9L gene product, wherein said nucleic acid sequence comprise at least one mutation (e.g. 1, 2, or 3 mutation(s)) resulting in an/at least one amino acid sequence modification (e.g. 1, 2, or 3 amino acid modification(s)) of said gene products (i.e. said A3L gene product, said A34R gene product and said A9L gene product), is detected, (iv) a MVA related virus comprising a nucleic acid sequence encoding a L3L gene product and an A3L gene product, wherein said nucleic acid sequence comprise at least one mutation (e.g. 1, 2, or 3 mutation(s)) resulting in an/at least one amino acid sequence modification (e.g. 1, 2, or 3 amino acid modification(s)) of said gene products (i.e. said L3L gene product and said A3L gene product), is detected, (v) a MVA related virus comprising a nucleic acid sequence encoding a L3L gene product and an A34R gene product, wherein said nucleic acid sequence comprise at least one mutation (e.g. 1, 2, or 3 mutation(s)) resulting in an/at least one amino acid sequence modification (e.g. 1, 2, or 3 amino acid modification(s)) of said gene products (i.e. said L3L gene product and said A34R gene product), is detected, or (vi) a MVA related virus comprising a nucleic acid sequence encoding a L3L gene product, an A3L gene product, an A34R gene product and an A9L gene product, wherein said nucleic acid sequence comprise at least one mutation (e.g. 1, 2, 3, or 4 mutation(s)) resulting in an/at least one amino acid sequence modification (e.g. 1, 2, 3, or 4 amino acid modification(s)) of said gene products (i.e. said 3L3 gene product, said A3L gene product, said A34R gene product and said A9L gene product), is detected.

As to the preferred embodiments of the amino acid modifications, it is referred to the first aspect of the present invention.

The MVA virus in step (a) may comprise a nucleic acid sequence according to accession number U94848 (version U94848.1 and GI: 2772662).

It is preferred that steps (a) to (c) are repeated at least 2 times, preferably at least 7 times, more preferably at least 14 times, most preferably at least 20 times, e.g. at least 2, 3, 4, 5, 6, 7, 8, 9, 10, 11, 12, 13, 14, 15, 16, 17, 18, 19, or 20 times.

It is further preferred that the cell is cultivated in virus production medium. The virus may be cultured in step (b) in virus production medium between 1 to 10 days, e.g. 1, 2, 3, 4, 5, 6, 7, 8, 9, or 10 days.

The cell in step (a) may be any cell in which the MVA virus is capable to replicate. It is preferred that said cell is not a primate cell, particularly a human cell. It is further preferred that said cell is an avian cell. Said avian cell is preferably a chicken, quail, goose, or duck cell (e.g. a duck somite or duck retina cell). Said avian cell (e.g. chicken, quail, goose, or duck cell such as duck somite or duck retina cell) may be a primary cell (or a cell from a primary cell culture), a secondary cell (or a cell from a secondary cell culture), or an immortalized cell (or a cell from a cell line). In preferred embodiments of the present invention, the cell is from a CR or CR.pIX cell line. The CR and CR.pIX cell lines are derived from immortalized Muscovy duck retina cells (Jordan, et al. 2009 in Vaccine 27, 748-756). The CR.pIX cell line has further stably integrated into its genome a gene encoding the Adenovirus pIX protein and expresses said gene. In other preferred embodiments of the invention, the cells are chicken embryo fibroblast (CEF) cells. Said cells are primary cells.

In a sixth aspect, the present invention relates to a pharmaceutical composition comprising the MVA related virus according to the first aspect or the genome according to the second aspect and one or more pharmaceutical acceptable excipient(s), diluent(s), and/or carrier(s).

As mentioned above, the MVA related virus according to the first aspect is highly host-restricted and, thus, highly attenuated. It is, therefore, ideal to treat a wide range of recipients. Preferably the recipients are primates, more preferably humans.

The pharmaceutical composition contemplated by the present invention may be formulated and/or administered in various ways well known to the skilled person. Preferably, the pharmaceutical composition of the present invention is in liquid form, e.g. in form of a solution such as an injection solution. Said solution may be injected, e.g. intramuscular or parenteral. The mode of administration, the dose, and the number of administrations of the pharmaceutical composition can be optimized by the skilled person in a known manner.

In a seventh aspect, the present invention relates to a vaccine comprising the MVA related virus according to the first aspect or the genome according to the second aspect. As mentioned above, the MVA related virus according to the first aspect is highly host-restricted and, thus, highly attenuated. It is, therefore, an ideal vaccine to treat a wide range of recipients.

Preferably the recipients are primates, more preferably humans. In this respect, it should be noted that the MVA related virus itself may be the vaccine. It confers protection against pox. However, said virus or said genome may further comprise a heterologous nucleic acid sequence, e.g. a sequence coding for an antigen, particularly an epitope of an antigen, against which a protective immunity, particularly an additional protective immunity, in the recipient may be elicited. Examples of such antigens cover, e.g. proteins of other viruses such as the Influenza virus, Hepatitis virus, e.g. Hepatitis C virus, Human immunodeficiency virus (HIV), Flavivirus, Paramyxovirus, Hantavirus or Filovirus, or proteins that are associated with the development of tumours and cancer such as Her2/neu or MUC-1. Examples of such epitopes cover, e.g. epitopes from proteins derived from other viruses such as the Influenza virus, Hepatitis virus, e.g. Hepatitis C virus, Human immunodeficiency virus (HIV), Flavivirus, Paramyxovirus, Hantavirus or Filovirus, or epitopes derived from proteins that are associated with the development of tumours and cancer such as extracellular peptides of Her2/neu or MUC-1. A MVA related virus comprising a heterologous nucleic acid sequence can also be designated as recombinant MVA related virus. After the administration of the vaccine into the body of the recipient, the antigens, particularly epitopes, are expressed and are presented to the immune system and a specific immune response against said antigens, particularly epitopes, may be induced. The recipient is, thus, immunized against said antigens, particularly epitopes.

Preferably, the vaccine comprising the MVA related virus according to the first aspect or the genome according to the second aspect is a pox virus, an Influenza virus, a Hepatitis virus, e.g. a Hepatitis C virus, a Human immunodeficiency virus (HIV), a Flavivirus, a Paramyxovirus, a Hantavirus, and/or a Filovirus vaccine. It may also be used in vaccination against breast cancer, melanoma, pancreatic cancer or prostate cancer.

The vaccine contemplated by the present invention may be formulated and administered in various ways well known to the skilled person. Preferably, the vaccine of the present invention is in liquid form, e.g. in form of a solution such as an injection solution. Said solution may be injected, e.g. intramuscular or parenteral. The mode of administration, the dose, and the number of administrations of the vaccine can be optimized by the skilled person in a known manner. For the formulation or preparation of the vaccine, the MVA virus, particularly the recombinant MVA virus, according to the first aspect is converted into a physiologically acceptable form. This can be done based on the experience in the preparation of poxvirus vaccines used for vaccination against pox (as described by (Stickl et al. 1974 in Dtsch Med Wochenschr 99, 2386-2392)). Said vaccine is particularly useful to induce immune responses in immuno-compromised recipients such as primates including humans. Immuno-compromised describes the status of the immune system of a recipient, which shows only incomplete immune responses or has a reduced efficiency in the defence against infectious agents.

In an eight aspect, the present invention relates to a MVA related virus according to the first aspect or a genome according to the second aspect for use in medicine. Preferably, the MVA related virus according to the first aspect or the genome according to the second aspect is for use in vaccination and/or therapy. Particularly, the recipient is challenged with the MVA related virus according to the first aspect or with the genome according to the second aspect to induce a specific immunity. Preferably the recipients are primates, more preferably humans. Said primates such as humans may be immuno-compromised. In this respect, it should be noted that the MVA related virus itself may be the vaccine. It confers protection against pox. However, said virus or said genome may further comprise a heterologous nucleic acid sequence, e.g. a sequence coding for an antigen, particularly an epitope of an antigen, against which a protective immunity, particularly an additional protective immunity, in the recipient may be elicited. Preferred antigens, particularly epitopes, are described in the first and seventh aspect of the present invention. Preferably, said MVA related virus or genome is for use in vaccination against pox virus, Influenza virus, Hepatitis virus, e.g. Hepatitis C virus, Human immunodeficiency virus (HIV), Flavivirus, Paramyxovirus, Hantavirus, Filovirus, tumours and/or cancer such as breast cancer, melanoma, pancreatic cancer or prostate cancer.

Alternatively or additionally, the recipient is challenged with the MVA related virus according to the first aspect or with the genome according to the second aspect to elicit a therapeutic effect. As mentioned above, the heterologous sequence comprised in said virus or genome may code for a therapeutic compound. For example, the therapeutic compound can be a compound that affects or participates in tissue growth, cell growth, cell differentiation, a compound that is able to invoke a biological action such as an immune response, or a compound that can play any other role in one or more biological processes. Particularly, said compound may be an anti-microbial compound, an anti-viral compound, an anti-fungal compound, an immunosuppressive compound, a growth factor, an enzyme, an anti-inflammatory compound, or an anti-allergic compound. The therapeutic compound may also be an antisense nucleic acid.

The mode of vaccination, the vaccination dose, and the vaccination number can be optimized by the skilled person in a known manner. The vaccine may be formulated and administered in various ways well known to the skilled person. Preferably, the vaccine is administered in liquid form. Preferably, the vaccine is injected, e.g. intramuscular or parenteral. It is preferred that the MVA related virus according to the first aspect or the genome according to the second aspect is administered at a pharmaceutically effective amount to the recipient. An amount of a MVA related virus or genome is effective in a particular route of administration when it elicits an immune response in the recipient.

The invention is summarized as follows:

1. A Modified Vaccinia Ankara (MVA) related virus comprising one or more of the following features:
   (i) a nucleic acid sequence corresponding to a region that includes the right Inverted Terminal Repeat (ITR) and extends to but excludes deletion site III instead of (replacing) a nucleic acid sequence that includes the left Inverted Terminal Repeat (ITR) and extends to but excludes deletion site V,
   (ii) two copies of a nucleic acid sequence comprising deletion site IV and the right ITR,
   (iii) no nucleic acid sequence comprising deletion site I and the left ITR,
   (iv) no deletion site I,
   (v) two deletion sites IV,
   (vi) no open reading frame for at least one gene product selected from the group consisting of C11R, C10L, and D7L,
   (vii) two open reading frames for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R, and/or
   (viii) a nucleic acid sequence encoding a L3L gene product, wherein said nucleic acid sequence comprises at least one mutation resulting in an amino acid sequence modification of said gene product.
2. The MVA related virus of item 1, wherein the region that includes the right ITR and extends to but excludes deletion site III comprises deletion site IV.
3. The MVA related virus of items 1 or 2, wherein the region that includes the right ITR and extends to but excludes deletion site III comprises an open reading frame for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R.
4. The MVA related virus of any one of items 1 to 3, wherein the region that includes the left ITR and extends to but excludes deletion site V comprises deletion site I.
5. The MVA related virus of any one of items 1 to 4, wherein the region that includes the left ITR and extends to but excludes deletion site V comprises at least one open reading frame for at least one gene product selected from the group consisting of C11R, C10L, and D7L.
6. The MVA related virus of any one of items 1 to 5, wherein the nucleic acid sequence comprising deletion site IV and the right ITR further comprises an open reading frame for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R.
7. The MVA related virus of any one of items 1 to 6, wherein the nucleic acid sequence comprising deletion site I and the left ITR further comprises an open reading frame for at least one gene product selected from the group consisting of C11R, C10L, and D7L.
8. The MVA related virus of any one items 1 to 7, wherein
   (i) the region that includes the right ITR and extends to but excludes deletion site III has a nucleic acid sequence according to SEQ ID NO: 37 or Genbank Accession number KY633487 (preferably ranging from nucleotide position 162221 to 190549 or a nucleotide position corresponding thereto) or is a variant thereof which is at least 95% identical to said nucleic acid sequence, (ii) the region that includes the left ITR and extends to but excludes deletion site V has a nucleic acid sequence according to SEQ ID NO: 37 or Genbank Accession number KY633487 (preferably ranging from nucleotide position 1 to 31261 or a nucleotide position corresponding thereto) or is a variant thereof which is at least 95% identical to said nucleic acid sequence, and/or
(iii) the nucleic acid sequence comprising deletion site IV and the right ITR has a nucleic acid sequence according to SEQ ID NO: 37 or Genbank Accession number KY633487 (preferably ranging from nucleotide position 179272 to 190549 or a nucleotide position corresponding thereto) or is a variant thereof which is at least 95% identical to said nucleic acid sequence.

9. The MVA related virus of any one items 1 to 8, wherein said virus comprises a nucleic acid sequence encoding an A3L gene product and/or an A34R gene product, wherein said nucleic acid sequence comprises at least one mutation resulting in an amino acid sequence modification of said gene product(s).
10. The MVA related virus of item 9, wherein the nucleic acid sequence further encodes an A9L gene product, wherein said nucleic acid sequence comprises at least one mutation resulting in an amino acid sequence modification of said gene product.
11. The MVA related virus of item 10, wherein
(i) the virus comprises a nucleic acid sequence encoding an A3L gene product and an A9L gene product, wherein said nucleic acid sequence comprises at least one mutation resulting in an amino acid sequence modification of said gene products, or
(ii) the virus comprises a nucleic acid sequence encoding an A34R gene product and an A9L gene product, wherein said nucleic acid sequence comprises at least one mutation resulting in an amino acid sequence modification of said gene products.
12. The MVA related virus of item 10, wherein the virus comprises a nucleic acid sequence encoding an A3L gene product, an A34R gene product and an A9L gene product, wherein said nucleic acid sequence comprise at least one mutation resulting in an amino acid sequence modification of said gene products.
13. The MVA related virus of any one of items 1 to 12, wherein the virus further comprises a heterologous nucleic acid sequence.
14. The MVA related virus of item 13, wherein the heterologous nucleic acid sequence is selected from a sequence coding for
(i) an antigen, particularly an epitope of an antigen,
(i) a diagnostic compound, and
(iii) a therapeutic compound.
15. The MVA related virus of any one of items 1 to 14, wherein the virus is capable of productive replication in avian cells.
16. The MVA related virus of any one of items 1 to 15, wherein the virus is not capable of productive replication in primate cells, more preferably human cells.
17. A genome of the MVA related virus according to any one of items 1 to 16.
18. A cell comprising the MVA related virus according to any one of items 1 to 16 or the genome according to item 17.
19. The cell of item 18, wherein the cell is a non-adherent/suspension cell.
20. The cell of items 18 or 19, wherein the cell is an avian cell.
21. A method for culturing a MVA related virus according to any one of items 1 to 16 comprising the steps of:
(a) providing a cell according to any one of items 18 to 20,
(b) culturing the cell, and
(c) isolating the MVA related virus.
22. The method of item 21, wherein the cell is cultured in cell proliferation medium and subsequently in virus production medium or the cell is solely cultured in cell proliferation medium.
23. The method of items 21 or 22, wherein the MVA related virus is isolated from the cell-free supernatant and/or cell lysate.
24. A method for producing a MVA related virus according to any one of items 1 to 16 comprising the steps of:
(a) infecting a cell with a MVA virus,
(b) culturing the cell,
(c) isolating the MVA virus, and
(d) repeating steps (a) to (c) with the MVA virus isolated in step (c) until a MVA related virus comprising one or more of the following features:
(i) a nucleic acid sequence corresponding to a region that includes the right Inverted Terminal Repeat (ITR) and extends to but excludes deletion site III instead of (replacing) a nucleic acid sequence that includes the left Inverted Terminal Repeat (ITR) and extends to but excludes deletion site V,
(ii) two copies of a nucleic acid sequence comprising deletion site IV and the right ITR,
(iii) no nucleic acid sequence comprising deletion site I and the left ITR,
(iv) no deletion site I,
(v) two deletion sites IV,
(vi) no open reading frame for at least one gene product selected from the group consisting of C11R, C10L, and D7L,
(vii) two open reading frames for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R, and/or
(viii) a nucleic acid sequence encoding a L3L gene product, wherein said nucleic acid sequence comprises at least one mutation resulting in an amino acid sequence modification of said gene product is detected.
25. The method of item 24, wherein steps (a) to (c) are repeated until a MVA related virus comprising a nucleic acid sequence encoding an A3L gene product and/or an A34R gene product, wherein said nucleic acid sequence comprises at least one mutation resulting in an amino acid sequence modification of said gene product(s), is detected.
26. The method of item 25, wherein steps (a) to (c) are repeated until a MVA related virus comprising a nucleic acid sequence further encoding an A9L gene product, wherein said nucleic acid sequence comprises at least one mutation resulting in an amino acid sequence modification of said gene product, is detected.
27. The method of any one of items 24 to 26, wherein the cell is cultivated in virus production medium.
28. A pharmaceutical composition comprising the MVA related virus according to any one of items 1 to 16 or the genome according to item 17 and one or more pharmaceutical acceptable excipient(s), diluent(s), and/or carrier(s).

29. A vaccine comprising the MVA related virus according to any one of items 1 to 16 or the genome according to item 17.
30. A MVA related virus according to any one of items 1 to 16 or a genome according to item 17 for use in medicine.
31. The MVA related virus or the genome of item 30 for use in vaccination.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

The following Figures and Examples are merely illustrative of the present invention and should not be construed to limit the scope of the invention as indicated by the appended claims in any way.

EXAMPLES

Figure 1:
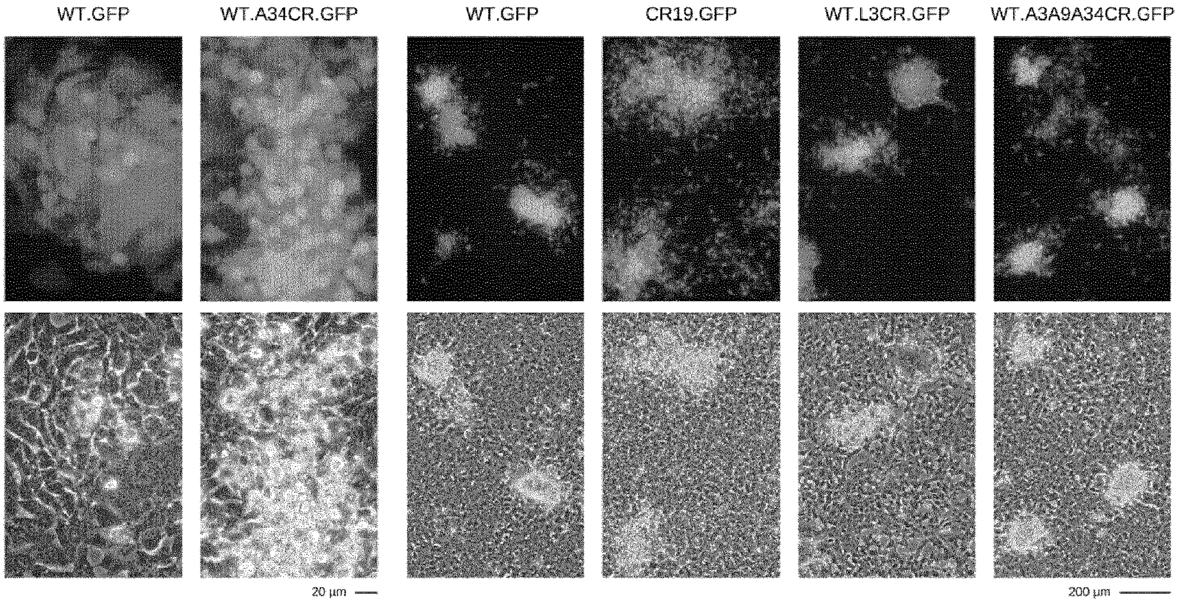
FIG. 1: CR-associated Mutations were inserted individually or in various combinations into the backbone of wildtype virus together with GFP to allow visualization of plaques without fixation and immunostaining. All infections were performed with MOI of 0.01 and plaque phenotype is shown 48 h PI. WT.GFP, wildtype MVA that expresses GFP, WT.A34CR, WT.L3CR and WT.A3A9A34CR denote WT.GFP viruses that contain the respective CR-associated mutations H639Y, K75E and D86Y in the genes A3L, A9L and A34R, CR19. GFP is MVA-CR19 that expresses GFP.

1. Materials and Methods 1.1 Cells and Viruses

CR.pIX cells from the muscovy duck (Jordan et al., 2009b) and MVA-CR19 (Jordan et al., 2013a) have been described previously. CR.pIX cells were maintained in adherent format in DMEM:F12 medium supplemented with 5% bovine serum (γ-irradiated, Gibco 26140-079), or in suspension cultures in CD-U4 medium (GE Healthcare

#G3321 or Biochrom #F9185) supplemented with 10 ng/mL LONG-R3IGF (Sigma, USA). Both media were also supplemented with 2 mM GlutaMAX I (Life Technology, USA). Infection and propagation of MVA was performed in 1:1 mixtures of CD-U4 and CD-VP4 (Merck-Millipore #F9127) as described previously, usually with 2×106 cells/mL, MOI of 0.01 to 0.1, and harvest 48 or 72 h post infection (Jordan et al., 2011). Suspension cultures were maintained in a shaking incubator (HT Multitron Cell, Infors AG, Switzerland) on a rotating platform with amplitude of 5 cm and rotation speed of 180 min-1. The CO2 atmosphere was set to 8% and temperature to 37° C. All culture vessels, shake tubes (Tubespin 50, TPP Techno Plastic Products AG, Switzerland) or baffled shake flasks (Corning, USA), were equipped with 0.2 μm filtered lids to allow gas exchange. Suspension culture volumes were maintained at 20-40% of the vessel size.

Infectious titers of MVA were determined in PFU/mL (plaque forming units) or FFU/mL (fluorescence forming units) as described previously (Jordan et al., 2013a) on Vero cells. Viruses were visualized in the non-permissive indicator cells by immunostaining or, where applicable, with help of the fluorescing reporters in deletion site III.

1.2 Generation of Recombinant MVA

Recombinant MVA was generated by homologous recombination in adherent CR.pIX cells by adaptation of published methods (Kremer et al., 2012). Briefly, 1×106 CR.pIX cells were seeded per well of a 6 well-plate. The culture monolayers were infected with receiving MVA with a MOI of 0.01 on the following day and transfected with 2.0 μg of shuttle plasmid for insertion into deletion site III.

Point mutations were introduced by homologous recombination with a synthetic fragment that also contained silent diagnostic sites for restriction enzymes to confirm successful insertion and maintenance (Table 1). The recombination events were promoted by framing the region of interest by flanks of 600 to 1000 bp on each side. The receiving viruses usually expressed a reporter gene from within deletion site III. A concurrent recombination was performed with a second shuttle plasmid designed to exchange this preexisting reporter gene for a different reporter gene (for example, blue fluorescence against green or red) to further facilitate recovery of recombined viruses. This marker plasmid was transfected at lower molar ratios compared to the main shuttle plasmid (1.8 μg of the shuttle plasmid with the point mutation and 0.2 μg of the reporter shuttle plasmid).

Transfections were performed with effectene (Qiagen, Germany) according to the manufacturer's instructions 90 min after infection, and the medium was replaced 24 h post transfection. The infected/transfected culture was harvested after 48 h to 72 h, sonicated, and used to infect cell monolayers in a 6-well plate at dilutions of 1000 to 10000-fold in PBS. The medium of this next generation infection was exchanged against medium containing 1% methylcellulose after 4 h to 16 h. Plaques of the appropriate fluorescent phenotype were picked usually after another 24 h to 48 h and total DNA was isolated from aliquots of individual plaques using QuickExtract DNA Extraction Solution 1.0 (Epicentre, USA). Another round of plaque purification was initiated with the candidate recombinant virus preparations that passed the PCR analysis. The material for infection was obtained by sonication of cell harvests using a Vial Tweeter (set to 20 s of 100% cycle and 90% amplitude) that allows handling of closed sample caps to avoid cross-contamination (Hielscher, Germany). Viruses with parental genotype or incomplete recombination were not detectable within 3 to 8 rounds of plaque purification.

Virus passages to assay genomic stability was performed in CR.pIX suspension cultures in a volume of 5 mL with 1:1 mixtures of CD-U4 and CD-VP4. Cell density was 2×106 cells/mL and MOI 0.01 (in blind passages a titer of 108 PFU/mL was assumed in the previous passage). The infected culture was sonicated 48 or 72 h post infection to harvest virus.

1.3 PCR Analysis of rMVA

80 μL of complete cell lysate was mixed with 20 μL of QuickExtract DNA Extraction Solution 1.0 (Epicentre, USA) and heated to 65° C. for 10 min and to 98° C. for 5 min. 4 μL of this preparation was subjected to PCR in a final volume of 25 μL with 0.15 μL Taq polymerase (Qiagen, Germany), 200 nM each primer, and 125 μM each nucleotide. The sequence of the primer pairs that span deletion sites I to VI of the viral genome were obtained from the literature (Kremer et al., 2012). The expected sizes of the amplification products are 291, 354, 447, 502, 603, and 702 bp for wildtype virus deletion sites I to VI (Kremer et al., 2012), and 1285 for deletion site III in MVA-CR19. GFP. Thermocycling was initiated with 94° C. for 80 s, followed by 35 cycles of 94° C. for 20 s, 55° C. for 20 s and 72° C. for 90 s, and terminated with 72° C. for 5 min. Amplicons were separated by electrophoreses in 1.5 agarose gels.

1.4 Cloning of Shuttle Plasmids

The shuttle plasmid for deletion site III was cloned stepwise via insertion of the left and right flanks into pEGFP-N1 (Clontech, USA). The flanks were amplified from the genomic DNA of wildtype MVA with the primers "LeftF" AGG ACA TGT-TTG GTG GTC GCC ATG GAT GGT (SEQ ID NO: 17) and "LeftR" TAC CGC TAG C-T ACC AGC CAC CGA AAG AG (SEQ IDNO: 18), and with primers "RightF" TGG GCG GCC GC-TTT GGA AAG TTT TAT AGG (SEQ IDNO: 19) and "RightR" TGG CAC GTA GTG-CCG GAG TCT CGT CTG TTG (SEQ IDNO: 20), respectively. The left flank was cut with NheI (all restriction enzymes used in this study were obtained from New England Biolabs or Roche) and PciI, the right flank with DraIII and NotI for sequential insertion into the same sites of pEGFP-N1 while maintaining the EGFP open reading frame. The artificial EL promoter (Chakrabarti et al., 1997) was generated by annealing two complementary 72 bp-oligonucleotides (TIP MolBiol, Germany) with the sequence "PromEL" ATC TGC TAG CAC GTG GAC TAG TAA AAA TTG AAA TTT TAT TTT TTT TTT TTG GAA TAT AAA TAA GAT CTT ACC (SEQ ID NO: 21) on the containing strand. The annealing was performed after denaturation at 95° C. for 2 min followed by a ramp down to 56° C. with −0.1° C. per second. This fragment was cut with BglII and NheI, precipitated with 300 mM sodium acetate in two volumes of ethanol, purified by polyacrylamide gel electrophoresis, and inserted into the same sites of the pEGFP-N1 plasmid already containing the deletion site III flanks. Sequencing confirmed integrity of the shuttle plasmid but revealed a transition from ttG aaa ttt to ttA aaa ttt in the EL promoter that was not corrected and maintained as GFP expression was strong in rMVAs. A viral transcription terminator signal (TSNT, (Yuen and Moss, 1987)) is contained in the right flank. The DsRed1 derivative mCherry was synthesized with codon-optimization for duck (Eurofins Genomic, Germany) and inserted in antisense orientation to GFP and under control of the late P11 promoter (Bertholet et al., 1985). The resulting dual expression cassette spans 1615 bp from EL to P11 promoter, the amplification product for deletion site III primers is 2087 bp long.

The shuttle plasmids for introduction of the point mutations D86Y in A34R and V110A in L3L into wildtype MVA were cloned only with fragments amplified out of MVA-CR19 genomic DNA. These mutations contain fortuitous diagnostic restriction enzyme sites to confirm successful recombination (Table 1). The A34R shuttle plasmid was cloned by amplification of 1393 bp with primers "A34F" AAT GCT AGC-GCG GAA TCA TCA ACA CTA CCC (SEQ IDNO: 22) and "A34R" GCT CTA G-ATT GTT CCC GCA ACT ACG GTC (SEQ IDNO: 23). The primers contained additional restriction sites for NheI and XbaI, respectively, at the 5' termini for insertion into pEGFP-N1 (out of dam(−) bacteria) using these sites. The L3L shuttle plasmid was cloned with primers "L3F" CTC TAC GGG CTA TTG TCT C (SEQ IDNO: 24) and "L3R" TGA ATA CCC GTA CCG ATG (SEQ IDNO: 25), the 717-bp fragment was cloned into pCR-Blunt II-Topo ("pTopo") as described in the Zero Blunt TOPO PCR Cloning Kit (Invitrogen, USA).

The shuttle plasmids for the other point mutations, H639Y in A3L and K75E in A9L, were cloned by insertion of synthetic DNA (Eurofins Genomic) that contained the desired point mutation and silent diagnostic mutations (designed using website: resitefinder.appspot.com).

For the generation of the shuttle plasmid for A3L a 2008 bp fragment of A3L was amplified with primers "A3F" GCA GAA GAA CAC CGC TTA GG (SEQ IDNO: 26) and "A3R" ATG GAA GCC GTG GTC AAT AG (SEQ IDNO: 27) and inserted into pTopo. A 274-bp fragment therein from SacI to SwaI was replaced with a synthetic DNA containing H639Y and the silent NcoI site. One flank of this shuttle plasmid had to be extended because first recombination attempts did not include the desired H639Y site: an additional synthetic DNA of 479 bp containing a new (but silent) AvaI site was appended to the NcoI-distal side using SwaI (in MVA) and SpeI (in pTopo).

Recombination of a 415 bp synthetic DNA that also contained a silent diagnostic mutation near to the desired K75E mutation transferred only the diagnostic mutation as well (revealed by sequencing of plaque purified viruses). The flanks were therefore extended and additional diagnostic mutations were inserted so that K75E is framed by markers: a 2905 bp fragment containing A9L and neighboring gene A10L was amplified out of wildtype MVA genomic DNA with primers "A9F" TTG AAA TAG CGC CAG TCC TCC (SEQ IDNO: 28) and "A10R" ACT ACG GCG GCA TTA TGT TCTC (SEQ IDNO: 29). This 2905 bp fragment was cloned into pTopo to yield pTA10L. A synthetic DNA containing the diagnostic sites in A10L was inserted via a three fragment ligation using PmeI (in the vector) to NsiI (in the MVA insert) of pTA10L as new vector backbone, SpeI to NsiI in the synthetic DNA to insert the silent StyI diagnostic marker, and NsiI to PmeI of the pTA10L to restore the initial amplification product. Three-fragment ligation to obtain pTLA10L-StyI was necessary to circumvent an additional SpeI site in the vector backbone. The A9L flank was inserted using a synthetic DNA fragment containing the K75E mutation framed by diagnostic silent mutations on both sides, EcoRI and BseRI. This fragment was inserted via a three-fragment ligation to circumvent a Tth111I site in the vector, using Tth111I in A9L to EcoRV in the multiple cloning site of the synthetic DNA vector, Tth111I to PmeI in pTA10L and Tth111I to PmeI in pTA10L to restore the vector. The resulting shuttle plasmid contains a MVA-derived fragment of 3620 bp.

1.5 Sequencing and RACE

Genomic DNA of plaque-purified MVA-CR19. GFP was isolated by polyethylene glycol precipitation out of 100 mL of infected CR.pIX cells at 2×106 cells/mL as described previously (Jordan et al., 2013a). Sequences were obtained by GATC Biotech AG (Germany) with the PacBio RSII technology and assembled using an unforced (without guide sequence) algorithm.

Because large gaps at the left side of the genome remained after sequence assembly, and because PCR against the deletion sites indicated a loss of deletion site I (that is located near the left terminus of MVA) 5'-end RACE was performed. Primer D2 RII (GGC GGC ATG TGG AGT GTC TTT ATC) (SEQ IDNO: 30) against a 5' terminal region still covered by the genomic sequence assembly was designed using the Clone Manager Professional suite version 9 (Sci-Ed Software, USA). This primer was extended on 500 ng of viral genomic DNA in 100 μL of 1×PCR buffer, 1×Q solution, and 5 U Taq and 0.2 U ProofStart Taq polymerase (all Qiagen, Germany), 0.4 μM primer D2 RII and 0.05 mM each dNTP. The thermocycler was programmed for 35 cylces of 94° C. for 10 s, 57° C. for 60 s, and 68° C. for 3 min (with 95° C. for 2 min at the start and 72° C. for 10 min at the end of the program). This PCR reaction was purified with the QIAquick PCR Purification Kit, 25 μL thereof were incubated with terminal transferase (TdT, New England Biolabs #M0315S) in a final volume of 50 μL of 1× Tailing Buffer, 0.25 mM CoCl2 and 0.1 mM dCTP. The tailing reaction was preceded by denaturation at 94° C. for 3 min, followed by addition of 0.5 μL of the TdT and incubation at 37° C. for 30 min, and termination at 70° C. for 10 min.

A nested PCR was next performed to recover the 5' extended and dC-tailed product using primers D2 (GGT GTA TAG AGT TCA CAG TAG) (SEQ IDNO: 31) and the universal anchored primer AAP (GCC ACG CGT CGA CTA GTA CGG Gnn GGG nnG GGn nG, wherein n stands for I=inosine, GCC ACG CGT CGA CTA GTA CGG GII GGG IIG GGI IG, with I for inosine) (SEQ IDNO: 32) in a final volume of 100 μL as described above for D2 RII primer extension but with an extension temperature of 59° C. for 60 s (instead of 57° C.).

This first nested PCR was diluted 1:50 and subjected to a second nested PCR in a final volume of 50 μL, without Q solution, primers GSPD2-R (GGA GGT GGC TCT CGA TGA AC) (SEQ IDNO: 33) and AAP, with the same thermocycler program as in the first nested PCR. A fragment of approx. 700 bp was isolated and purified by agarose gel electrophoresis with the Qiagen Gel Extraction kit and sequenced with primers AAP and GSPD2-R.

Primers "RS469F" ACG GTC CTG TAG TAT CTG (SEQ IDNO: 34) and "RS469R" CGG CAT GTG GAG TGT CTT TAT C (SEQ IDNO: 35) were designed on this sequence as a diagnostic pair for amplification of 469 bp spanning the newly discovered recombination site (RS469).

The long-PCR for amplification of the presumed left ITR of MVA-CR19 was performed with primers D2 RII and "ITR-M" (CTT GCA CAT GTC TCC GAT ACG) (SEQ IDNO: 36) to obtain 21312 bp on MVA-CR19 and 9360 bp on wildtype MVA (FIG. 1). The ITR-M primer binds in forward orientation from 533 to 553 and in reverse orientation from 165956 to 165976 in GenBank sequence AY603355 whereas primer D2 RII binds only once, in reverse orientation from 9869 to 9892. The possible amplicons are therefore 9360 bp and 165444 bp (ITR-M single-primer amplification) with wildtype MVA as template, but not 21312 bp. LongRange PCR (Qiagen) was performed in 50 μL final volume with 200 ng of viral genomic DNA according to the manual. The thermocycler program was initiated with 93° C. for 3 min; followed by 10 cycles of 93° C. for 10 s, 57° C. for 30 s and 68° C. for 15 min; followed by 25 cycles of 93° C. for 15 s, 57° C. for 30 s and 68° C. for 21 min with extension by 20 s per cycle. Restriction enzyme analysis with MI, NruI or ApaLI was performed with 3 μL of PCR product in 20 μL final volume and 0.5 μL of enzyme according to the manufacturer's instructions.

2. Results 2.1 Fusion Phenotype

A pronounced shift towards the novel strain in populations with mixtures of wildtype viruses and those that carry the MVA-CR mutations after repeated passage in suspension cultures was previously observed (Jordan et al., 2013a). Such a shift may be caused if a viral genotype replicates faster, is associated with higher specific infectivity or (as hypothesized) reduces the affinity of its progeny viruses for the host cells. The property of MVA to remain associated with host cells is well characterized (Blasco and Moss, 1991; Blasco et al., 1993; Husain et al., 2007; Meiser et al., 2003), with one consequence that syncytia can form if the viral fusion apparatus is activated in particles on the surface of a cell with contacts to neighboring cells (Ward, 2005). A prominent syncytia formation by induction of the fusion apparatus was only observed in cultures of CR.pIX cells infected with wildtype MVA but not with MVA-CR viruses (data not shown and (Jordan et al., 2013b)).

In a next step, the point mutations of MVA-CR (Table 1) were introduced into wildtype MVA to investigate the contribution of the mutations to the MVA-CR phenotype. The point mutations were inserted into the wildtype backbone by homolgous recombination of synthetic gene segments. These segments were designed to also contain silent mutations for diagnostic restriction enzyme polymorphism to confirm that plaque-purified recombinant viruses were of the intended genotype and without contaminating parental viruses. A GFP reporter gene was inserted under control of a synthetic promoter into deletion site III to facilitate study of life plaques without immunostaining. Adherent monolayers of the CR.pIX cell line were infected with recombinant viruses to a MOI of 0.01 and fluorescence images taken at various time points (48 h PI is shown in FIG. 1). The GFP signals from recombinant viruses that contained the A34RCR mutation were scattered over large areas and the plaques exhibited only negligible spontaneous syncytia formation. Plaques formed by recombinant viruses with the A3LCR, A9LCR and L3LCR mutations resembled those formed by wildtype viruses.

It has been concluded from these experiments that viruses with the CR genotype have a decreased tendency to form spontaneous or pH-induced syncitia.

2.2 Missing Deletion Site I

Figure 2:
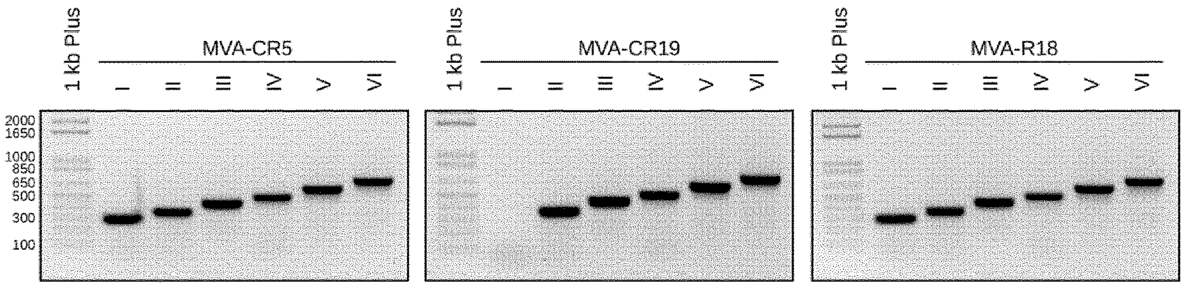
FIG. 2: Deletion site I is missing in MVA-CR19 but not in wildtype MVA (passage 5 in CR cells, MVA-CR5) or in a MVA obtained by serial passaging on adherent cells of the Egyptian fruit bat (MVA-R18 (Jordan et al., 2013a)).

Recombinant MVAs can be characterized by a set of PCRs that are designed to amplify across each of the six deletion sites (Kremer et al., 2012). These PCR reactions have been used to confirm insertion of the GFP-expression cassette into the commonly used deletion site III. As part of the recommended routine the other amplification fragments were also tested. Surprisingly, the signal expected for deletion site I was missing in MVA-CR19 derivatives, but not in an earlier passage or an isolate passaged 18 times on the permissive fruit bat cell line (MVA-R18 (Jordan et al., 2013a); FIG. 2). All other deletion sites gave signals of appropriate sizes in all tested viruses.

The deletion site I amplicon is localized at the boundary of the left inverted terminal repeat and partially overlaps with the core region of the genomic DNA. The previously reported sequence of the genomic DNA of MVA-CR11, an ancestor of MVA-CR19, has covered 135 kb of the genomic DNA that stretched downstream of deletion site I beyond deletion site III (FIG. 3A, contigs C-2412, C-131534 and C-1549) (Jordan et al., 2013a). The sequences of the core and partial ITR at the right end of the genome, including deletion site IV, were not part of the earlier reports. It was decided to include only sequences obtained by unguided sequence assembly. An additional sequence of 21 kb covering the right end of the genomic DNA was obtained by sequence assembly with GenBank entry U94848 as guide sequence and extended beyond deletion site IV into part of the ITR without any deviations from wildtype.

An earlier report has linked the absence of deletion site I to presence of ancestral (undeleted) chorioallantois vaccinia Ankara virus (CVA) sequences (Suter et al., 2009). However, a PCR for detection of CVA loci as described in that publication gave no signals with these primers in our preparations (data not shown). It was therefore suspected that a loss of deletion site I has occurred, and that this observation should be associated with genomic changes at the left end of the viral DNA. To elucidate potential mechanisms for the changes primer extension and TdT tailing, using the known sequence of C-2412 as a starting point, were next performed. The obtained PCR fragment from the genomic DNA of MVA-CR19 had a sequence that reads from within the core towards the left telomer but stopped at nucleotide 15322 (using GenBank #AY603355 as reference) and continued with the antisense strand going towards the right telomer and starting with nucleotide 150816 (FIG. 3B to D).

Figure 3:
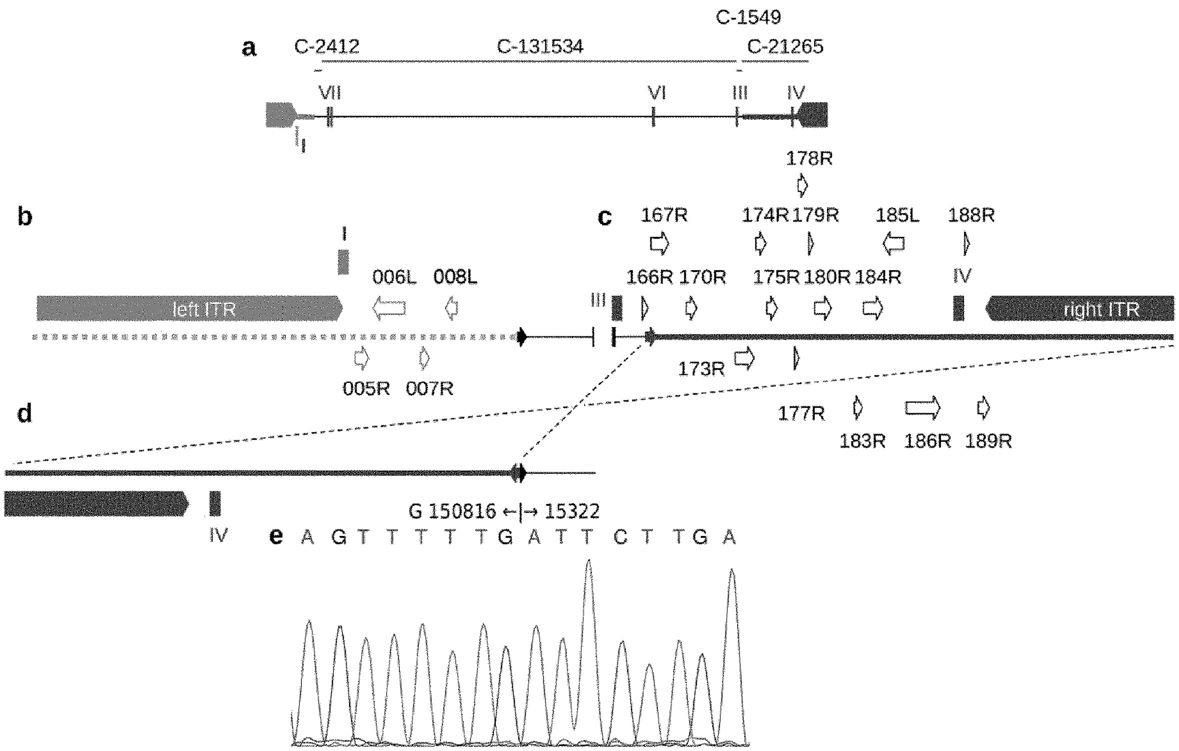
FIG. 3: Proposed recombination in MVA-CR19. (a) Schematic of the wildtype genome with inverted terminal repeats (ITRs) and expected amplification products that span the six deletion sites (roman numerals). The bars preceeded with "C-" indicate the contigs that were obtained in previous (Jordan et al., 2013a) sequence analysis. The recombined region in addition to the ITRs is shown by the bolded line. (b) Left and (c) right ITRs in greater detail. Open arrows indicate the open reading frames. (d) The proposed left ITR of MVA-CR19 after recombination. (e) Sequence chromatogram of the recombination site, numbering with reference to GenBank U94848. (a-d) Dark grey for sequences derived from the right side of the genome, light grey for those of the left side of the genome. The pointed rectangles symbolize the ITR, the recombined region in addition to the ITRs is shown by the bolded line. The filled opposing dark grey and black arrows ( ⇦➡ ) denote strand orientation and mark the recombination site.

A sequence as that obtained in FIG. 3D suggests that the left ITR of MVA-CR19 may have formed by recombination with the right ITR. The recombination site (RS) is downstream of deletion site I and upstream of deletion site IV.

Figure 4:
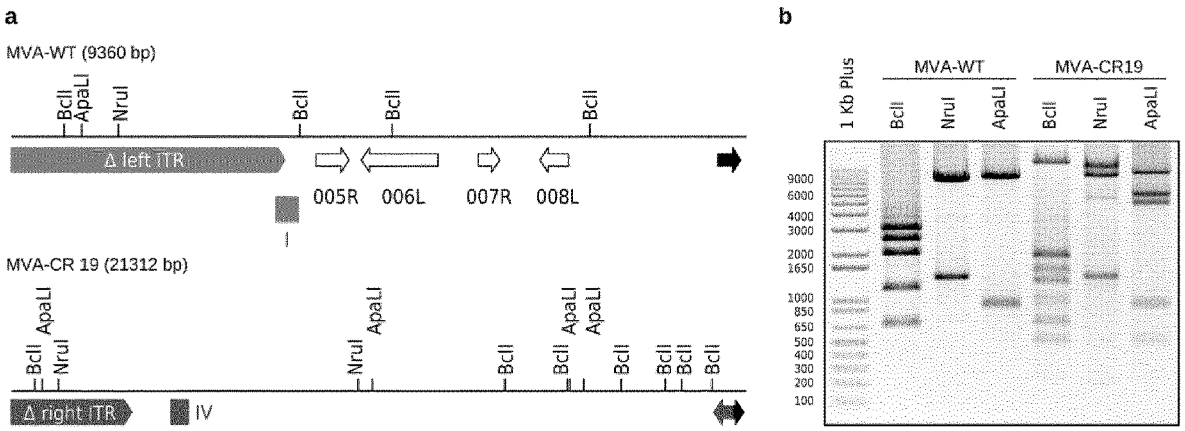
FIG. 4: Confirmation of ITR rearrangement as shown in the previous figure. (a) Proposed structures of a PCR amplication products derived from the left ITR of the GenBank sequence U94848 and of MVA-CR19. Shown are genes (open arrows), deletion sites I and IV (filled boxes), ITRs (pointed grey and dark grey rectangles), recombination site (bold dark grey and black arrows) and target sites for restriction enzymes that were used to confirm the proposed structure of the left ITR. (b) Agarose gel electrophoresis of the long-PCR product shown in (a). Expected sizes for wildtype cut with MI are 3007, 2518, 1992, 1172, and 671; with NruI are 7998 and 1362; with ApaLI are 8464 and 896; for MVA-CR19 cut with WI are 13634, 1890, 1498, 1269, 984, 886, 671 and 480; with NruI are 11257, 8693, and 1362; and with ApaLI are 9572, 5646, 4706, 896, and 492 bp.

Next a PCR has been performed intended to amplify fragments that should be unique for each of the genotypes to confirm that the proposed recombination has indeed occurred in MVA-CR19. One primer binds to a sequence that is found at the ends of both ITRs and faces towards the center independent of whether it annealed to the left or right ITR. The other primer is unique to a sequence in the core of the genome and faces towards the left ITR. The expected amplification products with GenBank AY603355 as template are 9360 bp (containing deletion site I) and 165444 bp, where 165 kb is the region that is spanned by the single primer that binds the termini. A rearrangement of the right ITR to the position of the left ITR increases the amplification product to 21312 bp (FIG. 4A). Such different amplicons were indeed obtained for MVA-WT, and MVA-CR19, respectively, and restriction fragment polymorphism with NruI, MI and ApaLI further confirmed the expected identity of the obtained fragments (FIG. 4B).

The lost fragment in the left ITR contains MAV001L to MVA013L (with MVA014L as the first gene not affected by the deletion). Only MVA005R (C11R), MVA006L (C10L) and MVA008L (D7L) therein appear to be functional genes (Antoine et al., 1998; Meisinger-Henschel et al., 2007). MVA001L, MVA002L and MVA003L are pseudogenes and also found duplicated in the C-21265 contig at the right end of the genome. MVA004L is a fragmented gene of 58 amino acids that are mirrored in a complete open reading frame of 188 amino acids in the right part of the genome (MVA189R, similar to vaccinia Copenhagen B22R according to the annotation of the Genbank entry U94848). MVA007R is a gene of 91 amino acids with homology to a gene of 242 amino acids, the p28 virulence factor of ectromelia (mousepox) virus (Senkevich et al., 1994, 1995). It has been reported to be already disrupted in vaccinia virus strains Copenhagen, Tian-Tan, WR and MVA (Esteban and Buller, 2005). The genes MVA009L to MVA013L appear to be non-functional fragments of host-range determinants with resemblance to D6L of variola virus or CP77 of cowpox virus (Antoine et al., 1998; Meisinger-Henschel et al., 2007).

2.3 Sequencing of MVA-CR19. GFP

With the proposed recombination another guide sequence starting from Genbank entry AY603355 was created, but were again not successful to recover terminal repeats with next generation sequencing. The new sequencing attempt was performed with DNA isolated of a MVA-CR19. GFP preparation and covered a total of 145636 bp (including telltale GFP expression cassette in deletion site III) in three contigs of 15557, 89342 and 40737 bp. The final remaining gap (a formality as there was no sequence overlap between C-2412 and C-131534) was closed by conventional PCR and sequencing.

Figure 6:
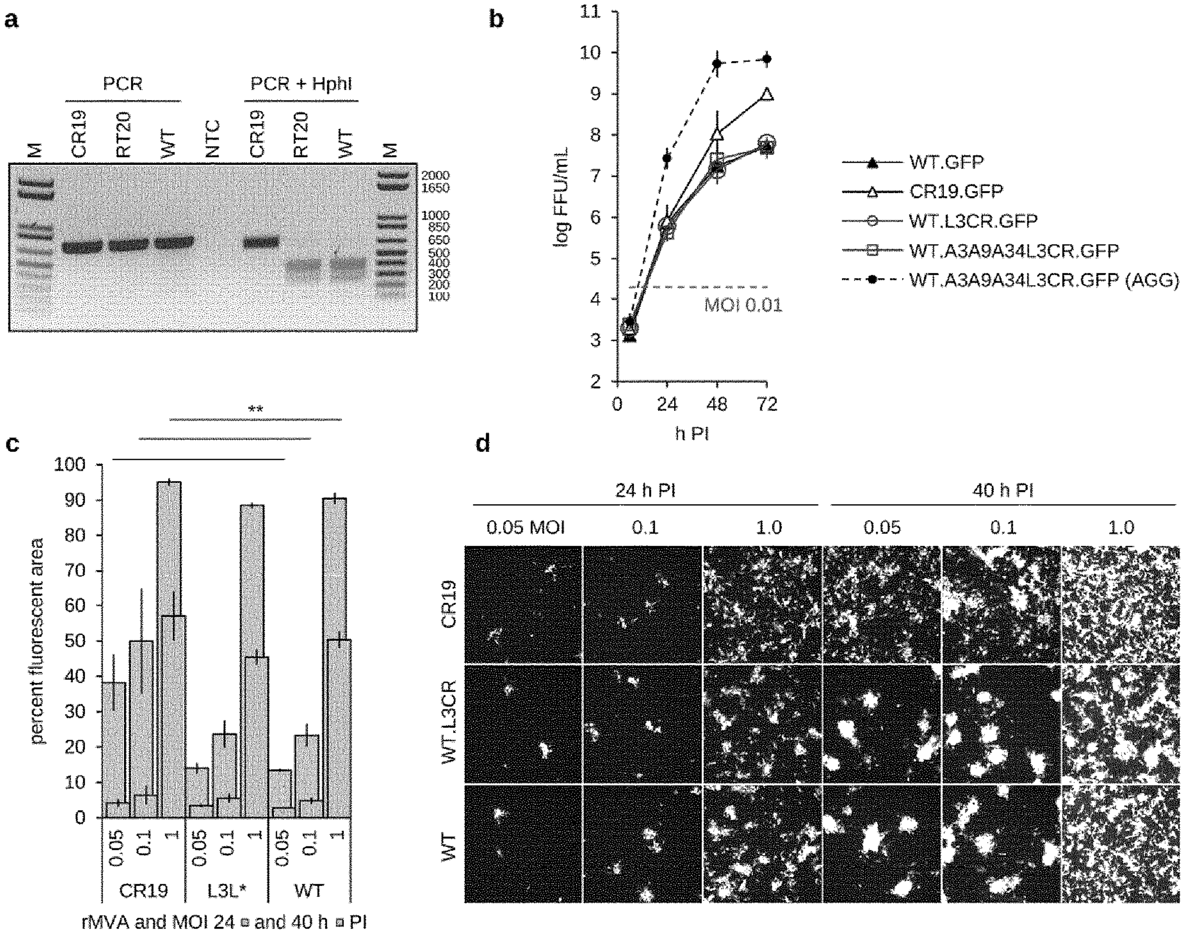
FIG. 6: Investigation of the L3 mutation. (a) Restriction fragment length polymorphism due to the mutation in L3L in MVA-CR19. The 717-bp amplicon is expected to yield HphI fragments of 649 and 68 bp for MVA-CR19 and 380, 269 and 68 bp for wildtype. (b-d) Two independent preparations of MVA-WT.L3LCR.GFP were used for these experiments. (b) Replication kinetic of the indicated recombinant viruses in single-cell suspension cultures. The dashed line shows replication of the indicated virus in the conventional process were aggregates are being induced. (c, d) Infection of adherent CR.pIX cells with GFP-expressing rMVAs. Depicted are mean and standard deviation of triplicates for MVA-WT.GFP and MVA-CR19. GFP, and of six values (two triplicates) of MVA-WT.L3CR.GFP. The $\log_{10}$ FFU/mL of the MVA preparations used for infection in this experiment were 8.5 (MVA-WT.GFP), 8.3 and 8.8 (MVA-WT.L3CR.GFP), and 9.8 (MVA-CR19. GFP). (**) indicates significant differences between the corresponding 40 h time points of CR19 and wildtype recombinant viruses in a two-tail, independent t-test; the differences were not significant in a comparison between L3L-mutant and wildtype.

All previous mutations could be confirmed and only one additional point mutation was discovered, V110A in MVA082L (L3L in vaccinia virus nomenclature). This point mutation is associated with a fortuitous restriction site polymorphism (HphI site is deleted) that allowed a comparison of MVA-CR19 and MVA-CR19. GFP to sequences obtained from wildtype virus or viruses passaged on the fruit bat cell line. The HphI polymorphism confirmed that this point mutation is not a sequencing artefact. The HphI site was detectable in wildtype and bat-cell passaged MVA viruses but not in MVA-CR19 (FIG. 6). L3L was sequenced in preparations of passage 2 MVA, passage 11 MVA and the plaque-purified MVA-CR19, and observed two notable differences to the previous three point mutations. First, there appeared to be no visibly mixed population of L3L genotypes in MVA-CR11, and there were no indications of the presence of L3L in the passage 2 preparation. (The A9L mutation of the CR-genotype was already visible in passage 2 of non-plaque purified MVA, and all CR genotype mutations were overlapping with wildtype sequence in chromatograms of MVA-CR11, see FIG. 2 of (Jordan et al., 2013a)).

2.4 Stability of the Different Virus Species

Figure 5:
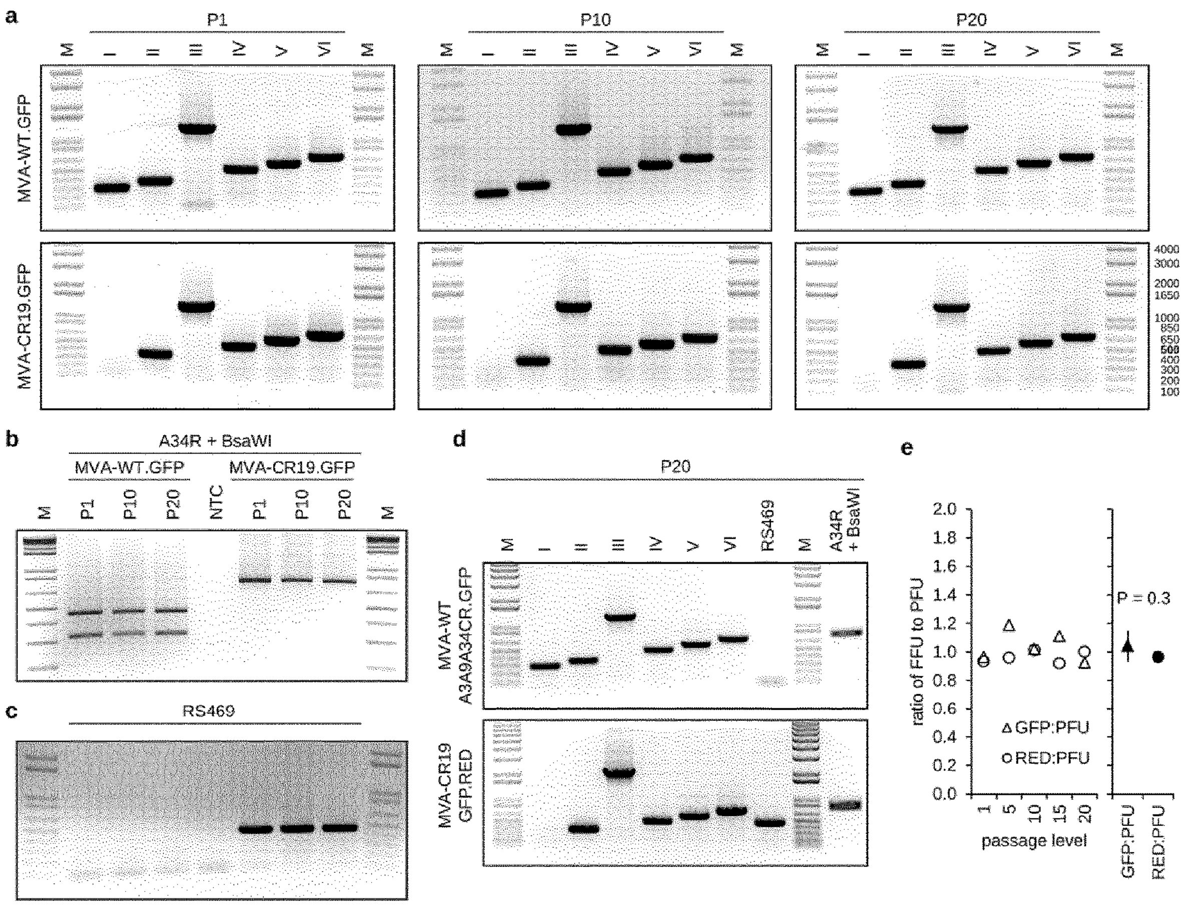
FIG. 5: Stability of MVA genotypes in CR.pIX cultures. (a) Plaque-purified recombinant wildtype and CR19 isolates that contain a GFP-expression cassette in deletion site III were passaged 20 times in CR.pIX suspension cultures. Note absence of deletion site I signal in CR19 derivatives and the expected shift in size of the deletion site III amplification product due to the GFP cassette. (b) The viral DNA that was purified in (a) also exhibits a stable pattern of the restriction fragment length polymorphism (RFLP) in the A34R gene for both isolates over the passaging interval. (c) The presence of the RS469 amplification product that replaces deletion site I in CR19 derivatives is found in passages of CR19 but not in those of the wildtype. The samples were applied in the same sequence as in (b). (d) Stable patterns of the deletion sites and the RFLP in recombinant viruses that carry the point mutations of the CR genotype in a wildtype backbone or a GFP and mCherry (RED) dual expression cassette in the CR19 derivative. (e) Infectious titers obtained with MVA-CR19.GFP.RED dual expression vector were determined at the indicated passage levels by determination of PFUs with immunostaining against vaccinia virus proteins, or via determination of the green or red fluorescence signals. The ratios of the infectious units is shown in the chart. A decrease of FFU relative to PFU would indicate loss of the expression cassettes. Titrations based on GFP tend to be higher than those based on mCherry in dual-expression constructs because some excitation of mCherry also occurred under GFP fluorescence conditions. The mean of all ratios is 1.00±0.09, there is no significant difference between the mean values of the ratios of GFP-FFU:PFU and mCherry-FFU:PFU at a 99% confidence level (paired t-test).

Maintenance of transgene expression, replication properties and degree of attenuation depend on the genomic stability of viral vectors. Although virus isolates with deletions and rearrangements in the ITR (Moss et al., 1981; Paez et al., 1985; Pickup et al., 1982; Qin et al., 2011) and transient gene amplification in response to selective pressures by the innate immune system (Elde et al., 2012) have been described previously, MVA is also known for high genetic stability (Antoine et al., 2006). Maintenance of genetic markers of wildtype MVA and MVA-CR19 was next investigated by propagation in the anatine continuous suspension cell line in chemically-defined medium (rather than galline primary adherent cultures in the presence of serum, the substrat used in generation of MVA). Plaque purified recombinant viruses that contained GFP or the dual GFP and mCherry expression cassette in deletion site III were passaged 20 times in the CR.pIX suspension cultures (FIG. 5). Background of the viruses were either wildtype or MVA-CR, or a wildtype virus with point mutations of the CR genotype in the affected structural genes. No changes in A34R (neither towards the CR genotype nor wildtype), no deletions in deletion site III, no changes at the recombination site in MVA-CR, and no loss of deletion site I in wildtype was observed. A retrospective study of the genomic DNAs of isolates obtained in the first round of plaque purification towards MVA-CR19 (where the point mutation in A34R was used as selection marker) furthermore revealed that the majority of the viruses did not contain deletion site I already, indicating that the rearrangement at the left ITR preceded isolation of MVA-CR19 (data not shown).

2.5 Effects of the L3L Mutation

An additional mutation was discovered in MVA-CR19. GFP, in the L3 protein, and its presence confirmed by restriction fragment length polymorphism in the parental MVA-CR19 and conventional sequencing (FIG. 6 *a*). The L3 protein is expressed predominantly in late phases of the infection but is only loosely incorporated (not as a structural

TABLE 1

Summary of observed mutations in MVA-CR19 and additionally introduced silent diagnostic mutations in wildtype virus

| gene | mutation | diagnostic site | WT (GenBank AY603355) | recombinant |
|---|---|---|---|---|
| MVA082L (L3L) | V110A | Δ HphI (ggtga) | ttg gTg aga<br>leu VAL arg | ttg gCg aga<br>leu ALA arg |
| MVA113L[1] | | AvaI* (ctcgag)<br>PspXI* (vc/tcgagb) | tgT tcT TCt<br>cys ser ser | tgC tcG AGt<br>cys ser ser |
| MVA114L (A3L) | H639Y | NcoI* (c/catgg) | tca atg gat<br>ser met asp<br>aga Cat att<br>arg HIS ile | tcc atg gat<br>ser met asp<br>aga Tat att<br>arg TYR ile |
| MVA120L (A9L) | K75E | EcoRI* (g/aattc)<br>Δ XcmI (ccan9tgg) | aag Aag aat<br>lys LYS asn<br>ccA aat tca ttt tgg<br>pro asn ser phe trp | aag Gag aat<br>lys GLU asn<br>ccG aat tca ttt tgg<br>pro asn ser phe trp |
| MVA121L (A10L)[1] | | K554K with<br>StyI (ccwwgg) | ccA aaG gtA<br>pro lys val | ccC aaG gtC<br>pro lys val |
| MVA145R (A34R) | D86Y | AccI* (gt/atac)<br>Δ BsaWI (a/ccgga) | aga ccg Gat act<br>arg pro ASP thr | aga ccg Tat act<br>arg pro TYR thr |

[1]The silent mutations in these genes are markers to confirm that recombination includes the complete flanks. Note that GenBank sequence U94848 lists a mutation (cca aGA gta, R554K) in A10L at this site. However, this deviation is corrected in a subsequent analysis so that U94848 and AY603355 are considered identical (Antoine et al., 2006).

component) into virions (Resch and Moss, 2005). Loss of L3L expression may reduce the infectious activity of the incoming particles, possibly because transcription or export of nascent mRNA of the newly infecting cores is disturbed (Resch and Moss, 2005). Conditional expression of L3L had no impact on the processing of virions, their association with the host cell membrane or the formation of actin tails that have been implicated in spread of the virus (Doceul et al., 2010; Resch and Moss, 2005).

Insertion of the L3 V110A mutation into wildtype virus did not result in obvious changes to the plaque phenotype 48 h PI (FIG. 1). It was next tested for enhanced initial infectivity by comparing the expansion of foci in adherent cells infected with different recombinant viruses. A NyONE cell imager (SynenTec GmbH, Germany) was used to quantify how much of the cell area is covered with GFP-expressing (infected) cells at two time points (24 and 40 h PI) and increasing MOI (0.05, 0.1 and 1). Because correct MOI is an important parameter in this study, two separate preparations of MVA-WT.L3LCR.GFP (the L3L mutation of MVA-CR19 in the backbone of wildtype virus) were used. As shown FIG. 6 *c* and *d*, there appeared to be no differences in the spread of viruses in the first 24 h and at a MOI below 1. Only MVA-CR19. GFP appeared to have a slight initial advantage at MOI of 1. At 40 h PI there were again no significant differences in the GFP-positive area between wildtype and the L3L mutant, independent of MOI. However, MVA-CR19. GFP has occupied a significantly larger area of the infected cell monolayer.

The L3L is an essential gene of vaccinia virus replication (Upton et al., 2003). However, the L3 mutation discovered here did not reduce infectious titers and viruses with that mutation in the wildtype backbone replicated with very high efficiencies and were not inferior to the wildtype reference in single-cell suspensions (FIG. 6 *b*). MVA-CR19. GFP replicated to the expected high titers also without induction of aggregates in the same experiment, and a wildtype virus with all of the observed mutations of the CR genotype replicated to very high titers only if cell aggregates were induced.

3. Discussion

A hitherto undescribed but highly stable vector strain has been isolated and characterized. A set of four mutations characterize the genomic DNA of the virus and have a major influence on the phenotype. Very extensive changes have occurred at the left side of the viral genome of MVA-CR19. When analysing GFP-recombinant viruses with the series of primers (Kremer et al., 2012) that are used to characterize the six deletion sites of MVA, no signal for deletion site I in MVA-CR19 derivatives could be detected. Further investigation suggested that a recombination has occurred in which the left side of the genomic DNA was replaced by the right side including the ITR. This event has led to an extensive symmetry and duplication of a number of genes (listed in FIG. 3C) and loss of MAV001L to MVA013L. The telomeres have not been sequenced. But by using Genbank sequence U94848 and the result of the diagnostic long-PCR as basis, then the left genomic region that characterizes MVA-CR19 may have expanded from 15327 bp to 27108 bp. The rearrangement may therefore have increased the area of complementarity between the two telomers but has not affected the GC content (16.3 vs. 16.6 and 17.7 vs 17.5%, for CR19 vs. wildtype left telomers).

Three functional genes, MVA005R (C11R), MVA006L (C10L) and MVA008L (D7L) (Antoine et al., 1998; Meisinger-Henschel et al., 2007), appear to have been irreversibly lost in this rearrangement and may impact biological properties of MVA-CR19. Deletion of the C11R gene may interfere with the capacity of MVA to engage extracellular signal-regulated kinase 2 (ERK2) that causes in NF-κB activation (Martin et al., 2012). The final effect on replication of viruses is difficult to predict since NF-κB activation furcates into several signaling pathways with different outcomes (Santoro et al., 2003). However, vaccinia viruses interfere with NF-κB activation (Mohamed and McFadden, 2009; Oie and Pickup, 2001; Shisler and Jin, 2004) whereas MVA is reported to have lost the defensive factors against NF-κB pathways (Antoine et al., 1998). A less vigorous activation of NF-κB may therefore improve reactogenicity because a potentially antiviral signal is not activated anymore by a virus that has lost part of its defenses against this particular signaling cascade.

The C10 protein appears to antagonize IL-1β by masking the cellular receptor for this proinflammatory cytokine (Kluczyk et al., 2002). Loss of C10 in MVA-CR19 may have only a limited effect in vivo because another viral factor also interferes with IL-1β, a soluble receptor expressed by the MVA184R gene (Blanchard et al., 1998). Inactivation of MVA184R was shown to augment the reactogenicity of MVA vectors and to prolonge T-cell memory responsens in mice (Staib et al., 2005). This observation may suggest that a knock-out of MVA184R in MVA-CR19 may act synergistically with loss of C10 and may have the potential to further improve the self-adjuvanting properties of MVA.

Deletion of D7L has also been used previously to augment reactogenicity of MVA (Falivene et al., 2012). The D7 protein is secreted by the infected host cell. It can bind to glycosaminoglycans in the extracellular matrix at the site of infection and may both delay inflammatory responses and interfere with the function of interleukin-18, a central signal molecule for antiviral responses by the innate and adaptive immune systems (Damon et al., 1998; Esteban et al., 2004; Smith et al., 2000).

Heterogeneity and rearrangements in the ITRs of vaccinia viruses has been described previously (for example, (Moss et al., 1981; Paez et al., 1985; Pickup et al., 1982; Qin et al., 2011)). The results here differ from some of the previous studies in that not only a deletion but an extensive rearrangement has been observed that appears to improve (rather than interfere with) the replication of the affected virus. The study confirms high mutational and genetic stability of diverse plaque-purified MVA vectors across several genetic markers and for different inserts in deletion site III. The recombination between the left and right parts of the genome of MVA-CR19 caused a diagnostic loss of deletion site I and is associated with deletion of C11R, C10L, and D7L. It is tempting to speculate that the observed combined disruption may improve the reactogenicity of vaccines based on the novel genotype.

The following abbreviations are used in this patent application:

MVA, MVA-WT: modified vaccinia virus Ankara, MVA-wildtype.

MVA-CR19: a novel strain at passage 19, related to MVA and isolated out of cultures of CR.pIX cells.

MVA-WT A3A9A34L3: A mutant of MVA-WT that contains point mutations H639Y, K75E and D86Y in the genes A3L, A9L and A34R.

MVA-WT L3: A mutant of MVA-WT that contains point mutation V110A in the gene L3L.

PI: post infection

MOI: multiplicity of infection

CR.pIX: *Cairina moschata* retina cell line that stably expresses the pIX protein, a minor structural protein of human adenovirus type 2.

GFP: green fluorescent protein

The following sequences are part of the sequence listing:
SEQ ID NO: 1 A3L gene product
SEQ ID NO: 2 A34R gene product
SEQ ID NO: 3 A9L gene product
SEQ ID NO: 4 H639Y A3L gene product mutant
SEQ ID NO: 5 D86Y A34R gene product mutant
SEQ ID NO: 6 K75E A9L gene product mutant
SEQ ID NO: 7 A3L gene
SEQ ID NO: 8 A34R gene
SEQ ID NO: 9 A9L gene
SEQ ID NO: 10 A3L gene mutant
SEQ ID NO: 11 A34R gene mutant
SEQ ID NO: 12 A9L gene mutant
SEQ ID NO: 13 L3L gene product
SEQ ID NO: 14 V110A L3L gene product mutant
SEQ ID NO: 15 L3L gene
SEQ ID NO: 16 L3L gene mutant
SEQ ID NO: 17: LeftF primer
SEQ ID NO: 18: LeftR primer
SEQ ID NO: 19: RightF primer
SEQ ID NO: 20: RightR primer
SEQ ID NO: 21: PromEL sequence
SEQ ID NO: 22: A34F primer
SEQ ID NO: 23: A34R primer
SEQ ID NO: 24: L3F primer
SEQ ID NO: 25: L3R primer
SEQ ID NO: 26: A3F primer
SEQ ID NO: 27: A3R primer
SEQ ID NO: 28: A9F primer
SEQ ID NO: 29: A10R primer
SEQ ID NO: 30: D2 RII primer
SEQ ID NO: 31: D2 primer
SEQ ID NO: 32: AAP primer
SEQ ID NO: 33: GSPD2-R primer
SEQ ID NO: 34: RS469F primer
SEQ ID NO: 35: RS469R primer
SEQ ID NO: 36: ITR-M primer
SEQ ID NO: 37: MVA related Virus (MVA-CR19. GFP)

REFERENCES

Antoine, G., Scheiflinger, F., Dorner, F., and Falkner, F. G. (1998). The complete genomic sequence of the modified vaccinia Ankara strain: comparison with other orthopoxviruses. Virology 244, 365-396.

Antoine, G., Scheiflinger, F., Dorner, F., and Falkner, F. G. (2006). Corrigendum to "The complete genomic sequence of the modified vaccinia Ankara (MVA) strain: Comparison with other orthopoxviruses" [Virology 244 (1998) 365-396]. Virology 350, 501-502.

Bertholet, C., Drillien, R., and Wittek, R. (1985). One hundred base pairs of 5' flanking sequence of a vaccinia virus late gene are sufficient to temporally regulate late transcription. Proc. Natl. Acad. Sci. U.S.A. 82, 2096-2100.

Blanchard, T. J., Alcami, A., Andrea, P., and Smith, G. L. (1998). Modified vaccinia virus Ankara undergoes limited replication in human cells and lacks several immunomodulatory proteins: implications for use as a human vaccine. J. Gen. Virol. 79 (Pt 5), 1159-1167.

Blasco, R., and Moss, B. (1991). Extracellular vaccinia virus formation and cell-to-cell virus transmission are prevented by deletion of the gene encoding the 37,000-Dalton outer envelope protein. J. Virol. 65, 5910-5920.

Blasco, R., Sisler, J. R., and Moss, B. (1993). Dissociation of progeny vaccinia virus from the cell membrane is regulated by a viral envelope glycoprotein: effect of a point mutation in the lectin homology domain of the A34R gene. J. Virol. 67, 3319-3325.

Byrd, C. M., Bolken, T. C., and Hruby, D. E. (2002). The vaccinia virus I7L gene product is the core protein proteinase. J. Virol. 76, 8973-8976.

Carroll, M. W., and Moss, B. (1997). Host range and cytopathogenicity of the highly attenuated MVA strain of vaccinia virus: propagation and generation of recombinant viruses in a nonhuman mammalian cell line. Virology 238, 198-211.

Cebere, I., Dorrell, L., McShane, H., Simmons, A., McCormack, S., Schmidt, C., Smith, C., Brooks, M., Roberts, J. E., Darwin, S. C., et al. (2006). Phase I clinical trial safety of DNA- and modified virus Ankara-vectored human immunodeficiency virus type 1 (HIV-1) vaccines administered alone and in a prime-boost regime to healthy HIV-1-uninfected volunteers. Vaccine 24, 417-425.

Chakrabarti, S., Sisler, J. R., and Moss, B. (1997). Compact, synthetic, vaccinia virus early/late promoter for protein expression. BioTechniques 23, 1094-1097.

Cyrklaff, M., Linaroudis, A., Boicu, M., Chlanda, P., Baumeister, W., Griffiths, G., and Krijnse-Locker, J. (2007). Whole cell cryo-electron tomography reveals distinct disassembly intermediates of vaccinia virus. PloS One 2, e420.

Damon, I., Murphy, P. M., and Moss, B. (1998). Broad spectrum chemokine antagonistic activity of a human poxvirus chemokine homolog. Proc. Natl. Acad. Sci. U.S.A. 95, 6403-6407.

Doceul, V., Hollinshead, M., van der Linden, L., and Smith, G. L. (2010). Repulsion of superinfecting virions: a mechanism for rapid virus spread. Science 327, 873-876.

Drexler, I., Heller, K., Wahren, B., Erfle, V., and Sutter, G. (1998). Highly attenuated modified vaccinia virus Ankara replicates in baby hamster kidney cells, a potential host for virus propagation, but not in various human transformed and primary cells. J. Gen. Virol. 79 (Pt 2), 347-352.

Drillien, R., Spehner, D., and Hanau, D. (2004). Modified vaccinia virus Ankara induces moderate activation of human dendritic cells. J. Gen. Virol. 85, 2167-2175.

Elde, N.C., Child, S. J., Eickbush, M. T., Kitzman, J. O., Rogers, K. S., Shendure, J., Geballe, A. P., and Malik, H. S. (2012). Poxviruses deploy genomic accordions to adapt rapidly against host antiviral defenses. Cell 150, 831-841.

Esteban, D. J., and Buller, R. M. L. (2005). Ectromelia virus: the causative agent of mousepox. J. Gen. Virol. 86, 2645-2659.

Esteban, D. J., Nuara, A. A., and Buller, R. M. L. (2004). Interleukin-18 and glycosaminoglycan binding by a protein encoded by Variola virus. J. Gen. Virol. 85, 1291-1299.

Falivene, J., Del Mêdico Zajac, M. P., Pascutti, M. F., Rodriguez, A. M., Maeto, C., Perdiguero, B., Gomez, C. E., Esteban, M., Calamante, G., and Gherardi, M. M. (2012). Improving the MVA vaccine potential by deleting the viral gene coding for the IL-18 binding protein. PloS One 7, e32220.

Gallego-Gómez, J. C., Risco, C., Rodriguez, D., Cabezas, P., Guerra, S., Carrascosa, J. L., and Esteban, M. (2003). Differences in virus-induced cell morphology and in virus maturation between MVA and other strains (WR, Ankara, and NYCBH) of vaccinia virus in infected human cells. J. Virol. 77, 10606-10622.

Heljasvaara, R., Rodriguez, D., Risco, C., Carrascosa, J. L., Esteban, M., and Rodriguez, J. R. (2001). The major core protein P4a (A10L gene) of vaccinia virus is essential for correct assembly of viral DNA into the nucleoprotein complex to form immature viral particles. J. Virol. 75, 5778-5795.

Husain, M., Weisberg, A. S., and Moss, B. (2006). Existence of an operative pathway from the endoplasmic reticulum to the immature poxvirus membrane. Proc. Natl. Acad. Sci. U.S.A. 103, 19506-19511.

Husain, M., Weisberg, A. S., and Moss, B. (2007). Resistance of a vaccinia virus A34R deletion mutant to spontaneous rupture of the outer membrane of progeny virions on the surface of infected cells. Virology 366, 424-432.

Jordan, I., Horn, D., Oehmke, S., Leendertz, F. H., and Sandig, V. (2009a). Cell lines from the Egyptian fruit bat are permissive for modified vaccinia Ankara. Virus Res. 145, 54-62.

Jordan, I., Vos, A., Beilfuss, S., Neubert, A., Breul, S., and Sandig, V. (2009b). An avian cell line designed for production of highly attenuated viruses. Vaccine 27, 748-756.

Jordan, I., Northoff, S., Thiele, M., Hartmann, S., Horn, D., Howing, K., Bernhardt, H., Oehmke, S., von Horsten, H., Rebeski, D., et al. (2011). A chemically defined production process for highly attenuated poxviruses. Biol. J. Int. Assoc. Biol. Stand. 39, 50-58.

Jordan, I., Horn, D., John, K., and Sandig, V. (2013a). A Genotype of Modified Vaccinia Ankara (MVA) that Facilitates Replication in Suspension Cultures in Chemically Defined Medium. Viruses 5, 321-339.

Jordan, I., Lohr, V., Genzel, Y., Reichl, U., and Sandig, V. (2013b). Elements in the Development of a Production Process for Modified Vaccinia Virus Ankara. Microorganisms 1, 100-121.

Kato, S. E. M., Strahl, A. L., Moussatche, N., and Condit, R. C. (2004). Temperature-sensitive mutants in the vaccinia virus 4b virion structural protein assemble malformed, transcriptionally inactive intracellular mature virions. Virology 330, 127-146.

Katz, E., Wolffe, E., and Moss, B. (2002). Identification of second-site mutations that enhance release and spread of vaccinia virus. J. Virol. 76, 11637-11644.

Kluczyk, A., Siemion, I. Z., Szewczuk, Z., and Wieczorek, Z. (2002). The immunosuppressive activity of peptide fragments of vaccinia virus C10L protein and a hypothesis on the role of this protein in the viral invasion. Peptides 23, 823-834.

Kremer, M., Volz, A., Kreijtz, J. H. C. M., Fux, R., Lehmann, M. H., and Sutter, G. (2012). Easy and efficient protocols for working with recombinant vaccinia virus MVA. Methods Mol. Biol. Clifton N.J. 890, 59-92.

Liu, L., Chavan, R., and Feinberg, M. B. (2008). Dendritic cells are preferentially targeted among hematolymphocytes by Modified Vaccinia Virus Ankara and play a key role in the induction of virus-specific T cell responses in vivo. BMC Immunol. 9, 15.

Martin, S., Harris, D. T., and Shisler, J. (2012). The C11R gene, which encodes the vaccinia virus growth factor, is partially responsible for MVA-induced NF-κB and ERK2 activation. J. Virol. 86, 9629-9639.

Mayr, A., and Munz, E. (1964). [Changes in the vaccinia virus through continuing passages in chick embryo fibroblast cultures]. Zentralblatt Für Bakteriol. Parasitenkd. Infekt. Hyg. 1 Abt Med.-Hyg. Bakteriol. Virusforsch. Parasitol. Orig. 195, 24-35.

McShane, H., Behboudi, S., Goonetilleke, N., Brookes, R., and Hill, A. V. S. (2002). Protective immunity against *Mycobacterium tuberculosis* induced by dendritic cells pulsed with both CD8(+)- and CD4(+)-T-cell epitopes from antigen 85A. Infect. Immun. 70, 1623-1626.

Meiser, A., Boulanger, D., Sutter, G., and Krijnse Locker, J. (2003). Comparison of virus production in chicken embryo fibroblasts infected with the WR, IHD-J and MVA strains of vaccinia virus: IHD-J is most efficient in trans-Golgi network wrapping and extracellular enveloped virus release. J. Gen. Virol. 84, 1383-1392.

Meisinger-Henschel, C., Schmidt, M., Lukassen, S., Linke, B., Krause, L., Konietzny, S., Goesmann, A., Howley, P., Chaplin, P., Suter, M., et al. (2007). Genomic sequence of chorioallantois vaccinia virus Ankara, the ancestor of modified vaccinia virus Ankara. J. Gen. Virol. 88, 3249-3259.

Meyer, H., Sutter, G., and Mayr, A. (1991). Mapping of deletions in the genome of the highly attenuated vaccinia virus MVA and their influence on virulence. J. Gen. Virol. 72 (Pt 5), 1031-1038.

Milligan, I. D., Gibani, M. M., Sewell, R., Clutterbuck, E. A., Campbell, D., Plested, E., Nuthall, E., Voysey, M., Silva-Reyes, L., McElrath, M. J., et al. (2016). Safety and Immunogenicity of Novel Adenovirus Type 26- and Modified Vaccinia Ankara-Vectored Ebola Vaccines: A Randomized Clinical Trial. JAMA 315, 1610-1623.

Mohamed, M. R., and McFadden, G. (2009). NFkB inhibitors: strategies from poxviruses. Cell Cycle Georget. Tex 8, 3125-3132.

Moss, B. (2012). Poxvirus cell entry: how many proteins does it take? Viruses 4, 688-707.

Moss, B., Winters, E., and Cooper, N. (1981). Instability and reiteration of DNA sequences within the vaccinia virus genome. Proc. Natl. Acad. Sci. U.S.A. 78, 1614-1618.

Oie, K. L., and Pickup, D. J. (2001). Cowpox virus and other members of the *orthopoxvirus* genus interfere with the regulation of NF-kappaB activation. Virology 288, 175-187.

Paez, E., Dallo, S., and Esteban, M. (1985). Generation of a dominant 8-MDa deletion at the left terminus of vaccinia virus DNA. Proc. Natl. Acad. Sci. U.S.A. 82, 3365-3369.

Pickup, D. J., Bastia, D., Stone, H. O., and Joklik, W. K. (1982). Sequence of terminal regions of cowpox virus DNA: arrangement of repeated and unique sequence elements. Proc. Natl. Acad. Sci. U.S.A. 79, 7112-7116.

Qin, L., Upton, C., Hazes, B., and Evans, D. H. (2011). Genomic analysis of the vaccinia virus strain variants found in Dryvax vaccine. J. Virol. 85, 13049-13060.

Resch, W., and Moss, B. (2005). The conserved poxvirus L3 virion protein is required for transcription of vaccinia virus early genes. J. Virol. 79, 14719-14729.

Roberts, K. L., and Smith, G. L. (2008). Vaccinia virus morphogenesis and dissemination. Trends Microbiol. 16, 472-479.

Santoro, M. G., Rossi, A., and Amici, C. (2003). NF-kappaB and virus infection: who controls whom. EMBO J. 22, 2552-2560.

Senkevich, T. G., Koonin, E. V., and Buller, R. M. (1994). A poxvirus protein with a RING zinc finger motif is of crucial importance for virulence. Virology 198, 118-128.

Senkevich, T. G., Wolffe, E. J., and Buller, R. M. (1995). Ectromelia virus RING finger protein is localized in virus factories and is required for virus replication in macrophages. J. Virol. 69, 4103-4111.

Shisler, J. L., and Jin, X.-L. (2004). The vaccinia virus K1L gene product inhibits host NF-kappaB activation by preventing IkappaBalpha degradation. J. Virol. 78, 3553-3560.

Smith, S. A., Mullin, N. P., Parkinson, J., Shchelkunov, S. N., Totmenin, A. V., Loparev, V. N., Srisatjaluk, R., Reynolds, D. N., Keeling, K. L., Justus, D. E., et al. (2000). Conserved surface-exposed K/R-X-K/R motifs and net positive charge on poxvirus complement control proteins serve as putative heparin binding sites and contribute to inhibition of molecular interactions with human endothelial cells: a novel mechanism for evasion of host defense. J. Virol. 74, 5659-5666.

Staib, C., Kisling, S., Erfle, V., and Sutter, G. (2005). Inactivation of the viral interleukin 1beta receptor improves CD8+ T-cell memory responses elicited upon immunization with modified vaccinia virus Ankara. J. Gen. Virol. 86, 1997-2006.

Suter, M., Meisinger-Henschel, C., Tzatzaris, M., Hülsemann, V., Lukassen, S., Wulff, N. H., Hausmann, J., Howley, P., and Chaplin, P. (2009). Modified vaccinia Ankara strains with identical coding sequences actually represent complex mixtures of viruses that determine the biological properties of each strain. Vaccine 27, 7442-7450.

Sutter, G., and Moss, B. (1992). Nonreplicating vaccinia vector efficiently expresses recombinant genes. Proc. Natl. Acad. Sci. U.S.A. 89, 10847-10851.

Sutter, G., Wyatt, L. S., Foley, P. L., Bennink, J. R., and Moss, B. (1994). A recombinant vector derived from the host range-restricted and highly attenuated MVA strain of vaccinia virus stimulates protective immunity in mice to influenza virus. Vaccine 12, 1032-1040.

Upton, C., Slack, S., Hunter, A. L., Ehlers, A., and Roper, R. L. (2003). Poxvirus orthologous clusters: toward defining the minimum essential poxvirus genome. J. Virol. 77, 7590-7600.

Ward, B. M. (2005). Visualization and characterization of the intracellular movement of vaccinia virus intracellular mature virions. J. Virol. 79, 4755-4763.

Webster, D. P., Dunachie, S., Vuola, J. M., Berthoud, T., Keating, S., Laidlaw, S. M., McConkey, S. J., Poulton, I., Andrews, L., Andersen, R. F., et al. (2005). Enhanced T cell-mediated protection against malaria in human challenges by using the recombinant poxviruses FP9 and modified vaccinia virus Ankara. Proc. Natl. Acad. Sci. U.S.A. 102, 4836-4841.

Wyatt, L. S., Earl, P. L., Eller, L. A., and Moss, B. (2004). Highly attenuated smallpox vaccine protects mice with and without immune deficiencies against pathogenic vaccinia virus challenge. Proc. Natl. Acad. Sci. U.S.A. 101, 4590-4595.

Yeh, W. W., Moss, B., and Wolffe, E. J. (2000). The vaccinia virus A9L gene encodes a membrane protein required for an early step in virion morphogenesis. J. Virol. 74, 9701-9711.

Yuen, L., and Moss, B. (1987). Oligonucleotide sequence signaling transcriptional termination of vaccinia virus early genes. Proc. Natl. Acad. Sci. U.S.A. 84, 6417-6421.

The invention claimed is:

1. A Modified Vaccinia Ankara (MVA) related virus comprising one or more of the following features:

(i) a nucleic acid sequence corresponding to a region that includes the right Inverted Terminal Repeat (ITR) and extends to but excludes deletion site III instead of a nucleic acid sequence that includes the left Inverted Terminal Repeat (ITR) and extends to but excludes deletion site V, wherein the region that includes the right ITR and extends to but excludes deletion site III has a nucleic acid sequence according to SEQ ID NO: 37 or Genbank Accession number KY633487 or is a variant thereof which is at least 95% identical to said nucleic acid sequence, and/or wherein the region that includes the left ITR and extends to but excludes deletion site V has a nucleic acid sequence according to SEQ ID NO: 37 or Genbank Accession number KY633487 or is a variant thereof which is at least 95% identical to said nucleic acid sequence, and (ii) two copies of a nucleic acid sequence comprising deletion site IV and the right ITR, wherein the nucleic acid sequence comprising deletion site IV and the right ITR has a nucleic acid sequence according to SEQ ID NO: 37 or Genbank Accession number KY633487 or is a variant thereof which is at least 95% identical to said nucleic acid sequence.

2. The MVA related virus of claim 1, wherein the virus further comprises a heterologous nucleic acid sequence.

3. The MVA related virus of claim 2, wherein the heterologous nucleic acid sequence is selected from a sequence coding for (i) an antigen, particularly an epitope of an antigen, (ii) a diagnostic compound, and (iii) a therapeutic compound.

4. The MVA related virus of claim 1, wherein the virus is capable of productive replication in avian cells.

5. The MVA related virus of claim 1, wherein the virus is not capable of productive replication in primate cells, more preferably human cells.

6. A genome of the MVA related virus of claim 1.

7. A cell comprising the MVA related virus of claim 1.

8. The cell of claim 7, wherein the cell is a non-adherent/suspension cell.

9. The cell of claim 7, wherein the cell is an avian cell.

10. A method for producing a MVA related virus of claim 1 comprising the steps of:

(a) infecting a cell with a MVA virus, (b) culturing the cell, (c) isolating the MVA virus, and (d) repeating steps (a) to (c) with the MVA virus isolated in step (c) until a MVA related virus comprising one or more of the following features:

(i) a nucleic acid sequence corresponding to a region that includes the right Inverted Terminal Repeat (ITR) and extends to but excludes deletion site III instead of a nucleic acid sequence that includes the left Inverted Terminal Repeat (ITR) and extends to but excludes deletion site V, wherein the region that includes the right ITR and extends to but excludes deletion site III has a nucleic acid sequence according to SEQ ID NO: 37 or Genbank Accession number KY633487 or is a variant thereof which is at least 95% identical to said nucleic acid sequence, and/or wherein the region that includes the left ITR and extends to but excludes deletion site V has a nucleic acid sequence according to SEQ ID NO: 37 or Genbank Accession number KY633487 or is a variant thereof which is at least 95% identical to said nucleic acid sequence, and (ii) two copies of a nucleic acid sequence comprising deletion site IV and the right ITR, wherein the nucleic acid sequence comprising deletion site IV and the right ITR has a nucleic acid sequence according to SEQ ID NO: 37 or Genbank Accession number KY633487 or is a variant thereof which is at least 95% identical to said nucleic acid sequence is detected.

11. A vaccine comprising the MVA related virus of claim 1.

12. A method for vaccinating or treating a subject comprising the steps of:

(i) providing the MVA related virus of claim 1, and (ii) administering a patient in need thereof a sufficient amount of the MVA related virus provided in step (i), thereby vaccinating or treating the subject.

13. The MVA related virus of claim 1, wherein the region that includes the right ITR and extends to but excludes deletion site III has a nucleic acid sequence according to SEQ ID NO: 37 or Genbank Accession number KY633487 ranging from nucleotide position 162221 to 190549 or a nucleotide position corresponding thereto, or is a variant thereof which is at least 95% identical to said nucleic acid sequence, and/or the region that includes the left ITR and extends to but excludes deletion site V has a nucleic acid sequence according to SEQ ID NO: 37 or Genbank Accession number KY633487 ranging from nucleotide position 1 to 31261 or a nucleotide position corresponding thereto, or is a variant thereof which is at least 95% identical to said nucleic acid sequence.

14. The MVA related virus of claim 1, wherein the nucleic acid sequence comprising deletion site IV and the right ITR has a nucleic acid sequence according to SEQ ID NO: 37 or Genbank Accession number KY633487 ranging from nucleotide position 179272 to 190549 or a nucleotide position corresponding thereto, or is a variant thereof which is at least 95% identical to said nucleic acid sequence.

15. The MVA related virus of claim 1, wherein the virus further comprises one or more of the following features:

(iii) no nucleic acid sequence comprising deletion site I and the left ITR, (iv) no deletion site I, (v) two deletion sites IV, (vi) no open reading frame for at least one gene product selected from the group consisting of C11R, C10L, and D7L, (vii) two open reading frames for at least one gene product selected from the group consisting of A57R, B1R, B2R, B3R, B4R, B5R, B6R, B7R, B8R, B9R, B10R, B11R, B12R, B15R, B16R, B17L, B18R, B19R, and B22R, and (viii) a nucleic acid sequence encoding a L3L gene product, wherein said nucleic acid sequence comprises at least one mutation resulting in an amino acid sequence modification of said gene product.

* * * * *

SEQUENCE LISTING

```
<160> NUMBER OF SEQ ID NOS: 37

<210> SEQ ID NO 1
<211> LENGTH: 644
<212> TYPE: PRT
<213> ORGANISM: Vaccinia virus

<400> SEQUENCE: 1

Met Glu Ala Val Val Asn Ser Asp Val Phe Leu Thr Ser Asn Ala Gly
1               5                   10                  15

Leu Lys Ser Ser Tyr Thr Asn Gln Thr Leu Ser Leu Val Asp Glu Asp
            20                  25                  30

His Ile His Thr Ser Asp Lys Ser Leu Ser Cys Ser Val Cys Asn Ser
        35                  40                  45

Leu Ser Lys Ile Val Asp Asp Asp Phe Ile Ser Ala Gly Ala Arg Asn
    50                  55                  60

Gln Arg Thr Lys Pro Lys Arg Ala Gly Asn Asn Gln Ser Gln Gln Pro
65                  70                  75                  80

Ile Lys Lys Asp Cys Met Val Ser Ile Asp Glu Val Ala Ser Thr His
                85                  90                  95

Asp Trp Ser Thr Arg Leu Arg Asn Asp Gly Asn Ala Ile Ala Lys Tyr
            100                 105                 110

Leu Thr Thr Asn Lys Tyr Asp Thr Ser Asn Phe Thr Ile Gln Asp Met
        115                 120                 125

Leu Asn Ile Met Asn Lys Leu Asn Ile Val Arg Thr Asn Arg Asn Glu
    130                 135                 140

Leu Phe Gln Leu Leu Thr His Val Lys Ser Thr Leu Asn Asn Ala Ser
145                 150                 155                 160

Val Ser Val Lys Cys Thr His Pro Leu Val Leu Ile His Ser Arg Ala
                165                 170                 175
```

-continued

```
Ser Pro Arg Ile Gly Asp Gln Leu Lys Glu Leu Asp Lys Ile Tyr Ser
            180                 185                 190

Pro Ser Asn His His Ile Leu Leu Ser Thr Thr Arg Phe Gln Ser Met
        195                 200                 205

His Phe Thr Asp Met Ser Ser Ser Gln Asp Leu Ser Phe Ile Tyr Arg
    210                 215                 220

Lys Pro Glu Thr Asn Tyr Tyr Ile His Pro Ile Leu Met Ala Leu Phe
225                 230                 235                 240

Gly Ile Lys Leu Pro Ala Leu Glu Asn Ala Tyr Val His Gly Asp Thr
                245                 250                 255

Tyr Ser Leu Ile Gln Gln Leu Tyr Glu Phe Arg Lys Val Lys Ser Tyr
            260                 265                 270

Asn Tyr Met Leu Leu Val Asn Arg Leu Thr Glu Asp Asn Pro Ile Val
        275                 280                 285

Ile Thr Gly Val Ser Asp Leu Ile Ser Thr Glu Ile Gln Arg Ala Asn
    290                 295                 300

Met His Thr Met Ile Arg Lys Ala Ile Met Asn Ile Arg Met Gly Ile
305                 310                 315                 320

Phe Tyr Cys Asn Asp Asp Asp Ala Val Asp Pro His Leu Met Lys Ile
                325                 330                 335

Ile His Thr Gly Cys Ser Gln Val Met Thr Asp Glu Glu Gln Ile Leu
            340                 345                 350

Ala Ser Ile Leu Ser Ile Val Gly Phe Arg Pro Thr Leu Val Ser Val
        355                 360                 365

Ala Arg Pro Ile Asn Gly Ile Ser Tyr Asp Met Lys Leu Gln Ala Ala
    370                 375                 380

Pro Tyr Ile Val Val Asn Pro Met Lys Met Ile Thr Thr Ser Asp Ser
385                 390                 395                 400

Pro Ile Ser Ile Asn Ser Lys Asp Ile Tyr Ser Met Ala Phe Asp Gly
                405                 410                 415

Asn Ser Gly Arg Val Val Phe Ala Pro Pro Asn Ile Gly Tyr Gly Arg
            420                 425                 430

Cys Ser Gly Val Thr His Ile Asp Pro Leu Gly Thr Asn Val Met Gly
        435                 440                 445

Ser Ala Val His Ser Pro Val Ile Val Asn Gly Ala Met Met Phe Tyr
    450                 455                 460

Val Glu Arg Arg Gln Asn Lys Asn Met Phe Gly Gly Glu Cys Tyr Thr
465                 470                 475                 480

Gly Phe Arg Ser Leu Ile Asp Asp Thr Pro Ile Asp Val Ser Pro Glu
                485                 490                 495

Ile Met Leu Asn Gly Ile Met Tyr Arg Leu Lys Ser Ala Val Cys Tyr
            500                 505                 510

Lys Leu Gly Asp Gln Phe Phe Asp Cys Gly Ser Ser Asp Ile Phe Leu
        515                 520                 525

Lys Gly His Tyr Thr Ile Leu Phe Thr Glu Asn Gly Pro Trp Met Tyr
    530                 535                 540

Asp Pro Leu Ser Val Phe Asn Pro Gly Ala Arg Asn Ala Arg Leu Met
545                 550                 555                 560

Arg Ala Leu Lys Asn Gln Tyr Lys Lys Leu Ser Met Asp Ser Asp Asp
                565                 570                 575

Gly Phe Tyr Glu Trp Leu Asn Gly Asp Gly Ser Val Phe Ala Ala Ser
            580                 585                 590

Lys Gln Gln Met Leu Met Asn His Val Ala Asn Phe Asp Asp Asp Leu
```

-continued

```
        595                 600                 605

Leu Thr Met Glu Glu Ala Met Ser Met Ile Ser Arg His Cys Cys Ile
    610                 615                 620

Leu Ile Tyr Ala Gln Asp Tyr Asp Gln Tyr Ile Ser Ala Arg His Ile
625                 630                 635                 640

Thr Glu Leu Phe


<210> SEQ ID NO 2
<211> LENGTH: 168
<212> TYPE: PRT
<213> ORGANISM: Vaccinia virus

<400> SEQUENCE: 2

Met Lys Ser Leu Asn Arg Gln Thr Val Ser Arg Phe Lys Lys Leu Ser
1               5                   10                  15

Val Pro Val Ala Ile Met Met Ile Leu Ser Thr Ile Ile Ser Gly Ile
            20                  25                  30

Gly Thr Phe Leu His Tyr Lys Glu Glu Leu Met Pro Ser Ala Cys Ala
        35                  40                  45

Asn Gly Trp Ile Gln Tyr Asp Lys His Cys Tyr Leu Asp Thr Asn Ile
    50                  55                  60

Lys Met Ser Thr Asp Asn Ala Val Tyr Gln Cys Arg Lys Leu Arg Ala
65                  70                  75                  80

Arg Leu Pro Arg Pro Asp Thr Arg His Leu Arg Val Leu Phe Ser Ile
                85                  90                  95

Phe Tyr Lys Asp Tyr Trp Val Ser Leu Lys Lys Thr Asn Asp Lys Trp
            100                 105                 110

Leu Asp Ile Asn Asn Asp Lys Asp Ile Asp Ile Ser Lys Leu Thr Asn
        115                 120                 125

Phe Lys Gln Leu Asn Ser Thr Thr Asp Ala Glu Ala Cys Tyr Ile Tyr
    130                 135                 140

Lys Ser Gly Lys Leu Val Lys Thr Val Cys Lys Ser Thr Gln Ser Val
145                 150                 155                 160

Leu Cys Val Lys Lys Phe Tyr Lys
                165


<210> SEQ ID NO 3
<211> LENGTH: 94
<212> TYPE: PRT
<213> ORGANISM: Vaccinia virus

<400> SEQUENCE: 3

Met Ser Cys Tyr Thr Ala Ile Leu Lys Ser Val Gly Gly Leu Ala Leu
1               5                   10                  15

Phe Gln Val Ala Asn Gly Ala Ile Asp Leu Cys Arg His Phe Phe Met
            20                  25                  30

Tyr Phe Cys Glu Gln Lys Leu Arg Pro Asn Ser Phe Trp Phe Val Val
        35                  40                  45

Val Arg Ala Ile Ala Ser Met Ile Met Tyr Leu Val Leu Gly Ile Ala
    50                  55                  60

Leu Leu Tyr Ile Ser Glu Gln Asp Asn Lys Lys Asn Thr Asn Asn Asp
65                  70                  75                  80

Lys Arg Asn Glu Ser Ser Ile Asn Ser Asn Ser Ser Pro Lys
                85                  90


<210> SEQ ID NO 4
```

-continued

```
<211> LENGTH: 644
<212> TYPE: PRT
<213> ORGANISM: Vaccinia virus

<400> SEQUENCE: 4

Met Glu Ala Val Val Asn Ser Asp Val Phe Leu Thr Ser Asn Ala Gly
1               5                   10                  15

Leu Lys Ser Ser Tyr Thr Asn Gln Thr Leu Ser Leu Val Asp Glu Asp
            20                  25                  30

His Ile His Thr Ser Asp Lys Ser Leu Ser Cys Ser Val Cys Asn Ser
        35                  40                  45

Leu Ser Lys Ile Val Asp Asp Asp Phe Ile Ser Ala Gly Ala Arg Asn
    50                  55                  60

Gln Arg Thr Lys Pro Lys Arg Ala Gly Asn Asn Gln Ser Gln Gln Pro
65                  70                  75                  80

Ile Lys Lys Asp Cys Met Val Ser Ile Asp Glu Val Ala Ser Thr His
                85                  90                  95

Asp Trp Ser Thr Arg Leu Arg Asn Asp Gly Asn Ala Ile Ala Lys Tyr
            100                 105                 110

Leu Thr Thr Asn Lys Tyr Asp Thr Ser Asn Phe Thr Ile Gln Asp Met
        115                 120                 125

Leu Asn Ile Met Asn Lys Leu Asn Ile Val Arg Thr Asn Arg Asn Glu
    130                 135                 140

Leu Phe Gln Leu Leu Thr His Val Lys Ser Thr Leu Asn Asn Ala Ser
145                 150                 155                 160

Val Ser Val Lys Cys Thr His Pro Leu Val Leu Ile His Ser Arg Ala
                165                 170                 175

Ser Pro Arg Ile Gly Asp Gln Leu Lys Glu Leu Asp Lys Ile Tyr Ser
            180                 185                 190

Pro Ser Asn His His Ile Leu Leu Ser Thr Thr Arg Phe Gln Ser Met
        195                 200                 205

His Phe Thr Asp Met Ser Ser Ser Gln Asp Leu Ser Phe Ile Tyr Arg
    210                 215                 220

Lys Pro Glu Thr Asn Tyr Tyr Ile His Pro Ile Leu Met Ala Leu Phe
225                 230                 235                 240

Gly Ile Lys Leu Pro Ala Leu Glu Asn Ala Tyr Val His Gly Asp Thr
                245                 250                 255

Tyr Ser Leu Ile Gln Gln Leu Tyr Glu Phe Arg Lys Val Lys Ser Tyr
            260                 265                 270

Asn Tyr Met Leu Leu Val Asn Arg Leu Thr Glu Asp Asn Pro Ile Val
        275                 280                 285

Ile Thr Gly Val Ser Asp Leu Ile Ser Thr Glu Ile Gln Arg Ala Asn
    290                 295                 300

Met His Thr Met Ile Arg Lys Ala Ile Met Asn Ile Arg Met Gly Ile
305                 310                 315                 320

Phe Tyr Cys Asn Asp Asp Asp Ala Val Asp Pro His Leu Met Lys Ile
                325                 330                 335

Ile His Thr Gly Cys Ser Gln Val Met Thr Asp Glu Glu Gln Ile Leu
            340                 345                 350

Ala Ser Ile Leu Ser Ile Val Gly Phe Arg Pro Thr Leu Val Ser Val
        355                 360                 365

Ala Arg Pro Ile Asn Gly Ile Ser Tyr Asp Met Lys Leu Gln Ala Ala
    370                 375                 380

Pro Tyr Ile Val Val Asn Pro Met Lys Met Ile Thr Thr Ser Asp Ser
```

```
385                 390                 395                 400

Pro Ile Ser Ile Asn Ser Lys Asp Ile Tyr Ser Met Ala Phe Asp Gly
                405                 410                 415

Asn Ser Gly Arg Val Val Phe Ala Pro Pro Asn Ile Gly Tyr Gly Arg
            420                 425                 430

Cys Ser Gly Val Thr His Ile Asp Pro Leu Gly Thr Asn Val Met Gly
        435                 440                 445

Ser Ala Val His Ser Pro Val Ile Val Asn Gly Ala Met Met Phe Tyr
    450                 455                 460

Val Glu Arg Arg Gln Asn Lys Asn Met Phe Gly Gly Glu Cys Tyr Thr
465                 470                 475                 480

Gly Phe Arg Ser Leu Ile Asp Asp Thr Pro Ile Asp Val Ser Pro Glu
                485                 490                 495

Ile Met Leu Asn Gly Ile Met Tyr Arg Leu Lys Ser Ala Val Cys Tyr
            500                 505                 510

Lys Leu Gly Asp Gln Phe Phe Asp Cys Gly Ser Ser Asp Ile Phe Leu
        515                 520                 525

Lys Gly His Tyr Thr Ile Leu Phe Thr Glu Asn Gly Pro Trp Met Tyr
    530                 535                 540

Asp Pro Leu Ser Val Phe Asn Pro Gly Ala Arg Asn Ala Arg Leu Met
545                 550                 555                 560

Arg Ala Leu Lys Asn Gln Tyr Lys Lys Leu Ser Met Asp Ser Asp Asp
                565                 570                 575

Gly Phe Tyr Glu Trp Leu Asn Gly Asp Gly Ser Val Phe Ala Ala Ser
            580                 585                 590

Lys Gln Gln Met Leu Met Asn His Val Ala Asn Phe Asp Asp Asp Leu
        595                 600                 605

Leu Thr Met Glu Glu Ala Met Ser Met Ile Ser Arg His Cys Cys Ile
    610                 615                 620

Leu Ile Tyr Ala Gln Asp Tyr Asp Gln Tyr Ile Ser Ala Arg Tyr Ile
625                 630                 635                 640

Thr Glu Leu Phe


<210> SEQ ID NO 5
<211> LENGTH: 168
<212> TYPE: PRT
<213> ORGANISM: Vaccinia virus

<400> SEQUENCE: 5

Met Lys Ser Leu Asn Arg Gln Thr Val Ser Arg Phe Lys Lys Leu Ser
1               5                   10                  15

Val Pro Val Ala Ile Met Met Ile Leu Ser Thr Ile Ile Ser Gly Ile
            20                  25                  30

Gly Thr Phe Leu His Tyr Lys Glu Glu Leu Met Pro Ser Ala Cys Ala
        35                  40                  45

Asn Gly Trp Ile Gln Tyr Asp Lys His Cys Tyr Leu Asp Thr Asn Ile
    50                  55                  60

Lys Met Ser Thr Asp Asn Ala Val Tyr Gln Cys Arg Lys Leu Arg Ala
65                  70                  75                  80

Arg Leu Pro Arg Pro Tyr Thr Arg His Leu Arg Val Leu Phe Ser Ile
                85                  90                  95

Phe Tyr Lys Asp Tyr Trp Val Ser Leu Lys Lys Thr Asn Asp Lys Trp
            100                 105                 110

Leu Asp Ile Asn Asn Asp Lys Asp Ile Asp Ile Ser Lys Leu Thr Asn
```

```
        115                 120                 125

Phe Lys Gln Leu Asn Ser Thr Thr Asp Ala Glu Ala Cys Tyr Ile Tyr
    130                 135                 140

Lys Ser Gly Lys Leu Val Lys Thr Val Cys Lys Ser Thr Gln Ser Val
145                 150                 155                 160

Leu Cys Val Lys Lys Phe Tyr Lys
                165


<210> SEQ ID NO 6
<211> LENGTH: 94
<212> TYPE: PRT
<213> ORGANISM: Vaccinia virus

<400> SEQUENCE: 6

Met Ser Cys Tyr Thr Ala Ile Leu Lys Ser Val Gly Gly Leu Ala Leu
1               5                   10                  15

Phe Gln Val Ala Asn Gly Ala Ile Asp Leu Cys Arg His Phe Phe Met
            20                  25                  30

Tyr Phe Cys Glu Gln Lys Leu Arg Pro Asn Ser Phe Trp Phe Val Val
        35                  40                  45

Val Arg Ala Ile Ala Ser Met Ile Met Tyr Leu Val Leu Gly Ile Ala
    50                  55                  60

Leu Leu Tyr Ile Ser Glu Gln Asp Asn Lys Glu Asn Thr Asn Asn Asp
65                  70                  75                  80

Lys Arg Asn Glu Ser Ser Ile Asn Ser Asn Ser Ser Pro Lys
                85                  90


<210> SEQ ID NO 7
<211> LENGTH: 1935
<212> TYPE: DNA
<213> ORGANISM: Vaccinia virus

<400> SEQUENCE: 7

atggaagccg tggtcaatag cgatgttttt ttaacatcta acgcaggact aaaatctagt     60

tatactaatc aaactctttc tttggtagat gaagatcata ttcacacttc tgataaatct    120

ttgtcttgta gtgtatgcaa ttcattatcc aaaattgtag acgatgactt tatatccgca    180

ggggctagaa atcaacgtac caaacctaaa cgtgcaggaa ataatcaatc tcaacagcct    240

atcaaaaagg attgtatggt ttccatcgac gaagtagcat ccacgcatga ttggagtacg    300

agattgagaa atgatgggaa tgcaattgct aaatatctaa ctactaacaa gtatgacaca    360

tctaacttta ctattcagga tatgcttaac attatgaata aactaaatat tgtcagaaca    420

aatagaaacg agctatttca actccttacc catgtaaaga gcacattgaa caatgctagt    480

gtttctgtga aatgtactca tcctttagta cttattcatt ctcgagctag tcctagaatc    540

ggtgaccaac tcaaagagtt agataaaata tactctccat ctaatcatca tattcttctg    600

tcgactacac gattccaatc catgcatttt accgatatgt ctagttcaca agatttgtct    660

tttatttata gaaaaccaga aactaattac tatattcatc ctattctgat ggcactattc    720

ggtattaaac ttcctgcgct cgagaacgcg tatgtacatg gagacaccta tagcctaatc    780

cagcaacttt atgaatttag aaaagtaaag tcttataatt atatgttgtt ggttaatcgt    840

cttacggagg ataatccgat agtgattaca ggtgtatcag atctaatttc cacagagatt    900

cagagagcaa acatgcatac catgattaga aaagcaatta tgaacattag aatgggaatt    960

ttttattgta acgatgatga tgcggtagat ccccatctaa tgaagattat tcatactgga   1020
```

-continued

```
tgctctcaag ttatgacaga tgaagaacag atattggctt ctattttgtc tatagttgga   1080

tttagaccta cgttggtttc tgtggctaga cctataaacg gcatcagtta cgatatgaaa   1140

cttcaggcgg caccatacat agttgttaat cctatgaaga tgatcacaac atccgacagt   1200

ccgatttcta tcaattccaa ggatatttat tctatggcat tcgatggcaa tagtggaaga   1260

gtggtgttcg ctcctcctaa cataggatat ggaagatgtt ctggagttac acacattgat   1320

ccattgggaa ctaatgtgat gggtagtgct gttcattccc ctgttatcgt taatggagca   1380

atgatgtttt atgtagaacg acgtcagaat aagaatatgt ttggtggaga atgttacacc   1440

ggctttagat ctctaataga tgatactccg attgacgtat caccagaaat catgctaaac   1500

ggtatcatgt ataggttaaa gtccgcagtt tgttacaaac tcggagacca attctttgat   1560

tgtggatcgt ctgatatctt cttgaaggga cattatacga ttctatttac agaaaatgga   1620

ccctggatgt acgatcctct ttctgttttc aatccgggag ctagaaatgc tagattgatg   1680

cgagctctca aaaaccagta caagaaatta tcaatggatt cagacgatgg tttttatgaa   1740

tggttgaatg gcgacggttc agtatttgct gcctcaaaac agcaaatgtt gatgaatcac   1800

gttgctaact ttgacgacga tcttctaact atggaagaag ccatgtcgat gatttcgaga   1860

cattgttgta tcttaattta tgcacaggat tatgatcaat atattagcgc tagacatatt   1920

acagaactat tttag                                                    1935
```

<210> SEQ ID NO 8
<211> LENGTH: 507
<212> TYPE: DNA
<213> ORGANISM: Vaccinia virus

<400> SEQUENCE: 8

```
atgaaatcgc ttaatagaca aactgtaagt aggtttaaga agttgtcggt gccggtcgct     60

ataatgatga tactctcaac cattattagt ggcataggaa catttctgca ttacaaagaa    120

gaactgatgc ctagtgcttg cgccaatgga tggatacaat acgataaaca ttgttattta    180

gatactaaca ttaaaatgtc tacagataat gcggtttatc agtgtcgtaa attacgagcc    240

agattgccta gaccggatac tagacatctg agagtattgt ttagtatttt ttataaagat    300

tattgggtaa gtttaaaaaa gaccaatgat aaatggttag atattaataa tgataaagat    360

atagatatta gtaaattaac aaattttaaa caactaaaca gtacgacgga tgctgaagcg    420

tgttatatat acaagtctgg aaaactggtt aaaacagtat gtaaaagtac tcaatctgta    480

ctatgtgtta aaaaattcta caagtga                                        507
```

<210> SEQ ID NO 9
<211> LENGTH: 285
<212> TYPE: DNA
<213> ORGANISM: Vaccinia virus

<400> SEQUENCE: 9

```
atgtcatgtt atacagctat attaaaatct gtaggaggac tggcgctatt tcaagtagcc     60

aatggcgcca tagatttatg tagacatttc tttatgtatt tttgtgaaca aaagctacga    120

ccaaattcat tttggttcgt cgttgttaga gccattgcaa gcatgataat gtatttagta    180

ttaggcatag cattgctgta tatttctgaa caagataaca agaagaatac taataatgat    240

aaacgaaatg agtcgtctat aaattctaac tccagtccta agtaa                    285
```

<210> SEQ ID NO 10
<211> LENGTH: 1935

-continued

<212> TYPE: DNA
<213> ORGANISM: Vaccinia virus

<400> SEQUENCE: 10
atggaagccg tggtcaatag cgatgttttt ttaacatcta acgcaggact aaaatctagt 60
tatactaatc aaactctttc tttggtagat gaagatcata ttcacacttc tgataaatct 120
ttgtcttgta gtgtatgcaa ttcattatcc aaaattgtag acgatgactt tatatccgca 180
ggggctagaa atcaacgtac caaacctaaa cgtgcaggaa ataatcaatc tcaacagcct 240
atcaaaaagg attgtatggt ttccatcgac gaagtagcat ccacgcatga ttggagtacg 300
agattgagaa atgatgggaa tgcaattgct aaatatctaa ctactaacaa gtatgacaca 360
tctaacttta ctattcagga tatgcttaac attatgaata aactaaatat tgtcagaaca 420
aatagaaacg agctatttca actccttacc catgtaaaga gcacattgaa caatgctagt 480
gtttctgtga aatgtactca tcctttagta cttattcatt ctcgagctag tcctagaatc 540
ggtgaccaac tcaaagagtt agataaaata tactctccat ctaatcatca tattcttctg 600
tcgactacac gattccaatc catgcatttt accgatatgt ctagttcaca agatttgtct 660
tttatttata gaaaaccaga aactaattac tatattcatc ctattctgat ggcactattc 720
ggtattaaac ttcctgcgct cgagaacgcg tatgtacatg gagacaccta tagcctaatc 780
cagcaacttt atgaatttag aaaagtaaag tcttataatt atatgttgtt ggttaatcgt 840
cttacggagg ataatccgat agtgattaca ggtgtatcag atctaatttc cacagagatt 900
cagagagcaa acatgcatac catgattaga aaagcaatta tgaacattag aatgggaatt 960
ttttattgta acgatgatga tgcggtagat ccccatctaa tgaagattat tcatactgga 1020
tgctctcaag ttatgacaga tgaagaacag atattggctt ctattttgtc tatagttgga 1080
tttagaccta cgttggtttc tgtggctaga cctataaacg gcatcagtta cgatatgaaa 1140
cttcaggcgg caccatacat agttgttaat cctatgaaga tgatcacaac atccgacagt 1200
ccgatttcta tcaattccaa ggatatttat tctatggcat tcgatggcaa tagtggaaga 1260
gtggtgttcg ctcctcctaa cataggatat ggaagatgtt ctggagttac acacattgat 1320
ccattgggaa ctaatgtgat gggtagtgct gttcattccc ctgttatcgt taatggagca 1380
atgatgtttt atgtagaacg acgtcagaat aagaatatgt ttggtggaga atgttacacc 1440
ggctttagat ctctaataga tgatactccg attgacgtat caccagaaat catgctaaac 1500
ggtatcatgt ataggttaaa gtccgcagtt tgttacaaac tcggagacca attctttgat 1560
tgtggatcgt ctgatatctt cttgaaggga cattatacga ttctatttac agaaaatgga 1620
ccctggatgt acgatcctct ttctgttttc aatccgggag ctagaaatgc tagattgatg 1680
cgagctctca aaaaccagta caagaaatta tcaatggatt cagacgatgg tttttatgaa 1740
tggttgaatg gcgacggttc agtatttgct gcctcaaaac agcaaatgtt gatgaatcac 1800
gttgctaact ttgacgacga tcttctaact atggaagaag ccatgtcgat gatttcgaga 1860
cattgttgta tcttaattta tgcacaggat tatgatcaat atattagcgc tagatatatt 1920
acagaactat tttag 1935

<210> SEQ ID NO 11
<211> LENGTH: 507
<212> TYPE: DNA
<213> ORGANISM: Vaccinia virus

<400> SEQUENCE: 11

-continued

```
atgaaatcgc ttaatagaca aactgtaagt aggtttaaga agttgtcggt gccggtcgct     60

ataatgatga tactctcaac cattattagt ggcataggaa catttctgca ttacaaagaa    120

gaactgatgc ctagtgcttg cgccaatgga tggatacaat acgataaaca ttgttattta    180

gatactaaca ttaaaatgtc tacagataat gcggtttatc agtgtcgtaa attacgagcc    240

agattgccta gaccgtatac tagacatctg agagtattgt ttagtatttt ttataaagat    300

tattgggtaa gtttaaaaaa gaccaatgat aaatggttag atattaataa tgataaagat    360

atagatatta gtaaattaac aaattttaaa caactaaaca gtacgacgga tgctgaagcg    420

tgttatatat acaagtctgg aaaactggtt aaaacagtat gtaaaagtac tcaatctgta    480

ctatgtgtta aaaaattcta caagtga                                        507
```

<210> SEQ ID NO 12
<211> LENGTH: 285
<212> TYPE: DNA
<213> ORGANISM: Vaccinia virus

<400> SEQUENCE: 12

```
atgtcatgtt atacagctat attaaaatct gtaggaggac tggcgctatt tcaagtagcc     60

aatggcgcca tagatttatg tagacatttc tttatgtatt tttgtgaaca aaagctacga    120

ccaaattcat tttggttcgt cgttgttaga gccattgcaa gcatgataat gtatttagta    180

ttaggcatag cattgctgta tatttctgaa caagataaca aggagaatac taataatgat    240

aaacgaaatg agtcgtctat aaattctaac tccagtccta agtaa                    285
```

<210> SEQ ID NO 13
<211> LENGTH: 350
<212> TYPE: PRT
<213> ORGANISM: Vaccinia virus

<400> SEQUENCE: 13

```
Met Asn Thr Arg Thr Asp Val Thr Asn Asp Asn Ile Asp Lys Asn Pro
1               5                   10                  15

Thr Lys Arg Gly Asp Lys Asn Ile Pro Gly Arg Asn Glu Arg Phe Asn
            20                  25                  30

Asp Gln Asn Arg Phe Asn Asn Asp Ile Pro Lys Pro Lys Pro Arg Leu
        35                  40                  45

Gln Pro Asn Gln Pro Pro Lys Gln Asp Asn Lys Cys Arg Glu Glu Asn
    50                  55                  60

Gly Asp Phe Ile Asn Ile Arg Leu Cys Ala Tyr Glu Lys Glu Tyr Cys
65                  70                  75                  80

Asn Asp Gly Tyr Leu Ser Pro Ala Tyr Tyr Met Leu Lys Gln Val Asp
                85                  90                  95

Asp Glu Glu Ile Ser Cys Trp Ser Glu Leu Ser Ser Leu Val Arg Ser
            100                 105                 110

Arg Lys Ala Val Gly Phe Pro Leu Leu Lys Ala Ala Lys Arg Ile Ser
        115                 120                 125

His Gly Ser Met Leu Tyr Phe Glu Gln Phe Lys Asn Ser Lys Val Val
    130                 135                 140

Lys Leu Thr Pro Gln Val Lys Cys Leu Asn Asp Thr Val Ile Phe Gln
145                 150                 155                 160

Thr Val Val Ile Leu Tyr Ser Met Tyr Lys Arg Gly Ile Tyr Ser Asn
                165                 170                 175

Glu Phe Cys Phe Asp Leu Val Ser Ile Pro Arg Thr Asn Ile Val Phe
            180                 185                 190
```

```
Ser Val Asn Gln Leu Met Phe Asn Ile Cys Thr Asp Ile Leu Val Val
        195                 200                 205

Leu Ser Ile Cys Gly Asn Arg Leu Tyr Arg Thr Asn Leu Pro Gln Ser
    210                 215                 220

Cys Tyr Leu Asn Phe Ile His Gly His Glu Thr Ile Ala Arg Arg Gly
225                 230                 235                 240

Tyr Glu His Ser Asn Tyr Phe Phe Glu Trp Leu Ile Lys Asn His Ile
                245                 250                 255

Ser Leu Leu Thr Lys Gln Thr Met Asp Ile Leu Lys Val Lys Lys Lys
            260                 265                 270

Tyr Ala Thr Gly Ala Pro Val Asn Arg Leu Leu Glu Pro Gly Thr Leu
        275                 280                 285

Val Tyr Val Pro Lys Glu Asp Tyr Tyr Phe Ile Gly Ile Ser Leu Thr
    290                 295                 300

Asp Val Ser Ile Ser Asp Asn Val Arg Val Leu Phe Ser Thr Asp Gly
305                 310                 315                 320

Ile Val Leu Glu Ile Glu Asp Phe Asn Ile Lys His Leu Phe Met Ala
                325                 330                 335

Gly Glu Met Phe Val Arg Ser Gln Ser Ser Thr Ile Ile Val
            340                 345                 350


<210> SEQ ID NO 14
<211> LENGTH: 350
<212> TYPE: PRT
<213> ORGANISM: Vaccinia virus

<400> SEQUENCE: 14

Met Asn Thr Arg Thr Asp Val Thr Asn Asp Asn Ile Asp Lys Asn Pro
1               5                   10                  15

Thr Lys Arg Gly Asp Lys Asn Ile Pro Gly Arg Asn Glu Arg Phe Asn
            20                  25                  30

Asp Gln Asn Arg Phe Asn Asn Asp Ile Pro Lys Pro Lys Pro Arg Leu
        35                  40                  45

Gln Pro Asn Gln Pro Pro Lys Gln Asp Asn Lys Cys Arg Glu Glu Asn
    50                  55                  60

Gly Asp Phe Ile Asn Ile Arg Leu Cys Ala Tyr Glu Lys Glu Tyr Cys
65                  70                  75                  80

Asn Asp Gly Tyr Leu Ser Pro Ala Tyr Tyr Met Leu Lys Gln Val Asp
                85                  90                  95

Asp Glu Glu Ile Ser Cys Trp Ser Glu Leu Ser Ser Leu Ala Arg Ser
            100                 105                 110

Arg Lys Ala Val Gly Phe Pro Leu Leu Lys Ala Ala Lys Arg Ile Ser
        115                 120                 125

His Gly Ser Met Leu Tyr Phe Glu Gln Phe Lys Asn Ser Lys Val Val
    130                 135                 140

Lys Leu Thr Pro Gln Val Lys Cys Leu Asn Asp Thr Val Ile Phe Gln
145                 150                 155                 160

Thr Val Val Ile Leu Tyr Ser Met Tyr Lys Arg Gly Ile Tyr Ser Asn
                165                 170                 175

Glu Phe Cys Phe Asp Leu Val Ser Ile Pro Arg Thr Asn Ile Val Phe
            180                 185                 190

Ser Val Asn Gln Leu Met Phe Asn Ile Cys Thr Asp Ile Leu Val Val
        195                 200                 205

Leu Ser Ile Cys Gly Asn Arg Leu Tyr Arg Thr Asn Leu Pro Gln Ser
```

```
    210                 215                 220

Cys Tyr Leu Asn Phe Ile His Gly His Glu Thr Ile Ala Arg Arg Gly
225                 230                 235                 240

Tyr Glu His Ser Asn Tyr Phe Phe Glu Trp Leu Ile Lys Asn His Ile
                245                 250                 255

Ser Leu Leu Thr Lys Gln Thr Met Asp Ile Leu Lys Val Lys Lys Lys
            260                 265                 270

Tyr Ala Thr Gly Ala Pro Val Asn Arg Leu Leu Glu Pro Gly Thr Leu
        275                 280                 285

Val Tyr Val Pro Lys Glu Asp Tyr Tyr Phe Ile Gly Ile Ser Leu Thr
    290                 295                 300

Asp Val Ser Ile Ser Asp Asn Val Arg Val Leu Phe Ser Thr Asp Gly
305                 310                 315                 320

Ile Val Leu Glu Ile Glu Asp Phe Asn Ile Lys His Leu Phe Met Ala
                325                 330                 335

Gly Glu Met Phe Val Arg Ser Gln Ser Ser Thr Ile Ile Val
            340                 345                 350


<210> SEQ ID NO 15
<211> LENGTH: 1053
<212> TYPE: DNA
<213> ORGANISM: Vaccinia virus

<400> SEQUENCE: 15

atgaataccc gtaccgatgt tacaaacgat aatatagaca aaaatccaac caaacgaggt     60

gataaaaata taccaggaag aaatgaaaga tttaatgacc aaaatagatt caacaacgat    120

ataccaaagc ctaaaccaag actacagcct aatcagccac cgaaacaaga taataaatgc    180

agagaagaga atggagattt tatcaatatt agattgtgtg cctacgaaaa ggaatattgc    240

aatgacggat atctatctcc tgcctattat atgttaaaac aggtggatga tgaagaaata    300

agttgctggt cagaactatc gtcgttggtg agatccagaa aggcggtggg atttcctcta    360

ttaaaggcgg ctaaacgtat ttctcatgga tcgatgctat attttgaaca gtttaaaaac    420

agtaaagttg tgaaattaac cccgcaagtt aaatgtttaa atgatactgt tatttttcaa    480

actgtagtta ttttatattc catgtataaa cgtggcatat attctaacga attttgtttt    540

gatctggttt ctattcccag aacgaacatt gttttttctg ttaatcaatt aatgtttaac    600

atttgtacag acatattggt agttctatct atttgcggca accggctcta tagaacaaat    660

ctaccacagt cgtgttactt aaatttcata cacggccatg agacaatagc ccgtagagga    720

tatgaacact ccaattactt ttttgagtgg ttgataaaaa atcacatatc gctattgacc    780

aagcaaacga tggatattct caaggtaaag aaaaagtatg ctacaggagc accagtaaat    840

aggttgttag aacctggtac actggtatat gtgcccaaag aagattatta ctttataggc    900

atatcactca ccgatgtgtc aattagcgat aatgtcagag tattattttc cacagatgga    960

atagtgttag aaatagaaga ctttaatatc aagcatttat ttatggcagg tgagatgttt   1020

gttagaagtc agtctagtac tattatagta taa                                1053


<210> SEQ ID NO 16
<211> LENGTH: 1053
<212> TYPE: DNA
<213> ORGANISM: Vaccinia virus

<400> SEQUENCE: 16

atgaataccc gtaccgatgt tacaaacgat aatatagaca aaaatccaac caaacgaggt     60
```

-continued gataaaaata taccaggaag aaatgaaaga tttaatgacc aaaatagatt caacaacgat 120
ataccaaagc ctaaaccaag actacagcct aatcagccac cgaaacaaga taataaatgc 180
agagaagaga atggagattt tatcaatatt agattgtgtg cctacgaaaa ggaatattgc 240
aatgacggat atctatctcc tgcctattat atgttaaaac aggtggatga tgaagaaata 300
agttgctggt cagaactatc gtcgttggcg agatccagaa aggcggtggg atttcctcta 360
ttaaaggcgg ctaaacgtat ttctcatgga tcgatgctat attttgaaca gtttaaaaac 420
agtaaagttg tgaaattaac cccgcaagtt aaatgtttaa atgatactgt tatttttcaa 480
actgtagtta ttttatattc catgtataaa cgtggcatat attctaacga attttgtttt 540
gatctggttt ctattcccag aacgaacatt gttttttctg ttaatcaatt aatgtttaac 600
atttgtacag acatattggt agttctatct atttgcggca accggctcta tagaacaaat 660
ctaccacagt cgtgttactt aaatttcata cacggccatg agacaatagc ccgtagagga 720
tatgaacact ccaattactt ttttgagtgg ttgataaaaa atcacatatc gctattgacc 780
aagcaaacga tggatattct caaggtaaag aaaaagtatg ctacaggagc accagtaaat 840
aggttgttag aacctggtac actggtatat gtgcccaaag aagattatta ctttataggc 900
atatcactca ccgatgtgtc aattagcgat aatgtcagag tattattttc cacagatgga 960
atagtgttag aaatagaaga ctttaatatc aagcatttat ttatggcagg tgagatgttt 1020
gttagaagtc agtctagtac tattatagta taa 1053

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
aggacatgtt tggtggtcgc catggatggt 30

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
taccgctagc taccagccac cgaaagag 28

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
tgggcggccg ctttggaaag ttttatagg 29

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
tggcacgtag tgccggagtc tcgtctgttg 30

<210> SEQ ID NO 21
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
atctgctagc acgtggacta gtaaaaattg aaattttatt tttttttttt ggaatataaa 60
taagatctta cc 72

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
aatgctagcg cggaatcatc aacactaccc 30

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
gctctagatt gttcccgcaa ctacggtc 28

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
ctctacgggc tattgtctc 19

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
tgaatacccg taccgatg 18

<210> SEQ ID NO 26
<211> LENGTH: 20
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 26
gcagaagaac accgcttagg 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
atggaagccg tggtcaatag 20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
ttgaaatagc gccagtcctc c 21

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
actacggcgg cattatgttc tc 22

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
ggcggcatgt ggagtgtctt tatc 24

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
ggtgtataga gttcacagta g 21

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (23)..(24)
<223> OTHER INFORMATION: Inosine
<220> FEATURE:
<221> NAME/KEY: modified_base
<222> LOCATION: (28)..(29)
<223> OTHER INFORMATION: Inosine
<220> FEATURE:
<221> NAME/KEY: modified_base
<222> LOCATION: (33)..(34)
<223> OTHER INFORMATION: Inosine

<400> SEQUENCE: 32
gccacgcgtc gactagtacg ggnngggnng ggnng 35

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
ggaggtggct ctcgatgaac 20

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
acggtcctgt agtatctg 18

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
cggcatgtgg agtgtcttta tc 22

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
cttgcacatg tctccgatac g 21

<210> SEQ ID NO 37
<211> LENGTH: 190550
<212> TYPE: DNA
<213> ORGANISM: Vaccinia virus

<400> SEQUENCE: 37

-continued

```
tatttattta gtgtctagaa aaaaatgtgt gaccaacgac cgtaggaaac tctagagggt     60
aagaaaaatc aatcgcttta tagagaccat cagaaagagg tttaatattt ttgtgagacc    120
atcgaaggag aaagagataa aactttttta cgactccatc agaaagaggt ttaatatttt    180
tgtgagacca tcgaagagag aaagagataa aactttttta cgactccatc agaaagaggt    240
ttaatatttt tgtgagacca tcgaagagag aaagagataa aactttttta cgactccatc    300
agaaagaggt ttaatatttt tgtgagacca tcgaaggaga aagagataaa acttttttac    360
gactccatca gaaagaggtt taatattttt gtgagaccat cgaaggagaa agagataaaa    420
cttttttacg actccatcag aaagaggttt aatatttttg tgagaccatc gaaggagaaa    480
gagataaaac tttttttacga ctccatcaga aagaggttta atatttttgt gagaccatcg    540
aagagagaaa gagataaaac tttttttacga ctccatcaga aagaggttta atatttttgt    600
gagaccatcg aaggagaaag agataaaact tttttacgac tccatcagaa agaggtttaa    660
tatttttgtg agaccatcga agagagaaag agaataaaaa tattttagtg acaccatcag    720
aaagaggttt aatatttttg tgagaccatc gaagagagaa agagataaaa cttttttacg    780
actccatcag aaagaggttt aatatttttg tgagaccatc gaaggagaaa gagataaaac    840
tttttttacga ctccatcaga aagaggttta atatttttgt gagaccatcg aagagagaaa    900
gagataaaac tttttttacga ctccatcaga aagaggttta atatttttgt gagaccatcg    960
aagagagaaa gagataaaac tttttttacga ctccatcaga aagaccatcg aagagagaaa   1020
gagaaagaga tagttagtct agatattttt cttagtacaa aagtcaatgt tttaaaatat   1080
atggacaaga atttgtctgt ataaaaactt gtgtgaaatt ttgtaccaaa gaaaaaatgt   1140
gagcagtatc ccctacatgg attttactag atcatttata taccaaaaaa tattatacga   1200
tctacgtttt attatatgat tttaacgtgt aaattataaa cattatttta tgatatacaa   1260
ttgtctggta acctagatgg gcatagggga tgagtatatg ttgttggacg ttattgttta   1320
agaaatagtt gatgcatcag aaagaggttt aatatttttg tgagaccatc gaagagagaa   1380
agagataaaa cttttttacg actccatcag aaagaggttt aatatttttg tgagaccatc   1440
gaagagagaa agagataaaa cttttttatg actccattga agagagaatg agaataaaaa   1500
tattttagtg acaccatcag aaagaggttt aatatttttt atgagaccat caaagagaga   1560
aagagaataa aaatatttta tgactccatt gaagagagaa agagaaaatg agaataaaaa   1620
tattttagtg acaccatcag aaagaggttt aatatttttt atgagaccat caaagagaga   1680
aagagaataa aaatattttt gtaaaacttt ttttatgaga ccatcaaaga gagaaagaga   1740
ataaaaatat ttttgtaaaa cttttttttat gagaccatca aagagagaaa gagaataaaa   1800
atatttttgt aaaacttttt ttatgagacc atcaaagaga gaaagagaat aaaaatattt   1860
ttgtaaaact ttttttatga gaccatcaaa gagagaaaga gaataaaaat atttttgtaa   1920
aacttttttt atgagaccat caaagagaga aagagaataa aaatattttt gtaaaacttt   1980
ttttatgaga ccatcaaaga gagaaagaga ataaaaatat ttttgtaaaa cttttttttat   2040
gagaccatca aagagagaaa gagaataaaa atattttatg actccattga agagagaaag   2100
agaataaaaa tattttagtg acaccatcag aaagaggttt aatatttttg tgagaccatc   2160
gaagagagaa agagaataaa aatattttat gactccattg aagagagaaa gagaataaaa   2220
atattttagt gacaccatca gaaagaggtt taatattttt tatgagacca tcaaagagag   2280
aaagagaata aaaatatttt tgtaaaactt tttttatgag accatcaaag agagaaagag   2340
```

-continued

```
aataaaaata tttttgtaaa actttttta tgagaccatc aaagagagaa agagaataaa    2400
aatattttg taaaactttt tttatgagac catcaaagag agaaagagaa taaaaatatt    2460
tttgtaaaac tttttttatg agaccatcaa agagagaaag agaataaaaa tatttttgta    2520
aaactttttt tatgagacca tcaaagagag aaagagaata aaaatatttt atgactccat    2580
tgaagagaga atgagaataa aaatatttta gtgacaccat cagaaagagg tttaatattt    2640
ttgtgagacc atcgaagaga gaaagagaat aaaaatattt tatgactcca ttgaagagag    2700
aaagagaata aaaatatttt agtgacacca tcagaaagag gtttaatatt ttttatgaga    2760
ccatcaaaga gagaaagaga ataaaaatat ttttgtaaaa cttttttat gagaccatca    2820
aagagagaaa gagaataaaa atatttttgt aaaacttttt ttatgagacc atcaaagaga    2880
gaaagagaat aaaaatattt ttgtaaaact tttttatga gaccatcaaa gagagaaaga    2940
gaataaaaat atttttgtaa aacttttttt atgagaccat caaagagaga aagagaataa    3000
aaatattttt gtaaaacttt ttttatgaga ccatcaaaga gagaaagaga ataaaaatat    3060
ttttgtaaaa cttttttat gagaccatca aagagagaaa gagaataaaa atatttttgt    3120
aaaacttttt ttatgagacc atcaaagaga gaaagagaat aaaaatattt tatgactcca    3180
ttgaagagag aatgagaata aaaatatttt agtgacacca tcagaaagag gtttaatatt    3240
tttgtgagac catcgaagag agaaagagaa taaaaatatt ttatgactcc attgaagaga    3300
gaatgagaat aaaaatattt tagtgacacc atcagaaaga ggtttaatat tttttatgag    3360
accatcaaag agagaaagag aataaaaata tttttgtaaa actttttta tgagaccatc    3420
aaagagagaa agagaataaa aatattttg taaaaattat aaacattatt ttatgatata    3480
caattgtctg gtaacctaga tgggcatagg ggatgttgat aagctcgacg agtatatgtt    3540
gttggacgtt attgtttaag aaatagttga tgcatcagaa agagaataaa aaatatttta    3600
gtgagaccat cgaagagaga aagagataaa actttttac gactccatca gaaagaggtt    3660
taatattttt gtgagaccat cgaagagaga aagagataaa actttttac gactccatca    3720
gaaagaggtt taatattttt gtgagaccat cgaaggagaa agagataaaa ctttttacg    3780
actccatcag aaagaggttt aatattttg tgagaccatc aaagagagaa agagaataaa    3840
aatattttg taaaactttt tttatgagac catcaaagag agaaagagaa taaaaatatt    3900
tttgtaaaac tttttttatg agaccatcaa agagagaaag agaataaaaa tatttttgta    3960
aaactttttt tatgagacca tcaaagagag aaagagaata aaaatatttt tgtaaaactt    4020
tttttatgag accatcaaag agagaaagag aataaaaata ttttatgact ccattgaaga    4080
gagaatgaga ataaaaatat tttagtgaca ccatcagaaa gaggtttaat atttttgtga    4140
gaccatcgaa gagagaaaga gaataaaaat attttatgac tccattgaag agagaatgag    4200
aataaaaata ttttagtgac accatcagaa agaggtttaa tattttttat gagaccatca    4260
aagagagaaa gagaataaaa atatttttgt aaaacttttt ttatgagacc atcaaagaga    4320
gaaagagaat aaaaatattt ttgtaaaact tttttatga gaccatcaaa gagagaaaga    4380
gaataaaaat atttttgtaa aacttttttt atgagaccat caaagagaga aagagaataa    4440
aaatattttt gtaaaacttt ttttatgaga ccatcaaaga gagaaagaga ataaaaatat    4500
tttatgactc cattgaagag agaatgagaa taaaaatatt ttagtgacac catcagaaag    4560
aggtttaata tttttgtgag accatcgaag agagaaagag aataaaaata ttttatgact    4620
ccattgaaga gagaaagaga ataaaaatat tttagtgaca ccatcagaaa gaggtttaat    4680
atttttatg agaccatcaa agagagaaag agaataaaaa tatttttgta aaactttttt    4740
```

```
tatgagacca tcaaagagag aaagagaata aaaatatttt atgactccat tgaagagaga   4800
atgagaataa aaatatttta gtgacaccat cagaaagagg tttaatattt ttgtgagacc   4860
atcgaagaga gaaagagaat aaaaatattt tatgactcca ttgaagagag aatgagaata   4920
aaaatatttt agtgacacca tcagaaagag gtttaatatt tttgtgagac catcgaagag   4980
agaaagagaa taaaaatatt ttatgactcc attgaagaga gaatgagaat aaaaatattt   5040
tagtgacacc atcagaaaga ggtttaatat tttttatgag accatcaaag agagaaagag   5100
aataaaaata tttttgtaaa actttttta tgagaccatc aaagagagaa agagaataaa   5160
aatatttttg taaaactttt tttatgagac catcaaagag agaaagagaa taaaaatatt   5220
tttgtaaaac ttttttatg agaccatcaa agagagaaag agaataaaaa tatttttgtg   5280
agaccatcaa agagagaaag agaataaaaa tatttttgtg agaccatcaa agagagaaag   5340
agaataaaaa tatttttgtg agaccatcaa agagagaaag agaataaaaa tattttatga   5400
ctccattgaa gagagaaaga gaataaaaat attttagtga caccatcaga aagaggttta   5460
atatttttgt gagaccatcg aagagagaaa gagaataaaa atattttatg actccattga   5520
agagagaaag agaataaaaa tattttagtg acaccatcag aaagaggttt aatatttttt   5580
atgagaccat caaagagaga aagagaataa aaatattttt tatgagacca tcaaagagag   5640
aaagagaata aaaatatttt atgagaccat caaagagaga aagagaataa aaatattttt   5700
tatgagacca tcaaagagag aaagagaata aaaatatttt atgagaccat caaagagaga   5760
aagagaataa aaatattttt tatgagacca tcaaagagag aaagagaata aaaatatttt   5820
tgtatgagac catcagaaag aggtttaata tttttgtgat accctgaaag gaaataggaa   5880
tagtgtcata atcgtatcac actattgaga cagaaaaaga agaagtcgcg agaggtaact   5940
ttttgttttg caaaccggaa tatagtgtcc ggtacacttt tttaattcgt ggtgtgcctg   6000
aatcgttcga ttaaccctac tcatccaatt tcagatgaat agagttatcg attcagacac   6060
acgctttgag ttttgttgaa tcgatgagtg aagtatcatc ggttgcacct tcagatgccg   6120
atccgtcgac atacttgacc tcaagttcag atgattcctt gcacatgtct ccgatacgaa   6180
cgctaaactc tagattcttg acacattttg tatcgacgat cgttgaaccg atgatatctt   6240
cgtaactcac tttcttatga gagatgttag acccgagtac tggatgggtc ttgatgtcgc   6300
tgtctttctc ttcttcgcta catctgatgt cgatagacac ctcacagtct ttccatcagc   6360
ggattctgag atggatttaa tctgaggaca tttggtgaat ccaaagttca ttctcagacc   6420
tccaccgatg atggagtaat aagtggtagg aggatctaca tcctcgactg attccacctc   6480
gggatctgga tctgactcgg actctgtaat ttccgttacg gattggcaaa tcttatcatc   6540
ggtcggtgtt tggtcttgct ttgtgacttt gataataaca tcgattccca tatgatgttt   6600
gttttcttct tccgtacacg atgaggatga ttgctgaaga ctggcaggca catgcatgcc   6660
agtacgatat attgtttcat gattgctatt gattgagtac tgttctttat gattctactt   6720
ccttaccgtg caataaatta gaatatattt tctactttta cgagaaatta attattgtat   6780
ttatgggtga aaaacttact ataaaaagcg ggtgggtttg gaattagtga tcagtttatg   6840
tatatcgcaa ctaccgggca tatggctaca ttacccacat gataagagat tgtatcagtt   6900
tcgtagtctt gagtattggt attactatat agtatataga tgtcgacgct agagttactg   6960
tctccgaatg cggcatgata gtatcattct ttgctttcgt taactgtttg gaggaagaat   7020
ctttgttatt gcatttaatc tcgaaattca gagtgcacac ctttctcctg taaagaaacc   7080
```

-continued

```
tgaagtcgct accttattaa gaagacggga tcgcagtctt tatgattcat agtaatagtt   7140
agttccgacg ttgagatgga ttcgctgaga ccggtagtgg tcgtccgagt acacgatgtg   7200
tcgttaactg gatacaggtt aatttccaca tcgatatagt taaaggtatt tctgggtacg   7260
ggttcgcatt tatctgcgga agagacggtg tgagaatatg ttccgagacc acacggagaa   7320
cagatgacgt ctccggatac tccgtatcct attccacatt ttgtttggga aacacatgcc   7380
ttgcatccat gatcgggaga gcattcacag attctattgt gagtcgtgtt acacgatcgc   7440
gtcgacattg ttgacagaaa cgtgaccttc attcttaccg tcgtccataa atacgttagg   7500
tatgtaccac atactgtcgc gaacgatgcg tccatctcat aatgatttac tttttcataa   7560
ttaaagatgt gaaagaaaac cgaacaatat attttttag taatgtttat gcgagacata   7620
taaaataaac tccgtgttta tgatgccggt aaatgttttt atcatcttgg acggaatcga   7680
ttttgtaata tgccatggaa acaggacatt atcactccat gataaattat ttaatggagt   7740
cgatcctctc attgttcttt gcgtatctca atctgtggcg tttgcttcgt ttaaataata   7800
tatcaaacat ggagacgcct gatatgtagg cattcttcat tctattaatg tctgctctat   7860
agcgctttag ttccttatga cgaccggcga tatcatactt actttagaag gaaaatcatc   7920
atctaggatt aaggcgtatc tgatacaggc gaataatggt tcaggatata gatagcgtat   7980
atctctatta aatgcgtcaa tcatagtctc tagagtggga tggtaactca gtaataaatc   8040
aactagcttc tctttggtaa ctgcttttct ggatggccgt attgattatc gagcgtgaca   8100
ctcgctccat attccaataa ccgctttgca aattgtatat tattgacatc gaccgcgtaa   8160
tatagtagag ttatcgatca tatctatatc atccatgtac ttgcttagta tatcaaatac   8220
atcttcataa cagtgatacc cgcaattatt aaatctcgat aatatcagac cgtacataca   8280
tagacggcca ttgttagata tgtgatttac agccgcgtgt ccatattttc cacgataaac   8340
cttacgacgt ttacatcgac gagattatta ttaacaaagt tgttgtccgt cgtcttatcc   8400
aacatgcatt gaatgatagg tatacttacc atatcgccgt aatgtaagta gtttatcagt   8460
atggcttgta cgatggattc atcctgttgt ctaaatctct ttagaatgtt atcgatgatg   8520
tagtggttat attctctgga atcgtacgaa gtaatactac gcattacgtc gacaagagta   8580
tgacgtctct caataagaag attaacgatt tccatgtcta cattatatgg ggttactcta   8640
aatcgcttgt ttagataata cgcctctaat atagggctga cgtcgtatac tctacacgtg   8700
tccacatcct ttattaataa tctctatatc tatggttgag caagaccagt agtattggat   8760
ggaaacattg ttatcgatca aacatttaat tacatccttg gatagagatt ctctatgaga   8820
cgatatatag taatgaagag agttcttaca catatcactg ttgtacatac aggtacgaaa   8880
tacgtaaccg gtgctgtaac attctgattt aagaagccat agcaatactt ctggtctcgg   8940
attaggcgtc gttacgtata tatccaccaa tccgagacca ttgattgcat aattcgtatt   9000
cttggacgga cgtatccgtt tatccacaat taggtatttt agcagacgta agtcgaaatc   9060
atttatattc gacttgagtt cgttagagga attcgaatag ctggatatca gtagatgcac   9120
aatctgagat tttacgtatc tatgcttact gtatgctcct agcggagtta atccttcgtt   9180
gtttctacaa agtctctcga ctccgcgaga gagtaacagt cgaacaatct taatgtctgt   9240
atcgcattta ttggagacgt aacaatgtag cgcattgttt cctcgtctat ctatatgttt   9300
tgataagttg tgacacgttt caatttctag ttttattttt ttgtacgtca catcttcatc   9360
cagtagacga catagaatac atgtgcaatc catagctatt ctggtgctaa ttattcctca   9420
taagatgata aaaagtgtag tgagagagca tgaaggagat ttagtattta gcagtgcgga   9480
```

```
tatgatccaa gagggtgaga tagtcgttct cgttcagaat ctttcgcagc ataagtagta   9540
tgtcgatata cttatcgttg aagactcttc cagagacgat agctgattga gtacaaagtc   9600
caatgattgc acgaagttct tcggcggttt tcatggagtc atttaatgat ctccacggaa   9660
gtgaatcctt caactcacca ccaaagagct ccgttgcatc agttctgaaa gagatgagaa   9720
gcctgtagag agaccctgcg ctttctctat gggtccatct atgagaaacc cacaggatgt   9780
attcagtcag acaatgtctg acgtcggcca cggtattcag ggagtcctta gtagcgtggc   9840
aatgacaggg tctgaactgg gcacaaggaa aggccattgt aaaggtagac ctgtagccgt   9900
ttatgctaat agagggcttt aatttccatt ttttaatggg ttgtggatga ggaatgagag   9960
tgatatcata ttgagatacg tagttatgta gaggtgtatt tcctatatta tttactttcg  10020
gtttcatatt ttaccaactc tttaataaat ttcttttcac gatgcatctt attaaatgac  10080
gttttctcat aagtggacat atagatgcag aagtattacc tctatcatct acataattag  10140
ggtctgctcc taacttatac agtacgtagt agtagtttat cggttttaaa tcaagtctag  10200
aatatatagt ggattaatat atttttatat tagctaaagc atatcattct caacttcatc  10260
atgagttaaa tatttgtgtc tactagtttg tttatatcac agcattctac aaacagtcta  10320
aacaatagag aagacggaca gactttaacg tataaatgac acatgttatc gatattcgtt  10380
gataaatgat tctaacgaca tctctcgcta gagataaaat ctagtatcgt atcatactcg  10440
catagcatag tttttcataa ttaatacaat atttaaaaga cttattcgga aagtatttta  10500
atacatgtat catcgatgga gatccatatg aggagtcact tgtagttctt cagtagtgct  10560
atcatcgata gtataattat atgttgttgt aattggagta actgttggta gttcttccgt  10620
ggaatcaata attatactaa cagcaatagt ataattatat aaatatgttc cgttgatatc  10680
acatatttta atgaactcat ttctaaagcc gtacatccac atctattagg atctgatatt  10740
ttacacaact gtttaataga gtctacattt atatgttctc tatcggtgag atacaaatac  10800
ctagatagtc gcgttatagc acaaatacga tataaataat aataataatt attcagtaat  10860
gtatataaaa atgcattgtg tatttactcc aatactactg tagttgtaag ggtttttttca  10920
aaataatagt tgtgtccacg acatttatat gtattaccta tatattcttc agtaacattt  10980
tcaaagtaca aggtcgcctc ggtgataccg cctctactag ttaaaacaga gtatacatca  11040
aaatcgaatc ctataagcca tccggatgga ttttcccatt caatcagtac atcgtcaatc  11100
aataatgacg ttgacacagc agtgcatgtt atattggcag gttctcctat cgttacgttg  11160
atttttggat ctagtattag tttaaacctg tggtcttgcg acggtataac cgtaagtatt  11220
ttacatcttg attctaacgt cgtcgtaatg aacgtaacag ttgtatcttc cactatcttc  11280
taactctgga ttatgaataa ttaatttctt tcccgtttgt gaatacttaa tatcgtcgat  11340
attaatttcc ttattatctt tataccaagt tatattatta taatgttttg cgtaaagaat  11400
tccacagtat aagtctatgc catacttatc atgagtacct agttcatatg tttttggaat  11460
gcatgaagga ggttttttaa tatgagatct aactataccc tgaacacagt caccattctt  11520
tgtagttacg gtacacaaat acctacggtt actgaattta gatgtatagt tggctatcca  11580
taaatcacca tgtttaacac gtttattaga aacctgtcgc cgtctatttt tttctagcct  11640
ctcccattta accacatagt ctttatatct gtgcgataaa agactgtctt caataggagg  11700
acactttgcg ctgaatggct ctcctagagc ggctatatca ttcattgtgc ctccgaacat  11760
acatgctgga ttcaaccatt tagagtcttt agctggtaga gtatctctca ttttattgaa  11820
```

-continued gaattctgtg atttcatttt cgatgtctat ggcgtaactg tggaatagca ataacaataa 11880
tgatacgaaa tatatatgta ccatcatttt catcgtcatc ttcattatac ggcactaaaa 11940
tatttatata atatcagttt ttttacacac atcgcatgag aaaaatacaa ctatactttg 12000
gtaggtggat acgatatatt ataaagatcg ttaattgtca gcatgtataa tatttcgtat 12060
ataatttctg aaggtagtaa tgttagtaga caatttttat ctgtgaaaac aggaaatagt 12120
ttatcatata cctttgacac gtacatatct ttataatata cattaaggta tctctcattc 12180
ataatattag aatatatttt aaaggactta tcgttattat attttttaa ctcgttgagg 12240
tatcttctta actttttcga attatggcat cttaaaactg catatagtgt agtgtctaga 12300
acagtggata gtttgagcaa tattgtttct ttatgacatt tagttattat accatcgtat 12360
ttatcaaacg acatgtattt tgaaaatgcg tatcgatacg ttttagaatt gcgattccta 12420
acgtgtctat tgtaaaatgt gtcatctaaa agtatacagt aggatatgaa tttctcaaat 12480
gattttatat cgaagatagg tagagatgga agttgatcca ccaacgatct tatcacattc 12540
ttatctacaa tatatctaag tatatacagt aaacaattaa tggtatatgg ggaattttct 12600
ttgttatcta taatgagttg tgtagcgtgt ttgttattgt cggttaacgc atttatatct 12660
ccgttgatac gtataagata atctattacg tgtgtattat tatattcaca tgctacgtgt 12720
aataatgtct ttccttcata gcgggtataa atatctatat ttttaaacct attcatcaaa 12780
taagttatcg aatctgccgg acgtgtagaa tatgttttga taaactcgaa tacgattata 12840
cgacgctcat ctatcggcat ttctccaaca tttgtttcat agtgatgtat taacataaca 12900
agaatatcgt gttgtatgta gtcggaagtt atataacata gtataggcgt taatccatga 12960
ttattacata ttttgaaatt cggattaaaa gtcaacagca ttttagtcat atgaatatta 13020
ttacacattt caatactaag atacaaatgg aatggtgtat taccacaatt atctaacgcg 13080
tttagattag ctccatgttg tataaacaaa gaaataattc gcttggcctt ttttatcgtt 13140
atcggttttc tacactcacc tggtttataa acgtgtgcga gacacaaata ataataatgt 13200
aacgctgtat atccgtcttg tttaaagtta ggatcgattc ccttatctaa taaagtggat 13260
actatgttct catcgatatc ctcttccttc aataacatgt aacgagattt tatatactct 13320
agtagtaggt tggaatagtc tctatgcgat aagtggtttt tatctttgtc tatcatatct 13380
atcactacat catgtgaaat attacaacat ctagtaagca atatataaac aggcatacgt 13440
ccgctactgg ttttcatcgt tacatccact ccatgattta ataatatctt cagtacatcg 13500
tttgtaaagt aattattata caaatagcag tgtagtgcag tatacccagt tacaggttgt 13560
cgtctgttta gatcatagtt tttaactaca aaatcaagtt ctgtagaagt atggtctata 13620
ttgcaatgac taaaatatgt atatatttca ttctcttgta ttttatgagt tgattcgcgg 13680
ttgatattta aaacataaat cagacgacga ctcattttta tgatgctttg tggtaaaagt 13740
cctcatataa ttgtttaata ttcattatta tagacgattc ccattaacta atctaacatc 13800
tttgatatac ccgtaaatat gtaaatatga tcctaaaata acacggattg taagatgtct 13860
agaaagttta tgcaggtgta tgaatatgac agagagcaat atctcgatga gttcattgaa 13920
gacagatata acgatagttt tatcactagt ccagaatact atagtgcgga aaaatacatg 13980
tgtagatata ctacactaaa tcacaattgt ataaacgtac gacgatgcgc gttagactcc 14040
aagttattac atgatatcat aaccaattgt aaaatatata acaatataga attagttagg 14100
gcgacaaaat ttgtttatta tctggatctg ataaaatgta attgggtatc taaggtaggt 14160
gattcagttc tatatcccgt tatatttata acacatacaa gcactagaaa tttagataaa 14220

-continued gtctctgtaa aaacatacaa gggcgttaaa gtaaaaaaac ttaatagatg cgcggatcat 14280
gctattgtaa ttaatccatt cgtcaagttt aaactaacgt tgccgaacaa aacaagtcat 14340
gcaaaggtat tggttacatt ttgtaagtta agaacggata taacgcagat agaggcaccg 14400
ctttcgggca atgttttagt ttatacattt cctgacatta ataaaagaat tcctggatat 14460
atacatgtca acatagaagg atgtatcgat ggaatgattt atataaattc ttcaaagttc 14520
gcgtgtgttt taaaactaca tagatcaatg tatcgcattc caccctttcc tatagatatc 14580
tgctcttgtt gttcacaata tattaacgat gacatagaaa ttcccattca tgatttaata 14640
aaggatgtgg caatttttaa aaataaggag acggtatatt atctaaaatt aaataataaa 14700
actatagcta gatttacgta ctttaataat atagataccg caattacaca agaacatgag 14760
tatgtcaaaa tagcactagg tatagtctgc aagttaatga ttaataatat gcatagtatc 14820
gtgggagtta atcatagcaa tacgttcgtc aattgtttgt tggaagataa tgtataaaaa 14880
ttcttataaa ctcaattgac atggaaatgt aacaacatac attcacgtta tactaacagt 14940
aactgttttg ctgatgctag gaatagtaaa cgccatacac gtaaacgttg tagcatcttc 15000
ttccttgaca ggattaatgt ttaaccggga tgtaataaca cgtctcttat cggtcatata 15060
gattttattt gctacactta ttctaccgtc tccgtcccca tcatcttctt cgtaatacat 15120
accattactt atccaaaaga cgtctgcatc cgttgtggga ggtctcaacg atactctaca 15180
cgcaatagtc aaattactac ctattgaagt tacaacacct tctggtaatt gcatagtaga 15240
aggtattatt ttatcccgta cctctaattt tacaattctg gttacgttat atgttttgcc 15300
accgtatata tattctaaaa cacatgtata ataaccagca tcatttttc taacatcttc 15360 tatggtaata attccaggtg tccgttgttt aagtctctta tttctaaggc gtcgatgccc 15420
gctccatata atatctgcgt ttacgttact agcaataaat gcattaatat tgggacatac 15480
catttcgcca gtagatctct catttactat ttgtggatac gagataagat ctatatttga 15540
ttctgagaca gacacgattg tcaaatttaa cgacatcatg tcacagtagg tttcgttcgt 15600
ggtaatgcat atataaatac cagagtctga ttgtgtcggg ttcagaatta gcatattgct 15660
accattatct atcggtataa ttctatcatt atccgctcct cgtttttccc ataaaatatc 15720
taatatatta tatccggatg atagcgtatt tatttgagga catggtaaga ttactggctc 15780
gttttctaac tccatgaatg atgcaaaata ttgccctttg tcgatacatt caggcgcgtt 15840
aaaagtctga acgaatgaag aataaaaaaa tatagaaaga aatataacag gtagtatact 15900
cattttattt tatagtgggt aaaaaaagtt tgtttctggg aaagggagaa gagaagaaag 15960
aagaaaatgt caagatgtac aactcatcaa ttcatacgcc ggaatatgat gttataatcc 16020
acgtaattta gcatctcaag catcacaaac aatgcgttca gactgttact agtgggatgg 16080
tcttcacctc cccagtaagt agcagcatat gcacaaagtc cgatgatggt tttttgctca 16140
tccggtatat aacaacggat gatttctaca caatctttga catcatccca cggcatattt 16200
tttaccagct cgcgaatgtc gatgaacact aattccgcat catctctaaa agagaggagt 16260
gtggaataca attgtccagc gcattgcctg ttgcggtatg cataggacga ccaataaata 16320
tattcagtca aacattgttt gacgtcatca atactggtca gtctgtcaca tccacagtgc 16380
tgtggtgaaa agacgtgggt actaaagttg gccgtcatct taccaattgc aattggaaga 16440
ataacgacct gcactaatac cacatgtttt ttctattttt ttaaaaaaaa tggttaacaa 16500
ttagttgtcg gagagcaata tctaccaacg aaaaaaattt ttccatcaac atgcctaatc 16560

-continued

```
acatagatga acggatgatc tacacagaac tcatttgtaa ttgttgatgc acagtctgac  16620
accagtgcac aagttgctgc agctgcttct gtatactctt cattgacatc tatatacgtt  16680
ttgtggatca tagcgtcgac actcacatct aaattacaca tattgctata atctccagtt  16740
gaaccgaaca cctctgtcag tcctgacttt actagagtat ccaccagatt atacgagcct  16800
gttaccttaa acttgggaat gtgaacatcg ataaacgtag cttccagaga gttacaccat  16860
ttcttaaaat ttgtatctgt tagattttgt tctatggatt ctaatccatc aatcttgtct  16920
ggaagaatga ccatcatact agtatctcca acatatggca gttctatgat tgaaaagtta  16980
ccgaatgatt cttttacaga tgcgtgatta aatagctcgc cgtacataga catcatactt  17040
acgtctacca tttccgttgg tgatacgtaa aagggataat cactggtaaa ttccttttcg  17100
aatggcgtca accattttgc tttaaagtat acggcactaa ttgctaggag acaattgttc  17160
atccaatagt ggattgattt tcccctcagt aaagatatct acacacttgt tgattgcatc  17220
tatagtgcga caatcagtga agtcaacagt ttgaaactta tcgccaattt ttctcaaaaa  17280
ggaatcttta aacacggcag aatatcgccc atatacttta ttcatggatt tgaatgagat  17340
attctgagcg ctaaccttat ccgtgttctc ctccttttct acatattttg atagctgttc  17400
agcagtggat ccattagctc cataatacag tattgtcaat actgacgaga ttgacgctgg  17460
agaaatgaat acattctctc ctttcataga agatatccat agtaatcgat attggtcgtg  17520
tagcgcgata gagatagtct aatattaata ttagatatcc gtaacactac cacactctat  17580
aaaaaaagaa tatttcaatc ttgtataaac agtctacgta gtctgtcata attaggagtt  17640
tgagaataat ctaacgtgta tactaattct atatatctaa ctaattccag aggttcattt  17700
ccttcaggaa aacagtcctc aaagaaagta gctataaatt ttttatattc tttttttgt  17760
tttattactt ttatactact ttcgtttttc catggaagtt tgccaccgaa ccattctatc  17820
atgcaatatc ccaacatttc taaatctcct cgttttgaaa ctgttgctcc aagatgattg  17880
tctacacaca tataattgat atttcctgaa gttatcatgt cctcgttgta atctatatgt  17940
gagtttccac tcttgtatag tttgttagtt ctagaatagt caattagtga aagacgttta  18000
tttctaatca gtatattcct cggttctatt tttccatggg taaatcctcg agagtgtata  18060
aactctaacg tgtttatcat agtgacgcat gcttcgaaga ctgattcagt atcctttggg  18120
gcgaatactc ttcccaaatt ctttataacg aagaacatat aatcatcggt ttctccaatt  18180
ccatacagat ctggaatagc caaatacttt ataccacgtt cccgtgtcca gttgtcgata  18240
gtcaaaggat ccaatacaga tatatagaat cgtatttcag acaacaatgg cttgtgtgat  18300
ttgtgatcta tcttcattac gtaattgtag aacgaactag tgaaattttt tctgacctta  18360
tagagtattg aattaccaga atataaagta tttccgataa tccatttctt gccatcgtta  18420
tcaaaacaat acttgaagga ttccatgcct gctatgtaat aacgagttgt tttttatgtt  18480
ttgtattgat tataaaaatt agtagatatg atctatattc ctacatcgtg actgatacat  18540
tctataactt ctttatcaat ggaatcacta ttactacttg tattaataac gagtgcttct  18600
ctaatatatt cattgggatg attcttgtta atgtttttat tattttcaat ttctacattt  18660
tttagtattt cttctttctc tctatctatt tcattcatga tatcttctac atttgtaaca  18720
tctgtatctg tatccatgtt agtagtaagc aataaaacta tagggtaata ctgctataca  18780
taaaaactat ttatatttc attttcaatc aataaggaga agttgataat gcctttatag  18840
cggggagacc atcatacttt tccacatatc caatgtcctt actaaataca tagaagacgt  18900
tatttagttt acacaatgat gatatggata tcttataaat agtatatgaa atatcaaacc  18960
```

-continued

```
acttattcgt tctaggattg taacaagata tctcgttgtt tttctctaaa ttaccatatt  19020
gttcggtaac ggatagacct ccggcaaaat ataacattcc aaatgtcgag tcgatgccgt  19080
gatataccct agccataggc atttctataa tcgaccattg tttgtcttta taaatgtcaa  19140
gtttttccat attgttaacc acgatcgtgc tattagagtt atttatgaat aatccgccag  19200
ttacgaaaat agtattatta acggaaacag cggacacatt gcttttttta taatttatcg  19260
gtgtttcgta tatccctgaa tccattgcct tcacttgcag ttgggagatg aacactgcaa  19320
tcagttcttt cgggatagaa atctttggca attatacaca accctatttt caatccccat  19380
gtttcctctt cagtcttctc acatcgtcta atagacatgg agtagatgat agaggggaac  19440
agaaggacta taatcaggga cctcatcttg aaaatggtta gagcctataa gggcgttaac  19500
cagtgtataa tatgcagttt tatttcgttt ttgtatcatt aataaaaatt agttatgaat  19560
atttagtcaa gttaagcatg ctaagaaaag tggtaacatc atttgatgtg ctaccgagaa  19620
atttagttaa attttctctt gataactctg gccattttgt ccttgaaatt gggaacatct  19680
tctttggatc taattgcgca tgtatataca ctctttttag gtgtcagaca tactttcgaa  19740
ctccatggag taatttttc gagaaaccct tctgtggctc cctgtgctgt cacgcacact  19800
ttttctgttg tgacaaagtc tatgctgcaa cctgtagacg tgcaatcgta gtcatcgata  19860
tcatatggta ctggttcttt agaatctccg aatgtgaagt tagccgtata caacaagtag  19920
atatcacaca tgtcaccgcg tttgtaaata ggaatctttt tgctacctct agtagcatac  19980
ggatggtcgt cgtattcagt taatgttaca gtcggtggtc ccgtacaata ctcttccact  20040
ttataatcgc cttgttcaaa tttaacccag aaagatacga aatcattctt tggaaatgcg  20100
gatatgtcgt atgttccttc tggtacattt gtatacattg tttgccacgt cttgatgcca  20160
taatttttaa gggatatatt gtatagacca tccccagtcc attcaatttt ggaatcaaaa  20220
ttgacggatt caaacttata actagttatt ttagcgtgta tactattaat gaacaaaact  20280
gcgagaatta taatatatct catggtgttg tttgttattt gactactgtc actgaagtga  20340
taatatattt taaattttta aaaatcatat tttgaataat atgtattact atgtccatga  20400
cgatcaaata tataagtaga tccaatttta agagtatgtt ttctcaatag agtatcatcg  20460
ttgatcatac ttatttcata ttttattcct ttatagcatt ttccctctgc agtaatagaa  20520
tattgtcgct catcaccatc atatttgtga atataagggt acttatcata atggcatgat  20580
aatttggtag atattctaca cgtgtgacct ctgcgttgaa tagtagacat atcaataatt  20640
ttatagtcgt ttataacatc tatatctatg gaatcaaatc cgacgtcgca tgactctgta  20700
ataatagaaa ttgtgtactc tttaaaattt aacaccaatt cattattatc atcagtatat  20760
gaattttcta tattatctac tccatctata tagagtttta cactcagttt attaaacgga  20820
gtgtactcat tattcgaata ggatgctaat gcacctatta caaataaaaa cgttattagt  20880
tttttataca tttaaaatct taaaatttta actagtatat tgaaataatt atttatacaa  20940
actaactaga tgcatcaaca gataataaca aacacctcca gcgatcgtgc caatagtagt  21000
tagagatgcg tatccgtaca acttgttaat catatttcta cggatgtata taccatcgtc  21060
gttaaaagcg cttctatatc tctcattagc tagaattata gatacgctat taattatatc  21120
atacattagt tgattgttga tactattttt attgtaatcg aaaaacattt ccatgaatag  21180
tattccggtg ccaacgctta cagaaacatc gcgttcattc atcattatac cattaagtgt  21240
atccatcacc cattgtttaa cacgtgattc atttggcata gtacgtacta tatcatcgaa  21300
```

-continued cggtataacg gcgcatcttg taaatagcct gtatatatta tgtaatatgg cgttacttct 21360
tccatacaca ataaatctct tgttataata gtgcctgagt aaaaatgctc taacggcatc 21420
gtagatatca acatccactg aagaagacat ctcaattgat tctagctata agtctttaat 21480
cttttgatac ttgtttgtta ttaaattatt aattattaat tattcattat tttaacggat 21540
ttatattcac ggtagcaatt tatggaactt atattggtca ttatttttgt cacaggaaca 21600
aactaatact ataacggaga ttaaaaatat gacgcccata attgttaacg ccactatgat 21660
tatatgataa gttgcttcta acgattctat ttcttgttca tattgtacaa cgtctttcga 21720
gagtttgctc aaatctgtct catcgtcggg accatcatcc actggatcaa atttttcgtt 21780
agatcgtaca catgttggga gtatgggatt ccatttaccg tcgatacatg tggatgatgg 21840
agatcccgtt agtataaaac cacttttaca actaagatgt ataacgccac cgatagaaaa 21900
tgtagatccg gaaattaatc cattagatag agacggtata tcacattttt gttgacatga 21960
tggaataaca ttccaagaat tagctgtaca acttatgtac gaagcaccaa taacctcata 22020
tccaacatca cagttgatag ttatatattc cccaaatgag tatttttctt taactggttg 22080
acacgatccg tgttctaatt gaagaggttg acattccgca ttaggacacg taacagtatc 22140
attccaagaa gtatttccat ttttttcttc gcaacgaaaa tattttgttt cgccgttgca 22200
acttagtgtc atggtggaat tcacttcgta tagcggttta ttatatagtt cagagatgta 22260
atcagaaact gtgcacattt ttttgcatgg attttcgtat ttccatttat ctgtttcgca 22320
gacagcattt ggatccgaag aatgatatcc ctgatcacat gtaaacgtaa ctttctggtt 22380
attattaaac gatgtttcgg tagacgttaa tttagcgtta ttcatagtgg gtacagtaca 22440
tgttgaataa acaacagcag gtagtacgca taacaacgta acaacggaaa tcgttttcat 22500
ttttatttat gagcgttaaa aatagtatac actgtcgagc actaaaagga aacaatgatg 22560
tagtgtgatt ttatatttta atagtgttta taagattttt agatatgtgg acagttcgtt 22620
atcgttatat tttatttcgt taggaaaaca cgaccattta tctccaggat ccagcttctt 22680
ggataataga ctaattaatc tctgacgata tctaatagat gctatgatat tacgtacacg 22740
acttccgtat acgtcgagac tagtgcactt cacgaaagaa ggatgtttac cgtatctcat 22800
taaagtatta atgtctttga tacaaaaaac taattggaat acagttttat tttttatata 22860
acatctcttc atgatatcta tttcatcgaa acatcttaaa atataccatt tatattgctg 22920
tagtgattgt acatctataa gagtatcata atcggtcata cacgcagtat attttataca 22980
cattttcaat aaatctgcat tatgctgttt atgtttagta attgctatca tagactgtat 23040
cataattttc aaagatggtc gtttagacaa tagtacttcc attattattt tgttgttgtt 23100
tgcgactgct tccgaaatac atgtacatcc actagtagta atcgtctcaa aatcaccatt 23160
tctgtttaat agatagacca acgtattata cgcattataa ctgacagcgt cgtaaatagt 23220
acgatagtta atatcaataa ctcctctgga taatagataa tctaaagatt caacagcatc 23280
aaaaattatt aaatgacgaa ctatatgttc attatctatt tctaactctg tgtctgattc 23340
caaatatagt tttataagcg agataccgtg tataattcca caataaaatg gagtagttcc 23400
gaatttatta cgcgcattaa catttgctcc tttagaaatt aataacttta caaaatcata 23460
tttattacga catgagacat aatgaagagg tgtatatcta ttaaagtcta cagagtctat 23520
attagcattc tctaaacata tctcaaacaa ttccacgttg ttgatatcgt gtttacataa 23580
taggataaaa ggtgtgtttc cgtacgtatc ttttttatct acatctgatc cattatttaa 23640
caatatctta attaattcat tgtatgattc tgattctgat tctgatttct tatagtgata 23700
tatacatcta tgtaataatg tacaaccgta actgtcttcg gcatctatat aaaatacata 23760
tatagatatt aactgtatct gatatatagg acaaaaaatg tcttgttcta cgtccatttt 23820
caagcattag tcttatccta ttatctggat gatcattatt aactaattga tatacatatt 23880
cttttatatt aatggatgat gataacctga gattgtgtat aaatgacccg ttcttattaa 23940
tatttaatac tctatctaga aaaaaaatta taatattcgt attagcatca tccatagaat 24000
aaatatgtag aatattttcc ccatattcta aaatatggaa taaatttggc aacctagata 24060
aaaaatcaac tattgtttta tccactttct cgtatgttcg aacgagatta taatcctgta 24120
ttatatggga tgtggaaaaa ttggaaaaca cgcgtgctat ataatgaaga gataaatata 24180
cactccagtc aagtatttcc tttttaaaaa aaatccatat ataatttata ttctgtaaca 24240
tgttatccct tttcaattaa caatgttggt ttataaaaaa ttaaagaagc gaatcaatga 24300
ttaatagatg ttaagaacta taattacgat gtattaatag gtatagttag ttagttaaaa 24360
agagataaca gttactaatt aattgttagt tattgtctat atgatattac aacctattat 24420
ttgttctcta tagttacatt aattaaaatt ttatatgtga cacctattca tctggagaat 24480
acttcttgat accatgattc tggccaatct gcaaacacag cacaacagca tctttccact 24540
ttgatagcgc acacgtatgt cgaggtagcc tcatccccag gtttatatac cttgatgaat 24600
cgacacgtgt acttgatgtc ctctttcttc tcacagaaat acacaacaca aagtcttttg 24660
atatgctttt ctatatcatt ctctatcagt ctgaggtagt cgtaacccac cgtgaatcca 24720
aatactttgt gtgtattatt atcaactcca atgaacaaat atccaccctc tgtgttggca 24780
aaagatgaga gtatacgtgt tcttagttgc ttagctgaaa cagatgtatg tttaacatta 24840
atagatttac cagcctgaag ttctgatcta ttgaagaact cctctaccaa tctctcaatt 24900
gattcagtgt cttccactcc atctggatat tcaaattcct gcatttctgg tctgggactc 24960
catccacctg attccttcag ttcgctaaga tactcatttg aatgcatgat cccatagtct 25020
tcatgtacaa atttgttttt acagtactcg gtataagatt ttgattagac aaatgcgtat 25080
gcacataaca gcattcttta ccattcacaa tatcaaaatg atcatataca acagaccaca 25140
tatggcgtat agattccaaa cgtttcatga gtacatgatt cacactgtct tccagagagg 25200
tggttacctc gatggtgccg ccgatatagt agaagaaaga ttttctgtat cattctcccc 25260
aagtttaact tttaccagat ttgggatcgg aagcaccgca ccctttttga atctcattct 25320
cataatttcc tttccatgta cgtccacagc agtaacttga cagatacaat ctcctatcca 25380
gacgtggtaa tcgatgatag gtcctgaact gagtgcattc atttctttgg ccttctcttt 25440
gatagtagaa taatcatgtt gaacttttcc atatacagcg ttttctgttt caagtacgtg 25500
atgatgaatc cctactcctt ccaaacacaa gtctagactc tcgtacccga ttccgcttag 25560
agcatagtag tttttgtggc gatatgtgat ttccttcttg atcatggatc ggatctccaa 25620
tttgtagata ttcattgcac tcaaacatag gcagcagtgc tccaatatat ctcttgttca 25680
cctgactgta acaccacata tatttgtctt ttacaatgtc atacttgtta ttataaactg 25740
acatcattgg caacagtcga tgatattcca ggaaaggcat gaagattctc gtcgtaccca 25800
ccgagagcgt gtgcgtaaaa catcgccatg atttcggttg tacacacgag atcaataata 25860
aattaagtta ttttttaatt tttatcgaca aaaattttac atcaaccaaa caccacactt 25920
aataatatac accctgcatt aatatgtgcc gaaacttgtc gtaattgggt tcctcaaaat 25980
atgtcaaaga gtttaccatg gtaatatatt gcagcaattc tctaggtgca tattgcaaac 26040

-continued

```
tggtcattaa caaagtcgca gtattgttaa catatttctg ttttgtggca cttactaatg  26100
cacaattctt tgtttcagat atcttagtcc atggcaagat acctcccaac catctaatca  26160
tacaatatcc aagtgtttct agatctccac gtctagatac aacgtatcct ttatgcgaat  26220
ctataggtgt aaattctaga gtaccgttat ccattttatt tggatttctt ataaatggaa  26280
catgttcgcc attagacatg aatttagaaa ccaatccgta atccactaga tataatttat  26340
tcttatctat ttgatccaag actatattac tcgctttaat atctccgtga gaatatcctt  26400
gctcgtgcat aaattgtatg gtatttaaga tttcgattcc gatcaacatc accgaccttt  26460
ttggtaatct attattattg gctctgatca ccgcatctag atctgcacct aatctattaa  26520
ttaccaagaa tcgatattcc acattaatgg atttgtatag accaaatgcc ttgcacgtga  26580
taagacctac gtgctttata ttgtgagatt ttttccattc ttcgataacg gatggtttaa  26640
gtactctagt ataaaatgcc tgttcggtaa ataatgatcc gttagctttg ggctctattt  26700
ttactacata attattgtca ttagtagtat aaatactacc aaatccacct tttcctatta  26760
atggtccaac gacccattga tttttgcaat tgtcagttaa cacaagtcct tgaaagttca  26820
taatgtgtga tctatctgtc aatgaaatat cattttaaat tttaagtttt acgtggtaag  26880
ttttaatatt taactaatac attagacgtt gaaatagcca catataaaaa cgagttatat  26940
tattaattat caagttttaa gtcttaagtc tctaattagt gttaaaatac attctaatac  27000
ggtcctgtag tatctgaatt aacttactat atgctaaatt cacatcatct tcaatgataa  27060
tagtgtcgaa tagaccggct tcacctgcct catccatgtc agtttttgat tcttgaattg  27120
gttcctggta tcattaggat ctctgtctct caacatctgt ttaagttcat cgagagccac  27180
ctcctcattt tccaaatagt caaacatttt gactgaatga gctactgtga actctataca  27240
cccacacaac taatgtcatt aaatatcatg tcaaaaactt gtacaattat taataaaaat  27300
aatttagtgt ttaaatttta ccagttccag attttacacc tccgttaacc ccacttttta  27360
caccactgga cgatcctcct ccccacattc caccgccacc agatgtataa gttttagatc  27420
ctttattact accatcatgt ccatggataa agacactcca catgccgcca ctacccccttt  27480
tagaagacat attaataaga cttaaggaca agtttaacaa taaaattaat cacgagtacc  27540
ctactaccaa cctacactat tatatgatta tagtttctat ttttacagta ccttaactaa  27600
agtctctagt cacaagagca atactaccaa cctacactat tatatgatta tagtttctat  27660
ttttatagga acgcgtacga gaaaatcaaa tgtctaattt ctaacggtag tgttgataaa  27720
cgattatcgt caatggatac ctcctctatc atgtcgtcta ttttcttact ttgttctatt  27780
aacttattag cattatatat tatttgatta taaaacttat attgcttatt agcccaatct  27840
gtaaatatcg gattattaac atatcgtttc tttgtaggtt tatttaacat gtacatcact  27900
gtaagcatgt ccgtaccatt tattttaatt tgacgcatat ccgcaatttc tttttcgcag  27960
tcggttataa attctatata tgatggatac atgctacatg tgtacttata atcgactaat  28020
atgaagtact tgatacatat tttcagtaac gatttattat taccacctat gaataagtac  28080
ctgtgatcgt ctaggtaatc aactgttttc ttaatacatt cgatggttgg taatttactc  28140
agaataattt ccaatatctt aatatataat tctgctattt ctgggatata tttatctgcc  28200
agtataacac aaatagtaat acatgtaaac ccatattttg ttattatatt aatgtctgcg  28260
ccattatcta ttaaccattc tactaggctg acactatgcg acttaataca atgataaagt  28320
atactacatc catgtttata tcatcaatat acggcttaca aagttttagt atcgataaca  28380
catccaactc acgcatagag aaggtaggga ataatggcat aatatttatt aggttatcat  28440
```

cattgtcatt atctacaact aagtttccat tttttaaaat atactcgaca actttaggat 28500
ctctattgcc aaatttttga aaatatttat ttatatgctt aaatctatat aatgtagctc 28560
cttcatcaat catacattta ataacattga tgtatactgt atgataagat acatattcta 28620
acaatagatc ttgtatagaa tctgtatatc ttttaagaat tgtggatatt attacgtaaa 28680
ctattacaca attctaaaat ataaaacgta tcacggtcga ataatagttg atcaactata 28740
taattatcga ttttgtgatt tttcttccta aactgtttac gtaaatagtt agatagaata 28800
ttcattagtt catgaccact atagttacta tcgaataacg cgtcaaatat ttcccgttta 28860
atatcgcatt tgtcaagata ataatagagt gtggtatgtt cacgataagt ataataacgc 28920
atctcttttt cgtgtgaaat taaatagttt attacgtcca aagatgtagc ataaccatct 28980
tgtgacctag taataatata ataatagaga actgttttac ccattctatc atcataatca 29040
gtggtgtagt cgtaatcgta attgtctaat tcatcatccc aattataata ttcaccagca 29100
cgtctaatct gttctatttt gatcttgtat ccatactgta tgttgctaca tgtaggtatt 29160
cctttatcca ataatagttt aaacacatct acattgggat ttgatgttgt agcgtatttt 29220
tctacaatat taataccatt tttgatacta tttatttcta tacctttcga aattagtaat 29280
ttcaataagt ctatatcgat gttatcagaa catagatatt cgagtatatc aaaatcattg 29340
atatttttat agtcgactga cgacaataac aaaatcacaa catcgttttt gatattatta 29400
tttttcttgg taacgtatgc ctttaatgga gtttcaccat catactcata taatggattt 29460
gcaccacttt ctatcaatga ttgtgcactg ctggcatcga tgttaaatgt tttacaacta 29520
tcatagagta tcttatcgtt aaccatgatt ggttgttgat gctatcgcat tttttggttt 29580
ctttcatttc agttatgtat ggatttagca cgtttgggaa gcatgagctc atatgatttc 29640
agtactgtag tgtcagtact attagtttca ataagatcaa tctctagatc tatagaatca 29700
aaacacgata ggtcagaaga taatgaatat ctgtaggctt cttgttgtac tgtaacttct 29760
cgttttgtta gatgtttgca tcgtgcttta acatcaatgg tacaaatttt atcctcgctt 29820
tgtgtatcat attcgtccct actataaaat tgtatattca gattatcatg agatgtgtat 29880
acgctaacgg tatcaataaa cggagcacac catttagtca taaccgtaat ccaaaaattt 29940
ttaaagtata tcttaacgaa agaagttgtg tcattgtcta cggtgtatgg tactagatcc 30000
tcataagtgt atatatctag agtaatgttt aatttatcaa atggttgata atatggatcc 30060
tcatgacaat ttccgaagat ggaaatgaga tatagacatg caataaatct aattgcggac 30120
atggttactc cttaaaaaaa tacgaataat caccttggct atttagtaag tgtcatttaa 30180
cactatactc atattaatcc atggactcat aatctctata cgggattaac ggatgttcta 30240
tatacgggga tgagtagttt tcttctttaa ctttatactt tttactaatc atatttagac 30300
tgatgtatgg gtaatagtgt ttaaagagtt cgttctcatc atcagaataa atcaatatct 30360
ctgttttttt gttatacaga tgtattacag cctcatatat tacgtaatag aacgtgtcat 30420
ctaccttatt aactttcacc gcatagttgt ttgcaaatac ggttaatcct ttgacctcgt 30480
cgatttccga ccaatctggg cgtataatga atctaaactt taatttcttg taatcattcg 30540
aaataatttt tagtttgcat ccgtagttat cccctttatg taactgtaaa tttctcaacg 30600
cgatatctcc attaataatg atgtcgaatt cgtgctgtat acccatactg aatggatgaa 30660
cgaataccga cggcgttaat agtaatttac tttttcatct ttacatattg ggtactagtt 30720
ttactatcat aagtttataa attccacaag ctactatgga ataagccaac catcttagta 30780

-continued

```
taacacacat gtcttaaagt ttattaatta attacatgtt gttttatata tcgctacgaa  30840
tttaaacaga gaaatcagtt taggaaaaaa aaatatctat ctacatcatc acgtctctgt  30900
attctacgat agagtgctac tttaagatga gacatatccg tgtcatcaaa aatatactcc  30960
attaaaatga ttattccggc agcgaacttg atattggata tatcacaacc tttgttaata  31020
tctacgacaa tagacagcag tcccatggtt ccataaacag tgagtttatc tttctttgaa  31080
gagatatttt gtagagatct tataaaactg tcgaatgaca tcgcatttat atctttagct  31140
aaatcgtata tgttaccatc gtaatatcta accgcgtcta tcttaaacgt ttccatcgct  31200
ttaaagacgt ttccgataga tggtctcatt tcatcagtca tactgagcca acaaatataa  31260
tcgtgtataa catctttgat agaatcagac tctaaagaaa acgaatcggc tttattatac  31320
gcattcatga taaacttaat gaaaaatgtt tttcgttgtt taagttggat gaatagtatg  31380
tcttaataat tgttattatt tcattaatta atatttagta acgagtacac tctataaaaa  31440
cgagaatgac ataactagtt atcaaagtgt ctaggacgcg taattttcat atggtataga  31500
tcctgtaagc attgtctgta ttctggagct attttctcta tatctaattt ctgaacgttc  31560
accaatgtct ctagccactt tggcactaat agcgatcatt cgcttagcgt cttctatatt  31620
attaactggt tgattcaatc tatctagcaa tggaccgtcg gacagcgtca ttctcatgtt  31680
cttaatcaat gtacatacat cgccgtcatc taccaattca tccaacaaca taagcttttt  31740
aaaatcatca ttataatagg tttgatcgtt gtcatttctc caaagaatat atctaataag  31800
tagagtcctc atgattagtt aacaactatt ttttatgtta aatcaattag tacaccgcta  31860
tgtttaatac ttattcatat tttagttttt aggattgaga atcaatacaa aaattaatgc  31920
atcattaatt ttagaaatac ttagtttcca cgtagtcaat gaaacatttg aactcatcgt  31980
acaggacgtt ctcgtacagg acgtaactat aaaccggttt atatttgttc aagatagata  32040
caaatccgat aacttttttt acgaattcta cgggatccac tttaaaagtg tcataccggg  32100
ttctttttat ttttttaaac agattaatgg tgtgatgttg attaggtctt ttacgaattt  32160
gatatagaat agcgtttaca tattctccat aatggtcaat cgccatttgt tcgtatgtca  32220
taaattcttt aattatatga cactgtgtat tatttagttc atccttgttc atcattagga  32280
atctatccaa tatggcaatt atactagaac tataggtgcg ttgtatacac atattgatgt  32340
gtctgtttat acaatccatg ctactacctt cgggtaaaat tgtagcatca tataccattt  32400
ctagtacttt aggttcattg ttatccattg cagaggacgt catgatcgca tcctaaaaaa  32460
atatattatt tttatgttat tttgttaaaa ataatcatcg aatacgaatc atccagtcca  32520
ctgaatagca aaatctttac tattttggta tcttccaatg tggctgcctg atgtaatgga  32580
aattcattct ctagaagatt tttcaatgct ccagcgttca acaacgtaca tactagacgc  32640
acgttattat cagctattgc ataatacaag gcactatgtc catggacatc cgccttaaat  32700
gcatctttgc tagagagaaa gcttttcagc tgcttagact tccaagtatt aattcgtgac  32760
agatccatgt ctgaaacgag acgctaatta gtgtataatt tttgtcatat tgcaccagaa  32820
ttaataatat ctctaataga tctgattagt agatacatgg ctatcgcaaa acaacatata  32880
cacatttaat aaaaataata tttattaaga aaattcagat ttcacgtacc catcaatata  32940
aataaaataa tgattcctta caccgtaccc atattaagga gattctacct tacccataaa  33000
caatataaat ccagtaatat catgtctgat gatgaacaca aatggtgtat taaattccag  33060
tttttcagga gatgatctcg ccgtagctac cataatagta gatgcctctg ctacagttcc  33120
ttgttcgtcg acatctatct ttgcattctg aaacatttta taaatatata atgggtccct  33180
```

agtcatatgt ttaaacgacg cattatctgg attaaacata ctaggagcca tcatttcggc 33240
tatcgactta atatccctct tattttcgat agaaaattta gggagtttaa gattgtacac 33300
tttattccct aattgaaacg accaatagtc taattttgca gccgtaatag aatctgtgaa 33360
atgggtcata ttatcaccta ttgccaggta catactaata ttagcatcct tatacggaag 33420
gcgtaccatg tcatattctt tgtcatcgat tgtgattgta tttccttgca atttagtaac 33480
tacgttcatc atgggaaccg ttttcgtacc gtacttatta gtaaaactag cattgcgtgt 33540
tttagtgata tcaaacggat attgccatat acctttaaaa tatatagtat taatgattgc 33600
ccatagagta ttattgtcga gcatattaga atctactaca ttagacatac cggatctacg 33660
ttctactata gaattaattt tattaaccgc atctcgtcta aagtttaatc tatataggcc 33720
gaatctatga tattgttgat aatacgacgg tttaatacac acagtattat ctacgaaact 33780
ttgataagtt agatcagtgt acgtatattt agatgttttc agcttagcta atcctgatat 33840
taattctgta aatgctggac ccagatctct ttttctcaaa tccatagtct tcaataattc 33900
tattctagta ttacctgatg caggcaatag cgacataaac atagaaaacg aataaccaaa 33960
cggtgagaag acaatattat catcttgaat atttttatac gctactatac cggcattggt 34020
aaatccttgt agacgatagg tagacgctga acacgttaac gatagtatca ataacgcaat 34080
catgatttta tggtattaat aattaacctt atttttatgt tcggtataaa aattattgat 34140
gtctacacat ccttttgtaa ttgacatcta tatatccttt tgtataatca actctaatca 34200
ctttaacttt tacagttttc cctaccagtt tatccctata ttcaacatat ctatccatat 34260
gcatcttaac actctctgcc aagatagctt cagagtgagg atagtcaaaa agataaatat 34320
atagagcata atcattctcg tatactctgc cctttattac atcgcccgca ttgggcaacg 34380
aataacaaaa tgcaagcatc ttgttaacgg gctcgtaaat tgggataaaa attatgtttt 34440
tatatctatt ttattcaaga gaatattcag gaatttcttt ttccggttgt atctcatcgc 34500
agtatatatc atttgtacat tgtttcatat tttttaatag tttacacctt ttagtaggac 34560
tagtatcgta caattcatag ctgtattttg aattccaatc acgcataaaa atatcttcta 34620
attgttgacg aagacctaat ccatcatccg gtgtaatatt aatagatgct ccacatgtat 34680
ccgtaaagta atttcctgtc caatttgagg tacctatata ggccgtttta tcggttacca 34740
tatatttggc atggtttacc ctagaatacg gaatgggagg atcagcatct ggtacaataa 34800
atagctttac ttctatattt atgtttttag attttagcat agcgatagat cttaaaaagt 34860
ttctcatgat aaacgaagat cgttgccagc aactaatcaa tagcttaacg gatacttgtc 34920
tgtctatagc ggatcttctt aattcatctt ctatataagg ccaaaacaaa attttacccg 34980
ccttcgaata aataataggg ataaagttca taacagatac ataaacgaat ttactcgcat 35040
ttctaataca tgacaataaa gcggttaaat cattggttct ttccatagta catagttgtt 35100
gcggtgcaga agcaataaat acagagtgtg gaacaccact tacgttaata ctaagaggat 35160
gatctgtatt ataatacgac ggataaaagt ttttccaatt atatggtaga ttgttaactc 35220
caagatacca gtatacctca aaaatttgag tgagatccgc tgccaagttc ctattattga 35280
agatcgcaat acccaattct ttgacctgag ttagtgatct ccaatccatg ttagcgcttc 35340
ctaaataaat atgtgtatta tcagatatcc aaaattttgt atgaagaact cctcctagga 35400
tatttgtaat atctatgtat cgtacttcaa ctccggccat ttgtagtctt tcaacatcct 35460
ttaatggttt gttagattta ttgacggcta ctctaactcg tactcctctt ttgggtaatt 35520

-continued

```
gtacaatctc gtttaatatt atcgtgccga aattcgtacc cacttcatcc gataaactcc  35580
aataaaaaga tgatatatct agtgtttttg tggtattgga tagaatttcc ctccacatgt  35640
taaatgtaga caaatatact ttatcaaatt gcatacctat aggaatagtc tctgtaatca  35700
ctgcgattgt attatccgga ttcattttat ttgttaaaag aataatccta tatcacttca  35760
ctctattaaa aatccaagtt tctatttctt tcatgactga ttttttaact tcatccgttt  35820
ccttatgaag atgatgtttg gcaccttcat aaatttttat ttctctatta caatttgcat  35880
gttgcatgaa ataatatgca cctaaaacat cgctaatctc attgtttgtt ccctggagta  35940
tgagagtcgg ggtgttaatc ttggaaatta tttttctaac cttgttggta gccttcaaga  36000
cctgactagc aaatccagcc ttaatttttt catgattgat taatgggtcg tattggtatt  36060
tataaacttt atccatatct ctagatactg attctggaca tagctttccg actggcgcat  36120
ttggtgtgat ggttcccata agtttggcag ctagcagatt cagtcttgaa acagcatctg  36180
cattaactag aggagacatt agaatcattg ctgtaaacaa gtttggatta tcgtaagagg  36240
ctagtataga aattgttgct cccatggaat gacccaataa gtagatttaa tagttaccac  36300
gtgctgtacc aaagtcatca atcatcattt tttcaccatt acttcttcca tgtccaatat  36360
gatcatgtga gaatactaaa attcctaacg atgatatgtt ttcagctagt tcgtcataac  36420
gtccagaatg tttaccagct ccatgactta tgaatactaa tgccttagga tatgtaatca  36480
ttgtccagat tgaacataca gtttgcactc atgattcacg ttatataact atcaatatta  36540
acagttcgtt tgatgatcat attattttta tgttttattg ataattgtaa aaacatacaa  36600
ttaaatcaat atagaggaag gagacggcta ctgtcttttg tgagatagtc atggcgacta  36660
aattagatta tgaggatgct gtttttttact ttgtggatga tgataaaata tgtagtcgcg  36720
actccatcat cgatctaata gatgaatata ttacgtggag aaatcatgtt atagtgttta  36780
acaaagatat taccagttgt ggaagactgt acaaggaatt gatgaagttc gatgatgtcg  36840
ctatacggta ctatggtatt gataaaatta atgagattgt cgaagctatg agcgaaggag  36900
accactacat caattttaca aaagtccatg atcaggaaag tttattcgct accataggaa  36960
tatgtgctaa aatcactgaa cattggggat acaaaaagat ttcagaatct agattccaat  37020
cattgggaaa cattacagat ctgatgaccg acgataatat aaacatcttg atactttttc  37080
tagaaaaaaa attgaattga tgatataggg gtcttcataa cgcataatta ttacgttagc  37140
attctatatc cgtgttaaaa aaaattatcc tatcatgtat ttgagagttt tatatgtagc  37200
aaacatgata gctgtgatgc caataagctt tagatattca cgcgtgctag tgttagggat  37260
ggtattatct ggtggtgaaa tgtccgttat ataatctaca aaacaatcat cgcatatagt  37320
atgcgatagt agagtaaaca tttttatagt ttttactgga ttcatacatc gtctacccaa  37380
ttcggttatg aatgaaattg tcgccaatct tacacccaac cccttgttat ccattagtat  37440
agtattaact tcgttattta tgtcataaac tgtaaatgat tttgtagatg ccatatcata  37500
catgatattc atgtccctat tataatcatt actaacttta tcacaatata tgttgataat  37560
atctatatat gatctagtct ttgtgggcaa ctgtctatac aagtcgtcta aacgttgttt  37620
actcatatag tatcgaacag ccatcattac atggtcccgt tccgttgata gataatcgag  37680
tatgttagtg gacttgtcaa atctatatac catattttct ggaagtggat atacatagtc  37740
gtgatcaaca ttattgctag cctcatcttc tatatcctgt actataccat ctacataatc  37800
tacgatatta ttacacataa acatcgacaa catactattg tttattatct aagtcctgtt  37860
gatccaaacc cttgatctcc tctatttgta ctatctagag attgtacttc ttccagttct  37920
```

ggataatata tacgttgata gattagctga gctattctat ctccagtatt tacattaaac 37980
gtacattttc cattattaat aagaatgact cctatgtttc ccctataatc ttcgtctatt 38040
acaccacctc ctatatcaat gccttttagt gacagaccag acctaggagc tattctacca 38100
tagcaaatct taggcatgga catactaata tctgtcttaa ttaactgtct ttctcctgga 38160
gggatagtat aatcgtaagc gctatacaaa tcatatccgg cagcacccgg cgattgccta 38220
gtaggagatt tagctctgtt agtttcctta acaaatctaa ctggtgagtt aatattcatg 38280
ttgaacataa aactaatatt ttatttcaaa attatttacc atcccatata ttccatgaat 38340
aagtgtgatg attgtacact tctatagtat ctatatacga ttcacgataa aatcctccta 38400
tcaatagcag tttattatcc actatgatca attctggatt atccctcgga taaataggat 38460
catctatcag agtccatgta ttgctggatt cacaataaaa ttccgcattt ctaccaacca 38520
agaataacct tctaccgaac actaacgcgc atgatttata atgaggataa taagtggatg 38580
gtccaaactg ccactgatca tgattgggta gcaaatattc tgtagttgta tcagtttcag 38640
aatgtcctcc cattacgtat ataacattgt ttatggatgc cactgctgga ttacatctag 38700
gtttcagaag actcggcata ttaacccaag cagcatcccc gtggaaccaa cgctcaacag 38760
atgtgggatt tggtagacct cctactacgt ataatttatt gttagcgggt atcccgctag 38820
catacagtct ggggctattc atcggaggaa ttggaatcca attgtttgat atataattta 38880
cagctatagc attgttatgt atttcattgt tcatccatcc accgatgaga tatactactt 38940
ctccaacatg agtacttgta cacatatgga atatatctat aatttgatcc atgttcatag 39000
gatactctat gaatggatac ttgtatgatt tgcgtggttg tttatcacaa tgaaatattt 39060
tggtacagtc tagtatccat tttacattat ttatacctct gggagaaaga taatttgacc 39120
tgattacatt tttgataagg agtagcagat ttcctaattt atttcttcgc tttatatacc 39180
acttaatgac aaaatcctca tctggaacat ttagttcatc gctttctaga ataagtttca 39240
tagatagata atcaaaattg tctatgatgt catcttccag ttccaaaaag tgtttggcaa 39300
taaagttttt agtatgacat aagagattgg atagtccgta ttctataccc atcatgtaac 39360
actcgacaca atattccttt ctaaaatctc gtaggataaa gtttatacaa gtgtagatga 39420
taaattctac agaggttaat atagaagcac gtaataaatt gacgacgtta tgactatcta 39480
tatatacctt tccagtatat gagtaaataa ctatagaagt tagactgtga atgtcaaggt 39540
ctagacaaac cctcgtaact ggatctttat ttttcgtgta tttttgacgt aaatgtgtgc 39600
gaaagtaagg agataacttt ttcaatatcg tagaattgac tattatattg cctcctatgg 39660
catcaataat tgttttgaat ttcttagtca tagacaatgc taatatattc ttacagtaca 39720
cagtattgac aaatatcggc atttatgttt ctttaaaagt caacatctaa agaaaaatga 39780
ttatcttctt gagacataac tcccattttt tggtattcac ccacacgttt ttcgaaaaaa 39840
ttagttttac cttctaatga tatattttcc atgaaatcaa acggattggt aacattataa 39900
attttttaa atcccaattc agaaatcaat ctatccgcga cgaattctat atatgttttc 39960
atcatttcac aattcattcc tataagttta actggaagag ccgcagtaag aaattcttgt 40020
tcaatggata ccgcatctgt tataatagat ctaacggttt cttcactcgg tggatgcaat 40080
aaatgtttaa acatcaaaca tgcgaagtcg cagtgtagac cctcgtctct actaatcaat 40140
tcgttggaaa acgtgagtcc gggcattagg ccacgctttt taagccaaaa tatggaagcg 40200
aatgatccgg aaaagaagat tccttctact gcagcaaagg caataagtct ctctccataa 40260

-continued

```
ccggcgctgt catgtatcca cttttgagcc caatcggcct tctttttttac acaaggcatc  40320
gtttctatgg cattaaagag atagtttttt tcattactat ctttaacata agtatcgatc  40380
aaaagactat acatttccga atgaatgttt tcaatggcca tctgaaatcc gtagaaacat  40440
ctagcctcgg taatctgtac ttctgtacaa aatcgttccg ccaaattttc attcactatt  40500
ccgtcactgg ctgcaaaaaa cgccaataca tgttttataa aatatttttc gtctggtgtt  40560
agtttattcc aatcattgat atctttagat atatctactt cttccactgt ccaaaatgat  40620
gcctctgcct ttttatacat gttccagatg tcatgatatt ggattgggaa aataacaaat  40680
ctatttggat ttggtgcaag gatgggttcc ataactaaat taacaataac aataaatttt  40740
ttttcagtta tctatatgcc tgtacttgga tcttttgtac atcgatatcg ccgcaatcac  40800
tacaataatt acaagtatta ttgatagcat tgttattagt actatcataa ttaaattatc  40860
gttattatca ttttgtaatt gtgacatcat actagataaa tcgtttgcga gattgttgtg  40920
ggaagcgggc atggaggatg aattatcgtt attattattt aaagcctccc attcggattc  40980
acaaatatgg cgcgcgttca acattttatg gaaacagata acaagaaaac tcgtcatcgt  41040
tcaaattttt aacgatagta aaccgattaa acgtcgagct aatttctaac gctagcgact  41100
ctgttggata tgggtttcca gatatatatc ttttcagttc ccctacgtat ctataatcat  41160
ctgtaggaaa tggaagatat ttccatttat ctactgttcc taatatcata tgtggtggtg  41220
tagtagaacc attaagcgcg aaagatgtta tttcgcatcg tattttaact tcgcaataat  41280
ttctggttag ataacgcact ctaccagtca agtcaatgat attagccttt acagatatat  41340
tcatagtagt cgtaacgatg actccatctt ttagatgcga tactcctttg tatgtaccag  41400
aatcttcgta cctcaaactc gatatattta aacaagttaa tgagatatta acgcgtttta  41460
tgaatgatga tatataacca gaagttttat cctcggtggc tagcgctata accttatcat  41520
tataatacca actagtgtga ttaatatgtg acacgttagt gtgggtacaa atatgtacat  41580
tatcgtctac gtcgtattcg atacatccgc atacagccaa caaatataaa atgacaaata  41640
ctctaacgcc gttcgtaccc atcttgatgc ggtttaataa atgttttgat ttcaatttat  41700
tgtaaaaaaa gattcggttt tatactgttc gatattctca ttgcttatat tttcatctat  41760
catctccaca cagtcaaatc cgtggttagc atgcacctca tcaaccggta aaagactatc  41820
ggactcttct atcattataa ctctagaata tttaatttgg tcattattaa tcaagtcaat  41880
tatcttattt ttaacaaacg tgagtatttt actcattttt tataaaaact tttagaaata  41940
tacagactct atcgtgtgtc tatatcttct ttttatatcc aatgtattta tgtctgattt  42000
ttcttcattt atcatatata atggtccaaa ttctacacgt gcttcggatt catccagatc  42060
attaaggttc ttataattgt aacatccttc tcttccctct tctacatctt ccttcttatt  42120
cttattctta gcgtcacaga atctaccaca gcaggatccc atgacgagcg tcatattaaa  42180
ctaatccatt ttcaattata atatacgatt agtaatgacc attaaaataa aaatattctt  42240
cataaccggc aagaaagtga aaagttcaca ttgaaactat gtcagtagta tacatcatga  42300
aatgatgata tatatatact ctattttggt ggaggattat atgatataat tcgtggataa  42360
tcattcttaa gacacatttc ttcattcgta aatcttttca cgttaaatga gtgtccatat  42420
tttgcaattt cttcatatga tggcggtgta cgtggacgag gctgctcctg ttcttgttgt  42480
agtcgccgac tgtcgtgtct gcgtttagat ccctccatta tcgcgattgc gtagatggag  42540
tactatttta taccttgtaa ttaaattttt ttattaatta aacgtataaa aacgttccgt  42600
atctgtattt aagagccaga tttcgtctaa tagaacaaat agctacagta aaaataacta  42660
```

gaataattgc tacacccact agaaaccacg gatcgtaata cggcaatcgg ttttcgataa 42720
taggtggaac gtatatttta tttaaggact taacaattgt ctgtaaacca caatttgctt 42780
ccgcggatcc tgtattaact atctgtaaaa gcatatgttg accgggcgga gccgaacatt 42840
ctccgatatc caatttctgt atatctataa tattattaac ctccgcatac gcattacagt 42900
tcttttctag cttggatacc gcactaggta catcgtctag atctattcct atttcctcag 42960
cgatagctct tctatccttt tccggaagca atgaaatcac ttcaataaat gattcaacca 43020
tgagtgtgaa actaagtcga gaattactca tgcatttgtt agttattcgg agcgcgcaat 43080
ttttaaactg tcctataacc tctcctatat gaatagcaca agtgacatta gtagggatag 43140
aatgttgagc taatttttgt aaataactat ctataaaaag attatacaaa gttttaaact 43200
ctttagtttc cgccatttat ccagtctgag aaaatgtctc tcataataaa tttttccaag 43260
aaactaattg ggtgaagaat ggaaaccttt aatctatatt tatcacagtc tgttttggta 43320
cacatgatga attcttccaa tgccgtacta aattcgatat ctttttcgat ttctggatat 43380
gtttttaata aagtatgaac aaagaaatgg aaatcgtaat accagttatg tttaactttg 43440
aaattgtttt ttattttctt gttaatgatt ccagccactt gggaaaagtc aaagtcgttt 43500
aatgccgatt taatacgttc attaaaaaca aactttttat cctttagatg aattattatt 43560
ggttcattgg aatcaaaaag taagatatta tcgggtttaa gatctgcgtg taaaaagttg 43620
tcgcagcatg gtagttcgta aattttaatg tataacagag ccatctgtaa aaagataaac 43680
tttatgtatt gtaccaaaga tttaaatcct aatttgatag ctagctcggt atctacttta 43740
tctgccgaat acagtgctag ggaaaaaatt ataatatttc ctctttcgta ttcgtagtta 43800
gttctctttt catgttcgaa aaagtgaaac atgcggttaa aatagtttat aacattaata 43860
ttactgttaa taactgccgg ataaaagtgg gatagtaatt tcacgaattt gatactgtcc 43920
tttctctcgt taaacgcctt taaaaaaact ttagaagaat atctcaatga tagttcctga 43980
ccatccatag tttgtatcaa taatagcaac atatgaagaa cacgtttata cagagtatgt 44040
aaaaatgtta atttatagtt taatcccatg gcccacgcac acacgattaa tttttttca 44100 tctccctta gattgttgta tagaaatttg ggtactgtga actccgccgt agtttccatg 44160
ggactatata attttgtggc ctcgaataca aattttacta catagttatc tatcttaaag 44220
actataccat atcctcctgt agatatgtga taaaaatcgt cgtttatagg ataaaatcgt 44280
ttatcctttt gttggaaaaa ggatgaatta atgtaatcat tctcttctat ctttagtagt 44340
gtttccttat taaaattctt aaaataattt aacaatctaa ctgatggagc ccaattttgg 44400
tgtaaatcta attgggacat tatattgtta aaatacaaac agtctcctaa tataacagta 44460
tctgataatc tatggggaga catccattga tattcagggg atgaatcatt ggcaacaccc 44520
atttattgta caaaaagccc caatttacaa acgaaagtcc aggtttgata gagacaaact 44580
attaactatt ttgtctctgt ttttaatttc tttggtaatg aaattattca caatatcagt 44640
atcttcttta tctaccagag attttactaa cttgataacc ttggctgtct cattcaatag 44700
ggtagtaata tttgtatgtg tgatattgat atcttttaga agtgattctt tgatggtgcc 44760
agcatacgaa ttacaataat gcagaaactc ggttaacatg caggaattat agtaagccaa 44820
ttccaattgt tgcctgtgtt gtattagagt gtcaatatga gcaatggtgt ccttgcgttt 44880
ctctgataga atgcgagcag cgattttggc gttatcattt gacgatattt ctggaatgac 44940
gaatcctgtt tctactaact ttttggtagg acaaagtgaa acaatcaaga agatagcttc 45000

-continued

```
tcctcctatt tgtggaagaa attgaactcc tctagatgat ctccttgaca gatattggac  45060
cgaattacag aagtacctgg aatgtaaagc cctgaaaccc cctcattttt taagcagatt  45120
gttgccgtaa atcctgcact atgcccaaga tagagagctc ctttggtgaa tccatctcta  45180
tgtttcagtt taaccaagaa acagtcagct ggtctaaaat ttccatctct atctaataca  45240
gcatctaact tgatgtcagg aactatgacc ggttatgtta tatgtaacat tgagtaaatc  45300
cttaagttca taatcatcac tgtcatcagt tatgtacgat ccaaacaatg tttctactgg  45360
catagtggat acgaagatgc tatccatcag aatgtttccc tgattagtat tttctatata  45420
gctattcttc tttaaacgat tttccaaatc agtaactatg ttcatttttt taggagtagg  45480
acgcctagcc agtatggaag aggattttct agatcctctc ttcaacatct ttgatctcaa  45540
tggaatgcaa aaccccatag tgtaacaacc aacgataaaa ataatattgt ttttcacttt  45600
ttataatttt accatctgac tcatggattc attaatatct ttataagagc tactaacgta  45660
taattcttta taactgaact gagatatata caccggatct atggtttcca taattgagta  45720
aatgaatgct cggcaataac taatggcaaa tgtataaaac aacgaaatta tactagagtt  45780
gttaaagtta atattttcta tgagctgttc caataaatta tttgttgtaa ctgcgttcaa  45840
gtcataaatc atcttgatac tatccagtaa accgttttta agttctggaa tattattatc  45900
ccattgtaaa gcccctaatt cgactatcga atatcctgct ctgatagcag tttcaatatc  45960
gacggacgtc aatactgtaa taaaggtggt agtattgtca tcatcgtgat aaactactgg  46020
aatatggtcg ttagtaggta cggtaacttt acacaacgcg atatataact ttccttttgt  46080
accattttta acgtagttgg gacgtcctgc agggtattgt tttgaagaaa tgatatcgag  46140
aacagatttg atacgatatt tgttggattc ctgattattt actataatat aatctagaca  46200
gatagatgat tcgataaata gagaaggtat atcgttggta ggataataca tccccattcc  46260
agtattctcg gatactctat taatgacact agttaagaac atgtcttcta ttctagaaaa  46320
cgaaaacatc ctacatggac tcattaaaac ttctaacgct cctgattgtg tctcgaatgc  46380
ctcgtacaag gatttcaagg atgccataga ttctttgacc aacgatttag aattgcgttt  46440
agcatctgat tttttatta aatcgaatgg tcggctctct ggtttgctac cccaatgata  46500
acaatagtct tgtaaagata aaccgcaaga aaatttatac gcatccatcc aaataaccct  46560
agcaccatcg gatgatatta atgtattatt atagattttc catccacagt tattgggcca  46620
gtatactgtt agcaacggta tatcgaatag attactcatg taacctacta gaatgatagt  46680
tcgtgtacta gtcataatat ctttaatcca atctaagaaa tttaaaatta gatttttttac  46740
actgttaaag ttaacaaagg tattacccgg atacgtggat atcatatatg gtattggtcc  46800
attatcagta atagctccat aaactgatac ggcgatggtt tttatatgtg tttgatctaa  46860
cgaggaagaa attcgcgccc acaattcatc tctagatatg tatttaatat caaacggtaa  46920
cacatcaatt tcgggacgcg tatatgtttc taaattttta atccaaatat aatgatgacc  46980
tatatgccct attatcatac tgtcaactat agtacaccta gagaacttac gatacatctg  47040
tttcctataa tcgttaaatt ttacaaatct ataacatgct aaaccttttg acgacaacca  47100
ttcattaatt tctgatatgg aatctgtatt ctcaataccg tatcgttcta aagccagtgc  47160
tatatctccc tgttcgtgag aacgctttcg tataaatatcg atcaacggat aatctgaagt  47220
ttttggagaa taatatgact catgatctat ttcgtccata aacaatctag acataggaat  47280
tggaggcgat gatcttaatt ttgtgcaatg agtcgtcaat cctataactt ctaatattgt  47340
aatattcatc atcgacataa cactatctat gttatcatcg tatattagta taccatgacc  47400
```

ttcttcattt cgtgccaaaa tgatatacag tcttaaatag ttacgcaata tctcaatagt 47460
ttcataattg ttagctgttt tcatcaaggt ttgtatcctg tttaacatga tggcgttcta 47520
tacgtttcta ttttttaaat ttttaacgat ttactgtggc tagataccca atctctctca 47580
aatatttttt tagcctcgct tacaagctgt ttatctatac tattaaaact gacgaatccg 47640
tgattttggt aatgggttcc gtcgaaattt gccgaagtga tatgaacata ttcgtcgtcg 47700
actatcaaca attttgtatt attctgaata gtgaaaacct tcacagatag atcattttga 47760
acacacaacg cgtctagact tctggcggtt gccatagaat atacgtcgtt cttatcccaa 47820
ttaccaacta gaagtctgat cttaactcct ctattaatgg ctgcttctat aatggagttg 47880
taaatgtcgg gccaatagta gctattaccg tcgacacgtg tagtgggaac tatggccaaa 47940
tgttcaatat ctatactagt cttagccgac ttgagtttat caataactac atcagtgtct 48000
agatctctag aatatcccaa taggtgttcc ggagaatcag taaagaacac tccacctata 48060
ggattcttaa tatgatacgc agtgctaact ggcagacaac aagccgcaga gcataaattc 48120
aaccatgaat tttttgcgct attaaaggct ttaaaagtat caaatcttct acgaagatct 48180
gtggccagcg ggggataatc agaatataca cctaacgttt taatcgtatg tatagatcct 48240
ccagtaaatg acgcgtttcc tacataacat ctttcattat ctgacaccca aaaacaaccg 48300
agtagtagtc ccacattatt ttttttatct atattaacgg ttataaaatt tatatccggg 48360
cagtgacttt gtagctctcc cagatttctt ttccctcgtt catctagcaa aactattatt 48420
ttaatccctt tttcagatgc ctcttttagt ttatcaaaaa taagcgctcc cctagtcgta 48480
ctcagaggat tacaacaaaa agatgctatg tatatatatt tcttagctag agtgataatt 48540
tcgttaaaac attcaaatgt tgttaaatga tcggatctaa aatccatatt ttctggtagt 48600
gtttctacca gcctacattt tgctcccgca ggtaccggtg caaatggcca catttagtta 48660
acataaaaac ttatacatcc tgttctatca acgattctag aatatcatcg gctatatcgc 48720
taaaatttc atcaaagtcg acatcacaac ctaactcagt caatatatta agaagttcca 48780
tgatgtcatc ttcgtctatt tctatatccg tatccattgt agattgttga ccgattatcg 48840
agtttaaatc attactaata ctcaatcctt cagaatacaa tctgtgtttc attgtaaatt 48900
tataggcggt gtatttaagt tggtagattt tcaattatgt atcaatatag caacagtagt 48960
tcttgctcct ccttgattct agcatcctct tcattatttt cttctacgta cataaacatg 49020
tccaatacgt tagacaacac accgacgatg gcggccgcca cagacacgaa tatgactaaa 49080
ccgatgacca tttaaaaacc cctctctagc tttcacttaa actgtatcga ttattctttt 49140
agaacatgta taatataaaa acattattct atttcgaatt taggcttcca aaaatttttc 49200
atccgtaaac cgataataat atatatagac ttgttaatag tcggaataaa tagattaatg 49260
cttaaactat catcatctcc acgattagag atacaatatt tacatttttt ttgctgtttc 49320
gaaactttat caatacacgt taatacaaac ccaggaagga gatattgaaa ctgaggctgt 49380
tgaaaatgaa acggtgaata caataattca gataatgtaa aatcatgatt ccgtattctg 49440
atgatattag aactgctaat ggatgtcgat ggtatgtatc taggagtatc tattttaaca 49500
aagcatcgat ttgctaatat acaattatca ttttgattaa ttgttatttt attcatattc 49560
ttaaaaggtt tcatatttat caattcttct acattaaaaa tttccatttt taatttatgt 49620
agccccgcaa tactcctcat tacgtttcat tttttgtcta taatatccat tttgttcatc 49680
tcggtacata gattatccaa ttgagaagcg catttagtag ttttgtacat tttaagttta 49740
ttgacgaatc gtcgaaaact agttatagtt aacattttat tatttgatac cctgatatta 49800
ataccccctgc cgttactatt atttataact gatgtaatcc acgtaacatt ggaattaact 49860
atcgatagta atgcatcgac gcttccaaaa ttgtctatta taaactcacc gataattttt 49920
ttattacatg ttttcatatt cattaggatt attaaatctt taatcttact acgattgtat 49980
gcgttgatat tgcaagacgt cattctaaaa gacggaggat ctccatcaaa tgccagacaa 50040
tcacgtacaa agtacatgga aataggtttt gttctattgc gcatcataga tttatataga 50100
acacccgtag aaatactaat ttgttttact ctataaaata ctaatgcatc tatttcatcg 50160
ttttgtataa cgtctttcca agtgtcaaat tccaaatttt tttcattgat agtaccaaat 50220
tcttctatct ctttaactac ttgcatagat aggtaattac agtgatgcct acatgccgtt 50280
ttttgaaact gaatagatgc gtctagaagc gatgctacgc tagtcacaat caccactttc 50340
atatttagaa tatatatatg taaaaatata gtagaatttc attttgtttt ttttctatgc 50400
tataaatgaa ttctcatttt gcatctgctc atactccgtt ttatatcaat accaaagaag 50460
gaagatatct ggttctaaaa gccgttaaag tatgcgatgt tagaactgta gaatgcgaag 50520
gaagtaaagc ttcctgcgta ctcaaagtag ataaaccctc atcacccgcg tgtgagagaa 50580
gaccttcgtc cccttccaga tgcgagagaa tgaataaccc aggaaaacaa gttccgttta 50640
tgaggacgga catgctacaa aatatgttcg cggctaatcg cgataatgta gcttctagac 50700
ttttgtccta aaatacaatt atatcctttt cgatattaat aaatccgtgt cgtccaggtt 50760
ttttatctct ttcagtatgt gaatagatag gtattttatc tctattcatc atcgaattta 50820
agagatccga taaacattgt ttgtattctc cagatgtcag catctgatac aacaatatat 50880
gtgcacataa acctctggca cttatttcat gtaccttccc cttatcacta aggagaatag 50940
tatttgagaa atatgtatac atgatattat catgaattag atatacagaa tttgtaacac 51000
tctcgaaatc acacgatgtg tcggcgttaa gatctaatat atcactcgat aacacatttt 51060
catctagata cactagacat tttttaaagc taaaatagtc tttagtagta acagtaacta 51120
tgcgattatt ttcatcgatg atacatttca tcggcatatt attacgctta ccatcaaaga 51180
ctataccatg tgtatatcta acgtattcta gcatggttgc catacgcgca ttaaactttt 51240
caggatcttt ggatagatct tccaatctat ctatttgaga aaacattttt atcatgttca 51300
atagttgaaa cgtcggatcc actatataga tattatctat aaagatttta ggaactacgt 51360
tcatggtatc ctggcgaata ttaaaactat caatgatatg attatcgttt tcatctttta 51420
tcaccatata gtttctaaga tatgggattt tacttaatat aatattattt cccgtaataa 51480
attttattag aaatgccaaa tctataagaa aagtcctcga attagtttga agaatatcta 51540
tatcgccgta ccgtatattt ggattaatta gatatagaga atatgatccg taacatatac 51600
aacttttatt atggcgtcta agatattctt ccatcaactt attaacattt ttgactaggg 51660
aagatacatt atgacgtccc attacttttg ccttgtctat tactgcgacg ttcatagaat 51720
ttagcatatc tcttgccaat tcttccattg atgttacatt ataagaaatt ttagatgaaa 51780
ttacatttgg agctttaata gtaagaactc ctaatatgtc cgtgtatgtg gtcactaata 51840
cagattgtag ttctataatc gtaaataatt tacctatatt atatgtttga gtctgtttag 51900
aaaagtagct aagtatacga tcttttattt ctgatgcaga tgtatcaaca tcggaaaaaa 51960
atcttttttt attcttttttt actaaagata caaatatgtc tttgttaaaa acagttattt 52020
tctgaatatt tctagcttgt aattttaaca tatgatattc gttcacacta ggtactctgc 52080
ctaaatatggt ttctataatc tttaatgtaa tattaggaaa agtattctga tcaggattcc 52140
tattcatttt gaggatttaa aactctgatt attgtctaat atggtctcaa cacaaacttt 52200
ttcacagagc gatagagttt ttgataactc gtttttctta agaaatataa aactactgtc 52260
tccagagctc gctctatctt ttatttttatt taattcgata caaactcctg atactggttc 52320
agaaagtaat tcattaattt tcagtccttt atagaagata tttaatatag ataatacaaa 52380
atcttcagtt tttgatatcg atctgattga tcctagaact agatatatta ataacgtgct 52440
cattaggcag tttatggcag cttgataatt agatatagta tattccagtt catatttatt 52500
agataccgca ttgcccagat tttgatattc tatgaattcc tctgaaaata aatccaaaat 52560
aactagacat tctatttttt gtggattagt gtactctctt ccctctatca tgttcactac 52620
tggtgtccac gatgataaat atctagaggg aatataatat agtccatagg atgccaatct 52680
agcaatgtcg aataactgta attttattct tcgctcttca ttatgaattg attcttgagg 52740
tataaaccta acacaaatta tattattaga cttttcgtat gtaatgtctt tcatgttata 52800
agtttttaat cctggaatag aatctatttt aatgaggctt ttaaacgcag agttctccaa 52860
cgagtcaaag cataatactc tgttggtttt cttatatacg atgttacgat tttcttcttt 52920
gaatggaata ggtttttgaa ttagtttata attacaacat aatagataag gaagtgtgca 52980
aatagtacgc ggaaaaaaca taatagctcc cctgttttca tccatggttt taagtaaatg 53040
atcactggct tctttagtca atggatattc gaacattaac cgtttcatca tcattggaca 53100
gaatccatat ttcttaatgt aaagagtgat caaatcattg tgtttattgt accatcttgt 53160
tgtaaatgtg tattcggtta tcggatctgc tcctttttct attaaagtat cgatgtcgat 53220
ctcgtctaag aattcaacta tatcgacata tttcatttgt atacacataa ccattactaa 53280
cgtagaatgt ataggaagag atgtaacggg aacagggttt gttgattcgc aaactattct 53340
aatacataat tcttctgtta atacgtcttg cacgtaatct attatagatg ccaagatatc 53400
tatataatta ttttgtaaga tgatgttaac tatgtgatct atataagtag tgtaataatt 53460
catgtatttc gatatatgtt ccaactctgt ctttgtgatg tctagtttcg taatatctat 53520
agcatcctca aaaaatatat tcgcatatat tcccaagtct tcagttctat cttctaaaaa 53580
atcttcaacg tatggaatat aataatctat tttacctctt ctgatatcat taatgatata 53640
gtttttgaca ctatcttctg tcaattgatt cttattcact atatctaaga aacggatagc 53700
gtccctagga cgaactactg ccattaatat ctctattata gcttctggac ataattcatc 53760
tattatacca gaattaatgg gaactattcc gtatctatct aacatagttt taagaaagtc 53820
agaatctaag acctgatgtt catatattgg ttcatacatg aaatgatctc tattgatgat 53880
agtgactatt tcattctctg aaaattggta actcattcta tatatgcttt ccttgttgat 53940
gaaggataga atatactcaa tagaatttgt accaacaaac tgttctctta tgaatcgtat 54000
atcatcatct gaaataatca tgtaaggcat acatttaaca attagagact tgtctcctgt 54060
tatcaatata ctattcttgt gataatttat gtgtgaggca aatttgtcca cgttctttaa 54120
ttttgttata gtagatatca aatccaatgg agctacagtt cttggcttaa acagatatag 54180
tttttctgga acgaattcta caacattatt ataaaggact ttgggtagat aagtgggatg 54240
aaatcctatt ttaattaatg cgatagcctt gtcctcgtgc agatatccaa acgcttttgt 54300
gatagtatgg cattcattgt ctagaaacgc tctacgaata tctgtgacag atatcatctt 54360
tagagaatat actagtcgcg ttaatagtac tacaatttgt attttttaat ctatctcaat 54420
aaaaaaatta atatgtatga ttcaatgtat aactaaacta ctaactgtta ttgataacta 54480

-continued gaatcagaat ctaatgatga cgtaaccaag aagtttatct actgccaatt tagctgcatt 54540
atttttagca tctcgtttag attttccatc tgccttatcg aatactcttc cgtcgatatc 54600
tacacaggca taaaatgtag gagagttact aggccccact gattcaatac gaaaagacca 54660
atctctctta gttatttggc agtactcatt aataatggtg acagggttag catctttcca 54720
atcaataatt tttttagccg gaataacatc atcaaaagac ttatgatcct ctctcattga 54780
tttttcgcgg gatacatcat ctattatggc gtcagccata acatcagcat ccggcttatc 54840
cgcctccgtt gtcataaacc aacgaggagg aatatcgtcg gagctgtaca ccatagcact 54900
acgttgaaga tcgtacagag ctttattaac ttctcgcttc tccatattaa gttgtctagt 54960
tagttgtgca gcagtagctc cttcgattcc aatgttttta atagccgcac acacaatctc 55020
tgcgtcagaa cgctcgtcaa tatagatctt agacattttt agagagaact aacacaacca 55080
gcaataaaac taatttattt tatcattttt ttattcatca tcctctggtg gttcgtcgtt 55140
tctatcgaat gtggatctga ttaacccgtc atctataggt gatgctggtt ctggagattc 55200
tggaggagat ggattattat ctggaagaat ctctgttatt tccttgtttt catgtatcga 55260
ttgcgttgta acattaagat tgcgaaatgc tctaaatttg ggaggcttaa agtgttgttt 55320
gcaatctcta cacgcatgtc taactagtgg aggttcgtca gcggctctag tttgaatcat 55380
catcggcgta gtattcctac ttttacagtt aggacacggt gtattgtatt tctcgtcgag 55440
aacgttaaaa taatcgttgt aactcacatc ctttatttta tctatattgt attctactcc 55500
tttcttaatg cattttatac cgaataagag atagcgaagg aattcttttt cggtgccgct 55560
agtaccctta atcatatcac atagtgtttt atattccaaa tttgtggcaa tagacggttt 55620
atttctatac gatagtttgt ttctggaatc ctttgagtat tctataccaa tattattctt 55680
tgattcgaat ttagtttctt cgatattaga ttttgtatta cctatattct tgatgtagta 55740
ctttgatgat ttttccatgg cccattctat taagtcttcc aagttggcat catccacata 55800
ttgtgatagt aattctcgga tatcagtagc ggctaccgcc attgatgttt gttcattgga 55860
tgagtaacta ctaatgtata cattttccat ttataacact tatgtattaa ctttgttcat 55920
ttatattttt tcattattat gttgatatta acaaaagtga atatatatgt taataattgt 55980
attgtggtta tacggctaca atttcataat gagtggaagt cagtgtccga tgatcaatga 56040
cgatagcttt actctgaaaa gaaagtatca aatcgatagt gcggagtcaa caataaaaat 56100
ggataagaag aggataaagt ttcagaatag agccaaaatg gtaaaagaaa taaatcagac 56160
aataagagca gcacaaactc attacgagac attgaaacta ggatacataa aatttaagag 56220
aatgattagg actactactc tagaagatat agcaccatct attccaaata atcagaaaac 56280
ttataaacta ttctcggaca tttcagccat cggcaaagca tcacagaatc cgagtaagat 56340
ggtatatgct ctgctgcttt acatgtttcc caatttgttt ggagatgatc atagattcat 56400
tcgttataga atgcatccaa tgagtaaaat caaacacaag atcttctctc ctttcaaact 56460
taatcttatt agaatattag tggaagaaag attctataat aatgaatgca gatctaataa 56520
atggagaata attggaacac aagttgataa aatgttgata gctgaatctg ataaatatac 56580
aatagatgca aggtataacc taaaacccat gtatagaatc aagggaaaat ctgaagaaga 56640
taccctcttt atcaaacaga tggtagaaca atgtgtgaca tcccaggaat tggtggaaaa 56700
agtgttgaag atactgttta gagatttgtt caagagtgga gaatacaaag cgtacagata 56760
cgatgatgat gtagaaaatg gatttattgg attggataca ctaaaattaa acattgttca 56820
tgatatagtt gaaccatgta tgcctgttcg taggccagtg gctaagatac tgtgtaaaga 56880

```
aatggtaaat aaatactttg agaatccgct acatattatt ggtaaaaatc ttcaagagtg  56940
cattgacttt gttagtgaat aggcatttca tctttctcca atactaattc aaattgttaa  57000
attaataatg gatagtataa atagttatta gtgataaaat agtaaaaata attattagaa  57060
taagagtgta gtatcataga taactctctt ctataaaaat ggattttatt cgtagaaagt  57120
atcttatata cacagtagaa aataatatag attttttaaa ggatgataca ttaagtaaag  57180
taaacaattt taccctcaat catgtactag ctctcaagta tctagttagc aattttcctc  57240
aacacgttat tactaaggat gtattagcta ataccaattt ttttgttttc atacatatgg  57300
tacgatgttg taaagtgtac gaagcggttt tacgacacgc atttgatgca cccacgttgt  57360
acgttaaagc attgactaag aattatttat cgtttagtaa cgcaatacaa tcgtacaagg  57420
aaaccgtgca taaactaaca caagatgaaa aatttttaga ggttgccgaa tacatggacg  57480
aattaggaga acttataggc gtaaattatg acttagttct taatccatta tttcacggag  57540
gggaacccat caaagatatg gaaatcattt ttttaaaact gtttaagaaa acagacttca  57600
aagttgttaa aaaattaagt gttataagat tacttatttg ggcttaccta agcaagaaag  57660
atacaggcat agagtttgcg gataatgata gacaagatat atacactcta tttcaacaaa  57720
ctggtagaat agtccatagc aatctaacag aaacgtttag agattatatc tttcccggag  57780
ataagactag ctattgggtg tggttaaacg aaagtatagc taatgatgcg gatattgttc  57840
ttaatagaca cgccattacc atgtatgata aaattcttag ttatatatac tctgagataa  57900
aacaaggacg cgttaataaa aacatgctta agttagttta tatctttgag cctgaaaaag  57960
atatcagaga acttctgcta gaaatcatat atgatattcc tggagatatc ctatctatta  58020
ttgatgcaaa aaacgacgat tggaaaaaat attttattag tttttataaa gctaatttta  58080
ttaacggtaa tacatttatt agtgatagaa cgtttaacga ggacttattc agagttgttg  58140
ttcaaataga tcccgaatat ttcgataatg aacgaattat gtctttattc tctacgagtg  58200
ctgcggacat taaacgattt gatgagttag atattaataa cagttatata tctaatataa  58260
tttatgaggt gaacgatatc acattagata caatggatga tatgaagaag tgtcaaatct  58320
ttaacgagga tacgtcgtat tatgttaagg aatacaatac atacctgttt ttgcacgagt  58380
cggatcccat ggtcatagag aacggaatac taaagaaact gtcatctata aaatccaaga  58440
gtagacggct gaacttgttt agcaaaaaca ttttaaaata ttatttagac ggacaattgg  58500
ctcgtctagg tcttgtgtta gatgattata aaggagactt gttagttaaa atgataaacc  58560
atcttaagtc tgtggaggat gtatccgcat tcgttcgatt ttctacagat aaaaacccta  58620
gtattcttcc atcgctaatc aaaactattt tagctagtta taatatttcc atcatcgtct  58680
tatttcaaag gtttttgaga gataatctat atcatgtaga agaattcttg gataaaagca  58740
tccatctaac caagacggat aagaaatata tacttcaatt gataagacac ggtagatcat  58800
agaacagacc aaatatatta ttaataattt gtatatacat agatataatt atcacacatt  58860
tttgataaat gggaactgct gcaacaattc agactcccac caaattaatg aataaagaaa  58920
atgcagaaat gattttggaa aaaattgttg atcatatagt tatgtatatt agtgacgaat  58980
caagtgattc agaaaataat cctgaatata ttgattttcg taacagatac gaagactata  59040
gatctctcat tataaaaagt gatcacgagt ttgtaaagct atgtaaaaat catgcagaga  59100
aaagttctcc agaaacgcaa caaatgatta tcaaacacat atacgaacaa tatcttattc  59160
cagtatctga agtactatta aaacctataa tgtccatggg tgacataatt acatataacg  59220
```

gatgtaaaga caatgaatgg atgctagaac aactctctac cctaaacttt aacaatctcc 59280
gcacatggaa ctcatgtagc ataggcaatg taacgcgtct gttttataca ttttttagtt 59340
atctgatgaa agataaacta aatatataag tataatccca ttctaatact ttaacctgat 59400
gtattacctg catcttatta gaatattaac ctaactaaaa gacataacat agttgataaa 59460
aagcggtagg atataaatat tatggctgcc accgttccgc gttttgacga cgtgtacaaa 59520
aatgcacaaa gaagaattct agatcaagaa acatttttta gtagaggtct aagtagaccg 59580
ttaatgaaaa acacatatct atttgataat tacgcgtatg gatggatacc agaaactgca 59640
atttggagta gtagatacgc aaacttagat gcaagtgact attatcccat ttcgttggga 59700
ttacttaaaa agttcgagtt tctcatgtct ctatataaag gtcctattcc cgtatatgaa 59760
gaaaaagtaa atactgaatt cattgctaat ggatcgttct ctggtagata cgtatcatat 59820
cttcgaaagt tttctgccct tccaacaaac gagtttatta gttttttgtt actgacttcc 59880
attccaatct ataatatctt gttctggttt aaaaatactc agtttgatat tactaaacac 59940
acattattca gatacgtcta tacagataat gccaaacacc tggcgttggc taggtatatg 60000
catcaaacag gagactataa gcctttgttt agtcgtctca aagagaatta tatatttacc 60060
ggtcccgttc caataagtat caaagatata gatcacccta atcttagtag agcaagaagt 60120
ccatccgatt atgagacatt agctaatatt agtactatat tgtactttac caagtatgat 60180
ccggtattaa tgtttttatt gttttacgta cctgggtatt caattactac aaaaattact 60240
ccagccgtag aatatctaat ggataaactg aatctaacaa agagcgacgt acaactgttg 60300
taaattattt tatgcttcgt aaaatgtagg ttttgaacca aacattcttt caaagaatga 60360
gatgcataaa actttattat ccaatagatt gactatttcg gacgtcaatc gtttaaagta 60420
aacttcgtaa aatattcttt gatcactgcc gagtttaaaa cttctatcga taattgtttc 60480
atatgtttta atatttacaa gtttttggt ccatggtaca ttagccggac aaatatatgc 60540
aaaataatat cgttctccaa gttctatagt ttctggatta tttttattat attcagtaac 60600
caaatacata ttagggttat ctgcggattt ataatttgag tgatgcattc gactcaacat 60660
aaataattct agaggagacg atctactatc aaattcggat cgtaaatctg tttctaaaga 60720
acggagaata tctatacata cctgattaga attcatccgt ccttcagaca acatctcaga 60780
cagtctggtc ttgtatgtct taatcatatt cttatgaaac ttggaaacat ctcttctagt 60840
ttcactagta cctttattaa ttctctcagg tacagatttt gaattcgacg atgctgagta 60900
tttcatcgtt gtatatttct tcttcgattg cataatcaga ttcttatata ccgcctcaaa 60960
ctctatttta aaattattaa acaatactct attattaatc agtcgttcta actctttcgc 61020
tatttctata gacttatcga catcttgact gtctatctct gtaaacacgg agtcggtatc 61080
tccatacacg ctacgaaaac gaaatctgta atctataggc aacgatgttt tcacaatcgg 61140
attaatatct ctatcgtcca tataaaatgg attacttaat ggattggcaa accgtaacat 61200
accgttagat aactctgctc catttagtac cgattctaga tacaagatca ttctacgtcc 61260
tatggatgtg caactcttag ccgaagcgta tgagtataga gcactatttc taaatcccat 61320
cagaccatat actgagttgg ctactatctt gtacgtatat tgcatggaat catagatggc 61380
cttttcagtt gaactggtag cctgttttag catcttttta tatctggctc tctctgccaa 61440
aaatgttctt aatagtctag gaatggttcc ttctatcgat ctatcgaaaa ttgctatttc 61500
agagatgagg ttcggtagtc taggttcaca atgaaccgta atatatctag gaggtggata 61560
tttctgaagc aagagctgat tatttatttc ttcttccaat ctattggtac taacaacgac 61620
accgactaat gtttccggag atagatttcc aaagatacac acattaggat acagactgtt 61680
ataatcaaag attaatacat tattactaaa catttttttgt tttggagcaa ataccttacc 61740
gccttcataa ggaaactttt gttttgtttc tgatctaact aagatagttt tagtttccaa 61800
caatagcttt aacagtggac ccttgatgac tgtactcgct ctatattcga ataccatgga 61860
ttgaggaagc acatatgttg acgcacccgc gtctgttttt gtttctactc cataatactc 61920
ccacaaatac tgacacaaac aagcatcatg aatacagtat ctagccatat ctaaagctat 61980
gtttagatta taatccttat acatctgagc taaatcaacg tcatcctttc cgaaagataa 62040
tttatatgta tcattaggta aagtaggaca tgatagtacg actttaaatc catttcccca 62100
aatatcttta cgaattactt tacatataat atcctcatca acagtcacat aattacctgt 62160
ggttaaaacc tttgcaaatg cagcggcttt gcctttcgcg tccgtagtat cgtcaccgat 62220
gaacgtcatt tctctaactc ctctatttaa tactttaccc atgcaactga acgcgttctt 62280
ggatatagaa tccaatttgt acgaatccaa tttttcagat ttttgaatga atgaatatag 62340
atcgaaaaat atagttccat tattgttatt aacgtgaaac gtagtattgg ccatgccgcc 62400
tactccctta tgactagact gatttctctc ataaatacag agatgtacag cttccttttt 62460
gtccggagat ctaaagataa tcttctctcc tgttaataac tctagacgat tagtaatata 62520
tctcagatca aagttatgtc cgttaaaggt aacgacgtag tcgaacgtta gttccaacaa 62580
ttgtttagct attcgtaaca aaactatttc agaacataga actagttctc gttcgtaatc 62640
catttccatt agtgactgta tcctcaaaca tcctctatcg acggcttctt gtatttcctg 62700
ttccgttaac atctcttcat taatgagcgt aaacaataat cgtttaccac ttaaatcgat 62760
ataacagtaa cttgtatgcg agattgggtt aataaataca gaaggaaact tcttatcgaa 62820
gtgacactct atatctagaa ataagtacga tcttgggata tcgaatctag gtattttttt 62880
agcgaaacag ttacgtggat cgtcacaatg ataacatcca ttgttaatct ttgtcaaata 62940
ttgctcgtcc aacgagtaac atccgtctgg agatatcccg ttagaaatat aaaaccaact 63000
aatattgaga aattcatcca tggtggcatt ttgtatgctg cgtttctttg gctcttctat 63060
caaccacata tctgcgacgg agcattttct atctttaata tctagattat aacttattgt 63120
ctcgtcaatg tctatagttc tcatctttcc caacggcctc gcattaaatg gaggaggaga 63180
caatgactga tatatttcgt ccgtaactac gtaataaaag taatgaggaa atcgtataaa 63240
tacggtctcg ccatttcgac atctggattt cagatataaa aatctgtttt caccgtgact 63300
ttcaaaccaa ttaatgcacc gaacatccat ttatagaatt tagaaatata ttttcattta 63360
aatgaatccc aaacattggg gaagagccgt atggaccatt atttttatag tactttcgca 63420
agcgggttta gacggcaaca tagaagcgtg taaacgaaaa ctatatacta tagtcagcac 63480
tcttccatgt cctgcatgta gacggcacgc gactatcgct atagaggaca ataatgtcat 63540
gtctagcgat gatctgaatt atatttatta ttttttcatc agattattta acaatttggc 63600
atctgatccc aaatacgcga tcgatgtgac aaaggttaac cctttataaa cttaacccat 63660
tataaaactt atgattagtc acgactgaaa taaccgcgtg attatttttt ggtataattc 63720
tacacggcat ggtttctgta actatgaatt caaccccccgt tacattagtg aaatctttaa 63780
caaacagcaa gggttcgtca aagacataaa actcattgtt tacaatcgaa atagaccccc 63840
tatcacactt aaaataaaaa atatccttat cctttaccac caaataaaat tctgattggt 63900
caatgtgaat gtattcactt aacagttcca caaatttatt tattaactcc gaggcacata 63960
catcgtcggt attttttatg gcaaacttta ctcttccagc atccgtttct aaaaaaatat 64020
taacgagttc catttatatc atccaatatt attgaaatga cgttgatgga cagatgatac 64080
aaataagaag gtacggtacc tttgtccacc atctcctcca attcatgctc tattttgtca 64140
ttaactttaa tgtatgaaaa cagtacgcca catgcttcca tgacagtgtg taacactttg 64200
gatacaaaat gtttgacatt agtataattg tccaagactg tcaatctata atagatagta 64260
gctataatat attctatgat ggtattgaag aagatgacaa tcttggcata ttgatcattt 64320
aacacagaca tggtatcaac agatagcttg aatgaaagag aatcagtaat tggaataagc 64380
gtcttctcga tagagtgtcc gtataccaac atgtctgata ttttgatgta ttccattaaa 64440
ttatttagtt ttttcttttt attctcgtta aacagcattt ctgtcaacgg accccaacat 64500
cgttgaccga ttaagttttg attgattttt ccgtgtaagg cgtatctagt cagatcgtat 64560
agcctatcca ataatccatc atctgtgcgt agatcacatc gtacactttt taattctcta 64620
tagaagagcg acagacagca atttctttat tctctacaga tgtaagatac ttgaagacat 64680
tcctatgatg atgcagaatt ttggataaca cggtattgat ggtatctgtt accataattc 64740
ctttgatggc tgatagtgtc agagcacaag atttccaatc tttgttttga tatctatatc 64800
agacagcatg gtgcgtctga caacacaagg attaagacgg aaagatgaaa tgattctctc 64860
aacatcttca atggatacct tgctattttt tctggcatta tctatatgtg cgagaatatc 64920
ctctagagaa tcagtatcct ttttgatgat agtggatctc aatgacatgg gacgtctaaa 64980
ccttcttatt ctatcaccag attgcatggt gatttgtctt ctttctttta tcataatgta 65040
atctctaaat tcatcggcaa attgtctata tctaaaatca taatatgaga tgtttacctc 65100
tacaaatatc tgttcgtcca atgttagagt atctacatca gttttgtatt ccaaattaaa 65160
catggcaacg gatttaattt tatattcctc tattaagtcc tcgtcgataa taacagaatg 65220
tagataatca tttaatccat cgtacatggt tggaagatgc ttgttgacaa aatctttaat 65280
tgtcttgatg aaggtgggac tatatctaac atcttgatta ataaaattta taacattgtc 65340
cataggatac tttgtaacta gttttataca catctcttca tcggtaagtt tagacagaat 65400
atcgtgaaca ggtggtatat tatattcatc agatatacga agaacaatgt ccaaatctat 65460
attgtttaat atattatata gatgtagcgt agctcctaca ggaatatctt taactaagtc 65520
aatgatttca tcaaccgtta gatctatttt aaagttaatc atataggcat tgatttttaa 65580
aaggtatgta gccttgacta cattctcatt aattaaccat tccaagtcac tgtgtgtaag 65640
aagattatat tctatcataa gcttgactac atttggtccc gataccatta aagaattctt 65700
atgatataag gaaacagatt ttaggtactc atctactcta caagaatttt ggagagcctt 65760
aacgatatca gtgacgttta ttatttcagg aggaaagaat ctaacattga gaatatcgga 65820
attaatagct tccagataca gtgattttgg caatagtccg tgtaatccat aatccagtaa 65880
cacgagctgg tgcttgctag acaccttttc aatgtttaat ttttttgaaa taagctttga 65940
taaagccttc ctcgcaaatt ccggatacat gaacatgtcg gcgacatgat taagtattgt 66000
tttttcatta ttttctcaac aagttctcaa taccccaata gatgatagaa tatcacccaa 66060
tgcgtccatg ttgtctattt ccaacaggtc gctatatcca ccaatagaag tttttccaaa 66120
aaagattcta ggaacagttc taccaccagt aatttgttca aaatagtcac gcaattcatt 66180
ttcgggttta aattctttaa tatcgacaat ttcatacgct cctcttttga aactaaactt 66240
atttagaata tccagtgcat ttctacaaaa aggacatgta tacttgacaa aaattgtcac 66300
tttgttattg gccaaccttt gttgtacaaa ttcctcggcc attttaatat ttaagtgata 66360

```
taaaactatc tcgacttatt taactcttta gtcgagatat atggacgcag atagctatat  66420
gatagccaac tacagaaggc aaacgctata aaaaacataa ttacgacgag catatttata  66480
aatattttta ttcagcatta cttgatatag taatattagg cacagtcaaa cattcaacca  66540
ctctcgatac attaactctc tcattttctt taacaaattc tacaatatct tcgtaaaaag  66600
attcttgaaa ctttttagaa tatctatcga ctctagatga aatagcgttc gtcaacatac  66660
tatgttttgt atacataaag gcgcccattt taacagtttc tagtgacaaa atgctagcga  66720
tcctaggatc ctttagaatc acatagattg acgattcgtc tctcttagta actctagtaa  66780
aataatcata caatctagta cgcgaaataa tattatcctt gacttgagga gatctaaaca  66840
atctagtttt gagaacatcg ataagttcat cgggaatgac atacatacta tctttaatag  66900
aactcttttc atccagttga atggattcgt ccttaaccaa ctgattaatg agatcttcta  66960
ttttatcatt ttccagatga tatgtatgtc cattaaagtt aaattgtgta gcgcttcttt  67020
ttagtctagc agccaatact ttaacatcac taatatcgat atacaaagga gatgatttat  67080
ctatggtatt aagaattcgt ttttcgacat ctgtcaaaac caattccttt ttgcctgtat  67140
catccagttt tccatccttt gtaaagaaat tattttctac tagactatta ataagactga  67200
taaggattcc tccataattg cacaatccaa actttttaac aaaactagac tttacaagat  67260
ctacaggaat gcgtaattca ggtttcttag cttgtgattt tttcttttgt ggacattttc  67320
ttgtgaccaa ctcatctacc atttcattga ttttagcagt gaaataagct ttcaatgcac  67380
gggcactgat actattgaaa acgagttgat cttcaaattc cgccatttaa gttcaccaaa  67440
caacttttaa atacaaatat atcaatagta gtagaataag aactataaaa aaaataataa  67500
ttaaccaata ccaaccccaa caaccggtat tattagttga tgtgactgtt ttctcatcac  67560
ttagaacaga tttaacaatt tctataaagt ctgtcaaatc atcttccgga gaccccataa  67620
atacaccaaa tatagcggcg tacaacttat ccatttatac attgaatatt ggcttttctt  67680
tatcgctatc ttcatcatat tcatcatcaa tatcaacaag tcccagatta cgagccagat  67740
cttcttctac attttcagtc attgatacac gttcactatc tccagagagt ccgataacgt  67800
tagccaccac ttctctatca atgattagtt tcttgagtgc gaatgtaatt tttgtttccg  67860
ttccggatct atagaagacg ataggtgtga taattgcctt ggccaattgt ctttctcttt  67920
tactgagtga ttctagttca ccttctatag atctgagaat ggatgattct ccagtcgaaa  67980
catattctac catggatccg tttaatttgt tgatgaagat ggattcatcc ttaaatgttt  68040
tctctgtaat agtttccacc gaaagactat gcaaagaatt tggaatgcgt tccttgtgct  68100
taatgtttcc atagacggct tctagaagtt gatacaacat aggactagcc gcggtaactt  68160
ttatttttag aaagtatcca tcgcttctat cttgtttaga tttattttta taaagtttag  68220
tctctccttc caacataata aaagtggaag tcatttgact agataaacta tcagtaagtt  68280
ttatagagat agacgaacaa ttagcgtatt gagaagcatt tagtgtaacg tattcgatac  68340
attttgcatt agatttacta atcgattttg catactctat aacacccgca caagtctgta  68400
gagaatcgct agatgcagta ggtcttggtg aagtttcaac tctcttcttg attaccttac  68460
tcatgattaa acctaaataa ttgtactttg taatataatg atatatattt tcactttatc  68520
tcatttgaga ataaaaatgt ttttgtttaa ccactgcatg atgtacagat ttcggaatcg  68580
caaaccacca gtggttttat tttatccttg tccaatgtga attgaatggg agcggatgcg  68640
ggtttcgtac gtagatagta cattcccgtt tttagaccga gactccatcc gtaaaaatgc  68700
```

-continued atactcgtta gtttggaata actcggatct gctatatgga tattcataga ttgactttga 68760
tcgatgaagg ctcccctgtc tgcagccatt tttatgatcg tcttttgtgg aatttcccaa 68820
atagttttat aaactcgctt aatatcttct ggaaggtttg tattctgaat ggatccacca 68880
tctgccataa tcctattctt gatctcatca ttccataatt ttctctcggt taaaactcta 68940
aggagatgcg gattaactac ttgaaattct ccagacaata ctctccgagt gtaaatatta 69000
ctggtatacg gttccaccga ctcattattt cccaaaattt gagcagttga tgcagtcggc 69060
ataggtgcca ccaataaact atttctaaga ccgtatgttc tgattttatc ttttagaggt 69120
tcccaattcc aaagatccga cggtacaaca ttccaaagat catattgtag aataccgtta 69180
ctggcgtacg atcctacata tgtatcgtat ggtccttcct tctcagctag ttcacaactc 69240
gcctctaatg caccgtaata aatggtttcg aagatcttct tatttagatc ttgtgcttcc 69300
aggctatcaa atggataatt taagagaata aacgcgtccg ctaatccttg aacaccaata 69360
ccgataggtc tatgtctctt attagagatt tcagcttctg gaataggata ataattaata 69420
tctataattt tattgagatt tctgacaatt actttgacca catccttcag tttgagaaaa 69480
tcaaatcgcc catctattac aaacatgttc aaggcaacag atgccagatt acaaacggct 69540
acctcattag catccgcata ttgtattatc tcagtgcaaa gattactaca cttgatagtt 69600
cctaaatttt gttgattact ctttttgtta cacgcatcct tataaagaat gaatggagta 69660
ccagtttcaa tctgagattc tataatcgct ttccagacga ctcgagcctt tattatagat 69720
ttgtatctcc tttctctttc gtatagtgta tacaatcgtt cgaactcgtc tccccaaaca 69780
ttgtccaatc caggacattc atccggacac atcaacgacc actctccgtc atccttcact 69840
cgtttcataa agagatcagg aatccaaaga gctataaata gatctctggt tctatgttcc 69900
tcgtttcctg tattcttttt aagatcgagg aacgccataa tatcagaatg ccacggttcc 69960
aagtatatgg ccataactcc aggccgtttg tttcctccct gatctatgta tctagcggtg 70020
ttattataaa ctctcaacat tggaataata ccgtttgata taccattggt accggagata 70080
tagcttccac tggcacgaat attactaatt gatagaccta ttccccctgc cattttagag 70140
attaatgcgc atcgttttaa cgtgtcatag ataccctcta tgctatcatc gatcatgtta 70200
agtagaaaac agctagacat ttggtgacga ctagttcccg cattaaataa ggtaggagaa 70260
gcgtgcgtaa accatttttc agaaagtaga ttgtacgtct caatagctga gtctatatcc 70320
cattgatgaa ttcctactgc gacacgcatt aacatgtgct gaggtctttc aacgatcttg 70380
ttgtttattt tcaacaagta ggatttttcc aaagttttaa aaccaaaata gttgtatgaa 70440
aagtctcgtt cgtaaataat aaccgagttg agtttatcct tatatttgtt aactatatcc 70500
atggtgatac ttgaaataat cggagaatgt ttcccatttt taggattaac atagttgaat 70560
aaatcctcca tcacttcact aaatagtttt tttgtttcct tgtgtagatt tgatacggct 70620
attctggcgg ctagaatggc ataatccgga tgttgtgtag tacaagtggc tgctatttcg 70680
gctgccagag tgtccaattc taccgttgtt actccattat atattccttg aataaccttc 70740
atagctattt taataggatc tatatgatcc gtgtttaagc cataacataa ttttctaata 70800
cgagacgtga ttttatcaaa catgacattt tccttgtatc catttcgttt aatgacaaac 70860
atttttgttg gtgtaataaa aaaaattatt taacttttca ttaataggga tttgacgtat 70920
gtagcgtaca aaattatcgt tcctggtata tagataaaga gtcctatata tttgaaaatc 70980
gttacggctc gattaaactt taatgattgc atagtgaata tatcattagg atttaactcc 71040
ttgactatca tggcggcgcc agaaattacc atcaaaagca ttaatacagt tatgccgatc 71100

-continued

```
gcagttagaa cggttatagc atccaccatt tatatctaaa aattagatca aagaatatgt  71160
gacaaagtcc tagttgtata ctgagaattg acgaaacaat gtttcttaca tatttttttt  71220
ttattagtaa ccgacttaat agtaggaact ggaaaactag acttgattat tctataagta  71280
tagataccct tccaaataat attctctttg ataaaagttc cagaaaatgt agaatttttt  71340
aaaaagttat cttttgctat taccaagatt gtgtttagac gcttattatt aatatgagtg  71400
atgaaatcca caccgcctct agatatcgct tttatttcca cattagatgg taaatccaat  71460
agtgaaacta tctttttagg aatgtatgga ctcgcgttta gaggagtgaa cgtcttaggc  71520
gtcggaaagg atgattcatc aaacgaataa acaatttcac aaatggatgt taatgtatta  71580
gtaggaaatt ttttgacgct agtggaattg aagattctaa tggatgatgt tctacctatt  71640
tcatccgata acatgttaat ttccgacacc aacggtttta atatttcgat gatatacggt  71700
agtctctctt tcggacttat atagcttatt ccacaatacg agtcattata tactccaaaa  71760
aacaaaataa ctagtataaa atctgtatcg aatgggaaaa acgaaattat cgacataggt  71820
atagaatctg gaacattgaa cgtattaata cttaattctt tttctgtggt aagtaccgat  71880
aggttattga cattgtatgg ttttaaatat tctataactt gagacttgat agatattagt  71940
gatgaattga aaattatttt tatcaccacg tgtgtttcag gatcatcgtc gacgcccgtc  72000
aaccaaccga atggagtaaa ataaatatca ttaatatatg ctctagatat tagtattttt  72060
atcaatcctt tgattatcat cttctcgtag gcgaatgatt ccatgatcaa gagtgattta  72120
agaacatcct ccggagtatt aatgggctta gtaaacagtc catcgttgca ataataaaag  72180
ttatccaagt taaaggatat tatgcattcg tttaaagata tcacctcatc tgacggagac  72240
aatttttttgg taggttttag agactttgaa gctacttgtt taacaaagtt attcatcgtc  72300
gtttactatt ctatttaatt ttgtagttaa tttatcacat atcacattaa ttgacttttt  72360
ggtccatttt tccatacgtt tatattcttt taatcctgcg ttatccgttt ccgttatatc  72420
cagggataga tcttgcaagt taaatagaat gctcttaaat aatgtcattt tcttatccgc  72480
taaaaattta aagaatgtat aaaccttttt cagagatttg aaactcttag gtggtgtcct  72540
agtacacaat atcataaaca aactaataaa cattccacat tcagattcca acagctgatt  72600
aacttctaca ttaatacagc ctattttcgc tccaaatgta cattcgaaaa atctgaataa  72660
aacatcgatg tcacaatttg tattatccaa tacagaatgt ttgtgattcg tgttaaaacc  72720
atcggagaag gaataaaaat aaaaattatt atagtggtgg aattcagttg gaatattgcc  72780
tccggagtca taaaaggata ctaaacattg ttttttatca taaattacac atttccaatg  72840
agacaaataa caaaatccaa acattacaaa tctagaggta gaacttttaa ttttgtcttt  72900
aagtatatac gataagatat gtttattcat aaacgcgtca aatttttcat gaatcgctaa  72960
ggagtttaag aatctcatgt caaattgtcc tatataatcc acttcggatc cataagcaaa  73020
ctgagagact aagttcttaa tacttcgatt gctcatccag gctcctctct caggctctat  73080
tttcatcttg acgacctttg gattttcacc agtatgtatt cctttacgtg ataaatcatc  73140
gattttcaaa tccatttgtg agaagtctat cgccttagat actttttccc gtagtcgagg  73200
tttaaagaaa tacgctaacg gtatactagt aggtaactca aagacatcat atatagaatg  73260
gtaacgcgtc tttaactcgt cggttaactc tttcttttga tcgagttcgt cgctactatt  73320
gggtctgctc aggtgccccg actctactag ttccaacatc ataccgatag gaatacaaga  73380
cactttgccg gcggttgtag atttatcata tttctccact acatatccgt tacaatttgt  73440
```

-continued

```
taaaaattta gatacatcta tattgctaca taatccagct agtgaatata tatgacataa  73500
taaattggta aatcctagtt ctggtatttt actaattact aaatctgtat atctttccat  73560
ttatcatgga aaagaattta ccagatatct tctttttcc aaactgcgtt aatgtattct  73620
cttacaaata ttcacaagat gaattcagta atatgagtaa aacggaacgt gatagtttct  73680
cattggcggt gtttccagtt ataaaacata gatggcataa cgcacacgtt gtaaaacata  73740
aaggaatata caaagttagt acagaagcac gtggaaaaaa agtatctcct ccatcactag  73800
gaaaacccgc acacataaac ctaaccgcga agcaatatat atacagtgaa cacacaataa  73860
gctttgaatg ttatagtttt ctaaaatgta taacaaatac agaaatcaat tcgttcgatg  73920
agtatatatt aagaggacta ttagaagctg gtaatagttt acagatattt tccaattccg  73980
taggtaaacg aacagatact ataggtgtac tagggaataa gtatccattt agcaaaattc  74040
cattggcctc attaactcct aaagcacaac gagagatatt ttcagcgtgg atttctcata  74100
gacctgtagt tttaactgga ggaactggag tgggtaagac gtcacaggta cccaagttat  74160
tgctttggtt taattattta tttggtggat tctctactct agataaaatc actgactttc  74220
acgaaagacc agtcattcta tctcttccta ggatagcttt agttagattg catagcaata  74280
ccattttaaa atcattggga tttaaggtac tagatggatc tcctatttct ttacggtacg  74340
gatctatacc ggaagaatta ataaacaaac aaccaaaaaa atatggaatt gtattttcta  74400
cccataagtt atctctaaca aaactattta gttatggcac tcttattata gacgaagttc  74460
atgagcatga tcaaatagga gatattatta tagcagtagc gagaaagcat catacgaaaa  74520
tagattctat gtttttaatg actgccacgt tagaggatga cagggaacgg ctaaaagtat  74580
ttttacctaa tcccgcattt atacatattc ctggagatac actgtttaaa attagcgagg  74640
tatttattca taataagata aatccatctt ccagaatggc atacatagaa gaagaaaaga  74700
gaaatttagt tactgctata cagatgtata ctcctcctga tggatcatcc ggtatagtct  74760
ttgtggcatc cgttgcacag tgtcacgaat ataaatcata tttagaaaaa agattaccgt  74820
atgatatgta tattattcat ggtaaggtct tagatataga cgaaatatta gaaaaagtgt  74880
attcatcacc taatgtatcg ataattattt ctactcctta tttggaatcc agcgttacta  74940
tacgcaatgt tacacacatt tatgatatgg gtagagtttt tgtccccgct cctttggag  75000
gatcgcaaga atttatttct aaatctatga gagatcaacg aaaaggaaga gtaggaagag  75060
ttaatcctgg gacatacgta tatttctatg atctgtctta tatgaagtct atacagcgaa  75120
tagattcaga atttctacat aattatatat tgtacgctaa taagtttaat ctaacactcc  75180
ccgaagattt gtttataatc cctacaaatt tggatattct atggcgtaca aaggaatata  75240
tagactcgtt cgatattagt acagaaacat ggaataaatt attatccaat tattatatga  75300
agatgataga gtatgctaaa ctttatgtac taagtcctat tctcgctgag gagttggata  75360
attttgagag gacgggagaa ttaactagta ttgtacaaga agccatttta tctctaaatt  75420
tacgaattaa gattttaaat tttaaacata aagatgatga tacgtatata cacttttgta  75480
aaatattatt cggtgtctat aacggaacaa acgctactat atattatcat agacctctaa  75540
cgggatatat gaatatgatt tcagatacta tatttgttcc tgtagataat aactaaaaat  75600
caaactctaa tgaccacatc ttttttaga gatgaaaaat tttccacatc tccttttgta  75660
gacacgacta aacattttgc agaaaaaagt ttattagtgt ttagataatc gtatacttca  75720
tcagtgtaga tagtaaatgt gaacagataa aaggtattct tgctcaatag attggtaaat  75780
tccatagaat atattaatcc tttcttcttg agatcccaca tcatttcaac cagagacgtt  75840
```

-continued

```
ttatccaatg atttacctcg tactatacca catacaaaac tagattttgc agtgacgtcg 75900
tatctggtat tcctaccaaa caaaatttta cttttagttc ttttagaaaa ttctaaggta 75960
gaatctctat ttgccaatat gtcatctatg gaattaccac tagcaaaaaa tgatagaaat 76020
atatattgat acatcgcagc tggttttgat ctactatact ttaaaaacga atcagattcc 76080
ataattgcct gtatatcatc agctgaaaaa ctatgtttta cacgtattcc ttcggcattt 76140
ctttttaatg atatatcttg tttagacaat gataaagtta tcatgtccat gagagacgcg 76200
tctccgtatc gtataaatat ttcattagat gttagacgct tcattagggg tatacttcta 76260
taaggtttct taatcagtcc atcattggtt gcgtcaagaa ctactatcgg atgttgttgg 76320
gtatctctag tgttacacat ggccttacta aagtttgggt aaataactat gatatctcta 76380
ttaattatag atgcatatat ttcatttgtc aaggatatta gtatcgactt gctatcgtca 76440
ttaatacgtg taatgtaatc atataaatca tgcgatagcc aaggaaaatt taaatagatg 76500
ttcatcatat aatcgtcgct ataattcata ttaatacgtt gacattgact aatttgtaat 76560
atagcctcgc cacgaagaaa gctctcgtat tcagtttcat cgataaagga taccgttaaa 76620
tataactggt tgccgatagt ctcatagtct attaagtggt aagtttcgta caaatacaga 76680
atccctaaaa tattatctaa tgttggatta atctttacca taactgtata aaatggagac 76740
ggagtcataa ctattttacc gtttgtactt actggaatag acgaaggaat aatctccgga 76800
catgctggta aagacccaaa tgtctgtttg aagaaatcca atgttccagg tcctaatctc 76860
ttaacaaaaa ttacgatatt cgatcccgat atcctttgca ttctatttac cagcatatca 76920
cgaactatat taagattatc tatcatgtct attctcccac cgttatataa atcgcctccg 76980
ctaagaaacg ttagtatatc catacaatgg aatacttcat ttctaaaata gtattcgttt 77040
tctaattctt taatgtgaaa tcgtatacta gaaagggaaa aattatcttt gagttttccg 77100
ttagaaaaga accacgaaac taatgttctg attgcgtccg attccgttgc tgaattaatg 77160
gatttacacc aaaaactcat ataacttcta gatgtagaag cattcgctaa aaaattagta 77220
gaatcaaagg atataagtag atgttccaac aagtgagcaa ttcccaagat ttcatctata 77280
tcattctcga atccgaaatt agaaattccc aagtagatat ccttttttcat ccgatcgttg 77340
atgaaaatac gaactttatt cggtaagaca atcatttact aaggagtaaa ataggaagta 77400
atgttcgtat gtcgttatca tcgtataaat taaaggtgtg ttttttacca ttaagtgaca 77460
ttataatttt accaatattg gaattataat ataggtgtat ttgcgcactc gcgacggttg 77520
atgcatcggt aaatatagct gtatctaatg ttctagtcgg tatttcatca tttcgctgtc 77580
taataatagc gttttctcta tctgtttcca ttacagctgc ctgaagttta ttggtcggat 77640
aatatgtaaa ataataagaa atacatacga ataacaaaaa taaaataaga tataataaag 77700
atgccattta gagatctaat tttgtttaac ttgtccaaat tcctacttac agaagatgag 77760
gaatcgttgg agatagtgtc ttccttatgt agaggatttg aaatatctta tgatgacttg 77820
ataacttact ttccagatag gaaataccat aaatatattt ctaaagtatt tgaacatgta 77880
gatttatcgg aggaattaag tatggaattc catgatacaa ctctgagaga tttagtctat 77940
cttagattgt acaagtattc caagtgtata cggccgtgtt ataaattagg agataatcta 78000
aaaggcatag ttgttataaa ggacaggaat atttatatta gagaagcaaa tgatgacttg 78060
atagaatatc tcctcaagga atacactcct cagatttata catattctaa tgagcgcgtc 78120
cccataactg gttcaaaatt aattctttgt ggattttctc aagttacatt tatggcgtat 78180
```

-continued

```
acaacgtcgc atataacaac aaataaaaag gtagatgttc tcgtttccaa aaaatgtata  78240
gatgaactag tcgatccaat aaattatcaa atacttcaaa atttatttga taaaggaagc  78300
ggaacaataa acaaaatact caggaagata ttttattcgg taaccggtgg ccaaactcca  78360
taatttgctt tttctatttc ggattttaga atttccaaat tcaccagcga tttatcggtt  78420
ttggtgaaat ccaaggattt attaatgtcc acaaatgcca tttgttttgt ctgtggattg  78480
tatttgaaaa tggaaacgat gtagttagat agatgcgctg caaagtttcc tattagggtt  78540
ccgcgcttta cgtcacccag catacttgaa tcaccatcct ttaaaaaaaa tgataagata  78600
tcaacatgga gtatatcata ctcggatttt aattcttcta ctgcatcact gacattttca  78660
caaatactac aatacggttt accgaaaata atcagtacgt tcttcattta tgggtatcaa  78720
aaacttaaaa tcgttactgc tggaaaataa atcactgacg atattagatg ataatttata  78780
caaagtatac aatggaatat ttgtggatac aatgagtatt tatatagccg tcgccaattg  78840
tgtcagaaac ttagaagagt taactacggt attcataaaa tacgtaaacg gatgggtaaa  78900
aaagggaggg catgtaaccc tttttatcga tagaggaagt ataaaaaatta aacaagacgt  78960
tagagacaag agacgtaaat attctaaatt aaccaaggac agaaaaatgc tagaattaga  79020
aaagtgtaca tccgaaatac aaaatgttac cggatttatg gaagaagaaa taaaggcaga  79080
aatgcaatta aaaatcgata aactcacatt tcaaatatat ttatctgatt ctgataacat  79140
aaaaatatca ttgaatgaga tactaacaca tttcaacaat aatgagaatg ttacattatt  79200
ttattgtgat gaacgagacg cagaattcgt tatgtgtctc gaggctaaaa cacatttctc  79260
taccacagga gaatggccgt tgataataag taccgatcag gatactatgc tatttgcatc  79320
tactgataat catcctaaga tgataaaaaa cttaactcaa ctgtttaaat ttgttccctc  79380
ggcagaggat aactatttag caaaattaac ggcgttagtg aatggatgtg atttctttcc  79440
tggactctat ggggcatcta taacacccac caacttaaac aaaatacaat tgtttagtga  79500
ttttacaatc gataatatag tcactagttt ggcaattaaa aattattata gaaagactaa  79560
ctctaccgta gacgtgcgta atattgttac gtttataaac gattacgcta atttagacga  79620
tgtctactcg tatgttcctc cttgtcaatg cactgttcaa gaatttatat tttccgcatt  79680
agatgaaaaa tggaacaatt ttaaatcatc ttatttagag accgttccgt taccctgcca  79740
attaatgtat gcattagaac cacgcaagga gattgatgtt tcagaagtta aaactttatc  79800
atcttatata gatttcgaaa atactaaatc agatatcgat gttataaaat ctatatcttc  79860
gatcttcgga tattctaacg aaaactgtaa cactatagtg ttcggcatct ataaggataa  79920
tttactactg agtataaata gttcatttta ctttaacgat agtctgttaa taaccaatac  79980
taaaagtgat aatataataa atataggtta ctagattaaa aatggtgttc caactcgtgt  80040
gctctacgtg cggcaaagat atttctcacg aacgatataa attgattata cgaaaaaaat  80100
cattaaagga tgtactcgtc agtgtaaaga acgaatgttg taggttaaaa ttatctacac  80160
aaatagaacc tcaacgtaac ttaacagtgc aacctctatt ggatataaac taatatggat  80220
ccggttaatt ttatcaagac atatgcgcct agaggttcta ttatttttat taattatacc  80280
atgtcattaa caagtcattt gaatccatcg atagaaaaac atgtgggtat ttattatggt  80340
acgttattat cggaacactt ggtagttgaa tctacctata gaaaaggagt tcgaatagtc  80400
ccattggata gttttttga aggatatctt agtgcaaaag tatacatgtt agagaatatt  80460
caagttatga aaatagcagc tgatacgtca ttaactttat tgggtattcc gtatggattt  80520
ggtcatgata gaatgtattg ttttaaattg gtagctgaat gttataaaaa tgccggtatt  80580
```

gatacatcgt ctaaacgaat attaggtaaa gatatttttc tgagccaaaa cttcacagat 80640
gataatagat ggataaagat atatgattct aataatttaa cattttggca aattgattac 80700
cttaaagggt gagttaatat gcataactac tcctccgttg ttttttccct cgttcttttt 80760
cttaacgttg tttgccatca ctctcataat gtaaagatat tctaaaatgg taaacttttg 80820
catatcggac gcagaaattg gtataaatgt tgtaattgta ttatttcccg tcaatggact 80880
agtcacagct ccatcagttt tatatccttt agagtatttc tcactcgtgt ctaacattct 80940
agagcattcc atgatctgtt tatcgttgat attggccgga aagatagatt ttttattttt 81000
tattatatta ctattggcaa ttgtagatat aacttctggt aaatattttt ctaccttttc 81060
aatctcttct attttcaagc cggctatata ttctgctata ttgttgctag tatcaatacc 81120
ttttctggct aagaagtcat atgtggtatt cactatatca gttttaactg gtagttccat 81180
tagcctttcc acttctgcag aataatcaga aattggttct ttaccagaaa atccagctac 81240
tataataggc tcaccgatga tcattggcaa aatcctatat tgtaccagat taatgagagc 81300
atatttcatt tccaataatt ctgctagttc ttgagacatt gatttatttg atgaatctag 81360
ttggttctct agatactcta ccatttctgc cgcatacaat aacttgttag ataaaatcag 81420
ggttatcaaa gtgtttagcg tggctagaat agtgggcttg catgtattaa agaatgcggt 81480
agtatgagta aaccgtttta acgaattata tagtctccag aaatctgtgg cgttacatac 81540
atgagccgaa tgacatcgaa gattgtccaa tatttttaat agctgctctt tgtccattat 81600
ttctatattt gactcgcaac aattgtagat accattaatc actgattcct ttttcgatgc 81660
cggacaatag cacaattgtt tagctttgga ctctatgtat tcagaattaa tagatatatc 81720
tctcaataca gattgcacta tacattttga aactatgtca aaaattgtag aacgacgctg 81780
ttctgcagcc atttaacttt aaataattta caaaaattta aaatgagcat ccgtataaaa 81840
atcgataaac tgcgccaaat tgtggcatat ttttcagagt tcagtgaaga agtatctata 81900
aatgtagact cgacggatga gttaatgtat atttttgccg ccttgggcgg atctgtaaac 81960
atttgggcca ttatacctct cagtgcatca gtgttctacc gcggagccga aaacattgtg 82020
tttaatcttc ctgtgtccaa ggtaaaatcg tgtttgtgta gttttcacaa tgatgccatc 82080
atagatatag aacctgatct ggaaaataat ctagtaaaac tttctagtta tcatgtagta 82140
agtgtcgatt gtaacaagga actgatgcct attaggacag atactactat ttgtctaagt 82200
atagatcaaa agaaatctta cgtgtttaat tttcacaagt atgaagaaaa atgttgtggt 82260
agaaccgtca ttcatttaga atggttgttg ggctttatca agtgtattag tcagcatcag 82320
catttggcta ttatgtttaa agatgacaat attattatga agactcctgg taatactgat 82380
gcgttttcca gggaatattc tatgactgaa tgttctcaag aactacaaaa gttttctttc 82440
aaaatagcta tctcgtctct caacaaacta cgaggattca aaaagagagt caatgttttt 82500
gaaactagaa tcgtaatgga taatgacgat aacattctag gaatgttgtt ttcggataga 82560
gttcaatcct ttaagatcaa catctttatg acgtttttag attaatactt tcaatgagat 82620
aaatatgggt ggcagagtaa gtgttgagct ccctaaacgg gatccgcctc cgggagtacc 82680
cactgatgag atgttattaa acgtggataa aatgcatgac gtgatagctc ccgctaagct 82740
tttagaatat gtgcatatag gaccactagc aaaagataaa gaggataaag taaagaaaag 82800
atatccagag tttagattag tcaacacagg acccggtggt ctttcggcat tgttaagaca 82860
atcgtataat ggaaccgcac ccaattgctg tcgcactttt aatcgtactc attattggaa 82920

```
aaaggatgga aagatatcag ataagtatga agagggtgca gtattagaat cgtgttggcc  82980
agacgttcac gacactggaa aatgcgatgt tgatttattc gactggtgtc agggggatac  83040
gttcgataga aacatatgcc atcagtggat cggttcagcc tttaatagga gtgatagaac  83100
tgtagagggt caacaatcgt taataaatct gtataataag atgcaaacat tatgtagtaa  83160
agatgctagt gtaccaatat gtgaatcatt tttgcatcat ttacgcgcac acaatacaga  83220
agatagcaaa gagatgatcg attatattct aagacaacag tctgcggact ttaaacagaa  83280
atatatgaga tgtagttatc ccactagaga taagttagaa gagtcattaa aatatgcgga  83340
acctcgagaa tgttgggatc cagagtgttc gaatgccaat gttaatttct tactaacacg  83400
taattataat aatttaggac tttgcaatat tgtacgatgt aatactagcg tgaacaactt  83460
acagatggat aaaacttcct cattaagatt gtcatgtgga ttaagcaata gtgatagatt  83520
ttctactgtt cccgtcaata gagcaaaagt agttcaacat aatattaaac attcgttcga  83580
cctaaaattg catttgatca gtttattatc tctcttggta atatggatac taattgtagc  83640
tatttaaatg ggtgccgcgg caagcataca gacgacggtg aatacactca gcgaacgtat  83700
ctcgtctaaa ttagaacaag aagcgaacgc tagtgctcaa acaaaatgtg atatagaaat  83760
cggaaatttt tatatccgac aaaaccatgg atgtaacctc actgttaaaa atatgtgctc  83820
tgcggacgcg gatgctcagt tggatgctgt gttatcagcc gctacagaaa catatagtgg  83880
attaacaccg gaacaaaaag catacgtacc agctatgttt actgctgcgt taaacattca  83940
gacgagtgta aacactgttg ttagagattt tgaaaattat gtgaaacaga cttgtaattc  84000
tagcgcggtc gtcgataaca aattaaagat acaaaacgta atcatagatg aatgttacgg  84060
agccccagga tctccaacaa atttggaatt tattaataca ggatctagca aaggaaattg  84120
tgccattaaa gcgttgatgc aattgacgac taaggccact actcaaatag cacctagaca  84180
agttgctggt acaggagttc agttttatat gattgttatc ggtgttataa tattggcagc  84240
gttgtttatg tactatgcca agcgtatgtt gttcacatcc accaatgata aaatcaaact  84300
tattttagcc aataaggaaa acgtccattg gactacttac atggacacat tctttagaac  84360
ttctccgatg gttattgcta ccacggatat gcaaaactga aaatatattg ataatatttt  84420
aatagattaa catggaagtt atcgctgatc gtctagacga tatagtgaaa caaaatatag  84480
cggatgaaaa atttgtagat tttgttatac acggtctaga gcatcaatgt cctgctatac  84540
ttcgaccatt aattaggttg tttattgata tactattatt tgttatagta atttatattt  84600
ttacggtacg tctagtaagt agaaattatc aaatgttgtt ggcgttggtg gcgctagtca  84660
tcacattaac tatttttat tactttatac tataatagta ctagactgac ttctaacaaa  84720
catctcacct gccataaata aatgcttgat attaaagtct tctatttcta acactattcc  84780
atctgtggaa aataatactc tgacattatc gctaattgac acatcggtga gtgatatgcc  84840
tataaagtaa taatcttctt tgggcacata taccagtgta ccaggttcta acaacctatt  84900
tactggtgct cctgtagcat actttttctt taccttgaga atatccatcg tttgcttggt  84960
caatagcgat atgtgatttt ttatcaacca ctcaaaaaag taattggagt gttcatatcc  85020
tctacgggct attgtctcat ggccgtgtat gaaatttaag taacacgact gtggtagatt  85080
tgttctatag agccggttgc cgcaaataga tagaactacc aatatgtctg tacaaatgtt  85140
aaacattaat tgattaacag aaaaaacaat gttcgttctg ggaatagaaa ccagatcaaa  85200
acaaaattcg ttagaatata tgccacgttt atacatggaa tataaaataa ctacagtttg  85260
aaaaataaca gtatcattta aacatttaac ttgcggggtt aatttcacaa ctttactgtt  85320
```

-continued

```
tttaaactgt tcaaaatata gcatcgatcc atgagaaata cgtttagccg cctttaatag  85380
aggaaatccc accgcctttc tggatctcgc caacgacgat agttctgacc agcaacttat  85440
ttcttcatca tccacctgtt ttaacatata ataggcagga gatagatatc cgtcattgca  85500
atattccttt tcgtaggcac acaatctaat attgataaaa tctccattct cttctctgca  85560
tttattatct tgtttcggtg gctgattagg ctgtagtctt ggtttaggct ttggtatatc  85620
gttgttgaat ctattttggt cattaaatct ttcatttctt cctggtatat ttttatcacc  85680
tcgtttggtt ggatttttgt ctatattatc gtttgtaaca tcggtacggg tattcattta  85740
tcacaaaaaa aacttctcta aatgagtcta ctgctagaaa acctcatcga agaagatacc  85800
atattttttg caggaagtat atctgagtat gatgatttac aaatggttat tgccggcgca  85860
aaatccaaat ttccaagatc tatgctttct atttttaata tagtacctag aacgatgtca  85920
aaatatgagt tggagttgat tcataacgag aatatcacag gggcaatgtt taccacaatg  85980
tataatataa gaaacaattt gggtctagga gatgataaac taactattga agccattgaa  86040
aactatttct tggatcctaa caatgaggtt atgcctctta tcattaataa tacggatatg  86100
actgccgtca ttcctaaaaa aagtggtagg agaaagaata agaacatggt tattttccgt  86160
caaggatcat cacctatctt gtgtattttc gaaactcgta aaaagattaa tatttataaa  86220
gaaaatatgg aatccgcgtc gactgagtat acacctatcg gagacaacaa ggctttgata  86280
tctaaatatg cgggaattaa tgtcctgaat gtgtattctc cttccacatc catgagattg  86340
aatgccattt acggattcac caataaaaat aaactagaga aacttagtac taataaggaa  86400
ctagaatcgt atagttctag ccctcttcaa gaacccatta ggttaaatga ttttctggga  86460
ctattggaat gtgttaaaaa gaatattcct ctaacagata ttccgacaaa ggattgatta  86520
ctataaatgg agaatgttcc taatgtatac tttaatcctg tgtttataga gcccacgttt  86580
aaacattctt tattaagtgt ttataaacac agattaatag ttttatttga agtattcatt  86640
gtattcattc taatatatgt attttttaga tctgaattaa atatgttctt catgcctaaa  86700
cgaaaaatac ccgatcctat tgatagatta cgacgtgcta atctagcgtg tgaagacgat  86760
aaattaatga tctatggatt accatggatg acaactcaaa catctgcgtt atcaataaat  86820
agtaaaccga tagtgtataa agattgtgca aagcttttgc gatcaataaa tggatcacaa  86880
ccagtatctc ttaacgatgt tcttcgcaga tgatgattca tttttaagt atttggctag  86940
tcaagatgat gaatcttcat tatctgatat attgcaaatc actcaatatc tagactttct  87000
gttattatta ttgatccaat caaaaaataa attagaagcc gtgggtcatt gttatgaatc  87060
tctttcagag gaatacagac aattgacaaa attcacagac tttcaagatt ttaaaaaact  87120
gtttaacaag gtccctattg ttacagatgg aagggtcaaa cttaataaag gatatttgtt  87180
cgactttgtg attagtttga tgcgattcaa aaaagaatcc tctctagcta ccaccgcaat  87240
agatcctatt agatacatag atcctcgtcg cgatatcgca ttttctaacg tgatggatat  87300
attaaagtcg aataaagtga acaataatta attctttatt gtcatcatga acggcggaca  87360
tattcagttg ataatcggcc ccatgttttc aggtaaaagt acagaattaa ttagacgagt  87420
tagacgttat caaatagctc aatataaatg cgtgactata aaatattcta acgataatag  87480
atacggaacg ggactatgga cgcatgataa gaataatttt gaagcattgg aagcaactaa  87540
actatgtgat gtcttggaat caattacaga tttctccgtg ataggtatcg atgaaggaca  87600
gttctttcca gacattgttg aattctgtga gcgtatggca aacgaaggaa aaatagttat  87660
```

agtagccgca ctcgatggga catttcaacg taaaccgttt aataatattt tgaatcttat 87720
tccattatct gaaatggtgg taaaactaac tgctgtgtgt atgaaatgct ttaaggaggc 87780
ttccttttct aaacgattgg gtgaggaaac cgagatagag ataataggag gtaatgatat 87840
gtatcaatcg gtgtgtagaa agtgttacgt cggctcataa tattatattt tttatctaaa 87900
aaactaaaaa taaacattga ttaaatttta atataatact taaaaatgga tgttgtgtcg 87960
ttagataaac cgtttatgta ttttgaggaa attgataatg agttagatta cgaaccagaa 88020
agtgcaaatg aggtcgcaaa aaaactgccg tatcaaggac agttaaaact attactagga 88080
gaattatttt ttcttagtaa gttacagcga cacggtatat tagatggtgc caccgtagtg 88140
tatataggat ctgctcccgg tacacatata cgttatttga gagatcattt ctataattta 88200
ggagtgatca tcaaatggat gctaattgac ggccgccatc atgatcctat tttaaatgga 88260
ttgcgtgatg tgactctagt gactcggttc gttgatgagg aatatctacg atccatcaaa 88320
aaacaactgc atccttctaa gattatttta atttctgatg tgagatccaa acgaggagga 88380
aatgaaccta gtacggcgga tttactaagt aattacgctc tacaaaatgt catgattagt 88440
attttaaacc ccgtggcgtc tagtcttaaa tggagatgcc cgtttccaga tcaatggatc 88500
aaggactttt atatcccaca cggtaataaa atgttacaac cttttgctcc ttcatattca 88560
gctgaaatga gattattaag tatttatacc ggtgagaaca tgagactgac tcgagttacc 88620
aaatcagacg ctgtaaatta tgaaaaaaag atgtactacc ttaataagat cgtccgtaac 88680
aaagtagttg ttaactttga ttatcctaat caggaatatg actattttca catgtacttt 88740
atgctgagga ccgtgtactg caataaaaca tttcctacta ctaaagcaaa ggtactattt 88800
ctacaacaat ctatatttcg tttcttaaat attccaacaa catcaactga aaaagttagt 88860
catgaaccaa tacaacgtaa aatatctagc aaaaattcta tgtctaaaaa cagaaatagc 88920
aagagatccg tacgcagtaa taaatagaaa cgtactactg agatatacta ccgatataga 88980
gtataatgat ttagttactt taataaccgt tagacataaa attgattcta tgaaaactgt 89040
gtttcaggta tttaacgaat catccataaa ttatactccg gttgatgatg attatggaga 89100
accaatcatt ataacatcgt atcttcaaaa aggtcataac aagtttcctg taaattttct 89160
atacatagat gtggtaatat ctgacttatt tcctagcttt gttagactag atactacaga 89220
aactaatata gttaatagtg tactacaaac aggcgatggt aaaaagactc ttcgtcttcc 89280
caaaatgtta gagacggaaa tagttgtcaa gattctctac cgtcctaata taccattaaa 89340
aattgttaga tttttccgca ataacatggt aactggagta gagatagccg atagatctgt 89400
tatttcagtc gctgattaat caattagtag agatgagata agaacattat aataatcaat 89460
aatatatttt atatcttata tcttgtttag aaaaatgcta atattaaaat agctaacgct 89520
agtaatccaa tcggaagcca tttgatatct ataatagggt atctaatttc ctgattcaga 89580
tagcggacag ctatattctc ggtagctact cgtttggaat cacaaacatt atttacatct 89640
aatttactat ctgtaatgga aacgtttccc aatgaaatgg tacaatccga tacattgcat 89700
tttgttatat tttttttaa agaggctggt aacaacgcat cgcttcgttt acatggctcg 89760
taccaacaat aatagggtaa tcttgtatct attcctatcc gtactatgct tttatcagga 89820
taaatacatt tacatcgtat atcgtctttg ttagcatcac agaatgcata aatttgttcg 89880
tccgtcatga taaaaattta aagtgtaaat ataactatta ttttatagtt gtaataaaaa 89940
gggaaatttg attgtatact ttcggttctt taaaagaaac tgacttgata aaaatggctg 90000
taatctctaa ggttacgtat agtctatatg atcaaaaaga gattaatgct acagatatta 90060

-continued tcattagtca tgttaaaaat gacgacgata tcggtaccgt taaagatggt agactaggtg 90120
ctatggatgg ggcattatgt aaaacttgtg ggaaaacgga attggaatgt ttcggtcact 90180
ggggtaaagt aagtatttat aaaactcata tagttaagcc tgaatttatt tcagaaatta 90240
ttcgtttact gaattatata tgtattcact gcggattatt gcgttcacga gaaccgtatt 90300
ccgacgatat taacctaaaa gagttatcgg gacacgctct taggagatta aaggataaaa 90360
tattatccaa gaaaaagtca tgttggaaca gtgaatgtat gcaaccgtat caaaaaatta 90420
ctttttcaaa gaaaaaggtt tgtttcgtca acaagttgga tgatattaac gttcctaatt 90480
ctctcatcta tcaaaagtta atttctattc atgaaaagtt ttggccatta ttagaaattc 90540
atcaatatcc agctaactta ttttatacag actactttcc catccctccg ttgattatta 90600
gaccggctat tagtttttgg atagatagta tacccaaaga aaccaatgaa ttaacttact 90660
tattaggtat gatcgttaag aattgtaact tgaatgctga tgaacaggtt atccagaagg 90720
cggtaataga atacgatgat attaaaatta tttctaataa cacttccagt atcaatttat 90780
catatatcac atccggcaaa aataatatga ttagaagtta tatcgtcgcc cggcgaaaag 90840
atcagaccgc tagatctgta attggtccca gtacatctat caccgttaat gaggtaggaa 90900
tgcccgcata tattagaaat acacttacag aaaagatatt tgttaatgcc tttacagtgg 90960
ataaagttaa acaactatta gcgtcaaacc aagttaaatt ttactttaat aaacgattaa 91020
accaattaac aagaatacgc caaggaaagt ttatcaaaaa taaaatacat ttattgcctg 91080
gtgattgggt agaagtagct gttcaagaat atacaagtat tatttttgga agacagccgt 91140
ctctacatag atacaacgtc atcgcttcat ctatcagagc taccgaagga gatactatca 91200
aaatatctcc cggaattgtc aactctcaaa atgctgattt cgacggagat gaagaatgga 91260
tgatattgga gcaaaatcct aaagccgtaa ttgaacaaag tattcttatg tatccgacga 91320
cgttactcaa acacgatatt catggagccc ccgtttatgg atctattcaa gatgaaatcg 91380
tagcagcgta ttcattgttt aggatacaag atctttgttt agatgaagta ttgaacatct 91440
tggggaaata tggaagagag ttcgatccta aaggtaaatg taaattcagc ggtaaagata 91500
tctatactta cttgataggt gaaaagatta attatccggg tctcttaaag gatggtgaaa 91560
ttattgcaaa cgacgtagat agtaattttg ttgtggctat gaggcatctg tcattggctg 91620
gactcttatc cgatcataag tcgaacgtgg aaggtatcaa ctttattatc aagtcatctt 91680
atgtttttaa gagatatcta tctatttacg gttttggggt gacattcaaa gatctgagac 91740
caaattcgac gttcactaat aaattggagg ccatcaacgt agaaaaaata gaacttatca 91800
aagaagcata cgccaaatat ctcaacgatg taagagacgg gaaaatagtt ccattatcta 91860
aagctttaga ggcggactat gtggaatcca tgttatccaa cttgacaaat cttaatatcc 91920
gagagataga agaacatatg agacaaacgc tgatagatga tccagataat aacctcctga 91980
aaatggccaa agcgggttat aaagtaaatc ccacagaact aatgtatatt ctaggtactt 92040
atggacaaca gaggattgat ggtgaaccag cagagactcg agtattgggt agagtcttac 92100
cttactatct tccagactct aaggatccag aaggaagagg ttacattctt aattctttaa 92160
caaaaggatt aacgggttct caatattact tttcgatgct ggttgcaaga tctcaatcta 92220
ctgatatcgt ctgtgaaaca tcacgtaccg gaacactggc tagaaaaatc attaaaaaga 92280
tggaggatat ggtggtcgac ggatacggac aagtagttat aggtaatacg ctcatcaagt 92340
acgccgccaa ttataccaaa attctaggct cagtatgtaa acctgtagat cttatctatc 92400

-continued

```
cagatgagtc catgacttgg tatttggaaa ttagtgctct gtggaataaa ataaaacagg  92460
gattcgttta ctctcagaaa cagaaacttg caaaaaagac attggcgccg tttaatttcc  92520
tagtattcgt caaacccacc actgaggata atgctattaa ggttaaggat ctgtacgata  92580
tgattcataa cgtcattgat gatgtgagag agaaatactt ctttacggta tctaatatag  92640
attttatgga gtatatattc ttgacgcatc ttaatccttc tagaattaga attacaaaag  92700
aaacggctat cactatcttt gaaaagttct atgaaaaact caattatact ctaggtggtg  92760
gaactcctat tggaattatt tctgcacagg tattgtctga gaagtttaca caacaagccc  92820
tgtccagttt tcacactact gaaaaaagtg gtgccgtcaa acaaaaactt ggtttcaacg  92880
agtttaataa cttgactaat ttgagtaaga ataagaccga aattatcact ctggtatccg  92940
atgatatctc taaacttcaa tctgttaaga ttaatttcga atttgtatgt ttgggagaat  93000
taaatccaaa catcactctt cgaaaagaaa cagataggta tgtagtagat ataatagtca  93060
atagattata catcaagaga gcagaaatta ccgaattagt cgtcgaatat atgattgaac  93120
gattcatctc ctttagcgtc attgtaaagg aatggggtat ggaaacattc attgaggatg  93180
aggataatat tagatttact gtctacctaa atttcgttga accggaagaa ttgaatctta  93240
gtaagtttat gatggttctt ccgggtgccg ccaacaaggg caagattagt aaattcaaga  93300
ttcctatctc tgattatacg ggatatgacg acttcaatca aacaaaaaag ctcaataaga  93360
tgactgtaga actcatgaat ctaaaagaat tgggttcttt cgatttggaa aacgtcaacg  93420
tgtatcctgg agtatggaat acatacgata tcttcggtat cgaggccgct cgtgaatact  93480
tgtgcgaagc catgttaaac acctatggag aagggttcga ttatctgtat cagccttgtg  93540
atcttctcgc tagtttacta tgtgctagtt acgaaccaga atcagtgaat aaattcaagt  93600
tcggcgcagc tagtactctt aagagagcta cgttcggaga caataaagca ttgttaaacg  93660
cggctcttca taaaaagtca gaacctatta acgataatag tagctgccac ttttttagca  93720
aggtccctaa tataggaact ggatattaca aatactttat cgacttgggt cttctcatga  93780
gaatggaaag gaaactatct gataagatat cttctcaaaa gatcaaggaa atggaagaaa  93840
cagaagactt ttaattctta tcaataacat atttttctat gatctgtctt ttaaacgatg  93900
gattttccac aaatgcgcct ctcaagtccc tcatagaatg atacacgtat aaaaaatata  93960
gcataggcaa tgactcctta tttttagaca ttagatatgc caaaatcata gccccgcttc  94020
tatttactcc cgcagcacaa tgaaccaaca cgggctcgtt tcgttgatca catttagata  94080
aaaaggcggt tacgtcgtca aaatatttac taatatcggt agttgtatca tctaccaacg  94140
gtatatgaat aatattaata ttagagttag gtaatgtata tttatccatc gtcaaattta  94200
aaacatattt gaacttaact tcagatgatg gtgcatccat agcattttta taatttccca  94260
aatacacatt attggttact cttgtcatta tagtgggaga tttggctttg tgcatatctc  94320
cagttgaacg tagtagtaag tatttataca aacttttctt atccatttat aacgtacaaa  94380
tggataaaac tactttatcg gtaaacgcgt gtaatttaga atacgttaga gaaaaggcta  94440
tagtaggcgt acaagcagcc aaaacatcaa cacttatatt ctttgttatt atattggcaa  94500
ttagtgcgct attactctgg tttcagacgt ctgataatcc agtctttaat gaattaacga  94560
gatatatgcg aattaaaaat acggttaacg attggaaatc attaacggat agcaaaacaa  94620
aattagaaag tgatagaggt agacttctag ccgctggtaa ggatgatata ttcgaattca  94680
aatgtgtgga tttcggcgcc tattttatag ctatgcgatt ggataagaaa acatatctgc  94740
cgcaagctat taggcgaggt actggagacg cgtggatggt taaaaaggcg gcaaaggtcg  94800
```

atccatctgc tcaacaattt tgtcagtatt tgataaaaca caagtctaat aatgttatta 94860
cttgtggtaa tgagatgtta aatgaattag gttatagcgg ttattttatg tcaccgcatt 94920
ggtgttccga ttttagtaat atggaatagt gttagataaa tgcggtaacg aatgttcctg 94980
taaggaacca taacagctta gatttaacgt taaagatgag cataaacata ataaacaaaa 95040
ttacaatcaa acctataaca ttaatatcaa acaatccaaa aaatgaaatc agtggagtag 95100
taaacgcgta cataactcct ggataacgtt tagcagctgc cgttcctatt ctagaccaaa 95160
aattcggttt catgttttcg aaacggtatt ctgcaacaag tcgaggatcg tgttctacat 95220
atttggcggc gttatccagt atctgcctat tgatcttcat ttcgttttcg attctggcta 95280
tttcaaaata aaatcccgat gatagacctc cagactttat aatttcatct acgatgttca 95340
gcgccgtagt aactctaata atataggctg ataagctaac atcataccct cctgtatatg 95400
tgaatatggc atgatttttg tccattacaa gctcggtttt aactttattg cctgtaataa 95460
tttctctcat ctgtaggata tctatttttt tgtcatgcat tgccttcaag acgggacgaa 95520
gaaacgtaat atcctcaata acgttatcgt tttctacaat aactacatat tctacctttt 95580
tattttctaa ctcggtaaaa aaattagaat cccatagggc taaatgtcta gcgatatttc 95640
ttttcgtttc ctctgtacac atagtgttac aaaaccctga aaagaagtga gtatacttgt 95700
catcatttct aatgtttcct ccagtccact gtataaacgc ataatccttg taatgatctg 95760
gatcatcctt gactaccaca acatttcttt tttctggcat aacttcattg tcctttacat 95820
catcgaactt ctgatcatta atatgctcat gaacattagg aaatgtttct gatggaggtc 95880
tatcaataac tggcacaaca ataacaggag ttttcaccgc cgccatttag ttattgaaat 95940
taatcatata caactcttta atacgagtta tattttcgtc tatccattgt ttcacattta 96000
catatttcga caaaaagata taaaatgcgt attccaatgc ttctctgttt aatgaattac 96060
taaaatatac aaacacgtca ctgtctggca ataaatgata tcttagaata ttgtaacaat 96120
ttattttgta ttgcacatgt tcgtgatcta tgagttcttc ttcgaatggc ataggatctc 96180
cgaatctgaa aacgtataaa taggagttag aataataata tttgagagta ttggtaatat 96240
ataaactctt tagcggtata attagttttt ttctctcgat ttctattttt agatgtgatg 96300
gaaaaatgac taattttgta gcattagtat catgaactct aatcgagatc ttaatatctt 96360
cgtcacacgt tagttctttg aagtttttaa gagatgcatc agttggttcg accgatggag 96420
taggtgcaac aattttttgt tcgatgtatg tatgtactgg agccattgtc ttaactataa 96480
tggtgcttgt atcgaaaaac tttaatgcag ataatggaag ctcttcgccg cgactttcta 96540
catcgtaatt gggttctaac gccgatctct gaatggatac tagttttcta agttctaatg 96600
tgattctctg aaaatgtaaa tccaattcct ccggcattat agatgtgtat acatcggtaa 96660
ataaaactat agtatccaac gatcccttct cgcaaattct agtcttaacc aaaaaatcgt 96720
atataaccac ggagatggcg tatttaagag tggattcttc taccgttttg ttcttggatt 96780
tcatataaga aactataaag tccgcactac tgttaagaat gattactaac gcaactatat 96840
agtttaaatt aagcatcttg gaaacataaa ataactctgt agacgatact tgactttcga 96900
ataagtttgc agacaaacga agaaagaaca gacctctctt aatttcagaa gaaaactttt 96960
tttcgtattc ctgacgtcta gagtttatat caataagaaa gttaagaatt agtcggttaa 97020
tgttgtattt cattacccaa gtttgagatt tcataatatt atcaaaagac atgataatat 97080
taaagataaa gcgctgacta tgaacgaaat agctatatgg ttcgctcaag aatatagtct 97140
tgttaaacgt ggaaacgata actgtatttt taatcacgtc agcggcatct aaattaaata 97200
taggtatatt tattccacac actctacaat atgccacacc atcttcataa taaataaatt 97260
cgttagcaaa attattaatt ttagtgaaat agttagcgtc aactttcata gcttccttca 97320
atctaatttg atgctcacac ggtgcgaatt ccactctaac atccctttc catgcctcag 97380
gttcatcgat ctctataata tctagttttt tgcgtttcac aaacacaggc tcgtctctcg 97440
cgatgagatc tgtatagtaa ctatgtaaat gataactaga tagaaagatg tagctatata 97500
gatgacgatc ctttaagaga ggtatgatga ctttacccca atcagataga ctgttgttat 97560
ggtcttcgga aaaagaattt ttataaattt ttccagtatt ttccaaatat acgtacttaa 97620
catctaaaaa atccttaatg ataataggaa tggataatcc gtctatttta taaagaaata 97680
catatcgcac attatacttt tttttggaaa tgggaatacc gatgtgtcta cataaatatg 97740
caaagtctaa atatttttta gagaatctta gttggtccaa attcttttcc aagtacggta 97800
atagattttt catattgaac ggtatcttct taatctctgg ttctagttcc gcattaaatg 97860
atgaaactaa gtcactattt ttataactaa cgattacatc acctctaaca tcatcattta 97920
ccagaatact gatcttcttt tgtcgtaaat acatgtctaa tgtgttaaaa aaaagatcat 97980
acaagttata cgtcatttca tctgtggtat tcttgtcatt gaaggataaa ctcgtactaa 98040
tctcttcttt aacagcctgt tcaaatttat atcctatata cgaaaaaata gcaaccagtg 98100
tttgatcatc cgcgtcaata ttctgttcta tcgtagtgta taacaatcgt atatcttctt 98160
ctgtgatagt cgatacgtta taaaggttga taacgaaaat atttttattt cgtgagataa 98220
agtcatcgta ggattttgga cttatattcg cgtctagtag atatgctttt atttttggaa 98280
tgatctcaat tagaatagtc tctttagagt ccatttaaag ttacaaacaa ctaggaaatt 98340
ggtttatgat gtataatttt tttagttttt atagattctt tattctatac ttaaaaaatg 98400
aaaataaata caaaggttct tgagggttgt gttaaattga aagcgagaaa taatcataaa 98460
ttatttcatt atcgcgatat ccgttaagtt tgtatcgtaa tggcgtggtc aattacaaat 98520
aaagcggata ctagtagctt cacaaagatg gctgaaatca gagctcatct aaaaaatagc 98580
gctgaaaata aagataaaaa cgaggatatt ttcccggaag atgtaataat tccatctact 98640
aagcccaaaa ccaaacgagc cactactcct cgtaaaccag cggctactaa aagatcaacc 98700
aaaaaggagg aagtggaaga agaagtagtt atagaggaat atcatcaaac aactgaaaaa 98760
aattctccat ctcctggagt cagcgacatt gtagaaagcg tggctgctgt agagctcgat 98820
gatagcgacg gggatgatga acctatggta caagttgaag ctggtaaagt aaatcatagt 98880
gctagaagcg atctttctga cctaaaggtg gctaccgaca atatcgttaa agatcttaag 98940
aaaattatta ctagaatctc tgcagtatcg acggttctag aggatgttca agcagctggt 99000
atctctagac aatttacttc tatgactaaa gctattacaa cactatctga tctagtcacc 99060
gagggaaaat ctaaagttgt tcgtaaaaaa gttaaaactt gtaagaagta aatgcgtgca 99120
ctttttata aagatggtaa actctttacc gataataatt ttttaaatcc tgtatcagac 99180
gataatccag cgtatgaggt tttgcaacat gttaaaattc ctactcattt aacagatgta 99240
gtagtatatg aacaaacgtg ggaggaggcg ttaactagat taatttttgt gggaagtgat 99300
tcaaaaggac gtagacaata cttttacgga aaaatgcatg tacagaatcg caacgctaaa 99360
agagatcgta tttttgttag agtatataac gttatgaaac gaattaattg ttttataaac 99420
aaaaatataa agaaatcgtc cacagattcc aattatcagt tggcggtttt tatgttaatg 99480
gaaactatgt tttttattag atttggtaaa atgaaatatc ttaaggagaa tgaaacagta 99540
gggttattaa cactaaaaaa taaacacata gaaataagtc ccgatgaaat agttatcaag 99600
tttgtaggaa aggacaaagt ttcacatgaa tttgttgttc ataagtctaa tagactatat 99660
aaaccgctat tgaaactgac ggatgattct agtcccgaag aatttctgtt caacaaacta 99720
agtgaacgaa aggtatacga atgtatcaaa cagtttggta ttagaatcaa ggatctccga 99780
acgtatggag tcaattatac gtttttatat aatttttgga caaatgtaaa gtccatatct 99840
cctcttccgt caccaaaaaa gttaatagcg ttaactatca aacaaactgc tgaagtggta 99900
ggtcatactc catcaatttc aaaaagagct tatatggcaa cgactatttt agaaatggta 99960
aaggataaaa attttttaga tgtagtatct aaaactacgt tcgatgaatt cctatctata 100020
gtcgtagatc acgttaaatc atctacggat ggatgatata gatctttaca caaataatta 100080
caagaccgat aaatggaaat ggataagcgt atgaaatctc tcgcaatgac agctttcttc 100140
ggagagctaa acacattaga tattatggca ttgataatgt ctatatttaa acgccatcca 100200
aacaatacca ttttttcagt ggataaggat ggtcagttta tgattgattt cgaatacgat 100260
aattataagg cttctcaata tttggatctg accctcactc cgatatctgg agatgaatgc 100320
aagactcacg catcgagtat agccgaacaa ttggcgtgtg tggatattat taaagaggat 100380
attagcgaat atatcaaaac tactccccgt cttaaacgat ttataaaaaa ataccgcaat 100440
agatcagata ctcgtatcag tcgagataca gaaaagctta aaatagctct agctaaaggc 100500
atagattacg aatatataaa agacgcttgt taataagtaa atgaaaaaaa actagtcgtt 100560
tataataaaa cacaatatgg atgccaacat agtatcatct tctactattg caacgtatat 100620
agacgcttta gcgaagaatg cttcagaatt agaacagagg tctaccgcat acgaaataaa 100680
taatgaattg gaactagtat ttattaagcc gccattaatt actttgacaa atgtagtgaa 100740
tatctctacg attcaggaat cgtttattcg atttaccgtt actaataagg aaggtgttaa 100800
aattagaact aagattccat tatctaaggt acatggtcta gatgtaaaaa atgtacagtt 100860
agtagatgct atagataaca tagtttggga aaagaaatca ttagtgacgg aaaatcgtct 100920
tcacaaagaa tgcttgttga gactatcgac agaggaacgt catatatttt tggattacaa 100980
gaaatatgga tcctctatcc gactagaatt agtcaatctt attcaagcaa aaacaaaaaa 101040
ctttacgata gactttaagc taaaatattt tctaggatcc ggtgcccagt ctaaaagttc 101100
tttattacac gctattaatc atccaaagtc aaggcctaat acatctctgg aaatagaatt 101160
cacacctaga gacaatgaaa aagttccata tgatgaacta ataaaggaat tgacgactct 101220
atcacgtcat atatttatgg cttctccaga gaatgtaatt ctttctccgc ctattaacgc 101280
gcctataaaa acctttatgt tgcctaaaca agatatagta ggtttggatc tggaaaatct 101340
atatgccgta actaagactg acggaattcc tataactatc agagttacat caaaagggtt 101400
gtattgttat tttacacatc ttggttatat tattagatat cctgttaaga gaataataga 101460
ttccgaagta gtagtctttg gtgaggcagt taaggataag aactggaccg tatatctcat 101520
taagctaata gagcctgtga atgcaatcaa tgatagacta gaagaaagta agtatgttga 101580
atctaaacta gtggatattt gtgatcggat agtattcaag tcaaagaaat acgaaggtcc 101640
gtttactaca actagtgaag tcgtcgatat gttatctaca tatttaccaa agcaaccaga 101700
aggtgttatt ctgttctatt caaagggacc taaatctaac attgatttta aaattaaaaa 101760
ggaaaatact atagaccaaa ctgcaaatgt agtatttagg tacatgtcca gtgaaccaat 101820
tatctttgga gaatcgtcta tctttgtaga gtataagaaa tttagcaacg ataaaggctt 101880

-continued tcctaaagaa tatggttctg gtaagattgt gttatataac ggcgttaatt atctaaataa 101940
tatctattgt ttggaatata ttaatacaca taatgaagtg ggtattaagt ccgtggttgt 102000
acctattaag tttatagcag aattcttagt taatggagaa atacttaaac ctagaattga 102060
taaaaccatg aaatatatta actcagaaga ttattatgga aatcaacata atatcatagt 102120
cgaacattta agagatcaaa gcatcaaaat aggagatatc tttaacgagg ataaactatc 102180
ggatgtggga catcaatacg ccaataatga taaatttaga ttaaatccag aagttagtta 102240
ttttacgaat aaacgaacta gaggaccgtt gggaatttta tcaaactacg tcaagactct 102300
tcttatttct atgtattgtt ccaaaacatt tttagacgat tccaacaaac gaaaggtatt 102360
ggcgattgat tttggaaacg gtgcggacct ggaaaaatac ttttatggag agattgcgtt 102420
attggtagcg acggatccgg atgctgatgc tatagctaga ggaaatgaaa gatacaacaa 102480
attaaactct ggaattaaaa ccaagtacta caaatttgac tacattcagg aaactattcg 102540
atccgataca tttgtctcta gtgtcagaga agtattctat tttggaaagt ttaatatcat 102600
cgactggcag tttgctatcc attattcttt tcatccgaga cattatgcta ccgtcatgaa 102660
taacttatcc gaactaactg cttctggagg caaggtatta atcactacca tggacggaga 102720
caaattatca aaattaacag ataaaaagac ttttataatt cataagaatt tacctagtag 102780
cgaaaactat atgtctgtag aaaaaatagc tgatgataga atagtggtat ataatccatc 102840
aacaatgtct actccaatga ctgaatacat tatcaaaaag aacgatatag tcagagtgtt 102900
taacgaatac ggatttgttc ttgtagataa cgttgatttc gctacaatta tagaacgaag 102960
taaaaagttt attaatggcg catctacaat ggaagataga ccgtctacaa aaaacttttt 103020
cgaactaaat agaggagcca ttaaatgtga aggtttagat gtcgaagact tacttagtta 103080
ctatgttgtt tatgtctttt ctaagcggta aataataata tggtatgggt tctgatatcc 103140
ccgttctaaa tgcattaaat aattccaata gagcgatttt tgttcctata ggaccttcca 103200
actgtggata ctctgtattg ttaatagata tattaatact tttgtcgggt aacagaggtt 103260
ctacgtcttc taaaaataaa agtttgataa catctggcct gttcataaat aaaaacttgg 103320
cgattctata tatactctta ttatcaaatc tagccattgt cttatagatg tgagctactg 103380
taggtgtacc atttgatttt ctttctaata ctatatattt ctctcgaaga agttcttgca 103440
catcatctgg gaataaaata ctactgttga gtaaatcagt tattttttt atatcgatat 103500 tgatggacat ttttatagtt aaggataata agtatcccaa agtcgataac gacgataacg 103560
aagtatttat actttagga aatcacaatg actttatcag atcaaaatta acaaaattaa 103620
aggagcatgt atttttttct gaatatattg tgactccaga tacatatgga tctttatgcg 103680
tcgaattaaa tgggtctagt tttcagcacg gtggtagata tatagaggtg gaggaattta 103740
tagatgctgg aagacaagtt agatggtgtt ctacatccaa tcatatatct gaagatatgc 103800
acactgataa atttgtcatt tatgatattt atacgtttga ttcgttcaag aataaacgat 103860
tggtatttgt acaggtgcct ccatcattag gagatgatag ctatttgact aatccgttat 103920
tgtctccgta ttatcgtaat tcagtagcca gacaaatggt caatgatatg atttttaatc 103980
aagattcatt tttaaaatat ttattagaac atctgattag aagccactat agagtttcta 104040
aacatataac aatagttaga tacaaggata ccgaagaatt aaatctaacg agaatatgtt 104100
ataatagaga taagtttaag gcgtttgtat tcgcttggtt taacggcgtt tcggaaaatg 104160
aaaaggtact agatacgtat aaaaaggtat ctaatttgat ataatgaatt cagtgactgt 104220
atcacacgcg ccatatacta ttacttatca cgatgattgg gaaccagtaa tgagtcaatt 104280

-continued ggtagagttt tataacgaag tagccagttg gctgctacga gacgagacgt cgcctattcc 104340
tgataagttc tttatacagt tgaaacaacc gcttagaaat aaacgagtat gtgtgtgtgg 104400
tatagatccg tatccgaaag atggaactgg tgtaccgttc gaatcaccaa attttacaaa 104460
aaaatcaatt aaggagatag cttcatctat atctagatta accggagtaa ttgattataa 104520
aggttataac cttaatataa tagacggggt tataccctgg aattattact taagttgtaa 104580
attaggagaa acaaaaagtc acgcgatcta ctgggataag atttccaagt tactgctgca 104640
gcatataact aaacacgtta gtgttcttta ttgtttgggt aaaacagatt tctcgaatat 104700
acgggcaaag ttagaatccc cggtaactac catagtcgga tatcatccag cggctagaga 104760
ccgccaattc gagaaagata gatcatttga aattatcaac gttttactgg aattagacaa 104820
caaggcacct ataaattggg ctcaagggtt tatttattaa tgctttagtg aaattttaac 104880
ttgtgttcta aatggatgca actattagag gtaatgatgt tatctttgtt cttaagacta 104940
taggtgtccc gtcagcgtgc agacaaaatg aagatccaag atttgtagaa gcatttaaat 105000
gcgacgagtt agaaagatat attgagaata atccagaatg tacactattc gaaagtctta 105060
gggatgagga agcatactct atagtcagaa ttttcatgga tgtagattta gacgcgtgtc 105120
tagacgaaat agattattta acggctattc aagattttat tatcgaggtg tcaaactgtg 105180
tagctagatt cgcgtttaca gaatgcggtg ccattcatga aaatgtaata aaatccatga 105240
gatctaattt ttcattgact aagtctacaa atagagataa aacaagtttt catattatct 105300
ttttagacac gtataccact atggatacat tgatagctat gaaacgaaca ctattagaat 105360
taagtagatc atctgaaaat ccactaacca gatcgataga cactgccgta tataggagaa 105420
aaacaactct tcgggttgta ggtactagga aaaatccaaa ttgcgacact attcatgtaa 105480
tgcaaccacc gcatgataat atagaagatt acctattcac ttacgtggat atgaacaaca 105540
atagttatta cttttctcta caacgacgat tggaggattt agttcctgat aagttatggg 105600
aaccagggtt tatttcattc gaagacgcta taaaaagagt ttcaaaaata ttcattaatt 105660
ctataataaa ctttaatgat ctcgatgaaa ataattttac aacggtacca ctggtcatag 105720
attacgtaac accttgtgca ttatgtaaaa aacgatcgca taaacatccg catcaactat 105780
cgttggaaaa tggtgctatt agaatttaca aaactggtaa tccacatagt tgtaaagtta 105840
aaattgttcc gttggatggt aataaactgt ttaatattgc acaaagaatt ttagacacta 105900
actctgtttt attaaccgaa cgaggagacc atatagtttg gattaataat tcatggaaat 105960
ttaacagcga agaacccttg ataacaaaac taattctgtc aataagacat caactaccta 106020
aggaatattc aagcgaatta ctctgtccga ggaaacgaaa gactgtagaa gctaacatac 106080
gagacatgtt aatagattca gtggagaccg atacctatcc ggataaactt ccgtttaaaa 106140
atggtgtatt ggacctggta gacggaatgt tttactctgg agatgatgct aaaaaatata 106200
cgtgtactgt atcaaccgga tttaaatttg acgatacaaa gttcgtcgaa gacagtccag 106260
aaatggaaga gttaatgaat atcattaacg atatccaacc attaacggat gaaaataaga 106320
aaaatagaga gttgtacgaa aaaactttat ctagttgttt atgcggtgct accaaaggat 106380
gtttaacatt ctttttggga gaaactgcaa ctggaaagtc gacaaccaaa cgtttgttaa 106440
agtctgctat cggtgacctg tttgttgaga cgggtcaaac aattttaaca gatgtattgg 106500
ataaaggacc taatccattt atcgctaaca tgcatttgaa aagatctgta ttctgtagcg 106560
aactacctga ttttgcctgt agtggatcaa agaaaattag atctgacaat attaaaaagt 106620

-continued tgacagaacc ttgtgtcatt ggaagaccgt gtttctccaa taaaattaat aatagaaacc 106680
atgcgacaat cattatcgat actaattaca aacctgtctt tgataggata gataacgcat 106740
taatgagaag aattgccgtc gtgcgattca gaacacactt ttctcaacct tctggtagag 106800
aggctgctga aaataatgac gcgtacgata aagtcaaact attagacgag gggttagatg 106860
gtaaaataca aaataataga tatagattcg catttctata cttgttggtg aaatggtaca 106920
aaaaatatca tgttcctatt atgaaactat atcctacacc ggaagagatt ccggactttg 106980
cattctatct caaaataggt actctgttag tatctagctc tgtaaagcat attccattaa 107040
tgacggacct ctccaaaaag ggatatatat tgtacgataa tgtggttact cttccgttga 107100
ctactttcca acagaaaata tccaagtatt ttaattctag actatttgga cacgatatag 107160
agagcttcat caatagacat aagaaatttg ccaatgttag tgatgaatat ctgcaatata 107220
tattcataga ggatatttca tctccgtaaa tatatgctca tatatttata gaagatatca 107280
catatctaaa tgaataccgg aatcatagat ttatttgata atcatgttga tagtatacca 107340
actatattac ctcatcagtt agctactcta gattatctag ttagaactat catagatgag 107400
aacagaagcg tgttattgtt ccatattatg ggatcaggta aaacaataat cgctttgttg 107460
ttcgccttgg tagcttccag atttaaaaag gtttacattc tagtgcctaa tattaacatt 107520
ttgaaaattt ttaattataa tatgggtgta gctatgaact tgtttaatga cgaattcata 107580
gctgagaata tctttattca ttccacaaca agtttttatt ctcttaatta taacgataac 107640
gtcattaatt ataacggatt atctcgctac aataactcta tttttatcgt tgatgaggca 107700
cataatatct ttgggaataa tactggagaa cttatgaccg tgataaaaaa taaaaacaag 107760
attccttttt tactattgtc tggatctccc attactaaca cacctaatac tctgggtcat 107820
attatagatt taatgtccga agagacgata gattttggtg aaattattag tcgtggtaag 107880
aaagtaattc agacacttct taacgaacga ggtgtgaatg tacttaagga tttgcttaaa 107940
ggaagaatat catattacga aatgcctgat aaagatctac caacgataag atatcacgga 108000
cgtaagtttc tagatactag agtagtatat tgtcacatgt ctaaacttca agagagagat 108060
tatatgatta ctagacgaca gctatgttat catgaaatgt ttgataaaaa tatgtataac 108120
gtgtcaatgg cagtattggg acaacttaat ctgatgaata atttagatac tttatttcag 108180
gaacaggata aggaattgta cccaaatctg aaaataaata atggcgtgtt atacggagaa 108240
gaattggtaa cgttaaacat tagttccaaa tttaaatact ttattaatcg gatacagaca 108300
ctcaacggaa aacattttat atacttttct aattctacat atggcggatt ggtaattaaa 108360
tatatcatgc tcagtaatgg atattctgaa tataatggtt ctcagggaac taatccacat 108420
atgataaacg gcaaaccaaa aacatttgct atcgttacta gtaaaatgaa atcgtcttta 108480
gaggatctat tagatgtgta taattctcct gaaaacgatg atggcagtca attgatgttt 108540
ttgttttcgt caaacattat gtccgaatcc tatactctga aagaggtaag gcatatttgg 108600
tttatgacta tcccagatac tttttctcaa tacaaccaaa ttcttggacg atctattaga 108660
aaattctctt acgccgatat ttctgaacca gttaatgtat atcttttagc cgccgtatat 108720
tccgatttca atgacgaagt gacgtcatta aacgattaca cacaggatga attaattaat 108780
gttttaccat ttgacatcaa aaagctgttg tatctaaaat ttaagactaa agaaacgaat 108840
agaatatact ctattcttca agagatgtct gaaacgtatt ctcttccacc acatccatca 108900
attgtaaaag ttttattggg agaattggtc agacaatttt tttataataa ttctcgtatt 108960
aagtataacg ataccaagtt acttaaaatg gttacatcag ttataaaaaa taaagaagac 109020
gctaggaatt acatagatga tattgtaaac ggtcacttct ttgtatcgaa taaagtattt 109080
gataaatctc ttttatacaa atacgaaaac gatattatta cagtaccgtt tagactttcc 109140
tacgaaccat ttgtttgggg agttaacttt cgtaaagaat ataacgtggt atcttctcca 109200
taaaactgat gagatatata aagaaataaa tgtcgagctt tgttaccaat ggataccttc 109260
cagttacatt ggagccacac gagctgacgt tagacataaa aactaatatt aggaatgccg 109320
tatataagac gtatctccat agagaaatta gtggtaaaat ggccaagaaa atagaaattc 109380
gtgaagacgt ggaattacct ctcggcgaaa tagttaataa ttctgtagtt ataaacgttc 109440
cgtgtgtaat aacctacgcg tattatcacg ttggggatat agtcagagga acattaaaca 109500
tcgaagatga atcaaatgta actattcaat gtggagattt aatctgtaaa ctaagtagag 109560
attcgggtac tgtatcattt agcgattcaa agtactgctt ttttcgaaat ggtaatgcgt 109620
atgacaatgg cagcgaagtc actgccgttc taatggaggc tcaacaaggt atcgaatcta 109680
gttttgtttt tctcgcgaat atcgttgact cataaaaaag agaatagcgg taagtataaa 109740
cacgaatact atggcaataa ttgcgaatgt tttattccct tcgatatatt tttgataata 109800
tgaaaaacat gtctctctca aatcggacaa ccatctcata aaatagttct cgcgcgctgg 109860
agaggtagtt gctgctcgta taatctcccc agaataatat acttgcgtgt cgtcgttcaa 109920
tttatacgga tttctatagt tctctgttat ataatgcggt tttccatcat gattagacga 109980
cgacaatagt gttctaaatt tagatagttg atcagaatga atgtttattg gcgttggaaa 110040
aattatccat acagcgtctg cagagtggtt gatagttgtt cctagatatg taaaataatc 110100
caacttacta ggcagcaaat tgtctagata aaatactgaa tcaaacggtg cagacgtatt 110160
ggtggatcta atggaatcca attgattaac tatcttttga aaatatacat ttttatgatc 110220
cgatacttgt aagaatatag aaataatgat aagtccatca tcgtgttttt ttgcctcttc 110280
ataagaacta tattttttct tattccaatg aacaagatta atctctccag agtatttgta 110340
cacatctatc aagtgattgg atccataatc gtcttccttt ccccaatata tacgtagtga 110400
tgataacaca tattcattgg ggagaaaccc tccacttata tatcctcctt taaaattaat 110460
ccttactagt tttccagtgt tctggatagt ggttggtttc gactcattat aatgtatgtc 110520
taacggcttc aatcgcgcgt tagaaattgc ttttttagtt tctatattaa taggagatag 110580
ttgttgcggc atagtaaaaa tgaaatgata actgtttaaa aatagctctt agtatgggaa 110640
ttacaatgga tgaggaagtg atatttgaaa ctcctagaga attaatatct attaaacgaa 110700
taaaagatat tccaagatca aaagacacgc atgtgtttgc tgcgtgtata acaagtgacg 110760
gatatccgtt aataggagct agaagaactt cattcgcatt ccaagcgata ttatctcaac 110820
aaaattcaga ttctatcttt agagtatcca ctaaactatt acggtttatg tactacaatg 110880
aactaagaga aatctttaga cggttgagaa aaggttctat caacgatatc gatcctcact 110940
ttgaagagtt aatattattg ggtggtaaac tagataaaaa ggaatctatt aaagattgtt 111000
taagaagaga attaaaagag gaaagtgatg aacgtataac agtaaaagaa tttggaaatg 111060
taattctaaa acttacaaca cgggataaat tatttaataa agtatatata agttattgca 111120
tggcgtgttt tattaatcaa tcgttggagg atttatcgca tactagtatt tacaatgtag 111180
aaattagaaa gattaaatca ttaaatgatt gtattaacga cgataaatac gaatatctgt 111240
cttatattta taatatgcta gttaatagta aatgaacttt tacagatcta gtataattag 111300
tcagattatt aagtataata gacgactagc taagtctatt atttgcgagg atgactctca 111360
aattattaca ctcacggcat tcgttaacca atgcctatgg tgtcataaac gagtatccgt 111420
gtccgctatt ttattaacta ctgataacaa aatattagta tgtaacagac gagatagttt 111480
tctctattct gaaataatta gaactagaaa catgtctaga aagaaacgat tatttctgaa 111540
ttattccaat tatttgtcca aacaggaaag aagtatacta tcgtcatttt tttctctaga 111600
tccagctact actgataatg atagaataga tgctatttat ccgggtggca tacccaaaag 111660
gggtgagaat gttccagagt gtttatccag ggaaattaaa gaagaagtta atatagacaa 111720
ttcttttgta ttcatagaca ctcggttttt tattcatggc atcatagaag ataccattat 111780
taataaattt tttgaggtaa tcttctttgt cggaagaata tctttaacga gtgatcaaat 111840
cattgataca tttaaaagta atcatgaaat caaggatcta atatttttag atccgaattc 111900
aggtaatgga ctccaatacg aaattgcaaa atatgctcta gatactgcaa aactcaaatg 111960
ttatggccat agaggatgtt attacgaatc attaaaaaaa ttaactgagg atgattgatt 112020
agaaaatata aattaattta ccatcgtgta tttttataac gggattgtcc ggcatatcat 112080
gtagatagtt accgtctaca tcgtatactc gaccatctac gcctttaaat cctctattta 112140
ttgacattaa tctattagaa ttggaatacc aaatattagt accctcaatt agtttattgg 112200
taatattttt tttagacgat agatcgatgg ctcttgaaac caaggttttc caaccggact 112260
cattgtcgat cggtgagaag tctttttcat tagcatgaat ccattctaat gatgtatgtt 112320
taaacactct aaacaattgg acaaattctt ttgatttgct ttgaatgatt tcaaataggt 112380
cttcgtctac agtaggcata ccattagata atctagccat tataaagtgc acgtttacat 112440
atctacgttc tggaggagta agaacgtgac tattgagacg aatggctctt cctactatct 112500
gacgaagaga cgcctcgttc catgtcatat ctaaaatgaa gatatcatta attgagaaaa 112560
aactaatacc ctcgcctcca ctagaagaga atacgcatgt tttaatgcat tctccgttag 112620
tgtttgattc ttggttaaac tcagccaccg ccttgattct agtatctttt gttctagatg 112680
agaactctat attagagata ccaaagactt tgaaatatag taataagatt tctattcctg 112740
actgattaac aaatggttca aagactagac atttaccatg ggatgctaat attcccaaac 112800
atacatctat aaatttgacg cttttctctt ttaattcagt aaatagagag atatcagccg 112860
cactagcatc ccctttcaat agttctccct ttttaaaggt atctaatgcg gatttagaaa 112920
actctctatc tcttaatgaa tttttaaaat cattatatag tgttgctatc tcttgcgcgt 112980
attcgcccgg atcacgattt tgtctttcag gaaagctatc gaacgtaaac gtagtagcca 113040
tacgtctcag aattctaaat gatgatatac ctgtttttat ttcagcgagt ttagcctttt 113100
gataaatttc ttcttgcttt ttcgacatat taacgtatcg cattaatact gttttcttag 113160
cgaatgatgc agacccttct acgtcatcaa aaatagaaaa ctcgttatta actatgtacg 113220
aacataggcc tcctagtttg gagactaatt ctttctcatc aactagacgt ttattctcaa 113280
atagcgattg gtgttgtaag gatcctggtc gtagtaagtt aaccaacatg gtgaattctt 113340
gcacactatt aacgataggt gtagccgata aacaaatcat cttatggttt tttaatgcga 113400
tggtcttaga taaaaaatta tatactgaac gagtaggacg gatcttacca tcttctttga 113460
ttaatgattt agaaatgaag ttatgacatt catcaataat gacgcatatt ctactcttgg 113520
aattaatagt tttgatatta gtaaaaaatt tatttctaaa attttgatca tcgtaattaa 113580
taaaaataca atccttcgtt atctctggag cgtatctgag tatagtgttc atccaaggat 113640
cttctatcaa agccttttc accaataaga taatagccca attcgtataa atatccttaa 113700
gatgtttgag aatatataca gtagtcattg ttttaccaac acccgtttca tggaacaata 113760
aaagagaatg catactgtct aatcctaaga aaactcttgc tacaaaatgt tgataatcct 113820
tgaggcgtac tacgtctgtt cccatcattt caacaggcat attagtagtt ctgcgcaatg 113880
cataatcgat ataggccgcg tgtgatttac tcatttatga gtgataagta ataactatgt 113940
tttaaaaatc acagcagtag tttaactagt cttctctgat gtttgttttc gatacttttt 114000
gaatcagaag tcatactaga ataaagcaac gagtgaacgt aatagagagc ttcgtatact 114060
ctattcgaaa actctaagaa cttattaatg aattccgtat ccactggatt gtttaaaata 114120
ctaaattgaa cactgttcac atccttccaa gaagaagact tagtgacgga cttaacatga 114180
gacataaata aatccaaatt ttttttacaa acatcactag ccaccataat ggcgctatct 114240
ttcaaccagc tatcgcttac gcattttagc agtctaacat ttttaaagag actacaatat 114300
attctcatag tatcgattac acctctaccg aataaagttg gaagtttaat aatacaatat 114360
ttttcgttta caaaatcaaa taatggtcga aacacgtcga aggttaacat cttataatcg 114420
ctaatgtata gattgttttc agtgagatga ttattagatt taatagcatc tcgttcacgt 114480
ttgaacagtt tattgtgtgc gctgaggtcg gcaactacgg cgtccgcttt agtactcctc 114540
ccataatact ttacgctatt aatctttaaa atttcataga ctttatctag atcgctttct 114600
ggtaacatga tatcatgtgt aaaaagtttt aacatgtcgg tcggcattct atttagatca 114660
ttaactctag aaatctgaag aaagtaatta gctccgtatt ccagactagg taatgggctt 114720
ttacctaaag acaagttaag ttctggcaat gtttcataaa atggaagaag gacatgcgtt 114780
ccctcccgga tattttttac aatttcatcc atttacaact ctatagtttg ttttcattat 114840
tattagttat tatctcccat aatcttggta atacttaccc cttgatcgta agatacctta 114900
tacaggtcat tacatacaac taccaattgt ttttgtacat aatagattgg atggttgaca 114960
tccatggtgg aataaactac tcgaacagat agtttatctt tccccctaga tacattggcc 115020
gtaatagttg tcggcctaaa gaatatcttt ggtgtaaagt taaaagttag ggttcttgtt 115080
ccattattgc tttttgtcag tagttcatta taaattctcg agatgggtcc gttctctgaa 115140
tatagaacat catttccaaa tctaacttct agtctagaaa taatatcggt cttattctta 115200
aaatctattc ccttgatgaa gggatcgtta atgaacaaat ccttggcctt tgattcggct 115260
gatctattat ctccgttata gacgttacgt tgactagtcc aaagacttac aggaatagat 115320
gtatcgatga tgttgatact atgtgatatg tgagcaaaga ttgttctctt agtggcatca 115380
ctatatgttc cagtaatggc ggaaaacttt ttagaaatgt tatatataaa agaatttttt 115440
cgtgttccaa acattagcag attagtatga agataaacac tcatattatc aggaacatta 115500
tcaattttta catacacatc agcatcttga atagaaacga taccatcttc tggaacctca 115560
acaatctcgg cagactccgg ataaccagtc ggtgggccat cactaacaat aactagatca 115620
tccaacaatc tactcacata tgcatctata taatcttttt catcttgtga gtaccctgga 115680
tacgaaataa atttattatc cgtatttcca taataaggtt tagtataaac agagagcgat 115740
gttgccgcat gaacttcagt tacagtcgcc gttggttggt ttatttgacc tattactctc 115800
ctaggtttct ctataaacga tggtttaatt tgtacattct taaccatata tccaataaag 115860
ctcaattcag gaacataaac aaattctttg ttgaacgttt caaagtcgaa cgaagagtca 115920
cgaataacga tatcggatac tggattgaag gttaccgtta cggtaatttt tgaatcggat 115980
agtttaagac tgctgaatgt atcttccaca tcaaacggag ttttaatata aacgtatact 116040
gtagatggtt ctttaatagt gtcattagga gttaggccaa tagaaatatc attaagttca 116100
ctagaatatc cagagtgttt caaagcaatt gtattattga tacaattatt atataattct 116160
tcgccctcaa tttcccaaat aacaccgtta cacgaagaga tagatacgtg attaatacat 116220
ttatatccaa catatggtac gtaaccgaat cttcccatac ctttaacttc tggaagttcc 116280
aaactcagaa ccaaatgatt aagcgcagta atatactgat ccctaatttc gaagctagcg 116340
atagcctgat tgtctggacc atcgtttgtc ataactccgg atagagaaat atattgcggc 116400
atatacaaag ttggaatttg actatcgact gcgaagacat tagaccgttt aatagagtca 116460
tccccaccga tcaaagaatt aatgatagta ttattcattt tctatttaaa atggaaaaag 116520
cttacaataa actccgtaga gaaatatcta taatttgtga gttttcctta aagtaacagc 116580
ttccgtaaac gccgtcttta tctcttagta ggtttattgt atttatgacc ttttccttat 116640
cttcatagaa tactaaaggc aacaaagaaa tttttggttc ttctctaaga gctacgtgag 116700
acttaaccat agaagccaac gaatccctac atattttaga acagaaatac ccaacttcac 116760
caccccttgaa tgtctcaata ctaataggtc taaaaaccaa atcttgatta caaaaccaac 116820
acttatcaat tacactattt gtcttaatag acacatctgc catagattta taatactttg 116880
gtagtataca agcgagtgct tcttctttag cgggcttaaa gactgcttta ggtgctgaaa 116940
taaccacatc tggaaggctt actcgcttag ccatttaatt acggaactat ttttttatac 117000
ttctaatgag caagtagaaa acctctcatc tacaaaaaca tactcgtgtc cataatcctc 117060
taccatagtt acacgttttt tagatctcat atgtgctaaa aagttttccc atactaattg 117120
gttactatta tttttcgtat aatttttaac agtttgaggt tttagatttt tagttacaga 117180
agtgatatcg aatattttat ccaaaaagaa tgaataatta attgtcttag aaggagtgtt 117240
ttcttggcaa aagaatacca agtgcttaaa tatttctact acttcattaa tcttttctgt 117300
actcagattc agtttctcat cttttacttg attgattatt tcaaagacta acttataatc 117360
ctttttattt attctctcgt tagccttaag aaaactagat acaaaatttg catctacatc 117420
atccgtggat atttgatttt tttccatgat atccaagagt tccgagataa tttctccaga 117480
acattgatga gacaataatc tccgcaatac atttctcaaa tgaataagtt tattagacac 117540
atggaagttt gacttttttt gtacctttgt acatttttga aatacagact cgcaaaaaat 117600
acaatattca tatccttgtt cagatactat accgttgtgt ctacaaccgc tacataatcg 117660
tagattcatg ttaacactct acgtatctcg tcgtccaata ttttatataa aaacatttta 117720
tttctagacg ttgccagaaa atcctgtaat atttttagtt ttttgggctg tgaataaagt 117780
atcgccctaa tatggttacc gtcctccgcc aatatagtag ttaaattatc cgcacatgca 117840
gaagaacacc gcttaggcgg attcagtaca atgttatatt tttcgtacca actcatttaa 117900
atatcataat ctaaaatagt tctgtaatat atctagcgct aatatattga tcataatcct 117960
gtgcataaat taagatacaa caatgtctcg aaatcatcga catggcttct tccatagtta 118020
gaagatcgtc gtcaaagtta gcaacgtgat tcatcaacat ttgctgtttt gaggcagcaa 118080
atactgaacc gtcgccattc aaccattcat aaaaaccatc gtctgaatcc attgataatt 118140
tcttgtactg gtttttgaga gctcgcatca atctagcatt tctagctccc ggattgaaaa 118200
cagaaagagg atcgtacatc cagggtccat tttctgtaaa tagaatcgta taatgtccct 118260
tcaagaagat atcagacgat ccacaatcaa agaattggtc tccgagtttg taacaaactg 118320
cggactttaa cctatacatg ataccgttta gcatgatttc tggtgatacg tcaatcggag 118380
tatcatctat tagagatcta aagccggtgt aacattctcc accaaacata ttcttattct 118440
gacgtcgttc tacataaaac atcattgctc cattaacgat aacaggggaa tgaacagcac 118500
tacccatcac attagttccc aatggatcaa tgtgtgtaac tccagaacat cttccatatc 118560
ctatgttagg aggagcgaac accactcttc cactattgcc atcgaatgcc atagaataaa 118620
tatccttgga attgatagaa atcggactgt cggatgttgt gatcatcttc ataggattaa 118680
caactatgta tggtgccgcc tgaagtttca tatcgtaact gatgccgttt ataggtctag 118740
ccacagaaac caacgtaggt ctaaatccaa ctatagacaa aatagaagcc aatatctgtt 118800
cttcatctgt cataacttga gagcatccag tatgaataat cttcattaga tggggatcta 118860
ccgcatcatc atcgttacaa taaaaaattc ccattctaat gttcataatt gcttttctaa 118920
tcatggtatg catgtttgct ctctgaatct ctgtggaaat tagatctgat acacctgtaa 118980
tcactatcgg attatcctcc gtaagacgat taaccaacaa catataatta taagacttta 119040
cttttctaaa ttcataaagt tgctggatta ggctataggt gtctccatgt acatacgcgt 119100
tctcgagcgc aggaagttta ataccgaata gtgccatcag aataggatga atatagtaat 119160
tagtttctgg ttttctataa ataaaagaca aatcttgtga actagacata tcggtaaaat 119220
gcatggattg gaatcgtgta gtcgacagaa gaatatgatg attagatgga gagtatattt 119280
tatctaactc tttgagttgg tcaccgattc taggactagc tcgagaatga ataagtacta 119340
aaggatgagt acatttcaca gaaacactag cattgttcaa tgtgctcttt acatgggtaa 119400
ggagttgaaa tagctcgttt ctatttgttc tgacaatatt tagtttattc ataatgttaa 119460
gcatatcctg aatagtaaag ttagatgtgt catacttgtt agtagttaga tatttagcaa 119520
ttgcattccc atcatttctc aatctcgtac tccaatcatg cgtggatgct acttcgtcga 119580
tggaaaccat acaatccttt ttgataggct gttgagattg attatttcct gcacgtttag 119640
gtttggtacg ttgatttcta gcccctgcgg atataaagtc atcgtctaca attttggata 119700
atgaattgca tacactacaa gacaaagatt tatcagaagt gtgaatatga tcttcatcta 119760
ccaaagaaag agtttgatta gtataactag attttagtcc tgcgttagat gttaaaaaaa 119820
catcgctatt gaccacggct tccattattt atattcgtag tttttactcg aaagcgtgat 119880
tttaatattc aatcttatta cttttggaat cgttcaaaac ctttgactaa ttgtagaatt 119940
tgatctattg ccctacgcgt atactccctt gcatcatata cgttcgtcac cagatcgttt 120000
gtttcggcct gaagttggtg catatctctt tcaacattcg acatgagatc cttaagggcc 120060
atatcgtcta gattttgttg agatgctgct cctggatttg gattttgttg tgctgttgta 120120
catactgtac caccagtagg tgtaggagta catacagtgg ccacaatagg aggttgagga 120180
ggtgtaaccg ttggagtagt acaagaaata cttccatccg attgttgtgt acatgtagtt 120240
gttggtaacg tctgagaagg ttgggtagat ggcggcgtcg tcgtcttttg atctttatta 120300
aatttagaga taatatcctg aacagcattg ctcggcgtca acgctggaag gagtgaactc 120360
gccggcgcat cagtatctgc agacagccaa tcaaaaagat tagacatatc agatgatgta 120420
ttagtttgtt gtcgtggttt tggtgtagga gccggtgtag ctgttggaac cggctgtgga 120480
gttatatgaa tagttggttg tagcggttgg ataggctgtc tgctggcggc catcatatta 120540
tctctagcta gttgttctcg caactgtctt tgataatacg actcttgaga ctttagtcct 120600
atttcaatcg cttcatcctt tttcgtatcc ggatcctttt cttcagaata atagattgac 120660
gactttggtg tagaggattc tgccagcccc tgtgagaact tgttaaagaa gtccatttaa 120720
ggctttaaaa ttgaattgcg attataagat taaatggcag acacagacga tattatcgac 120780
tatgaatccg atgatctcac cgaatacgag gatgatgaag aagaggaaga agatggagag 120840

```
tcactagaaa ctagtgatat agatcccaaa tcttcttata agattgtaga atcagcatcc 120900
actcatatag aagatgcgca ttccaatctt aaacatatag ggaatcatat atctgctctt 120960
aaacgacgct atactagacg tataagtcta tttgaaatag cgggtataat agcagaaagc 121020
tataacttgc ttcaacgagg aagattacct ctagtttcag aattttctga cgaaacgatg 121080
aagcaaaata tgctacatgt aattatacaa gagatagagg agggttcttg tcctatagtc 121140
atcgaaaaga acggagaatt gttgtcggta aacgattttg acaaagatgg tctaaaattc 121200
catctagact atattatcaa aatttggaaa cttcaaaaac gatattagaa tttatacgaa 121260
tatcgttctc taaatgtcac aatcaagtct cgcatgttca gcaatttatt gtcgtacttt 121320
atatcgtgtt cattaacgat atcttgcaaa atagtaatga ttctatcttc cttcgataga 121380
tattcttcag agattattgt cttatattct ttcttgttat cagatatgaa tttgataaga 121440
ctttgaacat tattgatacc cgtctgttta attttttcta cagatatttt agttttggca 121500
gattctatcg tatctgtcaa tagacatcca acatcgacat tcgacgtcaa ttgtctataa 121560
atcaacgtat aaattttaga aataacatta gcgaattgtt gtgcattgat gtcgttattc 121620
tgaaacagta tgattttagg tagcattttc ttaacaaaga gaacgtattt attgttactc 121680
agttgaacag atgatatatc cagattacta acgcatctga ttccatatac caaactttca 121740
gaagaaatgg tgtacaattg tttgtattca ttcaatgtct ctttttcaga aattagttta 121800
gagtcgaata ctgcaataat tttcaagaga tagttttcat cagataagat tttatttagt 121860
gtagatatga taaaactatt gttttgttgg agaacttgat acgccgcgtt ctctgtagtc 121920
gacgctctca aatgggaaac aatctccatt attttttgg aatcggatac aatatcttcg 121980
gtatcttgac gcaatctagt atacatagag ttaagagaaa ttagagtttg tacattaagc 122040
aacatgtctc taaatgtggc tgcaaacttt tccttttcca catcatctag tttattatat 122100
accgatttca caacggcacc agatttaagg aaccagaatg aaaaactctg ataactacaa 122160
tatttcatca tagttacgat tttatcatct tctatagttg gtgtaatagc gcataccttt 122220
ttctccaaga ctggaaccaa cgtcataaaa atgtttaaat caaaatccat atcaacatct 122280
gatgcgctaa gaccagtctc gcgttcaaga ttatctttac taatggtgac gaactcatcg 122340
tatagaactc taagtttgtc cattatttat ttacagattt agttgtttaa tttatttgtg 122400
ctcttccaga gttgggatag tatttttcta acgtcggtat tatattatta ggatctacgt 122460
tcatatgtat cataatatta atcatccacg ttttgataaa tctatcttta gcttctgaaa 122520
taacgtattt aaacaaagga gaaaaatatt tagctacggc atcagacgca ataacatttt 122580
ttgtaaatgt aacgtattta gacgacagat cttcgttaaa aagttttcca tctatgtaga 122640
atccatcggt tgttaacacc attcccgcgt cagattgaat aggagtttga atagtttgtt 122700
ttggaaatag atccttcaat aacttatagt tgggtgggaa aaaatcgatt ttatcactag 122760
actctttctt ttttactatc attacctcat gaactatttc ttgaatgagt atatgtattt 122820
tctttcctat atcggacgcg ttcattggaa aatataccat gtcgttaact ataagaatat 122880
ttttatcctc gtttacaaac tgaataatat cagatgtagt tcgtaaacga actatatcat 122940
caccagcaca acatctaact atatgatatc cactagtttc ctttagtcgt ttattatctt 123000
gttccatatt agcagtcatt ccatcattta agaaggcgtc aaagataata gggagaaatg 123060
acattttgga ttctgttaca actttaccaa aattaaggat atacggactt actatctttt 123120
tctcaacgtc gatttgatga acacacgatg aaaatgtact tcgatgagat tgatcatgta 123180
gaaaacaaca agggatacaa tatttccaca tatcatgaaa tatattaaga aatcccacct 123240
```

-continued tattatattt ccccaaagga tccatgcatg taaacattat gccgttatca ttaataaaga 123300
cttctttctc atcggatctg taaaagttgt tactgatttt tttcattcca ggatctagat 123360
aattaataat gatgggtttt ctattcttat tctttgtatt ttggcatatc ctagaccagt 123420
aaacagtttc cactttggta aaatcagcag acttttgaac gctattaaac atggcattaa 123480
tggcaataac taaaaatgta aaatattttt ctatgttagg aatatggttt ttcactttaa 123540
tagatatatg gtttttggcc aaaatgatag atattttttt atccgaggat agtaaaatat 123600
tattagtcgc cgtctctata aaaatgaagc tagtctcgat atccaatttt attctagaat 123660
tgataggagt cgccaaatgt accttatacg ttatatctcc cttgatgcgt tccatttgtg 123720
tatctatatc ggacacaaga tctgtaaata gttttacgtt attaatcatc acggtatcgc 123780
cgtcgctaga taacgctaat gtaccatcca agtcccaaat ggagagattt aactgttcat 123840
cgtttagaat aaaatgatta ccggtcatat taataaagtg ttcatcgtat ctagataaca 123900
acgacttata attaatgtcc aagtcttgaa ctcgctgaat gatctttttt aacccagtta 123960
gttttagatt ggtacgaaat atattgttaa actttgattc tacagtaatg tccaaatcta 124020
gttgtggaaa tacttccatc aacattgttt caaacttgat aatattatta tctacatctt 124080
catacgatcc aaattccgga atagatgtat cgcacgctct ggccacccag ataaccaaaa 124140
agtcacacgc tccaggatat acattgtata aaaagctatc gtttttttagt agtgtttttt 124200 tctgagtata tacgaaggga ttaaaaatag tattatcaac gtaactatat tccaaattat 124260
tcttatgaga atagataata atatcgtcct taatatctaa caaatttcct aaatatccct 124320
ttaattgagt cattcgaagc gtcaatagaa tatgtctctt aactatttcc ggctgttgta 124380
tatttaaatg acttcgtaaa aaataatata tgggcgactt ctcatctatg taatcatatg 124440
gagtgagata tagggctcgt tctacctcct gccccttacc cacctgtaat accaattgcg 124500
gacttactat atatcgcata tttatatcgt ggggtaaagt gaaaatctac taccgatgat 124560
gtaagtctta caatgttcga accagtacca gatcttaatt tggaggcctc cgtagaacta 124620
ggggaggtaa atatagatca aacaacacct atgataaagg aaaatagcgg ttttatatcc 124680
cgtagtagac gtctattcgc ccatagatct aaggatgatg agagaaaact agcactacga 124740
ttctttttac aaagacttta ttttttagat catagagaga ttcattattt gttcagatgc 124800
gttgacgctg taaaagacgt cactattacc aaaaaaaata acattatcgt ggcgccttat 124860
atagcacttt taactatcgc atcaaaagga tgcaaactta cagaaacaat gattgaagca 124920
ttctttccag aactatataa tgaacatagt aagaaattta aattcaactc tcaagtatcc 124980
atcatccaag aaaaactcgg ataccagttt ggaaactatc acgtttatga ttttgaaccg 125040
tattactcta cagtagctct ggctattcga gatgaacatt catctggcat ttttaatatc 125100
cgtcaagaga gttatctggt aagttcatta tctgaaataa catatagatt ttatctaatt 125160
aatctaaaat ctgatcttgt tcaatggagt gctagtacgg gcgctgtaat taatcaaatg 125220
gtaaatactg tattgattac agtgtatgaa aagttacaac tggtcataga aaatgattca 125280
caatttacat gttcattggc tgtggaatca aaacttccaa taaaattact taaagataga 125340
aatgaattat ttacaaaatt catcaacgag ttaaaaaaga ccagttcatt caagataagc 125400
aaacgcgata aggatacgct actaaaatat tttacttagg actggagtta gaatttatag 125460
acgactcatt tcgtttatca ttattagtat tctccttgtt atcttgttca gaaatataca 125520
gcaatgctat gcctaatact aaatacatta tcatgcttgc aatggctcta acaacgacga 125580

-continued accaaaatga atttggtcgt agcttttgtt cacaaaaata cataaagaaa tgtctacata 125640
aatctatggc gccattggct acttgaaata gcgccagtcc tcctacagat tttaatatag 125700
ctgtataaca tgacatttat tcatcatcaa aagagacaga gtcaccatct gtcatattta 125760
gatttttttt catgtgttca aagtatcctc tactcatttc attataatag tttatcatac 125820
ttagaatttt aggacggatc aatgagtaag acttgactag atcgtcagta gtaatttgtg 125880
catcgtctat tctgcatccg cttcgtcgaa taatgtatag catcgctttg agattctcca 125940
tagctatcaa gtctttatac aatgacatgg aaatatctgt gaatacttta tacttctcca 126000
acatcgatgc cttaacatca tcgcctactt tagcattgaa aatacgttct attgtgtaga 126060
tggatgtagc aagattttta aacaacaatg ccatcttaca cgatgattgc ctcaagtctc 126120
caatcgtttg tttagaacga ttagctacag agtccaatgc ttggctgact agcatattat 126180
tatctttaga aattgtattc ttcaatgagg cgtttatcat atctgtgatt tcgttagtca 126240
tattacagtc tgactgggtt gtaatgttat ccaacatatc acctatggat acggtacacg 126300
taccagcatt tgtaataatc ctatctaaga tgttgtatgg cattgcgcag aaaatatctt 126360
ctcctgtaat atttccactc tcgataaatc tactcagatt attcttaaat gccttattct 126420
ctggagaaaa gatatcagtg tccatcattt cattaatagt atacgcagaa aagataccac 126480
gagtatcaat tctatccaag atacttatcg gttccgagtc acagataatg gtttcctctc 126540
cttcgggaga tcctgcatag aaatatctag gacaatagtt tctatactgt ctgtaactct 126600
gataatctct aaagtcacta actgatacca tgaaattgag aagatcaaac gctgaagtaa 126660
ttaattttc tgcctcgttt ttactacaac tagttttcat caatgtagtg acgatgtatt 126720
gtttagttac ttttggtcta atactgatga tagagatatt attacttccc ataatggatc 126780
ttctagtagt caccttaaag cccattgatg caaatagcag atagataaag tcttggtatg 126840
actcctttct aatatagtac ggactacctt tgtcacccaa ctttataccc acataagcca 126900
taacaacctc tttaatagcc gtttcatgag gtttatcagc catgagcctg agtagttgga 126960
agaatctcat gaatcctgtc tcagaaagtc ctatatgcat gatagattta tctttcctgg 127020
gaaactctcg tatagtcata gatgaaatac tcttcaaagt ttctgaaata agattagtaa 127080
cagtcttacc tccgactact ctaggtaaca aacaaactct aataggtgtt ttctctgcgg 127140
agataatatc agaaaggata gagcaataag tagtattatt gtgattataa agaccgaata 127200
cataacaggt agaatttata aacatcatgt cctgaaggtt tttagacttg tattcctcgt 127260
aatccatacc gtcccaaaac atggatttgg taactttgat agccgtagat ctttgttcct 127320
tcgccaacag gttaaagaaa ttaataaaga atttgtggtt tctacctatg tctacaaatt 127380
gcacgtttgg aagcgccacg gttacattca ctgcagcatt ttgaggatcg cgagtatgaa 127440
gtacgatgtt attgtttact ggtatatctg gaaagaattc taccagtcta ggaataagag 127500
attgatatcg catagaaata caaaagttca taatctcatc atctaagagc attttgttac 127560
cattgtaata aatatccact ctgtcatatg tataaatgaa gtactgttca aacatgatga 127620
gatgtttata tgttggcata gtagtgagat ctacgtttgg taatggcaat gtattaagat 127680
taactccata atgtctagca gcatctgcga tgttataagc gttgtcaaag cggggtcgat 127740
cttgtgctgt tatatattgt ctaacaccta taagattatc aaaatcttgt ctgcttaata 127800
caccgttaac aatttttgcc ttgaattctt ttattggtgc attaataaca tccttataga 127860
ggatgttaaa caaataagtg ttatcaaagt taagatctgg atatttcttt tctgctagaa 127920
catccattga gtcggagcca tctggtttaa tataaccacc gataaatcta gctctgtatt 127980
ctgtatccgt caatctaata ttaagaaggt gttgagtgaa aggtggaaga tcgtaaaagc 128040
tgtgagtatt aatgatagga ttagtttccg aactaatgtt aattggggta ttaataatat 128100
ctatatttcc agcgttaagt gtaacattaa acagttttaa ttcacgtgac gtggtatcaa 128160
ttaaataatt aatgcccaat ttggatatag cagcctgaag ctcatcttgt ttagttacgg 128220
atcctaatga gttattaagc aatatatcga acggatgaac gaaggttgtt ttaagttggt 128280
cacatacttt gtaatctaga catagatgcg gaagaacggt agaaactata cgaaataaat 128340
attcagagtc ctctaattga tcaagagtaa ctattgactt aataggcatc atttatttag 128400
tattaaatga cgaccgtacc agtgacggat atacaaaacg atttaattac agagttttca 128460
gaagataatt atccatctaa caaaaattat gaaataactc ttcgtcaaat gtctattcta 128520
actcacgtta acaacgtggt agatagagaa cataatgccg ccgtagtgtc atctccagag 128580
gaaatatcct cacaacttaa tgaagatcta tttccagatg atgattctcc ggccactatt 128640
atcgaacgag tacaacctca tactactatt attgacgata ctccacctcc tacgtttcgt 128700
agagagttat tgatatcgga acaacgtcaa caacgagaaa aaagatttaa tattacagta 128760
tcgaaaaatg ctgaagcaat aatggaatct agatctatga tatcttctat gccaacacaa 128820
acaccatcct tgggagtagt ttatgataaa gataaaagaa ttcagatgtt ggaggatgaa 128880
gtggttaatc ttagaaatca acgatctaat acaaaatcat ctgataattt agataatttt 128940
accagaatac tatttggtaa gactccgtat aaatcaacag aagttaataa gcgtatagcc 129000
atcgttaatt atgcaaattt gaacgggtct ccccttatcag tcgaggactt ggatgtttgt 129060
tcagaggatg aaatagatag aatctataaa acgattaaac aatatcacga aagtagaaaa 129120
cgaaaaatta tcgtcactaa cgtgattatt attgtcataa atattatcga gcaagcattg 129180
ctaaaactcg gatttgaaga aatcaaagga ctgagtaccg atatcacttc agaaattatc 129240
gatgtggaga tcggagatga ctgcgatgct gtagcatcaa aactaggaat cggtaacagt 129300
ccggttctta atattgtatt gtttatactc aagatattcg ttaaacgaat taaaattatt 129360
taatttaata cattcccata tccagacaac aatcgtctgg attaatctgt tcctgtcgtc 129420
tcataccgga cgacatatta atctttttat tagtaggcat ctttttagat ggtttctttt 129480
tcccagcatt aactgagtcg atacctagaa gatcgtgatt gatctctccg accattccac 129540
gaacttctaa ttggccgtct ctgacggtac cataaactat tttaccagca ttagtaacag 129600
cttggacaat ctgaccatcc atcgcattgt acgatgtagt agtaactgtt gttctacgtc 129660
taggagcacc agaagtattt ttggagccct tggatgttga tgtagaagaa gacgaggatt 129720
ttgattttgg tttacatgta atacattttg tatcacatgc gccggcagtc acatctgttt 129780
gagaattaag attattgttg cctcctttga cggctgcatc tccaccgatt tgcgctagta 129840
gatttttaag ctgtggtgta atcttattaa ctgtttcgat ataatcatcg taactgcttc 129900
taacggctaa attttttta tccgccattt agaagctaaa aatattttta tttatgcaga 129960
agatttaact agattataca atgaactaat atgatccttt tccagattat ttacaaactt 130020
ggtatttttt ggttctggag gaggcgaatt taaattcgga cttggatttg gattttgtgg 130080
gttcttgatc ttattataca gcgcatatag gatggcgacg gtaactgcta cgcaaatacc 130140
gatcaacaaa agaataccaa tcatttattg acaataactt cactattgat caagtatgca 130200
atatatcatc ttttcactaa ataagtagta ataatgattc aacaatgtcg agatatatgg 130260
acgataataa tttagttcat ggaaatatcg ctatgattgg tatgaatgac tccgctaact 130320

-continued

```
ctgtggggcg cgcagtgctt tccccacata gaataaatta gcattccgac tgtgataata 130380
ataccaagta taaacgccat aatactcaat actttccatg tacgagtggg actggtagac 130440
ttactaaagt caataaaggc gaagatacac gaaagaatca aaagaatgat tccagcgatt 130500
agcacgccgg aaaaataatt tccaatcata agcatcatat ccatttaact aataaaaatt 130560
ttaaatcgcc gaatgaacaa agtggaatat aaaccatata aaaacaatag tttgtactgc 130620
aaaaataata tctatttttg ttttcgaaga tatggtaaaa ttaaatagta gtacacagca 130680
tgttataact aacagcagca acggctcgta attacttatc atttactaga cgaaaaggtg 130740
gtgggatatt ttcttgctca aataatacga atatatcacc catccatttt atgcgatgtt 130800
tatatactct aatctttaat agatctatag acgacgggtt taccaacaat atagatttta 130860
tcgattcatc taatttaaac ccttccttaa acgtgaatga tctattatct ggcataacga 130920
tgactctacc cgatgaatcg gacaatgtac tgggccatgt agaataaatt atcaacgaat 130980
tatcgtctac gaacatttat atcatttgtt ttaattttag tacgcgaata aatagatata 131040
aaatagaaaa taacagatat tacaaccaat gttatggccg cgcccaacca ggtaggcagt 131100
tttattttat cttttactac aggttctcct ggatgtacgt caccaacggc ggacgtagtt 131160
ctagtacaat tagacgtaag ttccgcttgg gaatttttta acgctaaaga gttaacgtta 131220
atcgtgcacc caacgtattt acatctagtt ctttgaacat cttgattata atataaccat 131280
tttctatctc tagattcgtc ggtgcactca tgtaaccaac ataccctagg tcctaaatat 131340
ttatctccgg aattagattt tggataattc gcgcaccaac aatttctatt tcctttatga 131400
tcgttacaaa agacgtataa tgccgtatcc ccaaaagtaa aataatcagg acgaataatt 131460
ctaataaact cagaacaata tctcgcatcc atatgtttgg agcaaatatc ggaataagta 131520
gacatagccg gtttccgttt tgcacgtaac cattctaaac aattggggtt tccaggatcg 131580
tttctacaaa atccagtcat gaaatcatca caatgttctg tcttgtaatt attattaaat 131640
atttttggac agtgtttggt atttgtctta gaacaacatt ttgccacgct atcactatcg 131700
cccaggagat aatccttttt tataaaatga catcgttgcc cggatgctat ataatcagta 131760
gcgtgtttta aatccttaat atattcagga gttacctcgt tctgataata gattaatgat 131820
ccaggacgaa atttgaaaga actacatggt tctccatgaa ttaatacata ttgtttagca 131880
aattcaggaa ctataaaact actacaatga tctatcgaca taccatctat caaacaaaac 131940
ttgggtttaa tttctcccgg agatgtttca taatagtacg tataactttc ttctgcaaac 132000
ttaacagctc tattatattc aggataatta aaacctaatt ccatatattt gtctcgtata 132060
tctgctattc ctggtgctat tttgattcta ttaagagtaa cggctgcccc catttttaat 132120
aatcgtcagt atttaaactg ttaaatgttg gtatatcaac atttacctta tttcccgcag 132180
tataaggttt gttgcaggta tactgttcag gaatggttac atttatactt tttctatagt 132240
cctgtctttc gatgttcatc acatatgcaa agaacagaat aaacaaaata atgtaagaaa 132300
taatattaaa tatctgtgaa ttcgtaaata cattgattgc cataataatt acagcagcta 132360
caatacatac aatagacatt cccacagtgt tgccattacc tccacgatac atttgagtta 132420
ctaagcaata ggtaataact aagctagtaa gaggcaatag aaaagatgag ataaatatca 132480
tcaatataga gattagagga gggctatata gagccaagac gaacaaaatc aaaccgagta 132540
acgttctaac atcattattt ttgaagattc ccaaataatc attcattcct ccataatcgt 132600
tttgcatcat acctccatct ttaggcataa acgattgctg ctgttcctct gtaaataaat 132660
ctttatcaag cactccagca cccgcagaga agtcgtcaag catattgtaa tatcttaaat 132720
```

aactcattta tatattaaaa aatgtcacta ttaaagatgg agtataatct ttatgccgaa 132780
ctaaaaaaaa tgacttgtgg tcaaccccta agtcttttta acgaagacgg ggatttcgta 132840
gaagttgaac cgggatcatc ctttaagttt ctgataccta agggatttta cgcctctcct 132900
tccgtaaaga cgagtctagt atttgaaaca ttaacaacga ccgataataa aattactagt 132960
atcaatccaa caaatgcgcc aaagttatat cctcttcaac gcaaagtcgt atctgaagta 133020
gtttctaata tgaggaaaat gatcgaatca aaacgtcctc tatacatcac tcttcacttg 133080
gcgtgtggat ttggtaagac tattaccacg tgttatctta tggctacaca cggtagaaaa 133140
accgtcattt gcgtacccaa taaaatgtta atacatcaat ggaagacaca ggtagaggca 133200
gtcggattgg aacataagat atccatagat ggagtaagta gtctattaaa ggaactaaag 133260
actcaaagtc cggatgtatt aatagtagtc agtagacatc tgacaaacga tgccttttgt 133320
aaatatatca ataagcatta tgatttgttc atcttggatg aatcacatac gtataatctg 133380
atgaacaata cagcagttac aagattttta gcgtattatc ctccgatgat gtgttatttt 133440
ttaactgcta cacctagacc atctaacaga atttattgta acagtattat taatattgcc 133500
aagttatccg atctaaaaaa aactatctat gcagtagata gtttttttga gccatattcc 133560
acagataata ttagacatat gataaaacga ttagatggac catctaataa atatcatata 133620
tataccgaga agttattatc tgtagacgag cctagaaatc aacttattct taataccctg 133680
gtagaagaat tcaagtcagg aactattaat cgcattttag ttattactaa actacgtgaa 133740
catatggtat tcttctacaa acgattatta gatttttcg gatcagaggt tgtatttata 133800
ggagacgccc aaaatagacg tactccagat atggtcaaat caatcaagga actaaataga 133860
tttatattcg tatccacctt attttattcc ggtactggtt tagatattcc tagtttggat 133920
tctttgttca tttgctcggc agtaatcaac aatatgcaaa tagagcaatt actagggagg 133980
gtatgtcgag aaacagaact attagatagg acggtatatg tatttcctag cacatccatc 134040
aaagaaataa agtacatgat aggaaatttc gttcaacgaa ttattagtct gtctgtagat 134100
aaactaggat ttaaacaaaa aagttatcgg aaacatcaag aatccgatcc cacttctgta 134160
tgtacaacat cctccagaga agaacgtgta ttaaatagaa tatttaactc gcaaaatcgt 134220
taagaagttt aagcgacgat ccgcatgctg cgcaggccag tgtattaccc ctcatagtat 134280
taatataatc caatgatact tttgtgatgt cggaaatctt aaccaattta gactgacagg 134340
cagaacacgt catgcaatca tcatcgtcat cgataactgt agtcttgggc ttctttttgc 134400
ggctcttcat tccggaacgc acattggtgc tatccattta ggtagtaaaa aataagtcag 134460
aatatgccct atagcacgat cgtgcaaaac ctggtatatc gtctctatct ttatcacaat 134520
atagtgtatc gacatcttta ttattattga cctcgtttat cttggaacat ggaatgggaa 134580
catttttgtt atcaacggcc acctttgcct taattccaga tgttgtaaaa ttataactaa 134640
acagtctatc atcgacacaa atgaaattct tgtttagacg tttgtagttt acgtatgcgg 134700
ctcgttcgcg tctcattttt tcagatattg caggtactat aatattaaaa ataagaatga 134760
aataacatag gattaaaaat aaagttatca tgacttctag cgctgattta actaacttaa 134820
aagaattact tagtctgtac aaaagtttga aattttcaga ttctgcggct atagaaaagt 134880
ataattcttt ggtagaatgg ggaacatcta cttactggaa aataggcgtg caaaaggtag 134940
ctaatgtcga gacgtcaata tctgattatt atgatgaggt aaaaaataaa ccgtttaata 135000
ttgatccggg ctattacatt ttcttaccgg tatattttgg gagcgtcttt atttattcga 135060

-continued agggtaaaaa tatggtagaa cttggatctg gaaactcttt tcaaatacca gatgatatgc 135120
gaagtgcgtg taacaaagta ttagacagcg ataacggaat agactttctg agatttgttt 135180
tgttaaacaa tagatggata atggaagatg ctatatcaaa atatcagtct ccagttaata 135240
tatttaaact agctagtgag tacggattaa acatacccaa atatttagaa attgaaatag 135300
aggaagacac attatttgac gacgagttat actctattat agaacgctct ttcgatgata 135360
aatttccaaa aatatccata tcgtatatta agttgggaga acttaggcgg caagttgtag 135420
actttttcaa attctcattc atgtatattg agtccatcaa ggtagatcgt ataggagata 135480
atatttttat tcctagcgtt ataacaaaat caggaaaaaa gatattagta aaagatgtag 135540
accatttaat acgatccaag gttagagaac atacatttgt aaaagtaaaa aagaaaaaca 135600
cattttccat tttatacgac tatgatggaa acggaacaga aactagagga gaagtaataa 135660
aacgaattat agacactata ggacgagact attatgttaa cggaaagtat ttctctaagg 135720
ttggtagtgc aggcttaaag caattgacta ataaattaga tattaatgag tgcgcaactg 135780
tcgatgagtt agttgatgag attaataaat ccggaactgt aaaacgaaaa ataaaaaacc 135840
aatcagcatt tgatttaagc agagaatgtt tgggatatcc agaagcggat tttataacgt 135900
tagttaataa catgcggttc aaaatagaaa attgtaaggt tgtaaatttc aatattgaaa 135960
atactaattg tttaaataac ccgagtattg agactatata tggaaacttt aaccagttcg 136020
tctcaatctt taatatcgtc accgatgtca aaaaaagatt attcgagtga aataatatgc 136080
gcctttgata taggtgcaaa aaatcctgcc agaactgttt tagaagtcaa ggataactcc 136140
gttagggtat tggatatatc aaaattagac tggagttctg attgggaaag gcacatagct 136200
aaagatttgt cacaatatga atacactaca gttcttctag aacgtcagcc tagaaggtcg 136260
ccgtacgtca aatttatcta ttttattaaa ggctttttat atcatacatc ggctgccaaa 136320
gttatttgcg tctcgcctgt catgtctggt aattcatata gagatcgaaa aaagagatcg 136380
gtcgaagcat ttcttgattg gatggacaca ttcggattgc gagactccgt tccggataga 136440
cgcaaattag acgatgtagc ggatagtttc aatttggcta tgagatacgt attagataaa 136500
tggaatacta attatacacc ttataatagg tgtaaatcta gaaattacat aaaaaaaatg 136560
taataacgtt agtaacgcca ttatggataa tctatttacc tttctacatg aaatagaaga 136620
tagatatgcc agaactattt ttaactttca tctaataagt tgcgatgaaa taggagatat 136680
atatggtctt atgaaagaac gcatttcctc agaggatatg tttgataata tagtgtataa 136740
taaagatata catcatgcca ttaagaaact agtgtattgc gacatccaac ttactaaaca 136800
cattattaat cagaatacgt atccggtatt taacgattct tcacaagtga aatgttgtca 136860
ttatttcgat ataaactcag ataatagcaa tattagctct cgtacagtag agatatttga 136920
gagggaaaag tcatctcttg tatcatatat taaaactacc aataagaaga gaaaggtcaa 136980
ttatggggaa ataaagaaaa ctgtacatgg aggcactaat gcaaattact tttccggtaa 137040
aaagtctgat gagtatctga gcactacagt caggtccaac attaatcaac cttggatcaa 137100
aaccatttct aagagaatga gagtagatat cattaatcac tctatagtaa cgcgtggaaa 137160
aagctctata ttacaaacta tagaaattat ttttactaat agaacatgtg tgaaaatatt 137220
caaggattct actatgcaca ttattctatc caaggacaag gatgaaaagg ggtgtataca 137280
catgattgac aaattattct atgtctatta taatttattt ctgttgttcg aggatatcat 137340
ccaaaacgag tactttaaag aagtagctaa tgttgtaaac cacgtactca cggctacggc 137400
attagatgag aaattattcc taattaagaa aatggctgaa cacgatgttt atggagttag 137460
caatttcaaa atagggatgt ttaacctgac atttattaag tcgttggatc ataccgtttt 137520
cccctctctg ttagatgagg atagcaaaat aaagtttttt aaggggaaaa agctcaatat 137580
tgtagcatta cgatctctgg aggattgtat aaattacgtg actaaatccg agaatatgat 137640
agaaatgatg aaggaaagat cgactatttt aaatagcata gatatagaaa cggaatcggt 137700
agatcgtcta aaagaattgc ttctaaaatg aaaaaaaaac actaattcag aaatggatca 137760
acgactcgga tataagtttt tggtgcctga tcctaaagcc ggagtttttt atagaccgtt 137820
acatttccaa tatgtatcgt attctaattt tatattgcat cgattgcatg aaatcttgac 137880
cgtcaagcgg ccactcttat cgtttaagaa taatacagaa cgaattatga tagaaattag 137940
caatgttaaa gtgactcctc cagattactc acctataatc gcgagtatta aaggtaagag 138000
ttatgacgca ttagccacgt tcactgtaaa tatctttaaa gaggtaatga ccaaagaggg 138060
tatatccatc actaaaataa gtagttatga gggaaaagat tctcatttga taaaaattcc 138120
gctactaata ggatacggga ataaaaatcc acttgataca gccaagtatc ttgttcctaa 138180
tgtcataggt ggagtcttta tcaataaaca atctgtcgaa aaagtaggaa ttaatctagt 138240
agaaaagatt acaacatggc caaaatttag ggttgttaag ccaaactcat tcactttctc 138300
gttttcctcc gtatcccctc ctaatgtatt accgacaaga tatcgccatt acaagatatc 138360
tctggatata tcacaattgg aagcgttgaa tatatcatcg acaaagacat ttataacggt 138420
caatattgtt ttgctgtctc aatatttatc tagagtgagt ctagaattca ttagacgtag 138480
tttatcatac gatatgcctc cagaagttgt ctatctagta aacgcgataa tagatagtgc 138540
taaacgaatt actgaatcta ttactgactt taatattgat acatacatta atgacctggt 138600
ggaagctgaa cacattaaac aaaaatctca gttaacgatc aacgagttca aatatgaaat 138660
gctgcataac tttttacctc atatgaacta tacacccgat caactaaagg gattttatat 138720
gatatcttta ctaagaaagt ttctctactg tatctaccac acttctagat atccagatag 138780
agattcgatg gtttgtcatc gcatcctaac gtacggcaaa tattttgaga cgttggcaca 138840
tgatgaatta gagaattaca taggcaacat ccgaaacgat atcatgaaca atcacaagaa 138900
cagaggcact tacgcggtaa acattcatgt actaacaact cctggactta atcatgcatt 138960
ttctagtcta ttgagtggaa agttcaaaaa gtcagacggt agttatcgaa cacatcctca 139020
ctattcatgg atgcagaata tttctattcc taggagtgtt ggattttatc cggatcaagt 139080
aaagatttca aagatgtttt ctgtcagaaa ataccatcca agtcaatatc tttacttttg 139140
ttcatcggac gttccggaaa gaggtcctca ggtaggttta gtatctcaat tgtctgtctt 139200
gagttccatt acaaatatac taacgtctga gtatttggat ttggaaaaga aaatttgtga 139260
gtatatcaga tcatattata aagatgatat aagttacttt gaaacaggat ttccaatcac 139320
tatagaaaat gctctagtcg catctcttaa tccaaatatg atatgtgatt ttgtaactga 139380
ctttagacgt agaaaacgga tggattcttt cggtaacttg gaggtaggta ttactttagt 139440
tagggatcac atgaatgaaa ttcgcattaa tattggagcg ggaagattag tcagaccatt 139500
cttggttgtg gataacggag agctcatgat ggatgtgtgt ccggagttag aaagcagatt 139560
agacgacatg acattctctg acattcagaa agagtttccg catgtcatcg aaatggtaga 139620
tatagaacaa tttactttta gtaacgtatg tgaatcggtt caaaaattta gaatgatgtc 139680
aaaggatgaa agaaagcaat acgatttatg tgactttcct gccgaattta gagatggata 139740
tgtagcatct tcactagtgg gaatcaatca caattctgga cccagagcta ttcttggatg 139800

-continued tgctcaagct aaacaagcta tctcttgtct gagctcggat atacgaaata aaatagacaa 139860
tggaattcat ttgatgtatc cagagaggcc aatcgtgatt agtaaggctt tagaaacttc 139920
aaagattgcg gctaattgct tcggccaaca tgttactata gcattaatgt cgtacaaagg 139980
tatcaatcaa gaggatggaa ttatcatcaa aaaacaattt attcagagag gcggtctcga 140040
tattgttaca gccaagaaac atcaagtaga aattccgttg gaaaacttta ataacaaaga 140100
aagagatagg tctaacgcct attcaaaatt agaaagtaat ggattagtta gactgaatgc 140160
tttcttggaa tccggagacg ctatagcacg aaatatctca tcaagaactc ttgaagatga 140220
ttttgctaga gataatcaga ttagctttga tgtttccgaa aaatataccg atatgtacaa 140280
atctcgcgtt gaacgagtac aagtagaact tactgacaaa gttaaggtac gagtattaac 140340
catgaaagaa agaagaccca ttctaggaga caaatttacc actagaacga gtcaaaaggg 140400
aacagtcgcg tatatcgcgg atgaaacgga acttccatac gatgaaaatg gtatcacacc 140460
agatgtcatt attaattcta catccatctt ctctagaaaa actatatcta tgttgataga 140520
ggttatttta acagccgcat attctgctaa gccgtacaac aataagggag aaaaccgacc 140580
tgtctgtttt cctagtagta acgaaacatc catcgataca tatatgcaat tcgctaaaca 140640
atgttatgag cattcaaatc cgaaattgtc tgatgaagaa ttatcggata aaatcttttg 140700
tgaaaagatt ctctatgatc ctgaaacgga taagccttat gcatccaaag tattttttgg 140760
accaatttat tacttgcgtc tgaggcattt aactcaggac aaggcaaccg ttagatgtag 140820
aggtaaaaag acgaagctca ttagacaggc gaatgaggga cgaaaacgtg gaggaggtat 140880
caagttcgga gaaatggaga gagactgttt aatagcgcat ggtgcagcca atactattac 140940
agaagttttg aaagattcgg aagaagatta tcaagatgtg tatgtttgtg aaaattgtgg 141000
agacatagca gcacaaatca agggtattaa tacatgtctt agatgttcaa aacttaatct 141060
ctctcctctc ttaacaaaaa ttgataccac gcacgtatct aaagtatttc ttactcaaat 141120
gaacgccaga ggcgtaaaag ttaaattaga tttcgaacga aggcctcctt cgttttataa 141180
accattagat aaagttgatc tcaaaccgtc ttttctggtg taatattcta gtttggtagt 141240
agatacatat caatatcatc aaattcgaga tccgaattat aaaatgggcg tggattgtta 141300
actatagaat cggacgtctg atattcgaaa atctgtggag ttttaggttt tggtggaggt 141360
gtaactgcta cttgggatac tgaagtctga tattcagaaa gctgggggat gttctggttc 141420
gacatccacc gatggtgtca catcactaat cggttcggta acgtctgtgg acgatggagg 141480
caccacttct acaggttctg gttctttatc ctcagtcatc aacggagcta cttcaatgcg 141540
aggaaatgta taatttggta atggtttctc atgtggatct gaagaagagg taagatatct 141600
actagaaaga taccgatcac gttctagttc tcttttgtag aacttaactt tttctttctc 141660
cgcatctagt tgatattcca acctcttcac gttcgcatgg gttacctccg cagtttttac 141720
gagcgatttc acgttcagcc ttcatgcgtc ttatagcatg aattcgctta tcgttatcgg 141780
gtttagcttc tgtcacctta gcaattcctt ttttattaaa ctctacataa tcatatccat 141840
ttctattgtt tgttctaata taaacgagta tagcatcatt gctaaatttt tcaatagtat 141900
cgaaaacaga atatcctaaa ccatataata tatattcagg aacactcaaa ctaaatgtcc 141960
aggattctcc taaatacgta aactttaata gtgcgaaatc attcaaaaat ctaccactta 142020
tagatagata gatagtacat aaatgcgtat agtagtctac ctatctcttt attatgaaaa 142080
ccggcattac gatcatatat gtcgtgatat acctgtgatc cgtttacgtt aaaccataaa 142140
tacatgggtg atcctataaa catgaattta tttctaattc tcagagctat agttaattga 142200

-continued ccgtgtaata tttgcttaca tgcatacttg atacgatcat taataagatt tttatcattg 142260
ctcgttattt cagaatcgta tatataagga gtaccatcgt gattcttacc agatattata 142320
caaaatacta tatataaaat atattgaccc acgttagtaa tcatgtaaat gtttaacgtt 142380
ttaaattttg tattcaatga tccattatca tacgctagca tggtcttatg atattcattc 142440
tttaaaatat aatattgtgt tagccattgc attggggctc ctaatggaga ttttttattc 142500
tcatccattt taggataggc tttcataaag tccctaataa cttcgtgaat aatgtttcta 142560
tgttttctac tgatgcatgt atttgcttcg attttttat cccatgtttc atctatcata 142620
gatttaaacg cagtaatgct cgcaacatta acatcttgaa ccgttggtac aattccgttc 142680
cataaattta taatgttcgc catttatata actcattttt tgaatatact tttaattaac 142740
aaaagagtta agttactcat atggacgccg tccagtctga acatcaatct ttttagccag 142800
agatatcata gccgctctta gagtttcagc gtgattttcc aacctaaata gaacttcatc 142860
gttgcgttta caacactttt ctatttgttc aaactttgtt gttacattag taatcttttt 142920
ttccaaatta gttagccgtt gtttgagagt ttcctcattg tcgtcttcat cggctttaac 142980
aattgcttcg cgtttagcct ctggcttttt agcagccgtt gtagaaaaaa attcagttgc 143040
tggaattgca agatcgtcat ctccggggaa aagagttccg tccatttaaa gtacagattt 143100
tagaaactga cactctgcgt tatttatatt tggtacaaca catggattat aaatattgat 143160
gttaataaca tcagaaaatg taaagtctat acattgttgc atcgtgttaa attttctaat 143220
ggatctagta ttattgggtc caacttctgc ctgaaatcca aatatggaag cggatacaaa 143280
accgtttcct ggataaacca cacatctcca cttttgcttt acatcagaaa ttgtgtcgtt 143340
gacatcttga actctcctat ctaatgccgg tgttccacct atagattttg aatattcgaa 143400
tgctgcatga gtagcattaa attccttaat attgccataa ttttcatata ttgagtaacc 143460
ctggataaaa agtaaacaca ccgcagccgt agctaccaca ataaaaaaaa ttgatagaga 143520
gttcatttat aatctattag aagctgacaa aattttttta cacgcatcag acaatgcttt 143580
aataaatagt tcaacatcta cttttgtcat atcgaaccga tggtatgatt ctaacctaga 143640
attacatccg aaaaagttga ctatgttcat agtcattaag tcattaacaa acaacattcc 143700
agactctgga ttataagacg atactgtttc gtcacaatta cctaccttaa tcatgtgatt 143760
atgaatattg gctattagag caccttctaa gaaatctata atatctttga aacacgattt 143820
aaaatcaaac cacgaatata cttctacgaa gaaagttagt ttacccatag gagaaataac 143880
tataaatgga gatctaaata caaaatccgg atctatgata gttttaacat tattatattc 143940
tctattaaat acctccacat ctaaaaatgt taattttgaa actatgtctt cgtttattac 144000
cgtacctgaa ctaaacgcta taagctctat tgtttgagaa ctctttaaac gatattcttg 144060
aaatacatgt aacaaagttt cctttaactc ggtcggttta tctaccatag ttacagaatt 144120
tgtatcctta tctataatat aataatcaaa atcgtataaa gttatataat tatcgcgttc 144180
agattgggat cttttcaaat agactaaaaa ccccatttct ctagtaagta tcttatgtat 144240
atgtttgtaa aatatcttca tggtgggaat atgctctacc gcagttagcc attcctcatt 144300
gacagcggta gatgtattag acaaaactat tccaatgttt aacaagggcc attttacgag 144360
attattaaat ccttgtttga taaatgtagc caatgagggt tcgagttcaa cgacgattga 144420
attctcttcc cgcggatgct gcatgatgaa cgacgggatg ttgttcgatt gatttggaat 144480
tctttttcga ctttttgttt atattaaata ttttaaaatt tatagcggat agcaattcat 144540

-continued gtaccacgga taatgtagac gcgtattgcg catcgatatc tttattatta gataaattta 144600
tcaataaatg tgagaagttt gcctcgttaa ggtcttccat ttaaatatta tataaacatt 144660
tgtgtttgta tcttattcgt cttttatgga atagtttttt actagtaaag ctgcaattac 144720
acactttgtc cgtaaaacat aaatataaac accagctttt atcaatcgtt ccaaaaagtc 144780
gacggcggac atttttaaca tggcatctat tttaaataca cttaggtttt tggaaaaaac 144840
atcattttat aattgtaacg attcaataac taaagaaaag attaagatta aacataaggg 144900
aatgtcattt gtattttata agccaaagca ttctaccgtt gttaaatact tgtctggagg 144960
aggtatatat catgatgatt tggttgtatt ggggaaggta acaattaatg atctaaagat 145020
gatgctattt tacatggatt tatcatatca tggagtgaca agtagtggaa caatttacaa 145080
attgggatcg tctatcgata gactttctct aaataggact attgttacaa aagttaataa 145140
ttataattat gatacatttt ttgacgatga tgattgatcg ctattgcaca attttgtttt 145200
tttactttct aatatagcgt ttagattctt tttcatgtgc gaatattgat ttactaaaat 145260
atctatgttt aacttttgtt ctataacgtc cttatcggcg gtatcggtac atatacgtaa 145320
ttcaccttca caaaatacgg agtcttcgat aataatagcc aatcgattat tggatctagc 145380
tgtctgtatc atattcaaca tgtttaatat atcctttcgt ttccccttta caggcatcga 145440
tcgtagcata ttttccgcgt ctgagatgga aatgttaaaa ctacaaaaat gcgtaatgtt 145500
agcccgtcct aatattggta cgtgtctata agtttggcat agtagaataa tagacgtgtt 145560
taaatgcctt ccaaagttta agaattctat tagagtattg cattttgata gtttatcgcc 145620
tacatcatca aaaataagta aaaagtgtgc tgattttttta tgattttgtg cgacagcaat 145680
acatttttct atgttacttt tagttcgtat cagattatat tctagagatt cctgactact 145740
aacgaaatta atatgatttg gccaaatgta tccatcataa tctggattat aaacgggtgt 145800
aaacaagaat acatgtttat attttttaac tagtgtagaa aacagagata gtaaatagat 145860
agtttttcca gatccagatc ctcccgttaa aaccattcta aacggcattt ttaataaatt 145920
ttctcttgaa aattgttttt cttggaaaca attcataatt atatttacag ttactaaatt 145980
aatttgataa taaatcaaaa tatggaaaac taaggtcgtt agtagggagg agaacaaaga 146040
aggcacatcg tgacataaat aacatttatt atcatgatga caccagaaaa cgacgaagag 146100
cagacatctg tgttctccgc tactgtttac agagacaaaa ttcagggaaa gaataaacgc 146160
aaacgcgtga ttggtctatg tattagaata tctatggtta tttcactact atctatgatt 146220
accatgtccg cgtttctcat agtgcgccta aatcaatgca tgtctgctaa cgaggctgct 146280
attactgacg ccgctgttgc cgttgctgct gcatcatcta ctcatagaaa ggttgcgtct 146340
agcactacgc aatatgatca caaagaaagc tgtaatggtt tatattacca gggttcttgt 146400
tatatattac attcagacta ccagttattc tcggatgcta aagcaaattg cactgcggaa 146460
tcatcaacac tacccaataa atccgatgtc ttgactacct ggctcattga ttatgttaag 146520
gatacatggg gatctgatgg taatccaatt acaaaaacta catccgatta tcaagattct 146580
gatgtatcac aagaagttag aaagtatttt tgtgttaaaa caatgaacta atatttattt 146640
ttgtacatta ataaatgaaa tcgcttaata gacaaactgt aagtaggttt aagaagttgt 146700
cggtgccggt cgctataatg atgatactct caaccattat tagtggcata ggaacatttc 146760
tgcattacaa agaagaactg atgcctagtg cttgcgccaa tggatggata caatacgata 146820
aacattgtta tttagatact aacattaaaa tgtctacaga taatgcggtt tatcagtgtc 146880
gtaaattacg agccagattg cctagaccgt atactagaca tctgagagta ttgtttagta 146940

-continued tttttataa agattattgg gtaagtttaa aaaagaccaa tgataaatgg ttagatatta 147000
ataatgataa agatatagat attagtaaat taacaaattt taaacaacta aacagtacga 147060
cggatgctga agcgtgttat atatacaagt ctggaaaact ggttaaaaca gtatgtaaaa 147120
gtactcaatc tgtactatgt gttaaaaaat tctacaagtg acaacaaaaa atgaattaat 147180
aataagtcgt taacgtacgc cgccatggac gccgcgtttg ttattactcc aatgggtgtg 147240
ttgactataa cagatacatt gtatgatgat ctcgatatct caatcatgga ctttatagga 147300
ccatacatta taggtaacat aaaaactgtc caaatagatg tacgggatat aaaatattcc 147360
gacatgcaaa aatgctactt tagctataag ggtaaaatag ttcctcagga ttctaatgat 147420
ttggctagat tcaacattta tagcatttgt gccgcataca gatcaaaaaa taccatcatc 147480
atagcatgcg actatgatat catgttagat atagaagata aacatcagcc attttatcta 147540
ttcccatcta ttgatgtttt taacgctaca atcatagaag cgtataacct gtatacagct 147600
ggagattatc atctaatcat caatccttca gataatctga aaatgaaatt gtcgtttaat 147660
tcttcattct gcatatcaga cggcaatgga tggatcataa ttgatgggaa atgcaatagt 147720 aatttttat cataaaagtt gtaaagtaaa taataaaaca ataaatattg aactagtagt 147780
acgtatattg agcaatcaga aatgatgctg gtacctctta tcacggtgac cgtagttgcg 147840
ggaacaatat tagtatgtta tatattatat atttgtagga aaaagatacg tactgtctat 147900
aatgacaata aaattatcat gacaaaatta aaaaagataa agagttctaa ttccagcaaa 147960
tctagtaaat caactgatag cgaatcagac tgggaggatc actgtagtgc tatggaacaa 148020
aacaatgacg tagataatat ttctaggaat gagatattgg acgatgatag cttcgctggt 148080
agtttaatat gggataacga atccaatgtt atggcgccta gcacagaaca catttacgat 148140
agtgttgctg gaagcacgct gctaataaat aatgatcgta atgaacagac tatttatcag 148200
aacactacag tagtacttaa tgaagatacc aaacagaatc ctaactattc atccaatcct 148260
ttcgtaaatt ataataaaac cagtatttgt agcaagtcaa atccgttcat tacagaactc 148320
aacaataaat ttagtgagaa taatccgttt agacgagcac atagcgatga ttatcttaat 148380
aagcaagaac aagatcatga acacgatgat atagaatcat tggtgtgatt agtttccttt 148440
ttataaaatt gaagtaatat ttagtattat tgctgccgtc acgttgtaca aatggagata 148500
ttccctgtat tcggcatttc taaaattagc aattttattg ctaataatga ctgtagatat 148560
tatatagata cagaacatca aaaaattata tctgatgaga tcaatagaca gatggatgaa 148620
acggtacttc ttaccaacat cttaagcgta gaagttgtaa atgacaatga gatgtaccat 148680
cttattcctc atagattatc gacgattata ctctgtatta gttctgtcgg aggatgtgtt 148740
atctctatag ataatgacgt caatggcaaa aatattctaa cctttcccat tgatcatgct 148800
gtaatcatat ccccactgag taaatgtgtc gtagttagca agggtcctac aaccatattg 148860
gttgttaaag cggatatacc tagcaaacga ttggtaacat cgtttacaaa cgacatactg 148920
tatgtaaaca atctatcact gattaattat tcgccgttgt ctgtattcat tattagacga 148980
gttaccgact atttggatag acacatatgc gatcagatat ttgcgaataa taagtggtat 149040
tccattataa ccatcgacaa taagcagttt cctattccat caaactgtat aggtatgtcc 149100
tctgccaagt acataaattc tagcatcgag caagatactt taatacatgt ttgtaacctc 149160
gagcatccat tcgacttagt atacaaaaaa atgcagtcgt acaattctgt acctatcaag 149220
gaacaaatat tgtacggtag aattgataat ataaatatga gcattagtat ttctgtggat 149280

-continued taatagattt ctagtatggg gatcattaat catctctaat ctctaaatac ctcataaaac 149340
gaaaaaaaag ctattatcaa atactgtacg gaatggattc attctcttct ctttttatga 149400
aactctgttg tatatctact gataaaactg gaagcaaaaa atctgataaa aagaataaga 149460
ataagatcaa ggattattat aaaataacaa tagttcctgg ttcctcttcc acgtctacta 149520
gctcgtggta ttatacacat gcctagtaat agtctctttg cgttgacgga aagcagacta 149580
gaaataacag gctaaaatgt tcagacacca taatagttcc caacccagat aataacagag 149640
taccatcaac acattccttt aaactcaatc ccaaacccaa aaccgttaaa atgtatccgg 149700
ccaattgata gtagataatg aggtgtacag cgcatgatga tttacacagt aaccaaaatg 149760
aaaatacttt agtaattata agaaatatag atggtaacgt catcatcaac aatccaataa 149820
tatgccggag agtaaacatt gacggataaa acaaaaatgc tccgcataac tctatcatgg 149880
caataacaca accaaatact tgtaagattc ctaaattagt agaaaataca acggatatcg 149940
atgtataagt gatctcgaga aataataaga ataaagtaat gcccgtaaag ataaacatca 150000
acattgtttg gtaatcatta aaccaattag tatgaagttg aactaatttc acagtagatt 150060
ttattccagt attatccccg catgtataag tacctggtaa gatatcttta tattccataa 150120
tcaatgagac atcactatct gataacgaat gaagtctagc actagtatgc catttactta 150180
atattgtcgt cttggaagtt ttattataag ttaaaatatc atggttatcc aatttccatc 150240
taatatactt tgtcggatta tctatagtac acggaataat gatggtatca ttacatgctg 150300
tatactctat ggtctttgta gttgttataa caaccaacgt atagaggtat atcaacgata 150360
ttctaactct tgacattttt tatttattta aaatgatacc tttgttattt attttattct 150420
attttgctaa cggtattgaa tggcataagt ttgaaacgag tgaagaaata atttctactt 150480
acttattaga cgacgtatta tacacgggtg ttaatggggc ggtatacaca ttttcaaata 150540
ataaactaaa caaaactggt ttaactaata ataattatat aacaacatct ataaaagtag 150600
aggatgcgga accaataacg gaaatcccaa atgttggaaa atagacggtt cagacgaccc 150660
aaaacataga ggtagaggat acgctcctta tcaaaatagc aaagtaacga taatcagtca 150720
caacggatgt gtactatctg acataaacat atcaaaagaa ggaattaaac gatggagaag 150780
atttgacgga ccatgtggtt atgatttata cacggcggat aacgtaattc caaaagatgg 150840
tttacgagga gcattcgtcg ataaagatgg tacttatgac aaagtttaca ttcttttcac 150900
tgatactatc ggctcaaaga gaattgtcaa aattccgtat atagcacaaa tgtgcctaaa 150960
cgacgaaggt ggtccatcat cattgtctag tcatagatgg tcgacgtttc tcaaagtcga 151020
attagaatgt gatatcgacg gaagaagtta tagacaaatt attcattcta gaactataaa 151080
aacagataat gatacgatac tatatgtatt cttcgatagt ccttattcca agtccgcatt 151140
atgtacctat tctatgaata ccattaaaca atctttttct acgtcaaaat tggaaggata 151200
tacaaagcaa ttgccgtctc cagctcctgg tatatgttta ccagctggaa aagttgttcc 151260
acataccacg tttgaagtca tagaaaaata taatgtacta gatgatatta taaagccttt 151320
atctaaccaa cctatcttcg aaggaccgtc tggtgttaaa tggttcgata taaaggagaa 151380
ggaaaatgaa catcgggaat atagaatata cttcataaaa gaaaattcta tatattcgtt 151440
cgatacaaaa tctaaacaaa ctcgtagctc gcaagtcgat gcgcgactat tttcagtaat 151500
ggtaacttcg aaaccgttat ttatagcaga tatagggata ggagtaggaa tgccacaaat 151560
gaaaaaaata cttaaaatgt aatcttaatc gagtacaccg cacgacaatg aacaaacata 151620
agacagatta tgctggttat gcttgctgcg taatatgcgg tctaattgtt ggaattattt 151680
ttacagcgac actattaaaa gttgtagaac gtaaattagt tcatacacca tcaatagata 151740
aaacgataaa agatgcatat attagagaag attgtcctac tgactggata agctataata 151800
ataaatgtat ccatttatct actgatcgaa aaacctggga ggaaggacgt aatgcatgca 151860
aagctctaaa tccaaattcg gatctaatta agatagagac tccaaacgag ttaagttttt 151920
taagaagcat tagacgcgga tattgggtag gagaatccga aatattaaac cagacaaccc 151980
catataattt tatagctaaa aatgccacga agaatggaac taaaaaacgg aaatatattt 152040
gtagtacaac gaatactccc aaactacatt tttatcatac cactacttcg gttagatgtt 152100
ttagaaaaaa ataaatatcg ccgtaccgtt cttgttttta taaaaataac aattaacaat 152160
tatcaaattt tttctttaat attttacgtg gttgaccatt cttggtggta aaataatctc 152220
ttagtgttgg aatggaatgc tgtttaatgt ttccgcactc atcgtatatt ttgacgtatg 152280
cagtcacatc gtttacgcaa tagtcagact gtagttctat catgcttcct acatcagaag 152340
gaggaacagt tttaaagtct cttggtttta atctattgcc attagttttc atgaaatcct 152400
ttgttttatc cacttcacat tttaaataaa tgtccactat acattcttct gttaatttta 152460
ctagatcgtc atgggtcata gaatttatag gttccgtagt ccatggatcc aaactagcaa 152520
acttcgcgta tacggtatcg cgattagtgt atacaccaac tgtatgaaaa ttaagaaaac 152580
agtttaataa atcaacagaa atatttaatc ctccgtttga tacagatgcg ccatatttat 152640
ggatttcgga ttcacacgtt gtttgtctga ggtgttcgtc tagtgttgct tctacgtaaa 152700
cttcgattcc catatattct ttattgtcag aatcgcatac cgatttatca tcatacactg 152760
tttgaaaact aaatggtata cacatcaaaa taataaataa taacgagtac attctgcaat 152820
attgttatcg taattggaaa aatagtgttc gagtgagttg gattatgtga gtattggatt 152880
gtatatttta ttttatattt tatattttgt agtaagaata gaatgctaat gtcaagttta 152940
ttccaataga tgtcttatta aaaaacatat ataataaata acaatggctg aatggcataa 153000
aattatcgag gatatctcaa aaaataataa gttcgaggat gccgccatcg ttgattacaa 153060
gactacaaag aatgttctag ctgctattcc taacagaaca tttgccaaga ttaatcctct 153120
catcactaat cgtaatattc taaaacctct tattggtcag aaatattgta ttgtatatac 153180
taactctcta atggatgaga acacgtatgc tatggagttg cttactgggt acgcccctgt 153240
atctccgatc gttatagcga gaactcatac cgcacttata tttttgatgg gtaagccaac 153300
aacatccaga cgtgacgtgt atagaacgtg tagagatcac gctacccgtg tacgtgcaac 153360
tggtaattaa aataaaaagt aatattcata tgtagtgtca attttaaatg atgatgatga 153420
aatggataat atccatattg acgatgtcaa taatgccggt attggcatac agttcatcga 153480
tttttagatt tcattcagag gatgtggaat tatgttatgg gcatttgtat tttgatagga 153540
tctataatgt agtaaatata aaatataatc cgcatattcc atatagatat aattttatta 153600
atcgcacgtt aaccgtagat gaactagacg ataatgtctt ttttacacat ggttattttt 153660
taaaacacaa atatggttca cttaatccta gtttgattgt ctcattatca ggaaacttaa 153720
aatataatga tatacaatgc tcagtaaatg tatcgtgtct cattaaaaat ttggcaacga 153780
gtacatctac tatattaaca tctaaacata agacttattc tctacatcgg tccacgtgta 153840
ttactataat aggatacgat tctattatat ggtataaaga tataaatgac atctatgatt 153900
ttactgcaat atgtatgcta atagcgtcta cattgatagt gaccatatac gtgtttaaaa 153960
aaataaaaat gaactcttaa ttatgctatg ctattagaaa tggataaaat caaaattacg 154020
gttgattcaa aaattggtaa tgttgttacc atatcgtata acttggaaaa gataactatt 154080
gatgtcacac ctaaaaagaa aaaagaaaag gatgtattat tagcgcaatc agttgctgtc 154140
gaagaggcaa aagatgtcaa ggtagaagaa aaaaatatta tcgatattga agatgacgat 154200
gatatggatg tagaaagcgc ataatacgat ctataaaaat aagtatataa atacttttta 154260
tttactgtac tcttactgtg tagtggtgat accctactcg attatttttt taaaaaaaaa 154320
tacttattct gattcttcta gccatttccg tgttcgttcg aatgccacat cgacgttaaa 154380
gataggggag tagttgaaat ctagttctgc attgttggta cgcacctcaa atgtagtgtt 154440
ggatatcttc aacgtatagt tgttgagtag tgatggtttt ctaaatagaa ttctcttcat 154500
atcattcttg cacgcgtaca tttttagcat ccatcttgga atcctagatc cttgttctat 154560
tcccaatggt ttcatcaata gaagattaaa catatcgtac gaacacgatg gagagtaatc 154620
gtagcaaaag taagcatttc ctttaatctc agatcccgga tactggatat attttgcagc 154680
caacacgtgc atccatgcag catttcctac atatacccgg ctatgtaccg cgttatcatc 154740
gactgtacga tacataatgt taccgtgttg cttacattgc tcgtaaaaga ctttcatcaa 154800
tttgtctcct tctccgtaaa ttccagtggg tcttaggcaa caagtataca attttgctcc 154860
attcatgatt acggaattat tggctttcat aaccagttgc tcggccatac gtttactttt 154920
tgcgtataca tgtcctggtg atatatcata aagggtatgc tcatggccga tgaatggatc 154980
accgtgttta ttgggtccta ttgcttccat gctactagta tagatcaaat acttgattcc 155040
taggtccaca caagctgcca atatagtctg tgttccataa tagtttactt tcatgatttc 155100
attatcggtg tattttccaa atacatccac tagagcagct gtatgaataa tcagatttac 155160
cccatctagc gcttctctta ccttatcaaa gtcgtttata tcacattgta tatagtttat 155220
aaccttaact ttcgaggtta ttggttgtgg atcttctaca atatctatga ctctgatttc 155280
ttgaacatca tctgcactaa ttaacagttt tactatatac ctgcctagaa atccggcacc 155340
accagtaacc gcgtacacgg ccattgctgc cactcataat atcagactac ttattctatt 155400
ttactaaata atggctgttt gtataataga ccacgataat atcagaggag ttatttactt 155460
tgaaccagtc catggaaaag ataaagttat tggattaaaa tccggaacgt atagtttgat 155520
aattcatcgt tacggagata ttagtcaagg atgtgattcc ataggcagtc cagaaatatt 155580
tatcggtaac atctttgtaa acagatatgg tgtagcatat gtttatttag atacagatgt 155640
aaatatatct acaattattg gaaaggcgtt atctatttca aaaaatgatc agagattagc 155700
gtgtggagtt attggtattt cttacataaa tgaaaagata atacattttc ttacaattaa 155760
cgagaatggc gtttgatata tcagttaatg cgtctaaaac aataaatgca ttagtttact 155820
tttctactca gcaaaataaa ttagtcatac gtaatgaagt taatgataca cactacactg 155880
tcgaatttga tagggacaaa gtagttgaca cgtttatttc atataataga cataatgact 155940
ccatagagat aagaggggtg cttccagagg aaactaatat tggttgcgcg gttaatacgc 156000
cggttagtat gacttacttg tataataagt atagttttaa actgatttta gcagaatata 156060
taagacacag aaatactata tccggcaata tttattcggc attgatgaca ctagatgatt 156120
tggctattaa acagtatgga gacattgatc tattatttaa tgagaaactt aaagtagact 156180
ccgattcggg actatttgac tttgtcaact ttgtaaagga tatgatatgt tgtgattcta 156240
gaatagtagt agctctatct agtctagtat ctaaacattg ggaattgaca aataaaaaat 156300
ataggtgtat ggcattagcc gaacatatat ctgatagtat tccaatatct gagctatcta 156360
gactacgata caatctatgt aagtatctac gcgggcacac tgagagcata gaggatgaat 156420
ttgattattt tgaagacgat gattcgtcta catgttctgc cgtaaccgac agggaaacgg 156480
atgtataatt ttttttatag cgtgaaggat atgataaaaa atataattgt tgtatttatc 156540
ccattccaat caccttatat gattctgtaa cacaatgaag gagtcttata gatgtataga 156600
ggtcagatac tggtttgata aactgtttat tccacataag tatgtttgac tttatggtta 156660
gacccgcata ctttaacaaa tcactgaaaa ttggagttag gtattgacct ctcagaatca 156720
gttgccgttc tggaacatta aatgtatttt ttatgatata ctccaacgca tttatgtggg 156780
catacaacaa gtcattacta atggagtatt ccaagagaag agatttcaac agactgttta 156840
tgaactcgaa tgccgcctca ttgtcgctta tattgatgat gtcgaattct cccaatatca 156900
tcaccgatga gtagctcatc ttgttatcgg gatccaagtt ttctaaagat gtcattaaac 156960
cctcgatcat gaatggattt atcatcatcg tttttatgtt ggacatgagc ttagtccgtt 157020
tgtccacatc tatagacgac gatttctgaa ttatttcata tatccctctc tttaactcca 157080
ggaacttgtc aggatggtct actttaatat gttctcgtct aagagatgaa aatctttgga 157140
tggttgcacg cgacttttct ctaaaggatc ctctcttaaa tgaatccatc ttatccttgg 157200
acaagatgga cagtctattt tccttagatg gtttaatatt tttgttaccc atgatctata 157260
aaggtagacc taatcgtctc ggatgaccat atatttattt tcagttttat tatacgcata 157320
aattgtaaaa aatatgttag gtttacaaaa atgtctcgtg gggcattaat cgtttttgaa 157380
ggattggaca aatctggaaa aacaacacaa tgtatgaaca tcatggaatc tataccggca 157440
aacacgataa aatatcttaa ctttcctcag agatccactg tcactggaaa gatgatagat 157500
gactatctaa ctcgtaaaaa aacctataat gatcatatag ttaatctatt attttgtgca 157560
aatagatggg agtttgcatc ttttatacaa gaacaactag aacagggaat tactttaata 157620
gttgatagat acgcattctc tggagtagcg tatgccgccg ctaaaggcgc gtcaatgact 157680
ctcagtaaga gttatgaatc tggattgcct aaacccgact tagttatatt cttggaatct 157740
ggtagcaaag aaattaatag aaacgtcggc gaggaaattt atgaagatgt tacattccaa 157800
caaaaggtat tacaagaata taaaaaaatg attgaagaag gagatattca ttggcaaatt 157860
atttcttctg aattcgagga agatgtaaag aaggagttga ttaagaatat agttatagag 157920
gctatacaca cggttactgg accagtgggg caactgtgga tgtaatagtg aaattacatt 157980
ttttataaat ggatgaagca tattactctg gcaacttgga atcagtactc ggatacgtgt 158040
ccgatatgca taccgaactc gcatcaatat ctcaattagt tattgccaag atagaaacta 158100
tagataatga tatattaaac aaggacattg taaattttat catgtgtaga tcaaacttgg 158160
ataatccatt tatctctttc ctagatactg tatatactat tatagatcaa gagatctatc 158220
agaccgaatt gattaattca ttagacgaca atgaaattat cgattgtata gttaacaagt 158280
ttatgagctt ttataaggat aacctagaaa atatagtaga tgctatcatt actctaaaat 158340
atataatgaa taatccagat tttaaaacta cgtatgccga agtactcggt tccagaatag 158400
cggatataga tattaaacaa gtgatacgtg agaatatact acaattgtct aataatatcc 158460
gcgaacgata tttgtgaaaa tattaaaaaa aaatactttt tttattaaat gacgtcgctt 158520
cgcgaattta gaaaattatg ctgtgatata tatcacgcat caggatataa agaaaaatct 158580
aaattaatta gagactttat aacagatagg gatgataaat atttgatcat taagctattg 158640
cttcccggat tagacgatag aatttataac atgaacgata aacaaattat aaaattatat 158700
agtataatat ttaaacaatc tcaggaagat atgctacaag atttaggata cggatatata 158760

-continued ggagacacta ttaggacttt cttcaaagag aacacagaaa tccgtccacg agataaaagc 158820
attttaactt tagaagaagt ggatagtttt ttaactacgt tatcatccgt aactaaagaa 158880
tcgcatcaaa taaaattatt gactgatatc gcatccgttt gtacatgtaa tgatttaaaa 158940
tgtgtagtca tgcttattga taaagatcta aaaattaaag cgggccctcg gtacgtactt 159000
aacgctatta gtcctcatgc ctatgatgtg tttagaaaat ctaataactt gaaagagata 159060
atagaaaatg catctaaaca aaatctagac tctatatcta tttctgttat gactccaatt 159120
aatcccatgt tagcggaatc gtgtgattct gtcaataagg cgtttaaaaa atttccatca 159180
ggaatgtttg cggaagtcaa atacgatggt gaaagagtac aagttcataa aaataataac 159240
gagtttgcct tctttagtag aaacatgaaa ccagtactct ctcataaagt ggattatctc 159300
aaagaataca taccgaaagc atttaaaaaa gctacgtcta tcgtattgga ttctgaaatt 159360
gttcttgtag acgaacataa tgtaccgctc ccgtttggaa gtttaggtat acacaaaaag 159420
aaagaatata aaaactctaa catgtgtttg ttcgtgtttg actgtttgta ctttgatgga 159480
ttcgatatga cggacattcc attgtacgaa cgaagatctt ttctcaaaga tgttatggtt 159540
gaaataccca atagaatagt attctcagag ttgacgaata ttagtaacga gtctcagtta 159600
actgacgtat tggatgatgc actaacgaga aaattagaag gattggtctt aaaagatatt 159660
aatggagtat acgaaccggg aaagagaaga tggttaaaaa taaagcgaga ctatttgaac 159720
gagggttcca tggcagattc tgccgattta gtagtactag gtgcttacta tggtaaagga 159780
gcaaagggtg gtatcatggc agtctttcta atgggttgtt acgacgatga atccggtaaa 159840
tggaagacgg ttaccaagtg ttcaggacac gatgataata cgttaaggga gttgcaagac 159900
caattaaaga tgattaaaat taacaaggat cccaaaaaaa ttccagagtg gttagtagtt 159960
aataaaatct atattcccga ttttgtagta gaggatccaa aacaatctca gatatgggaa 160020
atttcaggag cagagtttac atcttccaag tcccataccg caaatggaat atccattaga 160080
tttcctagat ttactaggat aagagaggat aaaacgtgga aagaatctac tcatctaaac 160140
gatttagtaa acttgactaa atcttaatag ttacatacaa attaaaataa cactatttag 160200
ttggtggtcg ccatggatgg tgttattgta tactgtctaa acgcgttagt aaaacatggc 160260
gaggaaataa atcatataaa aaatgatttc atgattaaac catgttgtga aaaagtcaag 160320
aacgttcaca ttggcggaca atctaaaaac aatacagtga ttgcagattt gccatatatg 160380
gataatgcgg tatccgatgt atgcaattca ctgtataaaa agaatgtatc aagaatatcc 160440
agatttgcta atttgataaa gatagatgac gatgacaaga ctcctactgg tgtatataat 160500
tattttaaac ctaaagatgc cattcctgtt attatatcca taggaaagga tagagatgtt 160560
tgtgaactat taatctcatc tgataaagcg tgtgcgtgta tagagttaaa ttcatataaa 160620
gtagccattc ttcccatgga tgtttccttt tttaccaaag gaaatgcatc attgattatt 160680
ctcctgtttg atttctctat cgatgcggca cctctcttaa gaagtgtaac cgataataat 160740
gttattatat ctagacacca gcgtctacat gacgagcttc cgagttccaa ttggttcaag 160800
ttttacataa gtataaagtc cgactattgt tctatattat atatggttgt tgatggatct 160860
gtgatgcatg caatagctga taatagaact tacgcaaata ttagcaaaaa tatattagac 160920
aatactacaa ttaacgatga gtgtagatgc tgttattttg aaccacagat taggattctt 160980
gatagagatg agatgctcaa tggatcatcg tgtgatatga acagacattg tattatgatg 161040
aatttacctg atgtaggcga atttggatct agtatgttgg ggaaatatga acctgacatg 161100
attaagattg ctctttcggt ggctggtagc tagcacgtgg actagtaaaa attaaaattt 161160 tattttttt ttttggaata taaataagat ctcgagctca agcttcgaat tctgcagtcg 161220
acggtaccgg tcgccaccat ggtgagcaag ggcgaggagc tgttcacagg ggtggtgccc 161280
atcctggtcg agctggacgg cgacgtaaac ggccacaagt tcagcgtgtc cggcgagggc 161340
gagggcgatg ccacctacgg caagctgacc ctgaagttca tctgcaccac cggcaagctg 161400
cccgtgccct ggcccaccct cgtgaccacc ctgacctacg gcgtgcagtg cttcagccgc 161460
taccccgacc acatgaagca gcacgacttc ttcaagtccg ccatgcccga aggctacgtc 161520
caggagcgca ccatcttctt caaggacgac ggcaactaca agacccgcgc cgaggtgaag 161580
ttcgagggcg acaccctggt gaaccgcatc gagctgaagg gcatcgactt caaggaggac 161640
ggcaacatcc tggggcacaa gctggagtac aactacaaca gccacaacgt ctatatcatg 161700
gccgacaagc agaagaacgg catcaaggcg aatttcaaga tccgccacaa catcgaggac 161760
ggcagcgtgc agctcgccga ccactaccag cagaacaccc ccatcggcga cggccccgtg 161820
ctgctgcccg acaaccacta cctgagcacc cagtccgccc tgagcaaaga ccccaacgag 161880
aagcgcgatc acatggtcct gctggagttc gtgaccgccg ccgggatcac tctcggcatg 161940
gacgagctgt acaagtaaag cggccgcttt ggaaagtttt ataggtagtt gatagaacaa 162000
aatacataat tttgtaaaaa taaatcactt ttttatactaa tatgacacga ttaccaatac 162060
ttttgttact aatatcatta gtatacgcta cacctttttcc tcagacatct aaaaaaatag 162120
gtgatgatgc aactttatca tgtaatcgaa ataatacaaa tgactacgtt gttatgagtg 162180
cttggtataa ggagcccaat tccattattc ttttagctgc taaaagcgac gtcttgtatt 162240
ttgataatta taccaaggat aaaatatctt acgactctcc atacgatgat ctagttacaa 162300
ctatcacaat taaatcattg actgctagag atgccggtac ttatgtatgt gcattcttta 162360
tgacatcgcc tacaaatgac actgataaag tagattatga agaatactcc acagagttga 162420
ttgtaaatac agatagtgaa tcgactatag acataatact atctggatct acacattcac 162480
cggaaactag ttctgagaaa cctgattata tagataattc taattgctcg tcggtattcg 162540
aaatcgcgac tccggaacca attactgata atgtagaaga tcatacagac accgtcacat 162600
acactagtga tagcattaat acagtaagtg catcatctgg agaatccaca acagacgaga 162660
ctccggaacc aattactgat aaagaagaag atcatacagt tacagacact gtctcataca 162720
ctacagtaag tacatcatct ggaattgtca ctactaaatc aaccaccgat gatgcggatc 162780
tttatgatac gtacaatgat aatgatacag taccatcaac tactgtaggc ggtagtacaa 162840
cctctattag caattataaa accaaggact ttgtagaaat atttggtatt accgcattaa 162900
ttatattgtc ggccgtggca atattctgta ttacatatta tatatataat aaacgttcac 162960
gtaaatacaa aacagagaac aaagtctaga tttttgactt acataaatgt ctgggatagt 163020
aaaatctatc atattgagcg ggccatctgg tttaggaaag acagccatag ccaaaagact 163080
atgggaatat atttggattt gtggtgtccc ataccactag atttcctcgt cctatggaac 163140
gagaaggtgt cgattaccat tacgttaaca gagaggccat ctggaaggga atagccgccg 163200
gaacatactg agtttttagg aaatatttac ggaacttcta aaactgctgt gaatacagcg 163260
gctattaata atcgtatttg tgtgatggat ctaaacatcg acggtgttag aagttttaaa 163320
aatacttacc taatgcctta ctcggtgtat ataagaccta cctctcttaa aatggttgag 163380
accaagcttc gttgtagaaa cactgaagcg gatgatgaga ttcatcgtcg tgtgatgttg 163440
gcaaaaactg acatggatga ggcaggtgaa gccggtctat tcgacactat tatcattgaa 163500

-continued gatgatgtga atttagcata tagtaagtta attcagatac tacaggaccg tattagaatg 163560
tattttaaca ctaattagag acttaagact taaaacttga taattaataa tataactcgt 163620
ttttatatgt ggctatttca acgtctaatg tattagttaa atattaaaac ttaccacgta 163680
aaacttaaaa tttaaaatga tatttcattg acagatagat cacacattat gaactttcaa 163740
ggacttgtgt taactgacaa ttgcaaaaat caatgggtcg ttggaccatt aataggaaaa 163800
ggtggatttg gtagtattta tactactaat gacaataatt atgtagtaaa aatagagccc 163860
aaagctaacg gatcattatt taccgaacag gcattttata ctagagtact taaaccatcc 163920
gttatcgaag aatggaaaaa atctcacaat ataaagcacg taggtcttat cacgtgcaag 163980
gcatttggtc tatacaaatc cattaatgtg gaatatcgat tcttggtaat taatagatta 164040
ggtgcagatc tagatgcggt gatcagagcc aataataata gattaccaaa aaggtcggtg 164100
atgttgatcg gaatcgaaat cttaaatacc atacaattta tgcacgagca aggatattct 164160
cacggagata ttaaagcgag taatatagtc ttggatcaaa tagataagaa taaattatat 164220
ctagtggatt acggattggt ttctaaattc atgtctaatg gcgaacatgt tccatttata 164280
agaaatccaa ataaaatgga taacggtact ctagaattta cacctataga ttcgcataaa 164340
ggatacgttg tatctagacg tggagatcta gaaacacttg gatattgtat gattagatgg 164400
ttgggaggta tcttgccatg gactaagata tctgaaacaa agaattgtgc attagtaagt 164460
gccacaaaac agaaatatgt taacaatact gcgactttgt taatgaccag tttgcaatat 164520
gcacctagag aattgctgca atatattacc atggtaaact ctttgacata ttttgaggaa 164580
cccaattacg acaagtttcg gcacatatta atgcagggtg tatattatta agtgtggtgt 164640
ttggttgatg taaaattttt gtcgataaaa attaaaaaat aacttaattt attattgatc 164700
tcgtgtgtac aaccgaaatc atggcgatgt tttacgcaca cgctctcggt gggtacgacg 164760
agaatcttca tgcctttcct ggaatatcat cgactgttgc caatgatgtc agtttataat 164820
aacaagtatg acattgtaaa agacaaatat atgtggtgtt acagtcaggt gaacaagaga 164880
tatattggag cactgctgcc tatgtttgag tgcaatgaat atctacaaat tggagatccg 164940
atccatgatc aagaaggaaa tcacatatcg ccacaaaaac tactatgctc taagcggaat 165000
cgggtacgag agtctagact tgtgtttgga aggagtaggg attcatcatc acgtacttga 165060
aacagaaaac gctgtatatg gaaaagttca acatgattat tctactatca aagagaaggc 165120
caaagaaatg aatgcactca gttcaggacc tatcatcgat taccacgtct ggataggaga 165180
ttgtatctgt caagttactg ctgtggacgt acatggaaag gaaattatga gaatgagatt 165240
caaaaagggt gcggtgcttc cgatcccaaa tctggtaaaa gttaaacttg gggagaatga 165300
tacagaaaat ctttcttcta ctatatcggc ggcaccatcg aggtaaccac ctctctggaa 165360
gacagtgtga atcatgtact catgaaacgt ttggaatcta tacgccatat gtggtctgtt 165420
gtatatgatc attttgatat tgtgaatggt aaagaatgct gttatgtgca tacgcatttg 165480
tctaatcaaa atcttatacc gagtactgta aaaacaaatt tgtacatgaa gactatggga 165540
tcatgcattc aaatgagtat cttagcgaac tgaaggaatc aggtggatgg agtcccagac 165600
cagaaatgca ggaatttgaa tatccagatg gagtggaaga cactgaatca attgagagat 165660
tggtagagga gttcttcaat agatcagaac ttcaggctgg taaatctatt aatgttaaac 165720
atacatctgt ttcagctaag caactaagaa cacgtatact ctcatctttt gccaacacag 165780
agggtggata tttgttcatt ggagttgata ataatacaca caaagtattt ggattcacgg 165840
tgggttacga ctacctcaga ctgatagaga atgatataga aaagcatatc aaaagacttt 165900
gtgttgtgta tttctgtgag aagaaagagg acatcaagta cacgtgtcga ttcatcaagg 165960
tatataaacc tggggatgag gctacctcga catacgtgtg cgctatcaaa gtggaaagat 166020
gctgttgtgc tgtgtttgca gattggccag aatcatggta tcaagaagta ttctccagat 166080
gaataggtgt cacatataaa attttaatta atgtaactat agagaacaaa taataggttg 166140
taatatcata tagacaataa ctaacaatta attagtaact gttatctctt tttaactaac 166200
taactatacc tattaataca tcgtaattat agttcttaac atctattaat cattgattcg 166260
cttctttaat tttttataaa ccaacattgt taattgaaaa gggataacat gttacagaat 166320
ataaattata tatggatttt ttttaaaaag gaaatacttg actggagtgt atatttatct 166380
cttcattata tagcacgcgt gttttccaat ttttccacat cccatataat acaggattat 166440
aatctcgttc gaacatacga gaaagtggat aaaacaatag ttgatttttt atctaggttg 166500
ccaaatttat tccatatttt agaatatggg gaaaatattc tacatattta ttctatggat 166560
gatgctaata cgaatattat aatttttttt ctagatagag tattaaatat taataagaac 166620
gggtcattta tacacaatct caggttatca tcatccatta atataaaaga atatgtatat 166680
caattagtta ataatgatca tccagataat aggataagac taatgcttga aaatggacgt 166740
agaacaagac atttttgtc ctatatatca gatacagtta atatctatat atgtatttta 166800
tatagatgcc gaagacagtt acggttgtac attattacat agatgtatat atcactataa 166860
gaaatcagaa tcagaatcag aatcatacaa tgaattaatt aagatattgt taaataatgg 166920
atcagatgta gataaaaaag atacgtacgg aaacacacct tttatcctat tatgtaaaca 166980
cgatatcaac aacgtggaat tgtttgagat atgtttagag aatgctaata tagactctgt 167040
agactttaat agatatacac ctcttcatta tgtctcatgt cgtaataaat atgattttgt 167100
aaagttatta atttctaaag gagcaaatgt taatgcgcgt aataaattcg gaactactcc 167160
attttattgt ggaattatac acggtatctc gcttataaaa ctatatttgg aatcagacac 167220
agagttagaa atagataatg aacatatagt tcgtcattta ataatttttg atgctgttga 167280
atctttagat tatctattat ccagaggagt tattgatatt aactatcgta ctatttacga 167340
cgctgtcagt tataatgcgt ataatacgtt ggtctatcta ttaaacagaa atggtgattt 167400
tgagacgatt actactagtg gatgtacatg tatttcggaa gcagtcgcaa acaacaacaa 167460
aataataatg gaagtactat tgtctaaacg accatctttg aaaattatga tacagtctat 167520
gatagcaatt actaaacata aacagcataa tgcagattta ttgaaaatgt gtataaaata 167580
tactgcgtgt atgaccgatt atgatactct tatagatgta caatcactac agcaatataa 167640
atggtatatt ttaagatgtt tcgatgaaat agatatcatg aagagatgtt atataaaaaa 167700
taaaactgta ttccaattag tttttgtat caaagacatt aatactttaa tgagatacgg 167760
taaacatcct tctttcgtga agtgcactag tctcgacgta tacggaagtc gtgtacgtaa 167820
tatcatagca tctattagat atcgtcagag attaattagt ctattatcca agaagctgga 167880
tcctggagat aaatggtcgt gttttcctaa cgaaataaaa tataacgata acgaactgtc 167940
cacatatcta aaaatcttat aaacactatt aaaatataaa atcacactac atcattgttt 168000
ccttttagtg ctcgacagtg tatactattt ttaacgctca taaataaaaa tgaaaacgat 168060
ttccgttgtt acgttgttat gcgtactacc tgctgttgtt tattcaacat gtactgtacc 168120
cactatgaat aacgctaaat taacgtctac cgaaacatcg tttaataata accagaaagt 168180
tacgtttaca tgtgatcagg gatatcattc ttcggatcca aatgctgtct gcgaaacaga 168240

-continued taaatggaaa tacgaaaatc catgcaaaaa aatgtgcaca gtttctgatt acatctctga 168300
actatataat aaaccgctat acgaagtgaa ttccaccatg acactaagtt gcaacggcga 168360
aacaaaatat tttcgttgcg aagaaaaaaa tggaaatact tcttggaatg atactgttac 168420
gtgtcctaat gcggaatgtc aacctcttca attagaacac ggatcgtgtc aaccagttaa 168480
agaaaaatac tcatttgggg aatatataac tatcaactgt gatgttggat atgaggttat 168540
tggtgcttcg tacataagtt gtacagctaa ttcttggaat gttattccat catgtcaaca 168600
aaaatgtgat ataccgtctc tatctaatgg attaatttcc ggatctacat tttctatcgg 168660
tggcgttata catcttagtt gtaaaagtgg ttttatacta acgggatctc catcatccac 168720
atgtatcgac ggtaaatgga atcccatact cccaacatgt gtacgatcta acgaaaaatt 168780
tgatccagtg gatgatggtc ccgacgatga gacagatttg agcaaactct cgaaagacgt 168840
tgtacaatat gaacaagaaa tagaatcgtt agaagcaact tatcatataa tcatagtggc 168900
gttaacaatt atgggcgtca tatttttaat ctccgttata gtattagttt gttcctgtga 168960
caaaaataat gaccaatata agttccataa attgctaccg tgaatataaa tccgttaaaa 169020
taatgaataa ttaataatta ataatttaat aacaaacaag tatcaaaaga ttaaagactt 169080
atagctagaa tcaattgaga tgtcttcttc agtggatgtt gatatctacg atgccgttag 169140
agcattttta ctcaggcact attataacaa gagatttatt gtgtatggaa gaagtaacgc 169200
catattacat aatatataca ggctatttac aagatgcgcc gttataccgt tcgatgatat 169260
agtacgtact atgccaaatg aatcacgtgt taaacaatgg gtgatggata cacttaatgg 169320
tataatgatg aatgaacgcg atgtttctgt aagcgttggc accggaatac tattcatgga 169380
aatgtttttc gattacaata aaaatagtat caacaatcaa ctaatgtatg atataattaa 169440
tagcgtatct ataattctag ctaatgagag atatagaagc gcttttaacg acgatggtat 169500
atacatccgt agaaatatga ttaacaagtt gtacggatac gcatctctaa ctactattgg 169560
cacgatcgct ggaggtgttt gttattatct gttgatgcat ctagttagtt tgtataaata 169620
attatttcaa tatactagtt aaaattttaa gattttaaat gtataaaaaa ctaataacgt 169680
ttttatttgt aataggtgca ttagcatcct attcgaataa tgagtacact ccgtttaata 169740
aactgagtgt aaaactctat atagatggag tagataatat agaaaattca tatactgatg 169800
ataataatga attggtgtta aattttaaag agtacacaat ttctattatt acagagtcat 169860
gcgacgtcgg atttgattcc atagatatag atgttataaa cgactataaa attattgata 169920
tgtctactat tcaacgcaga ggtcacacgt gtagaatatc taccaaatta tcatgccatt 169980
atgataagta cccttatatt cacaaatatg atggtgatga gcgacaatat tctattactg 170040
cagagggaaa atgctataaa ggaataaaat atgaaataag tatgatcaac gatgatactc 170100
tattgagaaa acatactctt aaaattggat ctacttatat atttgatcgt catggacata 170160
gtaatacata ttattcaaaa tatgattttt aaaaatttaa aatatattat cacttcagtg 170220
acagtagtca aataacaaac aacaccatga gatatattat aattctcgca gttttgttca 170280
ttaatagtat acacgctaaa ataactagtt ataagtttga atccgtcaat tttgattcca 170340
aaattgaatg gactggggat ggtctataca atatatccct taaaaattat ggcatcaaga 170400
cgtggcaaac aatgtataca aatgtaccag aaggaacata cgacatatcc gcatttccaa 170460
agaatgattt cgtatctttc tgggttaaat ttgaacaagg cgattataaa gtggaagagt 170520
attgtacggg accaccgact gtaacattaa ctgaatacga cgaccatccg tatgctacta 170580
gaggtagcaa aaagattcct atttacaaac gcggtgacat gtgtgatatc tacttgttgt 170640
atacggctaa cttcacattc ggagattcta aagaaccagt accatatgat atcgatgact 170700
acgattgcac gtctacaggt tgcagcatag actttgtcac aacagaaaaa gtgtgcgtga 170760
cagcacaggg agccacagaa gggtttctcg aaaaaattac tccatggagt tcgaaagtat 170820
gtctgacacc taaaaagagt gtatatacat gcgcaattag atccaaagaa gatgttccca 170880
atttcaagga caaaatggcc agagttatca agagaaaatt taactaaatt tctcggtagc 170940
acatcaaatg atgttaccac ttttcttagc atgcttaact tgactaaata ttcataacta 171000
atttttatta atgatacaaa aacgaaataa aactgcatat tatacactgg ttaacgccct 171060
tataggctct aaccatttc aagatgaggt ccctgattat agtccttctg ttcccctcta 171120
tcatctactc catgtctatt agacgatgtg agaagactga agaggaaaca tggggattga 171180
aaatagggtt gtgtataatt gccaaagatt tctatcccga aagaactgat tgcagtgttc 171240
atctcccaac tgcaagtgaa ggcaatggat tcagggatat acgaaacacc gataaattat 171300
aaaaaaagca atgtgtccgc tgtttccgtt aataatacta ttttcgtaac tggcggatta 171360
ttcataaata actctaatag cacgatcgtg gttaacaata tggaaaaact tgacatttat 171420
aaagacaaac aatggtcgat tatagaaatg cctatggcta gggtatatca cggcatcgac 171480
tcgacatttg gaatgttata ttttgccgga ggtctatccg ttaccgaaca atatggtaat 171540
ttagagaaaa acaacgagat atcttgttac aatcctagaa cgaataagtg gtttgatatt 171600
tcatatacta tttataagat atccatatca tcattgtgta aactaaataa cgtcttctat 171660
gtatttagta aggacattgg atatgtggaa aagtatgatg gtctccccgc tataaaggca 171720
ttatcaactt ctccttattg attgaaaatg aaaatataaa tagtttttat gtatagcagt 171780
attaccctat agttttattg cttactacta acatggatac agatacagat gttacaaatg 171840
tagaagatat catgaatgaa atagatagag agaaagaaga aatactaaaa aatgtagaaa 171900
ttgaaaataa taaaaacatt aacaagaatc atcccaatga atatattaga gaagcactcg 171960
ttattaatac aagtagtaat agtgattcca ttgataaaga agttatagaa tgtatcagtc 172020
acgatgtagg aatatagatc atatctacta atttttataa tcaatacaaa acataaaaaa 172080
caactcgtta ttacatagca ggcatggaat ccttcaagta ttgttttgat aacgatggca 172140
agaaatggat tatcggaaat actttatatt ctggtaattc aatactctat aaggtcagaa 172200
aaaatttcac tagttcgttc tacaattacg taatgaagat agatcacaaa tcacacaagc 172260
cattgttgtc tgaaatacga ttctatatat ctgtattgga tcctttgact atcgacaact 172320
ggacacggga acgtggtata aagtatttgg ctattccaga tctgtatgga attggagaaa 172380
ccgatgatta tatgttcttc gttataaaga atttgggaag agtattcgcc ccaaaggata 172440
ctgaatcagt cttcgaagca tgcgtcacta tgataaacac gttagagttt atacactctc 172500
gaggatttac ccatggaaaa atagaaccga ggaatatact gattagaaat aaacgtcttt 172560
cactaattga ctattctaga actaacaaac tatacaagag tggaaactca catatagatt 172620
acaacgagga catgataact tcaggaaata tcaattatat gtgtgtagac aatcatcttg 172680
gagcaacagt ttcaaaacga ggagatttag aaatgttggg atattgcatg atagaatggt 172740
tcggtggcaa acttccatgg aaaaacgaaa gtagtataaa agtaataaaa caaaaaaaag 172800
aatataaaaa atttatagct actttctttg aggactgttt tcctgaagga aatgaacctc 172860
tggaattagt tagatatata gaattagtat acacgttaga ttattctcaa actcctaatt 172920
atgacagact acgtagactg tttatacaag attgaaatat tcttttttta tagagtgtgg 172980
tagtgttacg gatatctaat attaatatta gactatctct atcgcgctac acgaccaata 173040
tcgattacta tggatatctt ctatgaaagg agagaatgta ttcatttctc cagcgtcaat 173100
ctcgtcagta ttgacaatac tgtattatgg agctaatgga tccactgctg aacagctatc 173160
aaaatatgta gaaaaggagg agaacacgga taaggttagc gctcagaata tctcattcaa 173220
atccatgaat aaagtatatg ggcgatattc tgccgtgttt aaagattcct ttttgagaaa 173280
aattggcgat aagtttcaaa ctgttgactt cactgattgt cgcactatag atgcaatcaa 173340
caagtgtgta gatatcttta ctgaggggaa aatcaatcca ctattggatg aacaattgtc 173400
tcctagcaat tagtgccgta tactttaaag caaaatggtt gacgccattc gaaaaggaat 173460
ttaccagtga ttatcccttt tacgtatcac caacggaaat ggtagacgta agtatgatgt 173520
ctatgtacgg cgagctattt aatcacgcat ctgtaaaaga atcattcggt aacttttcaa 173580
tcatagaact gccatatgtt ggagatacta gtatgatggt cattcttcca gacaagattg 173640
atggattaga atccatagaa caaaatctaa cagatacaaa ttttaagaaa tggtgtaact 173700
ctctggaagc tacgtttatc gatgttcaca ttcccaagtt taaggtaaca ggctcgtata 173760
atctggtgga tactctagta aagtcaggac tgacagaggt gttcggttca actggagatt 173820
atagcaatat gtgtaattta gatgtgagtg tcgacgctat gatccacaaa acgtatatag 173880
atgtcaatga agagtataca gaagcagctg cagcaacttg tgcactggtg tcagactgtg 173940
catcaacaat tacaaatgag ttctgtgtag atcatccgtt catctatgtg attaggcatg 174000
ttgatggaaa aatttttttc gttggtagat attgctctcc gacaactaat tgttaaccat 174060
tttttttaaa aaaatagaaa aaacatgtgg tattagtgca ggtcgttatt cttccaattg 174120
caattggtaa gatgacggcc aactttagta cccacgtctt ttcaccacag cactgtggat 174180
gtgacagact gaccagtatt gatgacgtca aacaatgttt gactgaatat atttattggt 174240
cgtcctatgc ataccgcaac aggcaatgcg ctggacaatt gtattccaca ctcctctctt 174300
ttagagatga tgcggaatta gtgttcatcg acattcgcga gctggtaaaa aatatgccgt 174360
gggatgatgt caaagattgt gtagaaatca tccgttgtta tataccggat gagcaaaaaa 174420
ccatcatcgg actttgtgca tatgctgcta cttactgggg aggtgaagac catcccacta 174480
gtaacagtct gaacgcattg tttgtgatgc ttgagatgct aaattacgtg gattataaca 174540
tcatattccg gcgtatgaat tgatgagttg tacatcttga cattttcttc tttcttctct 174600
tctccctttc ccagaaacaa actttttta cccactataa aataaaatga gtatactacc 174660
tgttatattt ctttctatat ttttttattc ttcattcgtt cagactttta acgcgcctga 174720
atgtatcgac aaagggcaat attttgcatc attcatggag ttagaaaacg agccagtaat 174780
cttaccatgt cctcaaataa atacgctatc atccggatat aatatattag atattttatg 174840
ggaaaaacga ggagcggata atgatagaat tataccgata gataatggta gcaatatgct 174900
aattctgaac ccgacacaat cagactctgg tatttatata tgcattacca cgaacgaaac 174960
ctactgtgac atgatgtcgt taaatttgac aatcgtgtct gtctcagaat caaatataga 175020
tcttatctcg tatccacaaa tagtaaatga gagatctact ggcgaaatgg tatgtcccaa 175080
tattaatgca tttattgcta gtaacgtaaa cgcagatatt atatggagcg ggcatcgacg 175140
ccttagaaat aagagactta aacaacggac acctggaatt attaccatag aagatgttag 175200
aaaaaatgat gctggttatt atacatgtgt tttagaatat atatacggtg gcaaaacata 175260
taacgtaacc agaattgtaa aattagaggt acgggataaa ataataccct ctactatgca 175320
attaccagaa ggtgttgtaa cttcaatagg tagtaatttg actattgcgt gtagagtatc 175380
gttgagacct cccacaacgg atgcagacgt cttttggata agtaatggta tgtattacga 175440
agaagatgat ggggacggag acggtagaat aagtgtagca aataaaatct atatgaccga 175500
taagagacgt gttattacat cccggttaaa cattaatcct gtcaaggaag aagatgctac 175560
aacgtttacg tgtatggcgt ttactattcc tagcatcagc aaaacagtta ctgttagtat 175620
aacgtgaatg tatgttgtta catttccatg tcaattgagt ttataagaat ttttatacat 175680
tatcttccaa caaacaattg acgaacgtat tgctatgatt aactcccacg atactatgca 175740
tattattaat cattaacttg cagactatac ctagtgctat tttgacatac tcatgttctt 175800
gtgtaattgc ggtatctata ttattaaagt acgtaaatct agctatagtt ttattattta 175860
attttagata atataccgtc tccttatttt taaaaattgc cacatccttt attaaatcat 175920
gaatgggaat ttctatgtca tcgttaatat attgtgaaca acaagagcag atatctatag 175980
gaaagggtgg aatgcgatac attgatctat gtagttttaa aacacacgcg aactttgaag 176040
aatttatata aatcattcca tcgatacatc cttctatgtt gacatgtata tatccaggaa 176100
ttcttttatt aatgtcagga aatgtataaa ctaaaacatt gcccgaaagc ggtgcctcta 176160
tctgcgttat atccgttctt aacttacaaa atgtaaccaa tacctttgca tgacttgttt 176220
tgttcggcaa cgttagttta aacttgacga atggattaat tacaatagca tgatccgcgc 176280
atctattaag ttttttttact ttaacgccct tgtatgtttt tacagagact ttatctaaat 176340
ttctagtgct tgtatgtgtt ataaatataa cgggatatag aactgaatca cctaccttag 176400
atacccaatt acattttatc agatccagat aataaacaaa ttttgtcgcc ctaactaatt 176460
ctatattgtt atatatttta caattggtta tgatatcatg taataacttg gagtctaacg 176520
cgcatcgtcg tacgtttata caattgtgat ttagtgtagt atatctacac atgtattttt 176580
ccgcactata gtattctgga ctagtgataa aactatcgtt atatctgtct tcaatgaact 176640
catcgagata ttgctctctg tcatattcat acacctgcat aaactttcta gacatcttac 176700
aatccgtgtt attttaggat catatttaca tatttacggg tatatcaaag atgttagatt 176760
agttaatggg aatcgtctat aataatgaat attaaacaat tatatgagga cttttaccac 176820
aaagcatcat aaaaatgagt cgtcgtctga tttatgtttt aaatatcaac cgcgaatcaa 176880
ctcataaaat acaagagaat gaaatatata catattttag tcattgcaat atagaccata 176940
cttctacaga acttgatttt gtagttaaaa actatgatct aaacagacga caacctgtaa 177000
ctgggtatac tgcactacac tgctatttgt ataataatta ctttacaaac gatgtactga 177060
agatattatt aaatcatgga gtggatgtaa cgatgaaaac cagtagcgga cgtatgcctg 177120
tttatatatt gcttactaga tgttgtaata tttcacatga tgtagtgata gatatgatag 177180
acaaagataa aaaccactta tcgcatagag actattccaa cctactacta gagtatataa 177240
aatctcgtta catgttattg aaggaagagg atatcgatga gaacatagta tccactttat 177300
tagataaggg aatcgatcct aactttaaac aagacggata tacagcgtta cattattatt 177360
atttgtgtct cgcacacgtt tataaaccag gtgagtgtag aaaaccgata acgataaaaa 177420
aggccaagcg aattatttct ttgtttatac aacatggagc taatctaaac gcgttagata 177480
attgtggtaa tacaccattc catttgtatc ttagtattga aatgtgtaat aatattcata 177540
tgactaaaat gctgttgact tttaatccga atttcaaaat atgtaataat catggattaa 177600
cgcctatact atgttatata acttccgact acatacaaca cgatattctt gttatgttaa 177660
tacatcacta tgaaacaaat gttggagaaa tgccgataga tgagcgtcgt ataatcgtat 177720
tcgagtttat caaaacatat tctacacgtc cggcagattc gataacttat ttgatgaata 177780
ggtttaaaaa tatagatatt tatacccgct atgaaggaaa gacattatta cacgtagcat 177840
gtgaatataa taatacacac gtaatagatt atcttatacg tatcaacgga gatataaatg 177900
cgttaaccga caataacaaa cacgctacac aactcattat agataacaaa gaaaattccc 177960
catataccat taattgttta ctgtatatac ttagatatat tgtagataag aatgtgataa 178020
gatcgttggt ggatcaactt ccatctctac ctatcttcga tataaaatca tttgagaaat 178080
tcatatccta ctgtatactt ttagatgaca cattttacaa tagacacgtt aggaatcgca 178140
attctaaaac gtatcgatac gcattttcaa aatacatgtc gtttgataaa tacgatggta 178200
taataactaa atgtcataaa gaaacaatat tgctcaaact atccactgtt ctagacacta 178260
cactatatgc agttttaaga tgccataatt cgaaaaagtt aagaagatac ctcaacgagt 178320
taaaaaaata taataacgat aagtccttta aaatatattc taatattatg aatgagagat 178380
accttaatgt atattataaa gatatgtacg tgtcaaaggt atatgataaa ctatttcctg 178440
ttttcacaga taaaaattgt ctactaacat tactaccttc agaaattata tacgaaatat 178500
tatacatgct gacaattaac gatctttata atatatcgta tccacctacc aaagtatagt 178560
tgtatttttc tcatgcgatg tgtgtaaaaa aactgatatt atataaatat tttagtgccg 178620
tataatgaag atgacgatga aaatgatggt acatatatat ttcgtatcat tattgttatt 178680
gctattccac agttacgcca tagacatcga aaatgaaatc acagaattct tcaataaaat 178740
gagagatact ctaccagcta aagactctaa atggttgaat ccagcatgta tgttcggagg 178800
cacaatgaat gatatagccg ctctaggaga gccattcagc gcaaagtgtc ctcctattga 178860
agacagtctt ttatcgcaca gatataaaga ctatgtggtt aaatgggaga ggctagaaaa 178920
aaatagacgg cgacaggttt ctaataaacg tgttaaacat ggtgatttat ggatagccaa 178980
ctatacatct aaattcagta accgtaggta tttgtgtacc gtaactacaa agaatggtga 179040
ctgtgttcag ggtatagtta gatctcatat taaaaaacct ccttcatgca ttccaaaaac 179100
atatgaacta ggtactcatg ataagtatgg catagactta tactgtggaa ttctttacgc 179160
aaaacattat aataatataa cttggtataa agataataag gaaattaata tcgacgatat 179220
taagtattca caaacgggaa agaaattaat tattcataat ccagagttag aagatagtgg 179280
aagatacaac tgttacgttc attacgacga cgttagaatc aagatgtaaa atacttacgg 179340
ttataccgtc gcaagaccac aggtttaaac taatactaga tccaaaaatc aacgtaacga 179400
taggagaacc tgccaatata acatgcactg ctgtgtcaac gtcattattg attgacgatg 179460
tactgattga atgggaaaat ccatccggat ggcttatagg attcgatttt gatgtatact 179520
ctgttttaac tagtagaggc ggtatcaccg aggcgacctt gtactttgaa aatgttactg 179580
aagaatatat aggtaataca tataaatgtc gtggacacaa ctattatttt gaaaaaaccc 179640
ttacaactac agtagtattg gagtaaatac acaatgcatt tttatataca ttactgaata 179700
attattatta ttatttatat cgtatttgtg ctataacgcg actatctagg tatttgtatc 179760
tcaccgatag agaacatata aatgtagact ctattaaaca gttgtgtaaa atatcagatc 179820
ctaatagatg tggatgtacg gctttagaaa tgagttcatt aaaatatgtg atatcaacgg 179880
aacatattta tataattata ctattgctgt tagtataatt attgattcca cggaagaact 179940
accaacagtt actccaatta caacaacata taattatact atcgatgata gcactactga 180000
agaactacaa gtgactcctc atatggatct ccatcgatga tacatgtatt aaaatacttt 180060
ccgaataagt cttttaaata ttgtattaat tatgaaaaac tatgctatgc gagtatgata 180120
cgatactaga ttttatctct agcgagagat gtcgttagaa tcatttatca acgaatatcg 180180
ataacatgtg tcatttatac gttaaagtct gtccgtcttc tctattgttt agactgtttg 180240
tagaatgctg tgatataaac aaactagtag acacaaatat ttaactcatg atgaagttga 180300
gaatgatatg ctttagctaa tataaaaata tattaatcca ctatatattc tagacttgat 180360
ttaaaaccga taaactacta ctacgtactg tataagttag gagcagaccc taattatgta 180420
gatgatagag gtaatacttc tgcatctata tgtccactta tgagaaaacg tcatttaata 180480
agatgcatcg tgaaaagaaa tttattaaag agttggtaaa atatgaaacc gaaagtaaat 180540
aatataggaa atacacctct acataactac gtatctcaat atgatatcac tctcattcct 180600
catccacaac ccattaaaaa atggaaatta aagccctcta ttagcataaa cggctacagg 180660
tctaccttta caatggcctt tccttgtgcc cagttcagac cctgtcattg ccacgctact 180720
aaggactccc tgaataccgt ggccgacgtc agacattgtc tgactgaata catcctgtgg 180780
gtttctcata gatggaccca tagagaaagc gcagggtctc tctacaggct tctcatctct 180840
ttcagaactg atgcaacgga gctctttggt ggtgagttga aggattcact tccgtggaga 180900
tcattaaatg actccatgaa aaccgccgaa gaacttcgtg caatcattgg actttgtact 180960
caatcagcta tcgtctctgg aagagtcttc aacgataagt atatcgacat actacttatg 181020
ctgcgaaaga ttctgaacga gaacgactat ctcaccctct tggatcatat ccgcactgct 181080
aaatactaaa tctccttcat gctctctcac tacacttttt atcatcttat gaggaataat 181140
tagcaccaga atagctatgg attgcacatg tattctatgt cgtctactgg atgaagatgt 181200
gacgtacaaa aaaataaaac tagaaattga aacgtgtcac aacttatcaa aacatataga 181260
tagacgagga aacaatgcgc tacattgtta cgtctccaat aaatgcgata cagacattaa 181320
gattgttcga ctgttactct ctcgcggagt cgagagactt tgtagaaaca acgaaggatt 181380
aactccgcta ggagcataca gtaagcatag atacgtaaaa tctcagattg tgcatctact 181440
gatatccagc tattcgaatt cctctaacga actcaagtcg aatataaatg atttcgactt 181500
acgtctgcta aaatacctaa ttgtggataa acggatacgt ccgtccaaga atacgaatta 181560
tgcaatcaat ggtctcggat tggtggatat atacgtaacg acgcctaatc cgagaccaga 181620
agtattgcta tggcttctta aatcagaatg ttacagcacc ggttacgtat ttcgtacctg 181680
tatgtacaac agtgatatgt gtaagaactc tcttcattac tatatatcgt ctcatagaga 181740
atctctatcc aaggatgtaa ttaaatgttt gatcgataac aatgtttcca tccaatacta 181800
ctggtcttgc tcaaccatag atatagagat tattaataaa ggatgtggac acgtgtagag 181860
tatacgacgt cagccctata ttagaggcgt attatctaaa caagcgattt agagtaaccc 181920
catataatgt agacatggaa atcgttaatc ttcttattga gagacgtcat actcttgtcg 181980
acgtaatgcg tagtattact tcgtacgatt ccagagaata taaccactac atcatcgata 182040
acattctaaa gagatttaga caacaggatg aatccatcgt acaagccata ctgataaact 182100
acttacatta cggcgatatg gtaagtatac ctatcattca atgcatgttg gataagacga 182160
cggacaacaa ctttgttaat aataatctcg tcgatgtaaa cgtcgtaagg tttatcgtgg 182220
aaaatatgga cacgcggctg taaatcacat atctaacaat ggccgtctat gtatgtacgg 182280
tctgatatta tcgagattta ataattgcgg gtatcactgt tatgaagatg tatttgatat 182340
actaagcaag tacatggatg atatagatat gatcgataac tctactatat tacgcggtcg 182400
atgtcaataa tatacaattt gcaaagcggt tattggaata tggagcgagt gtcacgctcg 182460

-continued

```
ataatcaata cggccatcca gaaaagcagt taccaaagag aagctagttg atttattact 182520
gagttaccat cccactctag agactatgat tgacgcattt aatagagata tacgctatct 182580
atatcctgaa ccattattcg cctgtatcag atacgcctta atcctagatg atgattttcc 182640
ttctaaagta agtatgatat cgccggtcgt cataaggaac taaagcgcta tagagcagac 182700
attaatagaa tgaagaatgc ctacatatca ggcgtctcca tgtttgatat attatttaaa 182760
cgaagcaaac gccacagatt gagatacgca aagaacaatg agaggatcga ctccattaaa 182820
taatttatca tggagtgata atgtcctgtt tccatggcat attacaaaat cgattccgtc 182880
caagatgata aaaacattta ccggcatcat aaacacggag tttattttat atgtctcgca 182940
taaacattac taaaaaaata tattgttcgg ttttctttca catctttaat tatgaaaaag 183000
taaatcatta tgagatggac gcatcgttcg cgacagtatg tggtacatac ctaacgtatt 183060
tatggacgac ggtaagaatg aaggtcacgt ttctgtcaac aatgtcgacg cgatcgtgta 183120
acacgactca caatagaatc tgtgaatgct ctcccgatca tggatgcaag gcatgtgttt 183180
cccaaacaaa atgtggaata ggatacggag tatccggaga cgtcatctgt tctccgtgtg 183240
gtctcggaac atattctcac accgtctctt ccgcagataa atgcgaaccc gtacccagaa 183300
atacctttaa ctatatcgat gtggaaatta acctgtatcc agttaacgac acatcgtgta 183360
ctcggacgac cactaccggt ctcagcgaat ccatctcaac gtcggaacta actattacta 183420
tgaatcataa agactgcgat cccgtcttct taataaggta gcgacttcag gtttctttac 183480
aggagaaagg tgtgcactct gaatttcgag attaaatgca ataacaaaga ttcttcctcc 183540
aaacagttaa cgaaagcaaa gaatgatact atcatgccgc attcggagac agtaactcta 183600
gcgtcgacat ctatatacta tatagtaata ccaatactca agactacgaa actgatacaa 183660
tctcttatca tgtgggtaat gtagccatat gcccggtagt tgcgatatac ataaactgat 183720
cactaattcc aaacccaccc gctttttata gtaagttttt cacccataaa tacaataatt 183780
aatttctcgt aaaagtagaa aatatattct aatttattgc acggtaagga agtagaatca 183840
taaagaacag tactcaatca atagcaatca tgaaacaata tatcgtactg gcatgcatgt 183900
gcctgccagt cttcagcaat catcctcatc gtgtacggaa gaagaaaaca aacatcatat 183960
gggaatcgat gttattatca aagtcacaaa gcaagaccaa acaccgaccg atgataagat 184020
ttgccaatcc gtaacggaaa ttacagagtc cgagtcagat ccagatcccg aggtggaatc 184080
agtcgaggat gtagatcctc ctaccactta ttactccatc atcggtggag gtctgagaat 184140
gaactttgga ttcaccaaat gtcctcagat taaatccatc tcagaatccg ctgatggaaa 184200
gactgtgagg tgtctatcga catcagatgt agcgaagaag agaaagacag cgacatcaag 184260
acccatccag tactcgggtc taacatctct cataagaaag tgagttacga agatatcatc 184320
ggttcaacga tcgtcgatac aaaatgtgtc aagaatctag agtttagcgt tcgtatcgga 184380
gacatgtgca aggaatcatc tgaacttgag gtcaagtatg tcgacggatc ggcatctgaa 184440
ggtgcaaccg atgatacttc actcatcgat tcaacaaaac tcaaagcgtg tgtctgaatc 184500
gataactcta ttcatctgaa attggatgag tagggttaat cgaacgattc aggcacacca 184560
cgaattaaaa aagtgtaccg gacactatat tccggtttgc aaaacaaaaa gttacctctc 184620
gcgacttctt ctttttctgt ctcaatagtg tgatacgatt atgacactat tcctatttcc 184680
tttcagggta tcacaaaaat attaaacctc tttctgatgg tctcatacaa aaatattttt 184740
attctctttc tctctttgat ggtctcataa aaaatatttt tattctcttt ctctctttga 184800
tggtctcata aaatattttt attctctttc tctctttgat ggtctcataa aaaatatttt 184860
```

tattctcttt ctctctttga tggtctcata aaatattttt attctctttc tctctttgat 184920
ggtctcataa aaaatatttt tattctcttt ctctctttga tggtctcata aaaaatatta 184980
aacctctttc tgatggtgtc actaaaatat ttttattctc tttctctctt caatggagtc 185040
ataaaatatt tttattctct ttctctcttc gatggtctca caaaaatatt aaacctcttt 185100
ctgatggtgt cactaaaata tttttattct ctttctctct tcaatggagt cataaaatat 185160
ttttattctc tttctctctt tgatggtctc acaaaaatat ttttattctc tttctctctt 185220
tgatggtctc acaaaaatat ttttattctc tttctctctt tgatggtctc acaaaaatat 185280
ttttattctc tttctctctt tgatggtctc ataaaaaaag ttttacaaaa atatttttat 185340
tctctttctc tctttgatgg tctcataaaa aaagttttac aaaaatattt ttattctctt 185400
tctctctttg atggtctcat aaaaaaagtt ttacaaaaat atttttattc tctttctctc 185460
tttgatggtc tcataaaaaa tattaaacct ctttctgatg gtgtcactaa aatattttta 185520
ttctcattct ctcttcaatg gagtcataaa atatttttat tctctttctc tcttcgatgg 185580
tctcacaaaa atattaaacc tctttctgat ggtgtcacta aaatattttt attctcattc 185640
tctcttcaat ggagtcataa aatattttta ttctctttct ctcttcgatg gtctcacaaa 185700
aatattaaac ctctttctga tggtgtcact aaaatatttt tattctcatt ctctcttcaa 185760
tggagtcata aaatattttt attctctttc tctctttgat ggtctcataa aaaaagtttt 185820
acaaaaatat ttttattctc tttctctctt tgatggtctc ataaaaaata ttaaacctct 185880
ttctgatggt gtcactaaaa tatttttatt ctctttctct cttcaatgga gtcataaaat 185940
atttttattc tctttctctc ttcgatggtc tcacaaaaat attaaacctc tttctgatgg 186000
tgtcactaaa atatttttat tctcattctc tcttcaatgg agtcataaaa tatttttatt 186060
ctctttctct ctttgatggt ctcataaaaa aagttttaca aaaatatttt tattctcttt 186120
ctctctttga tggtctcata aaaaaagttt tacaaaaata tttttattct ctttctctct 186180
ttgatggtct cataaaaaaa gttttacaaa aatattttta ttctctttct ctctttgatg 186240
gtctcataaa aaaagtttta caaaaatatt tttattctct ttctctcttt gatggtctca 186300
taaaaaatat taaacctctt tctgatggtg tcactaaaat atttttattc tcattctctc 186360
ttcaatggag tcataaaata tttttattct ctttctctct tcgatggtct cacaaaaata 186420
ttaaacctct ttctgatggt gtcactaaaa tatttttatt ctcattctct cttcaatgga 186480
gtcataaaat atttttattc tctttctctc tttgatggtc tcataaaaaa agttttacaa 186540
aaatattttt attctctttc tctctttgat ggtctcataa aaaaagtttt acaaaaatat 186600
ttttattctc tttctctctt tgatggtctc ataaaaaaag ttttacaaaa atatttttat 186660
tctctttctc tctttgatgg tctcataaaa aaagttttac aaaaatattt ttattctctt 186720
tctctctttg atggtctcac aaaaatatta aacctctttc tgatggagtc gtaaaaaagt 186780
tttatctctt tctccttcga tggtctcaca aaaatattaa acctctttct gatggagtcg 186840
taaaaaagtt ttatctcttt ctctcttcga tggtctcaca aaaatattaa acctctttct 186900
gatggagtcg taaaaaagtt ttatctcttt ctctcttcga tggtctcact aaaatatttt 186960
ttattctctt tctgatgcat caactatttc ttaaacaata acgtccaaca acatatactc 187020
gtcgagctta tcaacatccc ctatgcccat ctaggttacc agacaattgt atatcataaa 187080
ataatgttta taatttttac aaaaatattt ttattctctt tctctctttg atggtctcat 187140
aaaaaaagtt ttacaaaaat atttttattc tctttctctc tttgatggtc tcataaaaaa 187200
tattaaacct ctttctgatg gtgtcactaa aatattttta ttctcattct ctcttcaatg 187260
gagtcataaa atatttttat tctctttctc tcttcgatgg tctcacaaaa atattaaacc 187320
tctttctgat ggtgtcacta aaatattttt attctcattc tctcttcaat ggagtcataa 187380
aatattttta ttctctttct ctctttgatg gtctcataaa aaaagtttta caaaaatatt 187440
tttattctct ttctctcttt gatggtctca taaaaaaagt tttacaaaaa tatttttatt 187500
ctctttctct ctttgatggt ctcataaaaa aagttttaca aaaatatttt tattctcttt 187560
ctctctttga tggtctcata aaaaaagttt tacaaaaata tttttattct ctttctctct 187620
ttgatggtct cataaaaaaa gttttacaaa aatattttta ttctctttct ctctttgatg 187680
gtctcataaa aaaagtttta caaaaatatt tttattctct ttctctcttt gatggtctca 187740
taaaaaaagt tttacaaaaa tatttttatt ctctttctct ctttgatggt ctcataaaaa 187800
atattaaacc tctttctgat ggtgtcacta aaatattttt attctctttc tctcttcaat 187860
ggagtcataa aatattttta ttctctttct ctcttcgatg gtctcacaaa aatattaaac 187920
ctctttctga tggtgtcact aaaatatttt tattctcatt ctctcttcaa tggagtcata 187980
aaatattttt attctctttc tctctttgat ggtctcataa aaaaagtttt acaaaaatat 188040
ttttattctc tttctctctt tgatggtctc ataaaaaaag ttttacaaaa atatttttat 188100
tctctttctc tctttgatgg tctcataaaa aaagttttac aaaaatattt ttattctctt 188160
tctctctttg atggtctcat aaaaaaagtt ttacaaaaat atttttattc tctttctctc 188220
tttgatggtc tcataaaaaa agttttacaa aaatattttt attctctttc tctctttgat 188280
ggtctcataa aaaatattaa acctctttct gatggtgtca ctaaaatatt tttattctct 188340
ttctctcttc aatggagtca taaaatattt ttattctctt tctctcttcg atggtctcac 188400
aaaaatatta aacctctttc tgatggtgtc actaaaatat ttttattctc tttctctctt 188460
caatggagtc ataaaatatt tttattctct ttctctcttt gatggtctca taaaaaaagt 188520
tttacaaaaa tatttttatt ctctttctct ctttgatggt ctcataaaaa aagttttaca 188580
aaaatatttt tattctcttt ctctctttga tggtctcata aaaaaagttt tacaaaaata 188640
tttttattct ctttctctct ttgatggtct cataaaaaaa gttttacaaa aatattttta 188700
ttctctttct ctctttgatg gtctcataaa aaaagtttta caaaaatatt tttattctct 188760
ttctctcttt gatggtctca taaaaaaagt tttacaaaaa tatttttatt ctctttctct 188820
ctttgatggt ctcataaaaa aagttttaca aaaatatttt tattctcttt ctctctttga 188880
tggtctcata aaaaatatta aacctctttc tgatggtgtc actaaaatat ttttattctc 188940
attttctctt tctctcttca atggagtcat aaaatatttt tattctcttt ctctctttga 189000
tggtctcata aaaaatatta aacctctttc tgatggtgtc actaaaatat ttttattctc 189060
attctctctt caatggagtc ataaaaaagt tttatctctt tctctcttcg atggtctcac 189120
aaaaatatta aacctctttc tgatggagtc gtaaaaaagt tttatctctt tctctcttcg 189180
atggtctcac aaaaatatta aacctctttc tgatgcatca actatttctt aaacaataac 189240
gtccaacaac atatactcat cccctatgcc catctaggtt accagacaat tgtatatcat 189300
aaaataatgt ttataattta cacgttaaaa tcatataata aaacgtagat cgtataatat 189360
tttttggtat ataaatgatc tagtaaaatc catgtagggg atactgctca cattttttct 189420
ttggtacaaa atttcacaca agtttttata cagacaaatt cttgtccata tattttaaaa 189480
cattgacttt tgtactaaga aaaatatcta gactaactat ctctttctct ttctctcttc 189540
gatggtcttt ctgatggagt cgtaaaaaag ttttatctct ttctctcttc gatggtctca 189600

-continued

```
caaaaatatt aaacctcttt ctgatggagt cgtaaaaaag ttttatctct ttctctcttc 189660

gatggtctca caaaaatatt aaacctcttt ctgatggagt cgtaaaaaag ttttatctct 189720

ttctccttcg atggtctcac aaaaatatta aacctctttc tgatggagtc gtaaaaaagt 189780

tttatctctt tctctcttcg atggtctcac aaaaatatta aacctctttc tgatggtgtc 189840

actaaaatat ttttattctc tttctctctt cgatggtctc acaaaaatat taaacctctt 189900

tctgatggag tcgtaaaaaa gttttatctc tttctccttc gatggtctca caaaaatatt 189960

aaacctcttt ctgatggagt cgtaaaaaag ttttatctct ttctctcttc gatggtctca 190020

caaaaatatt aaacctcttt ctgatggagt cgtaaaaaag ttttatctct ttctccttcg 190080

atggtctcac aaaaatatta aacctctttc tgatggagtc gtaaaaaagt tttatctctt 190140

tctccttcga tggtctcaca aaaatattaa acctctttct gatggagtcg taaaaaagtt 190200

ttatctcttt ctccttcgat ggtctcacaa aaatattaaa cctctttctg atggagtcgt 190260

aaaaaagttt tatctctttc tctcttcgat ggtctcacaa aaatattaaa cctctttctg 190320

atggagtcgt aaaaaagttt tatctctttc tctcttcgat ggtctcacaa aaatattaaa 190380

cctctttctg atggagtcgt aaaaaagttt tatctctttc tccttcgatg gtctcacaaa 190440

aatattaaac ctctttctga tggtctctat aaagcgattg atttttctta ccctctagag 190500

tttcctacgg tcgttggtca cacatttttt tctagacact aaataaatag           190550
```